(12) United States Patent
Come et al.

(10) Patent No.: US 7,135,550 B2
(45) Date of Patent: Nov. 14, 2006

(54) THREE HYBRID ASSAY SYSTEM

(75) Inventors: Jon H. Come, Cambridge, MA (US); Frank Becker, Planegg (DE); Nikolai A. Kley, Wellesley, MA (US); Christoph Reichel, Planegg (DE)

(73) Assignees: GPC Biotech Inc., Waltham, MA (US); GPC Biotech AG, Munich (DE)

( * ) Notice: Subject to any disclaimer, the term of this patent is extended or adjusted under 35 U.S.C. 154(b) by 393 days.

(21) Appl. No.: 10/234,985

(22) Filed: Sep. 3, 2002

(65) Prior Publication Data
US 2004/0043388 A1   Mar. 4, 2004

Related U.S. Application Data

(63) Continuation-in-part of application No. 10/091,177, filed on Mar. 4, 2002.

(60) Provisional application No. 60/329,437, filed on Oct. 15, 2001, provisional application No. 60/278,233, filed on Mar. 23, 2001, provisional application No. 60/272,932, filed on Mar. 2, 2001.

(51) Int. Cl.
    *C01Q 1/68* (2006.01)
(52) U.S. Cl. .................. 530/350; 435/6; 536/23.4; 514/712
(58) Field of Classification Search ............ 435/6; 530/350
    See application file for complete search history.

(56) References Cited

U.S. PATENT DOCUMENTS

| | | | |
|---|---|---|---|
| 5,468,614 A | 11/1995 | Fields et al. | |
| 5,503,977 A | 4/1996 | Johnsson et al. | |
| 5,525,465 A | 6/1996 | Haralambidis et al. | |
| 5,585,245 A | 12/1996 | Johnsson et al. | |
| 5,629,157 A * | 5/1997 | Goodman et al. | 435/6 |
| 5,672,508 A * | 9/1997 | Gyuris et al. | 435/320.1 |
| 5,714,595 A | 2/1998 | Mak et al. | |
| 5,830,462 A | 11/1998 | Crabtree et al. | |
| 5,834,266 A | 11/1998 | Crabtree et al. | |
| 5,846,722 A | 12/1998 | Kauvar et al. | |
| 5,846,728 A | 12/1998 | Haralambidis et al. | |
| 5,869,337 A | 2/1999 | Crabtree et al. | |
| 5,871,753 A | 2/1999 | Crabtree et al. | |
| 5,955,280 A | 9/1999 | Vidal et al. | |
| 5,965,368 A | 10/1999 | Vidal et al. | |
| 5,994,313 A | 11/1999 | Crabtree et al. | |
| 6,011,018 A | 1/2000 | Crabtree et al. | |
| 6,015,709 A | 1/2000 | Natesan | |
| 6,043,082 A | 3/2000 | Crabtree et al. | |
| 6,046,047 A | 4/2000 | Crabtree et al. | |
| 6,054,436 A | 4/2000 | Crabtree et al. | |
| 6,063,625 A | 5/2000 | Crabtree et al. | |
| 6,117,680 A | 9/2000 | Natesan et al. | |
| 6,133,456 A | 10/2000 | Holt et al. | |
| 6,140,120 A | 10/2000 | Crabtree et al. | |
| 6,150,527 A | 11/2000 | Holt et al. | |
| 6,165,787 A | 12/2000 | Crabtree et al. | |
| 6,172,208 B1 | 1/2001 | Cook | |
| 6,270,964 B1 | 8/2001 | Michnick et al. | |
| 6,316,418 B1 | 11/2001 | Crabtree et al. | |
| 6,326,155 B1 | 12/2001 | Maclennan et al. | |
| 6,479,653 B1 | 11/2002 | Natesan et al. | |
| 6,891,021 B1 | 5/2005 | Crabtree et al. | |
| 2002/0004202 A1 | 1/2002 | Cornish | |
| 2002/0173474 A1 | 11/2002 | Schreiber et al. | |

FOREIGN PATENT DOCUMENTS

| | | |
|---|---|---|
| EP | 0646644 | 4/1995 |
| WO | WO 94/18317 | 8/1994 |
| WO | WO 96/02561 | 2/1996 |
| WO | WO 96/06097 | 2/1996 |
| WO | WO 96/13613 | 5/1996 |
| WO | WO 97/41255 | 11/1997 |
| WO | WO 98/07845 | 2/1998 |
| WO | WO-98/16835 | 4/1998 |
| WO | WO 98/25947 | 6/1998 |
| WO | WO-99/10510 | 3/1999 |
| WO | WO-00/01417 | 1/2000 |
| WO | WO-00/07018 | 2/2000 |
| WO | WO 01/53355 | 7/2001 |
| WO | WO 02/12902 | 2/2002 |
| WO | WO 02/059272 | 8/2002 |
| WO | WO-03/033499 | 4/2003 |

OTHER PUBLICATIONS

The Merck Index, Seventh Edition, 1960, Stecher et al. eds., pp. 180, 430 and 677.*
Bachmair, A. et al. In Vivo Half-Life of a Protein is a Function of its Amino-Terminal Residue. Science 234, 179-186 (1986).
Baker, R.T. et al. Ubiquitin-specific Proteases of *Saccharomyces cerevisiae*. J. Biol. Chem. 267, 23364-23375 (1992).
Baker, R.T. & Varshavsky, A. Yeast N-terminal Amidase. J. Biol. Chem. 270, 12065-12074 (1995).
Bartel, B. et al. The recognition component of the N-end rule pathway. EMBO J. 9, 3179-3189 (1990).

(Continued)

*Primary Examiner*—James Ketter
(74) *Attorney, Agent, or Firm*—Fish & Neave IP Group Ropes & Gray LLP

(57) ABSTRACT

The invention provides compositions and methods for isolating ligand binding polypeptides for a user-specified ligand, and for isolating small molecule ligands for a user-specified target polypeptide using an improved class of hybrid ligand compounds.

37 Claims, 18 Drawing Sheets

OTHER PUBLICATIONS

Bartel, P.L. & Fields, S., eds. The yeast-two-hybrid system. Oxford University Press, New York, NY (1997).

Bergmann, K.E. et al. Bivalent Ligands as Probes of Estrogen Receptor Action. J. Steroid Biochem. Molec. Biol. 49, 139-152 (1994).

Dohmen, R.J. et al. The N-end rule is mediated by the UBC2(RAD6) ubiquitin-conjugating enzyme, PNAS 88, 7351-7355 (Aug. 1991).

Fields, S. & Song, O. A novel genetic system to detect protein-protein interactions. Nature 340, 245-246 (1989).

Gyrius, J. et al. cdl1, a Human G1 and S Phase Protein Phosphatase that Associates with Cdk2. Cell 75, 791-803 (1993).

Johnsson, N. & Varshavsky, A. Split ubiquitin as a sensor of protein interactions in vivo. PNAS 91, 10340-10344 (Oct. 1994).

Kwon, Y.T, et al. The mouse and human genes encoding the recognition component of the N-end rule pathway. PNAS 95, 7898-7903 (Jul. 1998).

Laser, H. et al. A new screen for protein interactions reveals that the *Saccharomyces cerevisiae* high mobility group proteins Nhp6A/B are involved in the regulation of the GAL 1 promoter. PNAS 97, 13732-13737 (Dec. 5, 2000).

Licitra, et al. A three-hybrid system for detecting small ligand-protein receptor interactions. PNAS 93, 12817-12821 (Nov. 1996).

Lin et al. J. Am. Chem. Soc. 122, 4247-4248 (2000).

Ozkaynak, E. et al. The yeast ubiquitin genes: a family of natural gene fusions. EMBO J. 6, 1429 (1987).

Reichel, C. et al. Enhanced green fluorescence by the expression of an *Aequorea victoria* green fluorescent protein mutant in mono- and dicotyledonous plant cells. PNAS 93. 5888-5893 (Jun. 1996).

Stagljar, I. et al. A genetic system based on split-ubiquitin for the analysis of interactions between membrane proteins In vivo. PNAS 95, 5187-5192 (Apr. 1998).

Tobias, J.W. & Varshavsky, A. Cloning and Functional Analysis of the Ubiquitin-specific Protease Gene UBP1 of *Saccharomyces cerevisiae*. J. Biol. Chem. 266, 12021-12028 (1991).

Varshavsky, A. The N-End Rule. Cell 725-735 (1992).

Yang, M. et al. Protein-peptide interactions analyzed with the yeast two-hybrid system. Nucleic Acid Res. 23, 1152-1156 (1995).

Zhu, L. & Hannon, G.J., eds. Yeast hybrid technologies. Biotechniques Press, Westborough, Ma (2000).

Amara, J.F., et al., "A versatile synthetic dimerizer for the regulation of protein—protein interactions." PNAS 94: 10618-10623 (1997).

Baker, K., et al., "Chemical complementation: A reaction-independent genetic assay for enzyme catalysis." PNAS 99(26): 16537-16543 (2002).

Bertozzi, C.R., et al., "The Synthesis of Heterobifunctional Linkers for the Conjugation of Ligands to Molecular Probes." J. Org. Chem. 56: 4326-4329 (1991).

Griffith, E.C., et al., "Yeast Three-Hybrid System for Detecting Ligand-Receptor Interactions." Methods in Enzymology 328: 89-103 (2000).

Henthorn, D.C., et al., "A GAL4-based yeast three-hybrid system for the identification of small molecule-target protein interactions." Biochemical Pharmacology 63: 1619-1628 (2002).

MacBeath, G., et al., "Printing Proteins as Microassays for High-Throughput Function Determination." Science 289: 1760-1763 (2000).

Spencer, D.M., et al., "Controlling Signal Transduction with Synthetic Ligands." Science 262: 1019-1024 (1993).

Bierer et al., "Two district signal transmission pathways in T lymphocytes are inhibited by complexes formed between an immunophilin and either FK506 or rapamycin". Proc. Natl. Acad. Sci., vol. 87 pp. 9231-9235 (1990).

Keenan et al., "Synthesis and Activity of Bivalent FKBP12 Ligands for the Regulated Dimerization of Proteins", Bioorganic & Medicinal Chemistry vol. 6 pp. 1309-1335 (1998).

Lin et al., "Dexamethasone-Methotrexate: An Efficient Chemical Inducer of Protein Dimerization *In Vivo*", J. Am. Chem. Soc. vol. 122, pp. 4247-4248 (2000).

Matthews et al., "Dihydrofolate Reductase: X-ray Structure of the Binary complex with Methotrexate", Science, vol. 197 pp. 452-455 (1977).

Sota et al., "Detection of Conformational Changes in an Immobilized Protein Using Surface Plasmon Resonance", Analytical Chemistry, vol. 70, pp. 2019-2024 (1998).

ExPASy entry for Enzyme: EC 1.5.1.3., Dihydrofolate reductase, pp. 1-2, printed on Dec. 21, 2005.

* cited by examiner

Scheme 7

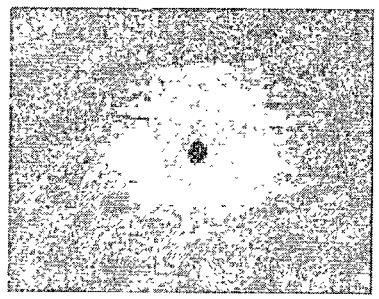
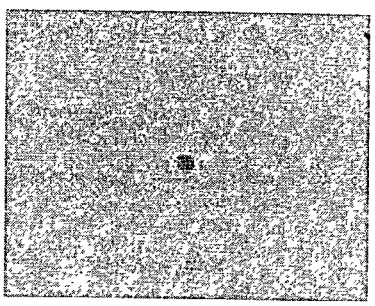
Fig. 4A      Fig. 4B
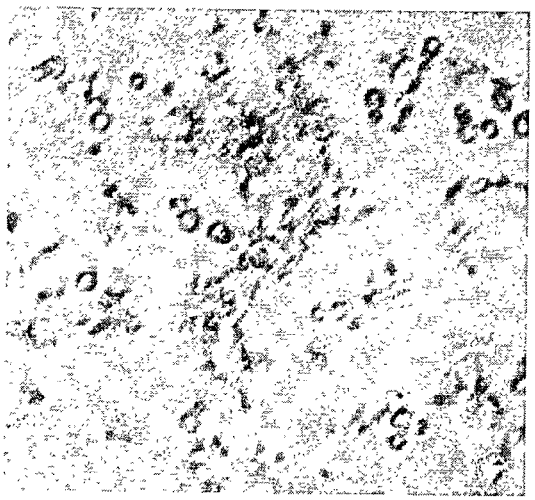
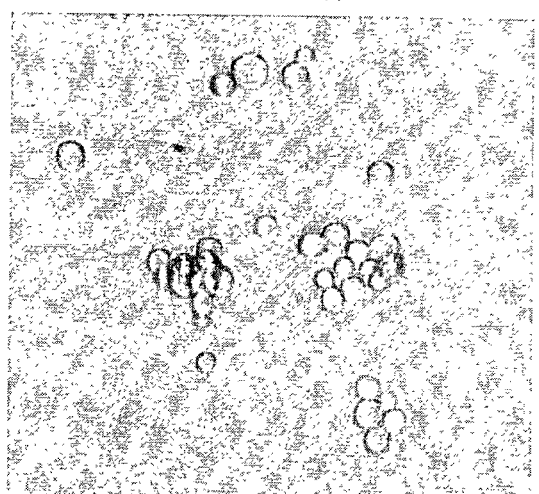
Fig. 5A      Fig. 5B

| GENELD.F orw | CLONE ID | LTH | 285985 | 285993 |
|---|---|---|---|---|
| GPC761 | MTP1E12 | ☐ | ☑ | ☐ |
| CDK2 | MTP1D6 | ☐ | ☑ | ☐ |
| GPC456 | MTP1D9 | ☑ | ☑ | ☑ |
|  | MTP1E7 | ☑ | ☑ | ☑ |
| GPC672 | MTP1C24 | ☐ | ☑ | ☑ |
| GPC556 | MTP1C14 | ☐ | ☑ | ☑ |
| GPC173 | MTP1F9 | ☑ | ☑ | ☑ |
| GPC553 | MTP1F7 | ☐ | ☑ | ☑ |
| GPC644 | MTP1C23 | ☑ | ☑ | ☑ |
|  | MTP1D16 | ☐ | ☐ | ☐ |

Fig. 12

```
        GAL4 AD
5089    (881)           5070          5060          5050
 *       →               *             *             *
AAA AAA GAG ATC TGT ATG GCT TAC CCA TAC GAT GTT CCA GAT TAC GCT
        Bgl II          ←─────────── HA epitope ───────────→

5040          5030          5020          5010          5000
 *             *             *             *             *
AGC TTG GGT GGT CAT ATG GCC ATG GAG GCC CCG GGG ATC CGA ATT C
                            Nco I       Sma I           EcoR I
                              Sfi I       Xma I   BamH I 4990          4980          4970
     *             *             *
GA GCT CGA GAG ATC TAT GAA TCG TAG ATA CTG AAA AAC
   Sac I          Bgl II  stop    stop    stop
     Xho I
```

THREE HYBRID ASSAY SYSTEM

REFERENCE TO RELATED APPLICATIONS

This application is a "continuation in part (CIP)" application of U.S. Ser. No. 10/091,177, filed on Mar. 4, 2002, which claims priority to U.S. Provisional applications No. 60/272,932, filed on Mar. 2, 2001; No. 60/278,233, filed on Mar. 23, 2001; and No. 60/329,437, filed on Oct. 15, 2001, the specifications of which are hereby incorporated by reference in their entirety.

BACKGROUND OF THE INVENTION

Protein interactions facilitate most biological processes including signal transduction and homeostasis. The elucidation of particular interacting protein partners facilitating these biological processes has been advanced by the development of in vivo "two-hybrid" or "interaction trap" methods for detecting and selecting interacting protein partners (see Fields & Song (1989) Nature 340: 245–6; Gyuris et al. (1993) Cell 75: 791–803; U.S. Pat. No. 5,468,614; and Yang et al. (1995) Nucleic Acid Research 23, 1152–1156). These methods rely upon the reconstitution of a nuclear transcriptional activator via the interaction of two binding partner polypeptides—i.e. a first polypeptide fused to a DNA binding domain (BD) and a second polypeptide fused to a transcriptional activation domain (AD). When the first and the second polypeptides interact, the interaction can be detected by the activation of a reporter gene containing binding sites for the DNA binding domain. For this method to work, both proteins need to be soluble and must be able to localized to the nucleus. Accordingly, the interaction of polypeptides which are normally localized to other compartments may not be detected because of the absence of other non-nuclear polypeptide components which facilitate the interaction or particular non-nuclear post-translational modifications which fail to occur in the nucleus or because the interacting proteins fail to fold properly when localized to the nuclear compartment. In particular, the nuclear two-hybrid assay is ill-suited to the detection of protein interactions occurring within or at the surface of cellular membranes. In addition, this assay is unsuited for screening small molecule-protein interactions because it relies solely on genetically encoded fusion proteins.

A fundamental area of inquiry in pharmacology and medicine is the determination of ligand-receptor interactions. The pharmacological basis of drug action, at the cellular level, is quite often the consequence of non-covalent interactions between therapeutically relevant small organic molecules and high affinity binding proteins within a specific cell type. These small organic ligands may function as agonists or antagonists of key regulatory events which orchestrate both normal and abnormal cellular functions. For years the pharmaceutical industry's approach to discovering such ligands has been one of the random screening of thousands of small molecules in specific in vitro and in vivo assays to determine a potent lead compound for their drug discovery efforts. Using these tools, a lead compound may be found to exert very well-defined effects with regard to a function in one particular cell type (e.g. inhibition of cytokine production or DNA replication in a particular cancer cell line). However, such results may give little indication as to the mechanism of action at the molecular (ligand-protein interaction) level. Furthermore, the screening for potent action on one cellular function may miss out on cross-reactivities of a lead compound giving rise to undesired side-effects. Such side-effects often are the consequence of proteins with closely similar structures having different functions, or of a protein fulfilling different functions when expressed in different cell types, or even when localized to different sub-cellular compartments. Therefore, the identification of the possibly various protein targets for a pharmacological agent displaying a given activity is challenging but highly desirable. There is an unmet need for a general and efficient method to identify the cellular targets for these pharmacological agents so as to accelerate the search for novel drugs both at the basic and applied levels of research.

Similarly, there is a need for a general approach to identify a small molecule capable of binding any selected cellular target regardless of its biological function. Fowlkes et al. (WO 94/23025) and Broach et al. (WO 95/30012) described a screening assay for identifying molecules capable of binding cell surface receptors so as to activate a selected signal transduction pathway. These references describe the modification of selected yeast signaling pathways so as to mimic steps in the mammalian signaling pathway. This latter approach is specific for certain signaling pathways and has limited utility for broadly discovering small molecules that interact with any cellular target. Thus, there is also an unmet need for a general screening method to determine the interaction between small molecules and target proteins so as to identify new drugs that are capable of specific therapeutic effects in a variety of disease states as well as to identify agonists and antagonists that may interfere or compete with the binding of the small molecules for these targets.

At this time, few (if any) efficient methodologies exist for rapidly identifying a biological target such as a protein for a particular small molecule ligand. Existing approaches include the use of affinity chromatography, radio-labeled ligand binding and photoaffinity labeling in combination with protein purification methods to detect and isolate putative target proteins. This is followed by cloning of the gene encoding the target protein based on the peptide sequence of the isolated target. These approaches require substantial re-development of matrices and the conditions of their use for each ligand under investigation, and are therefore laborious and painstaking.

Crabtree et al. (WO 94/18317) described a method to activate a target gene in cells comprising (a) the provision of cells containing and capable of expressing (i) at least one DNA construct comprising at least one receptor domain, capable of binding to a selected ligand, fused to a heterologous additional protein capable of initiating a biological process upon exposure of the fusion construct to the ligand, wherein the biological process comprises the expression of the target gene, wherein the ligand is capable of binding to two or more fusion proteins, and wherein the biological process is only initiated upon binding of the ligand to two or more fusion proteins, the two fusion proteins being the same or different, and (ii) the target gene under the expression control of a control element which is transcriptionally responsive to the initiation of said biological process; and (b) exposing said cells to said ligand in an amount effective to result in expression of the reporter gene. Further described are DNA constructs, ligands and kits useful for performing such method. Related documents U.S. Pat. No. 5,830,462, U.S. Pat. No. 5,869,337 U.S. Pat. No. 6,165,787 show these and other embodiments; specifically, Holt et al. (WO 96/06097) describes the synthesis of hybrid ligands for use with the subject methods. The purpose envisaged for these methods and compositions is restricted to the investigation of cellular processes, the regulation of the synthesis of proteins of therapeutic or agricultural importance and the regulation of cellular processes in gene therapy. Nothing therein suggests the use of these methods and compositions to study the interaction of proteins with small molecules, particularly in its application to pharmaceutical research and drug development.

Licitra and Liu (WO 97/41255) described a "three hybrid screen assay" in which the basic yeast two-hybrid assay system is implemented. The significant difference is: instead of depending on the interaction between a so-called "bait" and a so-called "prey" protein, the transcription of the reporter gene is conditioned on the proximity of the two proteins, each of which can bind specifically to one of the two moieties of a small hybrid ligand. The small hybrid ligand constitute the "third" component of the hybrid assay system. In that system, one known moiety of the hybrid ligand will bind to the "bait" protein, while the interaction between the other moiety and the "prey" protein can be exploited to screen for either a protein that can bind a known moiety, or a small moiety (pharmaceutical compound or drug) that can bind a known protein target.

However, the three hybrid system of Liu suffers from several limitations: 1) the use of a transcriptional activation reporter assay is ill-suited for non-nuclear proteins, for example, membrane-bound proteins and cytosolic proteins; 2) the hybrid ligand must be localized to the nucleus, and remains stable; and, 3) the interaction between the "bait" protein and its binding moiety on the hybrid ligand must have high affinity, preferably at the nanomolar level. For example, FK506-FKBP interaction was used which provides micromolar affinity. Higher affinity bewteen bait protein and its binding partner is desired for improving system performance.

Lin et al. (J. Am. Chem. Soc. 2000, 122:4247–8) improved upon the existing three hybrid system by replacing the FK506-FKBP pair with a hybrid ligand consisting of dihydrofolate-reductase (DHFR) linked to methotrexate (Mtx) (DHFR-Mtx), which provides picomolar affinity, thereby significantly improving system performance.

U.S. Pat No. 5,585,245 and U.S. Pat. No. 5,503,977 describe the "split ubiquitin" methods, which can detect protein-protein interactions by use of a ubiquitin specific protease to cleave a reporter polypeptide from a fusion protein. Two fusion proteins are constructed, one consisting of the N-terminal half of ubiquitin and a prey protein (Nub-prey or prey-Nub), and the other consisting of the C-terminal half of ubiquitin, a bait protein and the reporter (bait-Cub-reporter). Association of prey and bait reconstitutes a ubiquitin structure recognized by the ubiquitin specific protease, whereby the reporter is cleaved from the fusion protein. The cleavage of the reporter from the fusion protein can be detected by several techniques, e.g. cleavage or destabilizing the reporter or allow for its translocation.

A further working principle used in several assay systems developed to investigate protein-protein interactions is the reconstitution of an enzymatic activity from the induced spatial proximity of enzymatic fragments mediated by the interaction of two peptides fused to these fragments. Such an assay is termed an enzyme complementation assay. U.S. Pat. No. 6,270,964, WO 98/44350 and Wehrman et al., Proc. Natl. Acad. Sci. U.S.A. (2002), 99:3469–3474, show exemplary methods employing this principle.

WO 93/08278, WO 98/37186, WO 01/14539 and WO 02/22826 describe yet another biological system for the investigation of protein-protein interactions. Therein, genetic information encoding the peptides or proteins to be tested for interactions is cloned into a vector comprising genetic information encoding a nucleic acid binding protein as well as the nucleic acid sequence said nucleic acid binding protein binds to, such that the peptides or proteins are expressed as in-frame fusions with the nucleic acid binding domain. When cells are induced to express the fusion peptides/proteins, they will associate with the vector that encodes them. After isolation of these complexes from the cells and testing for interaction, the nucleic acid encoding interacting peptides/proteins is easily retrieved. WO 98/37186, WO 01/14539 and WO 02/22826 particularly describe systems wherein the nucleic acid binding protein forms a covalent bond with its recognition motif.

So called "pull-down" techniques are still frequently used in the investigation of protein-protein interactions. As opposed to the methods described above, these methods are carried out in vitro rather than in vivo. In essence, these methods rely on immobilizing the molecular species for which a binding or interaction partner is sought on a surface, and subsequently passing a solution containing potential binding partners/interactors over this surface. A binding/interaction partner will be retained on the solid support, while other constituents of the solution will be washed away. In a second step, the binding/interaction partner is isolated for further analysis, for example by passing a solution containing an excess of a substance known to competitively displace binding/interaction partners from the molecular species under investigation. Alternatively, the bond between the molecular species under investigation and the matrix may be severed and the complex isolated from the solid support for analysis. An example of the use of such a technique to identify intracellular targets of purvalanol B, an inhibitor of CDKs, is shown in Knockaert et al. (2000), Chem. Bio. 7:411–422.

SUMMARY OF THE INVENTION

One aspect of the instant invention provides a hybrid ligand represented by the general formula: R1-Y—R2, wherein:

R1 represents a first ligand selected from: a steroid, retinoic acid, beta-lactam antibiotic, cannabinoid, nucleic acid, polypeptide, FK506, FK506 derivative, rapamycin, tetracycline, methotrexate, novobiocin, maltose, glutathione, biotin, vitamin D, dexamethasone, estrogen, progesterone, cortisone, testosterone, nickel, 2,4-diaminopteridine or cyclosporin, or a derivative thereof with minor structural modifications;

Y represents a polyethylene linker having the general formula $(CH_2-X-CH_2)_n$, where X represents O, S, SO, or $SO_2$, and n is an integer from 2 to 25; and, R2 represents a user-specified second ligand different from R1 selected from: a peptide, nucleic acid, carbohydrate, polysaccharide, lipid, prostaglandin, acyl halide, alcohol, aldehyde, alkane, alkene, alkyne, alkyl, alkyl halide, alkaloid, amine, aromatic hydrocarbon, sulfonate ester, carboxylate acid, aryl halide, ester, phenol, ether, nitrile, carboxylic acid anhydride, amide, quaternary ammonium salt, imine, enamine, amine oxide, cyanohydrin, organocadmium, aldol, organometallic, aromatic hydrocarbon, nucleoside, or a nucleotide.

In one embodiment, the first ligand binds to a polypeptide. In a preferred embodiment, the binding affinity corresponds to a ligand/polypeptide dissociation constant $K_D$ of less than 1 µM. In another preferred embodiment, the first ligand is capable of forming a covalent bond with the polypeptide.

In another embodiment, X is O. In another embodiment, Y is $(CH_2-O-CH_2)_n$, where n=2 to 5. In another embodiment, R1 is dexamethasone. In another embodiment, R1 is methotrexate, a methotrexate derivative, FK506, an FK506 derivative or a 2,4-diaminopteridine derivative. In a preferred embodiment, R1 is dexamethasone, Y is $(CH_2OCH_2)_3$, and R2 is methotrexate or a 2,4-diaminopteridine derivative. In a most preferred embodiment, R1 is methotrexate, and Y is $(CH_2-O-CH_2)_n$, where n=2 to 5.

In another embodiment, R2 is a ligand chosen from: a compound with a known biological effect, a compound with an unknown mechanism of action, a compound which binds to more than one polypeptide, a drug candidate compound, or a compound that binds to an unknown protein.

In another embodiment, R2 binds to or inhibits a kinase.

The integer n can be from 2 to 20, or 2 to 15, or 2 to 10, or 2 to 5.

A related aspect of the invention provides a hybrid ligand represented by the general formula: R1-Y—R2, wherein:

R1 represents a first ligand selected from: a steroid, retinoic acid, beta-lactam antibiotic, cannabinoid, nucleic acid, polypeptide, FK506, FK506 derivative, rapamycin, tetracycline, methotrexate, novobiocin, maltose, glutathione, biotin, vitamin D, dexamethasone, estrogen, progesterone, cortisone, testosterone, nickel, 2,4-diaminopteridine derivative or cyclosporin, or a derivative with minor structural modifications;

Y represents a linker; and,

R2 represents a user-specified second ligand different from R1 selected from: a peptide, nucleic acid, carbohydrate, polysaccharide, lipid, prostaglandin, acyl halide, alcohol, aldehyde, alkane, alkene, alkyne, alkyl, alkyl halide, alkaloid, amine, aromatic hydrocarbon, sulfonate ester, carboxylate acid, aryl halide, ester, phenol, ether, nitrile, carboxylic acid anhydride, amide, quaternary ammonium salt, imine, enamine, amine oxide, cyanohydrin, organocadmium, aldol, organometallic, aromatic hydrocarbon, nucleoside, or a nucleotide;

wherein R2 binds to or inhibits a kinase.

In one embodiment, the kinase is a cyclin dependent kinase. In another embodiment, R2 is a compound selected from Table 2, which contains about 600 compounds known to be able to bind to or inhibit a kinase, or a derivative thereof with minor structural modifications. In another embodiment, Y represents a polyethylene linker having the general formula $(CH_2-X-CH_2)_n$, where X represents O, S, SO, or $SO_2$, and n is an integer from 2 to 25.

Another aspect of the invention provides a fusion polypeptide, comprising segments P1, Cub-Z, and RM, in an order wherein Cub-Z is closer to the N-terminus of the fusion polypeptide than RM, wherein 1) P1 is a ligand binding polypeptide that binds to a non-peptide ligand of a hybrid ligand, which has the general formula R1-Y—R2, where R1 and R2 are ligands, and Y is a linker, 2) Cub is a carboxy-terminal subdomain of ubiquitin, 3) Z is an amino acid residue, 4) RM is a reporter moiety.

Another aspect of the invention provides a fusion polypeptide, comprising segments P1 and Nux, wherein 1) Nux is the amino-terminal subdomain of a wild-type ubiquitin or a reduced-associating mutant ubiquitin amino-terminal subdomain, and 2) P1 is a ligand binding polypeptide that binds to a non-peptide ligand of a hybrid ligand, which has the general formula R1-Y—R2, where R1 and R2 are ligands, and Y is a linker.

In a preferred embodiment, the non-peptide ligands of the fusion proteins are: a steroid, retinoic acid, beta-lactam antibiotic, cannabinoid, nucleic acid, FK506, FK506 derivative, rapamycin, tetracycline, methotrexate, 2,4-diaminopteridine, novobiocin, maltose, glutathione, biotin, vitamin D, dexamethasone, estrogen, progesterone, cortisone, testosterone, nickel, cyclosporin, or a derivative thereof with minor structural modifications; or a carbohydrate, polysaccharide, lipid, prostaglandin, acyl halide, alcohol, aldehyde, alkane, alkene, alkyne, alkyl, alkyl halide, alkaloid, amine, aromatic hydrocarbon, sulfonate ester, carboxylate acid, aryl halide, ester, phenol, ether, nitrile, carboxylic acid anhydride, amide, quaternary ammonium salt, imine, enamine, amine oxide, cyanohydrin, organocadmium, aldol, organometallic, aromatic hydrocarbon, nucleoside, or a nucleotide.

In another embodiment, Z is a non-methionine amino acid. In another embodiment, RM is: a polypeptide capable of emitting light upon excitation, a polypeptide with an enzymatic activity, a detectable tag or a transcription factor. In another embodiment, RM is: green fluorescent protein, URA3 or PLV.

Another aspect of the invention provides a nucleic acid encoding the fusion polypeptide of any one of the instant invention.

In another embodiment, X is O. In another embodiment, Y is $(CH_2OCH_2)_3$. In another embodiment, R1 is dexamethasone, Y is $(CH_2OCH_2)_3$, and R2 is methotrexate or 2,4-diaminopteridine.

Another aspect of the invention provides a composition, comprising: 1) a hybrid ligand of the general formula R1-Y—R2, where R1 and R2 are ligands, R1 is different from R2 and at least one of R1 and R2 is not a peptide, Y is a linker; and, 2) at least one of two fusion polypeptides comprising: a) a first fusion polypeptide comprising segments P2, Cub-Z, and RM, in an order wherein Cub-Z is closer to the N-terminus of the first fusion polypeptide than RM, wherein P2 is a ligand binding polypeptide that may bind to ligand R1 or R2 of the hybrid ligand, Cub is a carboxy-terminal subdomain of ubiquitin and RM is a reporter moiety, and Z is an amino acid residue; b) a second fusion polypeptide comprising segments Nux and P1, wherein Nux is the amino-terminal subdomain of a wild-type ubiquitin or a reduced-associating mutant ubiquitin amino-terminal subdomain, and P1 is a ligand binding polypeptide that may bind to ligand R1 or R2 of the hybrid ligand.

A related aspect of the invention provides a composition, comprising: 1) a hybrid ligand represented by the general formula: R1-Y—R2, wherein: a) R1 represents a first ligand selected from: a steroid, retinoic acid, beta-lactam antibiotic, cannabinoid, nucleic acid, polypeptide, FK506, FK506 derivative, rapamycin, tetracycline, methotrexate, 2,4-diaminopteridine derivative, novobiocin, maltose, glutathione, biotin, vitamin D, dexamethasone, estrogen, progesterone, cortisone, testosterone, nickel, or cyclosporin, or a derivative thereof with minor structural modifications; b) Y represents a polyethylene linker having the general formula $(CH_2-X-CH_2)_n$, where X represents O, S, SO, or $SO_2$, and n is an integer from 2 to 25; c) R2 represents a user-specified second ligand different from R1 selected from: a peptide, nucleic acid, carbohydrate, polysaccharide, lipid, prostaglandin, acyl halide, alcohol, aldehyde, alkane, alkene, alkyne, alkyl, alkyl halide, alkaloid, amine, aromatic hydrocarbon, sulfonate ester, carboxylate acid, aryl halide, ester, phenol, ether, nitrile, carboxylic acid anhydride, amide, quaternary ammonium salt, imine, enamine, amine oxide, cyanohydrin, organocadmium, aldol, organometallic, aromatic hydrocarbon, nucleoside, or a nucleotide; 2) at least one fusion polypeptide selected from: a) a first fusion polypeptide comprising: a ligand binding domain P1 and a domain selected from the group consisting of: a DNA binding domain and a transcriptional activation domain, wherein the ligand binding domain may bind the first ligand R1; and, b) a second fusion polypeptide comprising: a candidate ligand-binding domain P2 which may bind the user-specified ligand R2 and a domain selected from the group consisting of: a DNA binding domain and a transcriptional activation domain, wherein one of the first and second fusion polypeptides contains a DNA binding domain and the other fusion polypeptide contains a transcription activation domain.

Another related aspect of the invention provides a composition comprising: 1) A hybrid ligand represented by the general formula: R1-Y—R2, wherein: a) R1 represents a first ligand selected from: a steroid, retinoic acid, beta-lactam antibiotic, cannabinoid, nucleic acid, polypeptide, FK506, FK506 derivative, rapamycin, tetracycline, methotrexate, 2,4-diaminopteridine derivative, novobiocin, maltose, glutathione, biotin, vitamin D, dexamethasone, estrogen, progesterone, cortisone, testosterone, nickel, or cyclosporin, or a derivative thereof with minor structural modifications; b) Y represents a polyethylene linker having the general formula $(CH_2-X-CH_2)_n$, where X represents O, S, SO, or SO2, and n is an integer from 2 to 25; c) R2 represents a user-specified second ligand different from R1 selected from: a peptide, nucleic acid, carbohydrate, polysaccharide, lipid, prostaglandin, acyl halide, alcohol, aldehyde, alkane, alkene, alkyne, alkyl, alkyl halide, alkaloid, amine, aromatic hydrocarbon, sulfonate ester, carboxylate acid, aryl halide, ester, phenol, ether, nitrile, carboxylic acid anhydride, amide, quaternary ammonium salt, imine, enamine, amine oxide, cyanohydrin, organocadmium, aldol, organometallic, aromatic hydrocarbon, nucleoside, or a nucleotide; and 2) a fusion polypeptide that includes: a) at least one ligand binding domain; and, b) a functional domain heterologous to the ligand binding domain which by itself is not capable of inducing or allowing the detection of a detectable event, but which is capable of inducing or allowing the detection of a detectable event when brought into proximity of a second functional domain.

In one embodiment, the composition is a complex. In another embodiment, the composition is provided in an environment chosen from: a cell, a container, a kit, a solution or a growth medium.

Another aspect of the invention provides method of identifying a polypeptide sequence that binds to a user-specified ligand comprising: 1) providing a hybrid ligand having the general formula R1-Y—R2, where R1 is a first ligand, R2 is a user-specified ligand, and Y is a polyethylene linker having the general formula $(CH_2-X-CH_2)_n$, where X represents O, S, SO, or $SO_2$, and n is an integer from 2 to 25; 2) introducing the hybrid ligand into a population of cells, each cell containing a hybrid ligand screening system including: a) a reporter gene operably linked to a transcriptional regulatory sequence, said regulatory sequence including a DNA sequence which binds to a DNA binding domain; b) a first chimeric gene encoding a first fusion polypeptide comprising: a ligand binding domain P1 and a domain selected from a DNA binding domain or a transcriptional activation domain, wherein the ligand binding domain binds the first ligand R1; and, c) a second chimeric gene encoding a second fusion polypeptide comprising: a candidate ligand-binding domain P2 for the user-specified ligand R2 and a domain selected from a DNA binding domain or a transcriptional activation domain; wherein one of the two fusion polypeptides contains a DNA binding domain and the other fusion polypeptide contains a transcription activation domain; 3) allowing the hybrid ligand to bind the ligand binding domain of the first fusion polypeptide through the first ligand R1 and to contact the candidate ligand binding domain of the second fusion polypeptide through the user-specified ligand R2 such that, if R2 binds to the candidate ligand binding domain, an increase in the level of transcription of the reporter gene occurs; 4) identifying a positive ligand binding cell in which an increase in the level of transcription of the reporter gene has occurred; and, 5) identifying the nucleic acid sequence of the second chimeric gene encoding the candidate ligand binding domain that binds to the user-specified ligand R2, thereby identifying a polypeptide sequence that binds to a user-specified ligand.

In one embodiment, the nucleic acid sequence encoding the candidate ligand binding domain polypeptide of the second fusion polypeptide is from a library selected from: a synthetic oligonucleotide library, a cDNA library, a bacterial genomic DNA fragment library, or a eukaryotic genomic DNA fragment library.

In another embodiment, the library has about 2–10 members, or about 10–500 members, or about 500–10,000 members, or at least 10,000 members.

In another embodiment, the nucleic acid sequence that encodes the candidate ligand binding domain polypeptide sequence represents a single user-selected drug target.

In another embodiment, the first ligand R1 of the hybrid ligand binds to the ligand binding domain P1 with a high affinity. In a preferred embodiment, the binding affinity corresponds to a ligand/ligand binding protein dissociation constant $K_D$ of less than 1 μM.

In another embodiment, the first ligand is capable of forming a covalent bond with the ligand binding domain P1.

In another embodiment, X is O. In another embodiment, Y is $(CH_2-O-CH_2)_n$, where n=2 to 5. In another embodiment, R1 is methotrexate, and Y is $(CH_2-O-CH_2)_n$, n=2 to 5. In another embodiment, the reporter gene is selected from: HIS3, LEU2, TRP2, TRP1, ADE2, LYS2, URA3, CYH1, CAN1, lacZ, gfp or CAT. In another embodiment, R2 binds to or inhibits a kinase.

Another aspect of the invention provides a method of identifying a polypeptide sequence that binds to a user-specified ligand comprising: 1) providing a hybrid ligand having the general formula R1-Y—R2, where R1 is a first ligand, R2 is a user-specified ligand different from R1 which binds to or inhibits a kinase, at least one of R1 and R2 is not a peptide, and Y is a linker; 2) introducing the hybrid ligand into a population of cells, each cell containing a hybrid ligand screening system including: a) a reporter gene operably linked to a transcriptional regulatory sequence, said regulatory sequence including a DNA sequence which binds to a DNA binding domain; b) a first chimeric gene encoding a first fusion polypeptide comprising: a ligand binding domain and a domain selected from the DNA binding domain or a transcriptional activation domain, wherein the ligand binding domain binds the first ligand R1; and, c) a second chimeric gene encoding a second fusion polypeptide comprising: a candidate ligand-binding domain for the user-specified ligand R2 and a domain selected from the DNA binding domain or the transcription activation domain; wherein one of the two fusion polypeptides contains a DNA binding domain and the other fusion polypeptide contains a transcription activation domain; 3) allowing the hybrid ligand to bind the ligand binding domain of the first fusion polypeptide through the first ligand R1 and to contact the candidate ligand binding domain of the second fusion polypeptide through the user-specified ligand R2 such that, if R2 binds to the candidate ligand binding domain, an increase in the level of transcription of the reporter gene occurs; 4) identifying a positive ligand binding cell in which an increase in the level of transcription of the reporter gene has occurred; and, 5) identifying the nucleic acid sequence of the second chimeric gene encoding the candidate ligand binding domain that binds to the user-specified ligand R2, thereby identifying a polypeptide sequence that binds to a user-specified ligand.

In one embodiment, the kinase is a cyclin dependent kinase. In one embodiment, R2 is a compound selected from Table 2. In one embodiment, Y is $(CH_2—X—CH_2)_n$, n=2 to 25. In one embodiment, R1 represents a first ligand selected from: a steroid, retinoic acid, beta-lactam antibiotic, cannabinoid, nucleic acid, polypeptide, FK506, FK506 derivative, rapamycin, tetracycline, methotrexate, novobiocin, maltose, glutathione, biotin, vitamin D, dexamethasone, estrogen, progesterone, cortisone, testosterone, nickel, 2,4-diaminopteridine derivative or cyclosporin, or a derivative thereof with minor structural modifications.

In another embodiment, the method further comprises determining the binding affinity of the hybrid ligand to the ligand binding domains P1 and/or P2. In a preferred embodiment, the determination of the binding affinity is performed by surface plasmon resonance.

In another embodiment, the method further comprises determining the effects of the hybrid ligand that are independent of the formation of a trimeric complex comprising the hybrid ligand, P1 and P2.

In another embodiment, the method further comprises the step of: performing at least one additional separate method to confirm that the transcription of the reporter gene is dependent on the presence of the hybrid ligand and the ligand binding domains P1 and P2. In a preferred embodiment, said additional separate method is selected from: a halo growth assay method or a fluorescence detection growth assay. In a most preferred embodiment, said additional separate method is individually conducted on greater than about 10, 100, 1000 or 10000 different positive ligand binding cell-types identified in step 4).

A related aspect of the invention provides a method of identifying a polypeptide sequence that binds to a user-specified ligand comprising: providing a hybrid ligand having the general formula R1-Y—R2, where R1 is a first ligand, R2 is a user-specified ligand, and Y is a linker; contacting the hybrid ligand with a cultured cell comprising: a first chimeric gene encoding a first fusion polypeptide comprising: segments P1, Cub-Z, and RM, in an order wherein Cub-Z is closer to the N-terminus of the first fusion polypeptide than RM, wherein P1 is a ligand binding polypeptide that binds to the first ligand R1, Cub is a carboxy-terminal subdomain of ubiquitin, Z is a non-methionine amino acid residue and RM is a reporter moiety, a second chimeric gene encoding a second fusion polypeptide comprising: segments Nux and P2, wherein Nux is the amino-terminal subdomain of a wild-type ubiquitin or a reduced-associating mutant ubiquitin amino-terminal subdomain, and P2 is a candidate ligand binding polypeptide for the user-specified ligand R2; and, a ubiquitin dependent proteolytic system comprising an N-end rule ubiquitin specific protease (UBP); allowing the hybrid ligand to bind the ligand binding polypeptide P1 of the first fusion polypeptide through the first ligand R1 and to contact the candidate ligand binding polypeptide P2 of the second fusion polypeptide through the user-specified ligand R2 such that, when R2 binds to the candidate ligand binding polypeptide P2, the Nux and Cub domains associate to form a reconstituted ubiquitin moiety and the ubiquitin specific protease cleaves the Cub-Z peptide bond so as to release an RM-containing fragment, said fragment being susceptible to N-end rule ubiquitin-dependent proteolytic degradation; maintaining the cultured cell under conditions wherein cleavage of the Cub-Z bond is necessary for growth of the cell; and, identifying the sequence of the chimeric gene encoding the candidate ligand binding polypeptide P2, thereby identifying a polypeptide sequence that binds to a user-specified ligand.

Another related aspect of the invention provides a method of identifying a polypeptide sequence that binds to a user-specified ligand comprising: providing a hybrid ligand having the general formula R1-Y-R2, where R1 is a first ligand, R2 is a user-specified ligand, and Y is a linker; contacting the hybrid ligand with cultured cell comprising: a first chimeric gene encoding a first fusion polypeptide comprising: segments Nux and PI, wherein Nux is the amino-terminal subdomain of a wild-type ubiquitin or a reduced-associating mutant ubiquitin amino-terminal subdomain, and P1 is a ligand-binding polypeptide for the first ligand R1, a second chimeric gene encoding a second fusion polypeptide comprising: segments P2, Cub-Z, and RM, in an order wherein Cub-Z is closer to the N-terminus of the second fusion polypeptide than RM, wherein P2 is a candidate ligand-binding polypeptide that binds to the user-specified ligand R2, Cub is a carboxy-terminal subdomain of ubiquitin, Z is a non-methionine amino acid residue and RM is a reporter moiety; and, a ubiquitin dependent proteolytic system comprising an N-end rule ubiquitin specific protease; allowing the hybrid ligand to bind the ligand binding polypeptide P1 of the first fusion polypeptide through the first ligand R1 and to contact the candidate ligand binding polypeptide P2 of the second fusion polypeptide through the user-specified ligand R2 such that, when R2 binds to the candidate ligand binding polypeptide P2, the Nux and Cub subdomains associate to form a reconstituted ubiquitin moiety and the ubiquitin specific protease cleaves the Cub-Z peptide bond so as to release an RM-containing fragment, said fragment being susceptible to N-end rule ubiquitin-dependent proteolytic degradation; maintaining the cultured cell under conditions wherein cleavage of the Cub-Z bond is necessary for growth of the cell; and, identifying the sequence of the second chimeric gene encoding the candidate ligand binding polypeptide P2, thereby identifying a polypeptide sequence that binds to a user-specified ligand.

In one embodiment, P2 is encoded by a nucleic acid from a library selected from the group consisting of: a synthetic oligonucleotide library, a cDNA library, a bacterial genomic DNA fragment library, and a eukaryotic genomic DNA fragment library. In another embodiment, the nucleic acid sequence that encodes the candidate ligand binding protein sequence represents a single user-selected drug-target. In another embodiment, the first ligand of the hybrid ligand binds to the ligand binding polypeptide with a high affinity. In another embodiment, the first ligand is methotrexate and the first ligand binding polypeptide is DHFR. In another embodiment, the binding affinity corresponds to a ligand/ligand binding protein dissociation constant of less than 1 µM. In another embodiment, the first ligand is capable of forming a covalent bond with the ligand binding polypeptide. In another embodiment, Y is $(CH_2OCH_2)_3$. Preferably, R1 is dexamethasone, Y is $(CH_2OCH_2)_3$, and R2 is methotrexate or 2,4-diaminopteridine. In another embodiment, the reporter moiety (RM) is a negative selectable marker expressed in a cell expressing the first and second fusion polypeptides, and wherein a decrease in the level of the reporter moiety causes an increase in the growth of said cell. In another embodiment, the reporter moiety (RM) is a positive selectable marker expressed in a cell expressing the first and second fusion polypeptides, and wherein a increase in the activity of the reporter moiety causes an increase in the growth of said cell.

Another related aspect of the invention provides a method of identifying a polypeptide sequence that binds to a user-specified ligand comprising: providing a hybrid ligand having the general formula R1-Y—R2, where R1 is a first ligand, R2 is a user-specified ligand, and Y is a linker; contacting the hybrid ligand with a cultured cell comprising: a first chimeric gene encoding a first fusion polypeptide comprising: segments P1, Cub-Z, and RM, in an order wherein Cub-Z is closer to the N-terminus of the first fusion polypeptide than RM, wherein P1 is a ligand binding polypeptide that binds to the first ligand R1, Cub is a carboxy-terminal subdomain of ubiquitin, Z is methionine and RM is a reporter moiety, a second chimeric gene encoding a second fusion polypeptide comprising: segments Nux and P2, wherein Nux is the amino-terminal subdomain of a wild-type ubiquitin or a reduced-associating mutant ubiquitin amino-terminal subdomain, and P2 is a candidate ligand binding polypeptide for the user-specified ligand R2; and, a ubiquitin dependent proteolytic system comprising an N-end rule ubiquitin specific protease (UBP); allowing the hybrid ligand to bind the ligand binding polypeptide P1 of the first fusion polypeptide through the first ligand R1 and to contact the candidate ligand binding polypeptide P2 of the second fusion polypeptide through the user-specified ligand R2 such that, when R2 binds to the candidate ligand binding polypeptide P2, the Nux and Cub domains associate to form a reconstituted ubiquitin moiety and the ubiquitin specific protease cleaves the Cub-Z peptide bond so as to release an RM-containing fragment, said fragment being non-susceptible to N-end rule ubiquitin-dependent proteolytic degradation is functional upon cleavage; maintaining the cultured cell under conditions wherein cleavage of the Cub-Z bond is necessary for growth of the cell; and, identifying the sequence of the chimeric gene encoding the candidate ligand binding polypeptide P2, thereby identifying a polypeptide sequence that binds to a user-specified ligand.

Another aspect of the invention provides a method of determining whether a polypeptide P2 and a ligand R2 bind to each other comprising: 1) translationally providing a first ligand-binding polypeptide comprising segments P1, Cub-Z, and RM, in an order wherein Cub-Z is closer to the N-terminus of the first ligand-binding polypeptide than RM, and a second ligand-binding polypeptide comprising segments Nux and P2, wherein P1 and P2 are polypeptides, Nux is the amino-terminal subdomain of a wild-type ubiquitin or a reduced-associating mutant ubiquitin amino-terminal subdomain, Cub is the carboxy-terminal subdomain of a wild-type ubiquitin, Z is an amino acid residue and RM is a reporter moiety; 2) providing a hybrid ligand represented by the general formula: R1-Y—R2, wherein R1 is a first ligand that binds the first ligand-binding polypeptide at P1, R2 is a second ligand different from R1, at least one of R1 and R2 is not a peptide, and Y is a linker; 3) allowing the hybrid ligand to contact the first and second ligand-binding polypeptides; 4) detecting the degree of cleavage by a ubiquitin-specific protease (UBP) of the first ligand-binding polypeptide between Cub and Z, wherein an increase of cleavage is indicative of polypeptide P2—ligand R2 binding.

Another aspect of the invention provides a method of determining whether a polypeptide P1 and a ligand R1 bind to each other comprising: 1) translationally providing a first ligand-binding polypeptide comprising segments P1, Cub-Z, and RM, in an order wherein Cub-Z is closer to the N-terminus of the first ligand-binding polypeptide than RM, and a second ligand-binding polypeptide comprising segments Nux and P2, wherein P1 and P2 are polypeptides, Nux is the amino-terminal subdomain of a wild-type ubiquitin or a reduced-associating mutant ubiquitin amino-terminal subdomain, Cub is the carboxy-terminal subdomain of a wild-type ubiquitin, Z is an amino acid residue and RM is a reporter moiety; 2) providing a hybrid ligand represented by the general formula: R1-Y—R2, wherein R1 is a first ligand, R2 is a second ligand different from R1 that binds the second ligand-binding polypeptide at P2, at least one of R1 and R2 is not a peptide, and Y is a linker; 3) allowing the hybrid ligand to contact the first and second ligand-binding polypeptides; 4) detecting the degree of cleavage by a ubiquitin-specific protease (UBP) of the first ligand-binding polypeptide between Cub and Z, wherein an increase of cleavage is indicative of protein P1—ligand R1 binding.

In one embodiment, step 1) involves the use of a cell providing an N-end rule degradation system. In one embodiment, the degree of cleavage between Cub and Z is determined by detecting the degree of activity of the RM. In one embodiment, the degree of cleavage between Cub and Z is determined by detecting the degree of enzymatic activity of the RM. In one embodiment, the degree of cleavage between Cub and Z is determined by detecting the amount of the cleaved form of RM.

Another aspect of the invention provides a method of inducing or allowing the detection of a biologically detectable event, comprising: 1) providing at least one cell comprising at least one nucleic acid sequence encoding a fusion polypeptide that includes: a) at least one ligand binding domain; and, b) a functional domain which by itself is not capable of inducing or allowing the detection of the detectable event; 2) providing a hybrid ligand of the general formula R1-Y—R2, wherein R1 is different from R2, at least one of R1 and R2 is not a peptide, R1 or R2 represents a ligand that binds to said ligand binding domain; Y represents a polyethylene linker having the general formula $(CH_2-X-CH_2)_n$, where X represents O, S, SO, or $SO_2$, and n is an integer from 2 to 25; and wherein the binding of said hybrid ligand to said ligand binding domain brings the first functional domain into proximity of a second functional domain, thereby inducing or allowing the detection of the detectable event; and, 3) exposing said at least one cell to an effective amount of said hybrid ligand to bring the first functional domain into proximity of a second functional domain, thereby inducing or allowing the detection of the detectable event.

Another aspect of the invention provides a method of identifying a ligand of a user-specified polypeptide, comprising: 1) providing at least one candidate hybrid ligand having the general formula R1-Y—R2, where R1 is a first ligand, R2 is a candidate ligand, and Y is a polyethylene linker having the general formula $(CH_2-X-CH_2)_n$, where X represents O, S, SO, or $SO_2$, and n is an integer from 2 to 25; 2) introducing the candidate hybrid ligand into at least one cell which contains a hybrid ligand screening system including: a) a reporter gene operably linked to a transcriptional regulatory sequence, said regulatory sequence including a DNA sequence which binds to a DNA binding domain; b) a first chimeric gene encoding a first fusion polypeptide comprising: a ligand binding domain and a domain selected from the DNA binding domain or a transcriptional activation domain, wherein the ligand binding domain binds the first ligand R1; and, c) a second chimeric gene encoding a second fusion polypeptide comprising: a user-specified ligand-binding domain for the candidate ligand R2 and a domain selected from the DNA binding domain or the transcription activation domain; wherein one of the two fusion polypeptides contains a DNA binding domain and the other fusion polypeptide contains a transcription activation domain; 3) allowing the candidate hybrid ligand to bind the ligand binding domain of the first fusion polypeptide through the first ligand R1 and to contact the user-specified ligand binding domain of the second fusion polypeptide through the candidate ligand R2 such that, if the user-specified ligand binding domain binds to the candidate ligand R2, an increase in the level of transcription of the reporter gene occurs; 4) identifying the candidate hybrid ligand which causes an increase in the level of transcription of the reporter gene in the cell, thereby identifying the candidate ligand on the candidate hybrid ligand as a ligand for the user-specified polypeptide.

A related aspect of the invention provides a method of identifying a ligand that binds to a user-specified polypeptide, comprising: providing a population of candidate hybrid ligand having the general formula R1-Y—R2, where R1 is a first ligand, R2 is a candidate ligand, and Y is a linker; contacting each individual candidate hybrid ligand with a split ubiquitin hybrid ligand binding system comprising: a first chimeric gene encoding a first fusion polypeptide comprising: segments PI, Cub-Z, and RM, in an order wherein Cub-Z is closer to the N-terminus of the first fusion polypeptide than RM, wherein P1 is a ligand binding polypeptide that binds to the first ligand R1, Cub is a carboxy-terminal subdomain of ubiquitin, Z is a non-methionine amino acid residue and RM is a reporter moiety, a second chimeric gene encoding a second fusion polypeptide comprising: segments Nux and P2, wherein Nux is the amino-terminal subdomain of a wild-type ubiquitin or a reduced-associating mutant ubiquitin amino-terminal subdomain, and P2 is a user-specified polypeptide for the candidate ligand; and, a ubiquitin dependent proteolytic system comprising an N-end rule ubiquitin specific protease (UBP); allowing the candidate hybrid ligand to bind the ligand binding polypeptide P1 of the first fusion polypeptide through the first ligand R1 and to contact the user-specified polypeptide P2 of the second fusion polypeptide through the candidate ligand R2 such that, when the user-specified polypeptide P2 binds to the candidate ligand R2, the Nux and Cub domains associate to form a reconstituted ubiquitin moiety and the ubiquitin specific protease cleaves the Cub-Z peptide bond so as to release an RM-containing fragment, said fragment being susceptible to N-end rule ubiquitin-dependent proteolytic degradation; measuring the level of the RM in the presence of the candidate hybrid ligand as compared to the level of the RM in the absence of the hybrid ligand, wherein a decrease in the level of the RM in the presence of the hybrid ligand as compared to the level of the RM in the absence of the hybrid ligand indicates that the user-specified polypeptide P2 binds to the candidate ligand R2, identifying the candidate hybrid ligand which causes a decrease in the level of the RM in the presence of the hybrid ligand as compared to the level of the RM in the absence of the hybrid ligand, thereby identifying a ligand that binds to a user-specified polypeptide.

A related aspect of the invention provides a method of identifying a ligand that binds to a user-specified polypeptide, comprising: providing a population of candidate hybrid ligand having the general formula R1-Y—R2, where R1 is a first ligand, R2 is a candidate ligand, and Y is a linker; contacting each individual candidate hybrid ligand with a split ubiquitin hybrid ligand binding system comprising: a first chimeric gene encoding a first fusion polypeptide comprising: segments Nux and P1, wherein Nux is the amino-terminal subdomain of a wild-type ubiquitin or a reduced-associating mutant ubiquitin amino-terminal subdomain, and P1 is a polypeptide that binds to the first ligand R1 of the hybrid ligand, a second chimeric gene encoding a second fusion polypeptide comprising: segments P2, Cub-Z, and RM, in an order wherein Cub-Z is closer to the N-terminus of the first fusion polypeptide than RM, wherein P2 is a user-specified ligand binding polypeptide for the candidate ligand R2 of the hybrid ligand, Cub is a carboxy-terminal subdomain of ubiquitin, Z is a non-methionine amino acid residue and RM is a reporter moiety; and, a ubiquitin dependent proteolytic system comprising an N-end rule ubiquitin specific protease (UBP); allowing the candidate hybrid ligand to bind the first ligand binding polypeptide P1 of the first fusion polypeptide through the first ligand R1 and to contact the user-specified polypeptide P2 of the second fusion polypeptide through the candidate ligand R2 such that, when the user-specified polypeptide P2 binds to the candidate ligand R2, the Nux and Cub domains associate to form a reconstituted ubiquitin moiety and the ubiquitin specific protease cleaves the Cub-Z peptide bond so as to release an RM-containing fragment, said fragment being susceptible to N-end rule ubiquitin-dependent proteolytic degradation; measuring the level of the RM in the presence of the candidate hybrid ligand as compared to the level of the RM in the absence of the hybrid ligand, wherein a decrease in the level of the RM in the presence of the hybrid ligand as compared to the level of the RM in the absence of the hybrid ligand indicates that the user-specified polypeptide P2 binds to the candidate ligand R2, identifying the candidate hybrid ligand which causes a decrease in the level of the RM in the presence of the hybrid ligand as compared to the level of the RM in the absence of the hybrid ligand, thereby identifying a ligand that binds to a user-specified polypeptide.

In one embodiment, P2 is encoded by a nucleic acid from a library selected from the group consisting of: a synthetic oligonucleotide library, a cDNA library, a bacterial genomic DNA fragment library, and a eukaryotic genomic DNA fragment library. In one embodiment, the split ubiquitin hybrid ligand binding system is provided by a cell.

Another aspect of the invention provides a method to investigate the structure activity relationship of a ligand to a ligand binding domain comprising: 1) providing a hybrid ligand R1-Y—R2, wherein a) R1 represents a first ligand selected from: a steroid, retinoic acid, beta-lactam antibiotic, cannabinoid, nucleic acid, polypeptide, FK506, FK506 derivative, rapamycin, tetracycline, methotrexate, novobiocin, maltose, glutathione, biotin, vitamin D, dexamethasone, estrogen, progesterone, cortisone, testosterone, nickel, 2,4-diaminopteridine derivative or cyclosporin, or a derivative thereof with minor structural modifications; b) Y represents a polyethylene linker having the general formula $(CH_2—X—CH_2)_n$, where X represents O, S, SO, or $SO_2$, and n is an integer from 2 to 25; and, c) R2 represents a user-specified second ligand which is different from R1 and is selected from: a peptide, nucleic acid, carbohydrate, polysaccharide, lipid, prostaglandin, acyl halide, alcohol, aldehyde, alkane, alkene, alkyne, alkyl, alkyl halide, alkaloid, amine, aromatic hydrocarbon, sulfonate ester, carboxylate acid, aryl halide, ester, phenol, ether, nitrile, carboxylic acid anhydride, amide, quaternary ammonium salt, imine, enamine, amine oxide, cyanohydrin, organocadmium, aldol, organometallic, aromatic hydrocarbon, nucleoside, or a nucleotide; 2) providing cells comprising a fusion protein that includes: a) at least one ligand binding domain; and, b) a functional domain heterologous to the ligand binding domain which by itself is not capable of inducing or allowing the detection of a detectable event, but which is capable of inducing or allowing the detection of a detectable event when brought into proximity of a second functional domain; 3) wherein either a plurality of hybrid ligands comprising structural variants of said second ligand R2 is provided in step 1), or a plurality of fusion proteins comprising structural variants of said ligand binding domain is provided in step 2); 4) exposing said cells comprising each fusion protein to an effective amount of each hybrid ligand such that the first functional domain may be brought into proximity of a second functional domain thereby inducing or allowing the detection of a detectable event; 5) measuring the presence, amount or activity of any detectable event so induced or allowed in step 4), thereby investigating the structure activity relationship between said second ligand and the ligand binding domain.

In one embodiment, said first functional domain of (b) is chosen from: a DNA binding domain, a transcription activation domain, a carboxy-terminal subdomain of a wild-type ubiquitin, an amino-terminal subdomain of a ubiquitin or a reduced-associating mutant ubiquitin amino-terminal subdomain.

Another aspect of the invention provides a method to identify a hybrid ligand having the general structure R1-Y—R2 suitable for an in-vivo assay, wherein said assay involves: 1) the use of a hybrid ligand, and 2) of at least one fusion polypeptide that includes: a) at least one ligand binding domain P; and, b) a functional domain which by itself is not capable of inducing or allowing the detection of the detectable event; and wherein said method involves the steps of: 3) synthesizing a plurality of hybrid ligands R1-Y—R2 differing by a plurality of different linkers Y, wherein R1 and R2 are different, and at least one of R1 and R2 is not a peptide; and 4) testing each hybrid ligand in said plurality of hybrid ligands individually for efficacy in inducing or allowing the detection of the detectable event; and 5) selecting a hybrid ligand with a particular linker that possesses suitable efficacy in inducing or allowing the detection of the detectable event.

In one embodiment, said linker has the general structure $(CH_2—X—CH_2)_n$, where X represents O, S, SO, or $SO_2$, and n is an integer from 2 to 25, and the plurality of linkers differ in n. In another embodiment, R1 represents a first ligand selected from: a steroid, retinoic acid, beta-lactam antibiotic, cannabinoid, nucleic acid, polypeptide, FK506, FK506 derivative, rapamycin, tetracycline, methotrexate, novobiocin, maltose, glutathione, biotin, vitamin D, dexamethasone, estrogen, progesterone, cortisone, testosterone, nickel, 2,4-diaminopteridine derivative or cyclosporin, or a derivative thereof with minor structural modifications.

Another aspect of the invention provides a kit comprising at least one polynucleotide including a DNA fragment linked to a coding sequence for a functional domain heterologous to the DNA fragment which by itself is not capable of inducing or allowing the detection of a detectable event, but which is capable of inducing or allowing the detection of a detectable event when brought into proximity of a second functional domain; further comprising instructions to synthesize a hybrid ligand of general structure R1-Y—R2, and to clone a ligand binding domain into the polynucleotide, and to test the binding between the hybrid ligand and the ligand binding domain, wherein R2 is different from R1, one of R1 and R2 is a non-peptide ligand, and wherein one of R1 and R2 binds to or inhibits a kinase.

Another aspect of the invention provides a kit comprising at least one polynucleotide including a DNA fragment linked to a coding sequence for a functional domain heterologous to the DNA fragment which by itself is not capable of inducing or allowing the detection of a detectable event, but which is capable of inducing or allowing the detection of a detectable event when brought into proximity of a second functional domain; further comprising instructions to synthesize a hybrid ligand of general structure R1-Y—R2, and to clone a ligand binding domain into the polynucleotide, and to test the binding between the hybrid ligand and the ligand binding domain, wherein R2 is different from R1, one of R1 and R2 is a non-peptide ligand, and wherein Y is of the general structure $(CH_2—X—CH_2)_n$, where X represents O, S, SO, or $SO_2$, and n is an integer from 2 to 25.

Another aspect of the invention provides a kit comprising at least one polynucleotide including a DNA fragment linked to a coding sequence for a functional domain heterologous to the DNA fragment which by itself is not capable of inducing or allowing the detection of a detectable event, but which is capable of inducing or allowing the detection of a detectable event when brought into proximity of a second functional domain; further comprising instructions to synthesize a hybrid ligand of general structure R1-Y—R2, and to clone a ligand binding domain into the polynucleotide, and to test the binding between the hybrid ligand and the ligand binding domain, wherein R2 is different from R1, one of R1 and R2 is a non-peptide ligand, and wherein the functional domain is the carboxy-terminal or the amino-terminal domain of ubiquitin.

Another aspect of the invention provides a kit comprising: 1) a compound of general structure R1-Y-L, wherein Y is of the general structure $(CH_2—X—CH_2)_n$ and L is a chemical group that is easily substituted by a different chemical group, and 2) instructions to use the compound for the synthesis of a hybrid ligand R1-Y—R2 where R1 is different from R2, and at least one of R1 and R2 is not a peptide.

Another aspect of the invention provides a method of doing business comprising: 1) the identification of polypeptides binding to a hybrid ligand of general formula R1-Y—R2, wherein Y is of the general structure $(CH_2—X—CH_2)_n$, R1 is different from R2, and at least one of R1 and R2 is not a peptide, X=O, S, SO or $SO_2$, and wherein said polypeptides were previously not known to bind to such hybrid ligand, and 2) providing access to data, nucleic acids or polypeptides so obtained to another party for consideration.

In one embodiment, said identification of polypeptides is performed using any one of the suitable methods of the instant invention.

A related aspect of the invention provides a method of doing business comprising: 1) the identification of at least one ligand binding to a user-specified polypeptide by using a plurality of hybrid ligands of general formula R1-Y—R2 differing in at least one of R1 and R2, wherein R1 and R2 are ligands, R1 is different from R2, at least one of R1 and R2 is not a peptide, Y is of the general structure $(CH_2—X—CH_2)_n$, X=O, S, SO or $SO_2$, and wherein said ligands were previously not known to bind to such polypeptide, and 2) providing access to data and ligands obtained from such identification to another party for consideration.

In a preferred embodiment, said identification of ligands is performed using any one of the suitable methods of the instant invention.

A related aspect of the invention provides a method to identify a polypeptide P2 which binds to a given small molecule ligand R2, comprising:

immobilizing a polypeptide P1 on a matrix, wherein the polypeptide P1 is known to bind a ligand R1, and contacting said matrix with a hybrid ligand of general structure R1-Y—R2, wherein Y is a linker, such that a R2-Y—R1::P1 complex is formed on the matrix, and contacting said complex with a sample comprising at least one candidate polypeptide P2, and washing said surface such that all constituents of said sample unable to bind to said complex are removed from contact with said complex, and determining whether at least one polypeptide P2 has bound to said complex, and if a polypeptide P2 was determined to bind to said complex in (v), identifying the polypeptide P2 thereby identifying a polypeptide P2 which binds to a given small molecule ligand R2.

In a preferred embodiment, Y is of the general structure $(CH_2—X—CH_2)_n$, and n is an integer from 2 to 25 Preferably, X=O, S, SO or $SO_2$ It is further preferred that said sample is a mixture of several different candidate polypeptides P2, more preferably a cell extract. In another preferred embodiment, R1 represents a first ligand selected from: steroid, retinoic acid, beta-lactam antibiotic, cannabinoid, FK506, FK506 derivative, rapamycin, tetracycline, methotrexate, novobiocin, maltose, glutathione, vitamin D, dexamethasone, estrogen, progesterone, cortisone, testosterone, 2,4-diaminopteridine derivative or cyclosporin, or a derivative of one of the above with minor modifications. In a further preferred embodiment, P1 is a fusion polypeptide, comprising at least two domains which are not found in combination in nature.

In a further preferred embodiment, said fusion polypeptide comprises one domain chosen from the group consisting of: β-lactamase, a steroid receptor, retinoic acid receptor, cannabinoid receptor, FKB 12, Tet-R, DHFR, GyrB, maltose binding protein, glutathione-S-transferase, vitamin D receptor, glucocorticoid receptor, estrogen receptor, progesterone receptor, testosterone receptor, or a fragment of one of the above retaining the binding capacity to its respective ligand, and a second domain comprising a tag which allows the immobilization of said fusion protein on a matrix.

Preferably, said tag is chosen from the group consisting of: strep tag, FLAG tag, $his_6$-tag, CBD tag, E tag, GFP tag, GST tag, haemagglutinin tag, Myc tag, T7 tag, Tag 100, V5 tag, Calmodulin binding peptide tag, S tag, Intein/chitin binding domain tag, Xpress tag, thioredoxin tag or VSV tag. In another related embodiment of said method, P2 is a fusion polypeptide comprising a user specified fragment and a DNA-binding domain. Preferably, P2 is bound, through said DNA-binding domain, to a DNA molecule encoding P2. Preferably, said DNA binding domain is chosen from the group consisting of: a lac repressor protein, a Rep protein, an NS1 or H-1 protein, a phi-29 terminal protein, a 55 Kd protein, and fragments and derivatives of one of the above, which fragments and derivatives retain the respective DNA binding activity.

A related aspect of the present invention provides a composition comprising:

a hybrid ligand of general structure R1-Y—R2, wherein Y is a linker, and a fusion polypeptide, comprising at least two domains which are not found in combination in nature, wherein one domain is a user specified polypeptide, and a second domain is a DNA binding domain.

Preferably, Y is of the general structure $(CH_2—X—CH_2)_n$, and n is an integer from 2 to 25. More preferably, X=O, S, SO or $SO_2$. In another preferred embodimant, R1 represents a first ligand selected from: steroid, retinoic acid, beta-lactam antibiotic, cannabinoid, FK506, FK506 derivative, rapamycin, tetracycline, methotrexate, novobiocin, maltose, glutathione, vitamin D, dexamethasone, estrogen, progesterone, cortisone, testosterone, 2,4-diaminopteridine derivative or cyclosporin, or a derivative of one of the above with minor modifications.

A related aspect of the present invention provides a method of determining whether a polypeptide P2 and a ligand R2 bind to each other comprising:

translationally providing a first ligand-binding polypeptide comprising segments P1 and a first fragment of a β-lactamase, and a second ligand-binding polypeptide comprising segments P2 and a second fragment of a β-lactamase, wherein said first and second fragments of a β-lactamase individually possess no β-lactamase activity, and wherein the enzymatic activity of a β-lactamase is reconstituted when P1 and P2 are brought into close spatial proximity; and providing a hybrid ligand represented by the general formula: R1-Y—R2, wherein R1 is a first ligand that binds the first ligand-binding polypeptide at P1, R2 is a second ligand different from R1, at least one of R1 and R2 is not a peptide, and Y is a linker; and allowing the hybrid ligand to contact the first and second ligand-binding polypeptides; and detecting the activity of a β-lactamase, wherein an increase in β-lactamase activity in the presence of said hybrid ligand compared to in its absence is indicative of polypeptide P2—ligand R2 binding, thereby determining whether the polypeptide P2 and a ligand R2 bind to each other.

Preferably, Y is of the general structure $(CH_2—X—CH_2)_n$, and n is an integer from 2 to 25. More preferably, X=O, S, SO or $SO_2$. In another preferred embodiment, R1 represents a first ligand selected from: steroid, retinoic acid, beta-lactam antibiotic, cannabinoid, nucleic acid, polypeptide, FK506, FK506 derivative, rapamycin, tetracycline, methotrexate, novobiocin, maltose, glutathione, biotin, vitamin D, dexamethasone, estrogen, progesterone, cortisone, testosterone, nickel, 2,4-diaminopteridine derivative or cyclosporin, or a derivative of one of the above with minor modifications.

A related aspect of the present invention provides a composition comprising a nucleic acid encoding a polypeptide comprising a fragment of a β-lactamase and a user specified polypeptide, and a second nucleic acid encoding a polypeptide comprising a second fragment of a β-lactamase and a domain chosen from the group consisting of: β-lactamase, a steroid receptor, retinoic acid receptor, cannabinoid receptor, FKB 12, Tet-R, DHFR, GyrB, maltose binding protein, glutathione-S-transferase, vitamin D receptor, glucocorticoid receptor, estrogen receptor, progesterone receptor, testosterone receptor, or a fragment of one of the above, which fragment retains the binding capacity to its respective ligand, wherein said first and second fragments of a β-lactamase individually possess no β-lactamase activity, and wherein the enzymatic activity of a β-lactamase is reconstituted when P1 and P2 are brought into close spatial proximity. In a preferred ambodiment, said composition further comprises a hybrid ligand of general structure R1-Y—R2, wherein Y is a linker. Preferably, Y is of the general structure (CH$_2$—X—CH$_2$)$_n$, and n is an integer from 2 to 25. More preferably, X=O, S, SO or SO$_2$. In another preferred ambodiment, R1 represents a first ligand selected from: steroid, retinoic acid, beta-lactam antibiotic, cannabinoid, nucleic acid, polypeptide, FK506, FK506 derivative, rapamycin, tetracycline, methotrexate, novobiocin, maltose, glutathione, biotin, vitamin D, dexamethasone, estrogen, progesterone, cortisone, testosterone, nickel, 2,4-diaminopteridine derivative or cyclosporin, or a derivative of one of the above with minor modifications.

A related aspect of the present invention provides a composition comprising a polypeptide comprising a fragment of a β-lactamase and a user specified polypeptide, and a second polypeptide comprising a second fragment of a β-lactamase and a domain chosen from the group consisting of: β-lactamase, a steroid receptor, retinoic acid receptor, cannabinoid receptor, FKB12, Tet-R, DHFR, GyrB, maltose binding protein, glutathione-S-transferase, vitamin D receptor, glucocorticoid receptor, estrogen receptor, progesterone receptor, testosterone receptor, or a fragment of one of the above, which fragment retains the binding capacity to its respective ligand, wherein said first and second fragments of a β-lactamase individually possess no β-lactamase activity, and wherein the enzymatic activity of a β-lactamase is reconstituted when P1 and P2 are brought into close spatial proximity. Preferably, said composition further comprises a hybrid, ligand of general structure R1-Y—R2, wherein Y is a linker. Preferably, Y is of the general structure (CH$_2$—X—CH$_2$)$_n$, and n is an integer from 2 to 25. More preferably, X=O, S, SO or SO$_2$.

In another preferred embodiment, R1 represents a first ligand selected from the group consisting of: a steroid, retinoic acid, beta-lactam antibiotic, cannabinoid, nucleic acid, polypeptide, FK506, FK506 derivative, rapamycin, tetracycline, methotrexate, novobiocin, maltose, glutathione, biotin, vitamin D, dexamethasone, estrogen, progesterone, cortisone, testosterone, nickel, 2,4-diaminopteridine derivative or cyclosporin, or a derivative of one of the above with minor modifications.

BRIEF DESCRIPTION OF THE FIGURES

FIGS. 4A and 4B. An example of a Halo Growth Assay. A visible halo of yeast cellular growth on medium lacking histidine indicates activation of the reporter HIS3 gene caused by the dimerization of the LexBD-DHFR and GalAD-GR2 fusion proteins in the presence of GPC 285937, but not in the presence of DMSO alone.

FIGS. 5A and 5B. Activation of the HIS3 reporter gene by compound induced dimerization of the LexA-BD-DHFR and Gal4-AD-GR2 fusion proteins in the presence of a hybrid ligand of the invention (GPC 285937) compared to a prior art hybrid ligand Mtx-mdbt-Dex (mdbt: metadibenzothioester). Microscope images of growth media where circular objects are individual yeast cells and dark woolly threads are precipitated Mtx-mdbt-Dex. Precipitation of Mtx-mdbt-Dex is seen at 100 µM.

FIG. 12. Results of a high throughout halo assay using clones recovered from a three-hybrid genetic screen. A library of fusion proteins was screened to isolated genes that encoded proteins, which bound to the hybrid ligand GPC 285985. The table shows a sample of the analysis performed on 2811 initial positive clones. 102 clones showed compound specific growth. The identity of all clones was confirmed by sequencing and contained genes encoding CDK2 and other genes.

DETAILED DESCRIPTION OF THE INVENTION

1. Overview

Figure 1A:
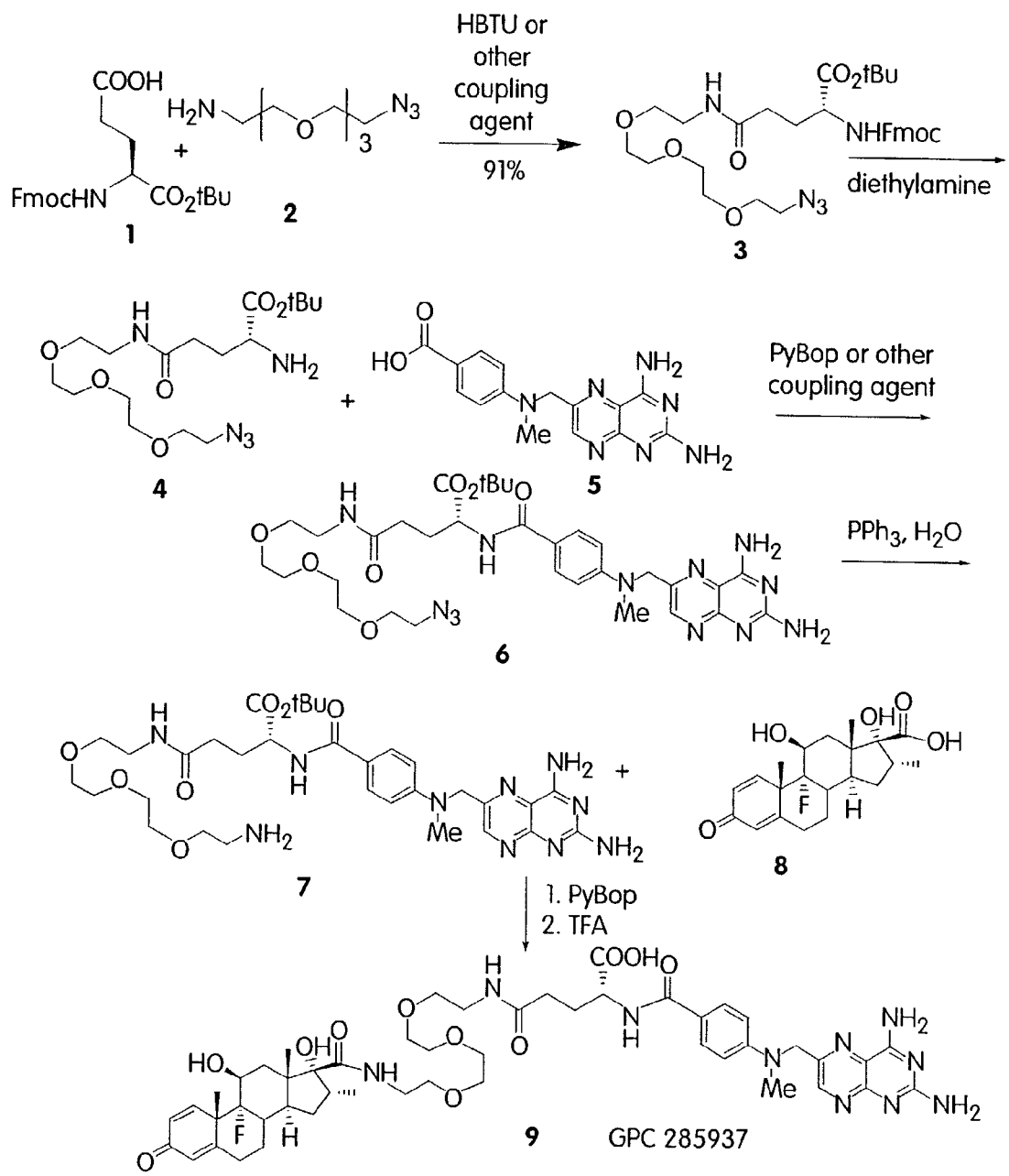
FIGS. 1A–1G. Synthetic schemes and structure representations for GPC 285937, 285985, 286004, 286026 and 285993 and Mtx-(CH$_2$—O—CH$_2$)$_5$-purvalanol B.

In general the invention provides a three hybrid assay system and reagents for the identification of the protein binding partner of a selected small pharmaceutical agent. Likewise, the invention also provides methods and reagents for the identification of a small pharmaceutical agent binding partner of a selected protein. Once detected, the invention further provides methods for monitoring the interaction of the pharmaceutical agent and its protein binding partner that can be used to detect competitors of the interaction.

According to one aspect of the invention, a compound binding to a known target polypeptide can be selected from a pool/library of candidate compounds. Preferably, the compound is a small molecule (see definition below). In this aspect of the invention, each candidate small molecule (designated "R2" hereafter) is linked to a known small molecule (designated "R1" hereafter) via a linker sequence (designated "Y" hereafter). The resulting R1-Y—R2 compound is then allowed to contact a fusion polypeptide P1-RS1, comprising the known polypeptide binding partner of R1, P1, fused to a first part of a reporter system (RS), RS1, and the target polypeptide (designated "P2" hereafter) fused to a second part of RS, RS2, in a suitable environment (such as a cell). The RS is designed such that when RS1 and RS2 are brought into spatial proximity in a suitable environment, the RS is activated and triggers a biologically detectable event. If R2 interacts with P2 with strong enough affinity, then RS1 is brought into close vicinity with RS2 via the bridging effect of the R1-Y—R2 hybrid, thereby triggering the activation of RS. Hence, contacting the environment (i.e., a cell) containing the RS, the P1-RS1-hybrid and the P2-RS2-hybrid with a pool/library of R1-Y—R2-hybrids and observing activation of RS facilitates the isolation of R1-Y—R2-hybrids, wherein R2 is able to specifically bind to P2.

In one embodiment, the RS is a transcription-based reporter system, such as yeast two-hybrid system. In another related embodiment, the RS is a split ubiquitin based reporter system.

In one embodiment, the linker sequence is particularly suitable for in vivo use of the chemical compound due to its increased solubility and enhanced membrane permeability.

In one embodiment, the P1-R1 interaction is a non-covalent interaction. In an alternative embodiment, the P1-R1 interaction results in a covalent bond.

In one embodiment, the chemical library is synthesized. In another embodiment, the chemical library is from natural sources.

According to another aspect of the invention, a polypeptide binding to a known target small molecule R2 can be selected from a library/libraries of test polypeptides. In this aspect, the target small molecule R2 is linked by a linker sequence Y to a known small molecule R1 to form an R1-Y—R2 hybrid compound, which is then allowed to contact polypeptide P1, the known binding partner of known small molecule R1, fused to RS1, in a suitable environment. A library or libraries of test polypeptides P2, each fused to RS2, are translationally provided to the same environment. Binding between the target small molecule R2 and any member polypeptide P2 of the library/libraries will bring the P2-RS2 hybrid into the vicinity of the P1-RS1-hybrid, thereby triggering the activation of a reporter system RS. Hence, contacting cells containing the RS, the P1-RS 1-hybrid and a pool/library of P2-RS2-hybrids with the R1-Y—R2-hybrid and observing activation of RS facilitates the isolation of P2-RS2-hybrids, wherein P2 is able to specifically bind to R2.

In one embodiment, the RS is a transcription-based reporter system, such as yeast two-hybrid system. In another related embodiment, the RS is a split ubiquitin based reporter system.

In one embodiment, the linker sequence is particularly suitable for in vivo use of the chemical compound due to its increased solubility and enhanced membrane permeability.

In one embodiment, the P1-R1 interaction is a non-covalent interaction. In a related embodiment, the P1-R1 interaction results in a covalent bond.

In one embodiment, the polypeptide library is cDNA library or genomic DNA library. In another embodiment, the polypeptide library is synthesized randomly or semi-randomly. The library may contain different number of members, preferably from 2 to 10 members, or 10 to 500 members, 500 to 10,000 members or more than 10,000 members.

The above described methods are not only suitable to identify an unknown member of a polypeptide—ligand pair (screen method), but also suitable to determine if a given polypeptide binds a given ligand (assay or test method).

According to yet another aspect of the invention, there is provided a kit for detecting and/or selecting interactions between polypeptides and small molecules using either one of the above mentioned methods.

According to another aspect of the invention, there is provided a method for pharmaceutical research wherein interactions between polypeptides and small molecules are monitored to facilitate further characterization and/or optimization of binding of at least one of the identified binding partners. This can be useful in a variety of situations. For example, many drugs or chemical compounds have noticeable, sometimes even severe, undesirable side-effects. This is likely caused by the fact that the drug may non-discriminately bind proteins other than the intended target. The instant invention provides a method to identify all potential binding partners of a given drug or chemical compound, thereby providing a basis to design other related drugs that do not bind these non-intended targets to avoid the undesirable side-effects. In other cases, a drug may have some efficacy for certain conditions, but the mechanism of action of the drug is unknown, thus, it is difficult to optimize the drug for a better efficacy. The instant invention provides a method to identify the target of the drug, thereby offering a means to further study the biology and the related signaling pathways so that drug optimization can be achieved based on knowledge gained through research on those signaling pathways. Furthermore, information on the binding of ligands to polypeptide ligand binding domains that is collected by practicing the methods of the invention may be used to understand or further understand the function or side effects of a ligand in a biological or therapeutic setting. Information thus collected may for example, be used to provide more informed prescription of medicaments comprising the ligand or with appropriate additional medicaments to provide more effective combination therapies. Thus, the instant invention can be used to identify or produce any one or more of the following: a compound with a known biological effect, a compound with an unknown mechanism of action, a compound which binds to more than one polypeptide, a drug candidate compound, or a compound that binds to an unknown protein.

The instant invention also provides hybrid ligands which binds to or inhibits a kinase. For example, R2 can be a compound chosen from Table 2, which is a list of compounds that is known to bind or inhibit kinases, or a derivative thereof with minor structural modifications. A typical kinase target can be a cyclin-dependent kinase.

Furthermore, the instant invention also provides a method to identify novel modulators of certain known proteins and a method to produce pharmaceutical formulations of such modulators.

Another aspect of the invention provides a method to identify a compound which inhibits the interaction between a ligand and a polypeptide, wherein the interaction is identified using any suitable method of the instant invention, comprising: 1) identifying, by any one of the suitable methods of the instant invention, a polypeptide that interacts with a user-specified ligand, or identifying a ligand that interacts with a user-specified polypeptide; 2) providing an environment wherein said interaction occurs; 3) contacting the environment with a test compound; 4) determining if said test compound inhibits said interaction, thereby identifying a compound which inhibits the interaction between a ligand and a polypeptide.

In one embodiment, the ligand is a non-peptide ligand. In a preferred embodiment, the ligand is of the general structure R1-Y—R2, wherein R1, Y, and R2 are as defined above.

In one embodiment, the test compound is from a variegated library, which, for example, can be a nucleic acid library (cDNA, genomic DNA, EST, etc.) encoding polypeptides; a polypeptide library (synthetic, natural, random, semi-random, etc.); a small chemical library (natural, synthetic, etc.).

In one embodiment, the environment is a cell. In a related embodiment, the environment contains any one of the suitable hybrid ligand screening system of the instant invention (including reporter systems).

The inhibitory effect of the test compound can be assessed based on the change of status of the reporter system (see detailed descriptions below).

This method can be useful in a variety of situations. For example, if a small chemical compound is initially identified as possessing certain biological activity when administered to a cell, its protein target(s) can be identified. In case that multiple targets are present and only one target interaction is desired (for example, other target protein interactions lead to undesirable side effects), a test compound can be identified using this method so that it may specifically blocks those undesirable interactions while still allow the intended interaction to occur. In another scenario, after the identification of the polypeptide target of a known ligand, a compound can be identified using the subject method to block the interaction between such ligand and polypeptide, either to eliminate the undesirable effect of ligand-polypeptide interaction, or to reversibly control such interaction.

Another aspect of the invention provides a method to identify a polypeptide sequence that binds to a user-specified ligand, comprising: 1) providing a hybrid ligand with the general structure R—Y—R, wherein R is a user-specified ligand and Y is a linker, preferably a linker having the general formula $(-CH_2-X-CH_2-)_n$, wherein X and n are as defined above; 2) introducing the hybrid ligand into a population of cells, each cell containing a ligand screening system as defined above, or a Nux-Cub split ubiquitin-based system as defined above, wherein both P1 and P2 (as defined above) represent the same test polypeptide; 3) allowing the hybrid ligand to contact P1 and P2 in said ligand screening system, 4) identifying a positive ligand binding cell in which a detectable change in the status of the reporter system of the ligand screen system occurs; thereby identifying a nucleic acid encoding the test polypeptide.

In a related aspect of the invention, there is provided a method to determine if a ligand binds to a polypeptide, comprising: 1) providing a hybrid ligand with the general structure R—Y—R, wherein R is a user-specified ligand and Y is a linker, preferably a linker having the general formula $(-CH_2-X-CH_2-)_n$, wherein X and n are as defined above; 2) introducing the hybrid ligand into an environment containing a test polypeptide, wherein multimerization (preferably dimerization) of the polypeptide lead to a detectable change; 3) determining if said detectable change occur, thereby determining if the ligand binds to the test polypeptide.

In a related aspect, a similar method can be used to determine if a known polypeptide interacts with a test hybrid ligand.

In one embodiment, the detectable change is an enzymatic activity of the test polypeptide, which activity is only present when said polypeptide is multimerized (for example, dimerized). In a related embodiment, the polypeptide can be linked to any one of the suitable hybrid ligand screen system described above so that multimerization of the polypeptide by the hybrid ligand lead to the activation of the reporter system.

In one embodiment, the polypeptide is an enzyme that is inactive as a monomer, and is only activated as a multimer, preferably a dimer. In this embodiment, it may suffice to use only a single polynucleotide in a method of the invention. For example, where one is searching for a new ligand for a polypeptide of interest for which a ligand is already known, one could use a polynucleotide encoding the polypeptide of interest fused to an enzyme that is active only as a multimer, preferably a dimer, and which does not dimerize spontaneously (e.g. a reduced affinity mutant). If this fusion polypeptide is contacted with a hybrid ligand R1-Y—R2 of the invention, where R1 is the known ligand for the polypeptide of interest, and R2 is a test ligand, activity of the enzyme will only be manifest if the test ligand binds the polypeptide of interest.

In one embodiment, the environment is a cell.

In one embodiment, the polypeptide comprises a receptor, preferably a receptor that requires multimerization to be functional or activated, such as a receptor that contains a cytoplasmic domain from one of the various cell surface membrane receptors as described in WO 94/18317. For example, many of these domains are tyrosine kinases or are complexed with tyrosine kinases, e.g. CD3 ζ, IL-2R, IL-3R, etc. For a review see Cantley, et al., Cell (1991) 64, 281. Tyrosine kinase receptors which are activated by cross-linking, e.g. dimerization (based on nomenclature first proposed by Yarden and Ulrich, Annit. Rev. Bioclin. (1988) 57, 443,include subclass 1: EGF-R, ATR2/neu, HER2/neu, HER3/c-erbB-3, Xmrk; subclass II: insulin-R, IGF R insulin-like growth factor receptor, IRR; subclass III: PDGF-R-A, PDGF-R-B, CSF R (M-CSF/c-Fms), c-kit, STK-1/Flk-2; and subclass IV: FGF-R, fig acidic FGFJ, bek [basic FGF]); neurotrophic tryosine kinases: Trk family, includes NGF-R, Ror1,2. Receptors which associate with tyrosine kinases upon cross-linking include the CD3 ζ-family: CD3 ζ and CD3 η (found primarily in T cells, associates with Fyn) β and -γ chains of Fcε RI (found primarily in mast cells and basophils); γ chain of Fcγ RIII/CD16 (found primarily in macrophages, neutrophils and natural killer cells); CD3 γ, δ, and ε (found primarily in T cells); Ig-a/MB-1 and Ig-P/B29 (found primarily in B cell). Alternatively, a cytokine-receptor may be utilized to detect ligand and receptor interactions as described in Eyckernan et al (Nature Cell Biology 2001; 3: 1114–1119).

2. Definitions

The term "agonist", as used herein, is meant to refer to an agent that mimics or up-regulates (e.g. potentiates or supplements) the bioactivity of a protein of interest, or an agent that facilitates or promotes (e.g. potentiates or supplements) an interaction among polypeptides or between a polypeptide and another molecule (e.g. a steroid, hormone, nucleic acids, small molecules etc.). An agonist can be a wild-type protein or derivative thereof having at least one bioactivity of the wild-type protein. An agonist can also be a small molecule that up-regulates the expression of a gene or which increases at least one bioactivity of a protein. An agonist can also be a protein or small molecule which increases the interaction of a polypeptide of interest with another molecule, e.g. a target peptide or nucleic acid.

"Antagonist" as used herein is meant to refer to an agent that down-regulates (e.g. suppresses or inhibits) the bioactivity of a protein of interest, or an agent that inhibits/suppresses or reduces (e.g. destabilizes or decreases) interaction among polypeptides or other molecules (e.g. steroids, hormones, nucleic acids, etc.). An antagonist can be a compound which inhibits or decreases the interaction between a protein and another molecule, e.g., a target peptide, such as interaction between ubiquitin and its substrate. An antagonist can also be a compound that down-regulates the expression of a gene of interest or which reduces the amount of the wild type protein present. An agonist can also be a protein or small molecule which decreases or inhibits the interaction of a polypeptide of interest with another molecule, e.g. a target peptide or nucleic acid.

The term "allele", which is used interchangeably herein with "allelic variant" refers to alternative forms of a gene or portions thereof. Alleles occupy the same locus or position on homologous chromosomes. When a subject has two identical alleles of a gene, the subject is said to be homozygous for that gene or allele. When a subject has two different alleles of a gene, the subject is said to be heterozygous for the gene. Alleles of a specific gene can differ from each other in a single nucleotide, or several nucleotides, and can include substitutions, deletions, and/or insertions of nucleotides. An allele of a gene can also be a form of a gene containing mutations.

The term "biologically detectable event" is a general term used to describe any biological event that can be detected in an assay system, such as for example, without limitation, in a transcription-based yeast two hybrid assay, a split ubiquitin assay, etc. A biologically detectable event means an event that changes a measurable property of a biological system, for example, without limitation, light absorbance at a certain wavelength, light emission after stimulation, presence/absence of a certain molecular moiety in the system, electrical resistance/capacitance etc., which event is conditional on another, possibly non-measurable or less easily measurable property of interest of the biological system, for example, without limitation, the presence or absence of an interaction between two proteins. Preferably, the change in the measurable property brought about by the biologically detectable event is large compared to natural variations in the measurable property of the system. Examples include the yellow color resultant from the action of β-galactosidase on o-nitrophenyl-b-D-galactopyranoside (ONPG) (J. H. Miller, Experiments in Molecular Genetics, 1972) triggered by transcriptional activation of the *E. coli* lacZ gene encoding β-galactosidase by reconstitution of a transcription factor upon binding of two proteins fused to the two functional domains of the transcription factor. Other examples of biologically detectable events are readily apparent to the person skilled in the art. Alternatively, other biological functions may be induced and detected following oligomerization, preferable dimerization, of the functional domains. For example, transcriptional regulation, secondary modification, cell localization, excocytosis, cell signaling, protein degradation or inactivation, cell viability, regulated apoptosis, growth rate, cell size. Such biological events may also be controlled by a variety of direct and indirect means including particular activities associated with individual proteins such as protein kinase or phosphatase activity, reductase activity, cyclooxygenase activity, protease activity or any other enzymatic reaction dependent on subunit association. Also, one may provide for association of G proteins with a receptor protein associated with the cell cycle, e.g. cyclins and cdc kinases, or multiunit detoxifying enzymes.

"Biological activity" or "bioactivity" or "activity" or "biological function", which are used interchangeably, for the purposes herein means a catalytic, effector, antigenic, molecular tagging or molecular interaction function that is directly or indirectly performed by a polypeptide (whether in its native or denatured conformation), or by any subsequence thereof.

The terms "cell death", "cell killing" or "necrosis" refer to the phenomenon of cells dying as a result of an extrinsically imposed loss of a particular cellular function essential for the survival of the cell.

"Cells," "host cells" or "recombinant host cells" are terms used interchangeably herein. It is understood that such terms refer not only to a particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

"Characterize" as used herein means a detailed study of a small molecule, a polypeptide or a nucleic acid (polynucleotide) encoding a polypeptide to reveal relevant chemical and biological information. This information generally includes one or more, but is not limited to, the following: sequence information for protein and nucleic acid, primary, secondary, tertiary, and quarternary structure information, molecular weight, solubility in various solvents, enzymatic or other activity, isoelectric focusing point, binding affinity to other molecules, binding partners, stability, expression pattern, tissue distribution, subcellular localization, expression regulation, developmental roles, phenotypes of transgenic animals overexpressing or devoid of a polypeptide or nucleic acid, size of nucleic acid, and hybridization property of nucleic acid. A variety of standard chemistry, cell and molecular biology protocols and methodologies can be used, such as gel electrophoresis, capillary electrophoresis, cloning, restriction enzyme digestion, expression profiling by hybridization, affinity chromatography, HPLC, isoelectric focusing, mass spectrometry, automated sequencing, and the generation of transgenic animals, the details of which can be found in many standard chemistry and molecular biology laboratory manuals (see below). Techniques employing the hybridization of nucleic acids may, for example, utilize arrayed libraries of nucleic acids, such as oligonucleotides, cDNA or others (See, for example, U.S. Pat. No. 5,837,832).

The term "chemically similar" is used to refer to chemical compounds with similar chemical structures and/or chemical properties. Similarity can be judged by comparison between two compounds of several characteristics, such as electronic charge, steric size, stereochemistry, hydrogen bond donor/acceptor capability, and polarity (i.e., hydrophobicity/hydrophilicity). For example, chemically similar amino acids would have side chains which, judged by at least three, four, or preferably all five of these characteristics, are categorized in the same way. For example, under physiological conditions, glycine and alanine are similar judged by all five characteristics, glycine and phenylalanine differ only judged by steric size, glycine and tyrosine differ by steric size and hydrogen bond donor capability, and glycine and glutamic acid differ by steric size, charge, polarity, and hydrogen bond acceptor capability. For example, steroids are generally similar in terms of conformation, polarity, stereochemistry, charge, steric size, etc., although some steroids (individually or as subclasses) may differ slightly from "average" steroids (e.g., steroidal alkaloids are typically charged under physiological conditions).

In certain embodiments, chemically similar small molecule compounds share similar functional groups and/or ring systems and thus display a combination of structural elements disposed in similar orientations or conformations, thereby defining a structural class of compounds which differ slightly, e.g., by substituents appended to the structural core, or by slight variations in the structural core (such as changes in ring size, heteroatom substitutions, homologation, etc.). For example, beta-lactam antibiotics all share a four-membered lactam ring, macrolide antibiotics have a macrocyclic lactone (e.g., 10 to 18 members) substituted with multiple methyl and/or hydroxyl groups (some of the latter of which may be hydroxylated), peptides are chains of alpha-amino acids linked by amide bonds, etc., and each such group of compounds comprises chemically similar members.

The term "derivative with minor modifications" with respect to a parent chemical compound, for example a small molecule, ligand, hybrid ligand, peptide or polypeptide, is used to refer to chemical compounds which are chemically similar to the parent chemical compound. Preferably, a derivative with minor modifications will have minor structural modifications and hence may be considered as "structural variants" of the original compound. Generally, such minor structural modifications are made in order to obtain a compound with overall similar properties as compared to the parent compound, but with a change with respect to a certain property of the parent compound that is disadvantageous or unwanted. For example, a hydrophilic side chain may be added to a certain chemical compound to increase its solubility, while retaining a desired biological activity as the side chain is added such as not to interfere with the binding between the compound and its biological target.

A "chimeric polypeptide", "fusion polypeptide" or "fusion protein" is a fusion of a first amino acid sequence encoding a first polypeptide with a second amino acid sequence defining a domain (e.g. polypeptide portion) foreign to and not substantially homologous with any domain of the first polypeptide. Such second amino acid sequence may present a domain which is found (albeit in a different polypeptide) in an organism which also expresses the first polypeptide, or it may be an "interspecies", "intergenic", etc. fusion of polypeptide structures expressed by different kinds of organisms. At least one of the first and the second polypeptides may also be partially or completely synthetic or random, i.e. not previously identified in any organism.

"To clone" as used herein, as will be apparent to skilled artisan, may be meant as obtaining exact copies of a given polynucleotide molecule using recombinant DNA technology. Furthermore, "to clone into" may be meant as inserting a given first polynucleotide sequence into a second polynucleotide sequence, preferably such that a functional unit combining the functions of the first and the second polynucleotides results, for example, without limitation, a polynucleotide from which a fusion protein may be translationally provided, which fusion protein comprises amino acid sequences encoded by the first and the second polynucleotide sequences. Details of molecular cloning can be found in a number of commonly used laboratory protocol books such as *Molecular Cloning: A Laboratory Manual*, 2nd Ed., ed. by Sambrook, Fritsch and Maniatis (Cold Spring Harbor Laboratory Press: 1989).

"To clone" as used herein, as will be apparent to skilled artisan, may be also meant as obtaining identical or nearly identical population of cells possessing a common given property, such as the presence or absence of a fluorescent marker, or a positive or negative selectable marker. The population of identical or nearly identical cells obtained by cloning is also called a "clone." Cell cloning methods are well known in the art as described in many commonly available laboratory manuals (see Current Protocols in Cell Biology, CD-ROM Edition, ed. by Juan S. Bonifacino, Jennifer Lippincott-Schwartz, Joe B. Harford, and Kenneth M. Yamada, John Wiley & Sons, 1999).

"Complementation screen" as used herein means genetic screening for one or several genes or source DNA that can confer a certain specified phenotype which will not exist without the presence of said one or several genes or source DNA. It is usually done in vivo, by introducing into cells lacking the specified phenotype a library of source DNA to be screened for, and identifying cells that have obtained a source DNA and now exhibit the specified phenotype. Alternatively, it could be done in vivo by randomly inactivating genes in the genome of the cell lacking the specified phenotype and identify cells that have lost the function of certain genes and exhibit the specified phenotype. However, a complementation screen can also be done in vitro in cell-free systems, either by testing each candidate individually or as pools of individuals.

"Recovering a clone of the cell . . . under conditions wherein a cell is selectable" as used herein is meant as selecting from a population of cells, a subpopulation or a single cell possessing a given property such as the presence or absence of fluorescent markers, or the presence or absence of positive or negative selectable markers, and obtaining a clone of each selected cell. The cells can be selected under conditions that will completely or nearly completely eliminate any cell that does not have the desired property of the cells to be selected. For example, by growing cells in selective media, only cells possessing a certain desired property will survive. The surviving cells can be cloned using standard cell and molecular biology protocols (see Current Protocols in Cell Biology, CD-ROM Edition, ed. by Juan S. Bonifacino, Jennifer Lippincott-Schwartz, Joe B. Harford, and Kenneth M. Yamada, John Wiley & Sons, 1999). Alternatively, cells possessing a desired property can be selected from a population based on the observation of a certain discernable phenotype, such as the presence or absence of fluorescent markers. The selected cells can then be cloned using standard cell and molecular biology protocols (see Current Protocols in Cell Biology, CD-ROM Edition, ed. by Juan S. Bonifacino, Jennifer Lippincott-Schwartz, Joe B. Harford, and Kenneth M. Yamada, John Wiley & Sons, 1999).

The term "equivalent" is understood to include polypeptides or nucleotide sequences that are functionally equivalent or possess an equivalent activity as compared to a given polypeptide or nucleotide sequence. Equivalent nucleotide sequences will include sequences that differ by one or more nucleotide substitutions, additions or deletions, such as allelic variants; and will, therefore, include sequences that differ from the nucleotide sequence of a particular gene, due to the degeneracy of the genetic code. Equivalent polypeptides will include polypeptides that differ by one or more amino acid substitutions, additions or deletions, which amino acid substitutions, additions or deletions leave the function and/or activity of the polypeptide substantially unaltered. A polypeptide equivalent to a given polypeptide could e.g. be the polypeptide that performs the same function in another species. For example, murine ubiquitin herein is considered an equivalent of human ubiquitin.

"FK506 derivative" as used herein means a structural homolog of native FK506 in its broadest sense. It has been reported that FKBP, the normal binding partner of FK506, can be modified to bind a FK506 derivative in such a way that the mutated binding pocket can only accommodate the FK506 derivative but not the wild type FK506 (Clackson et al., 1998, Proc. Natl. Acad. Sci. U.S.A. 95:10437–42; and Yang et al., 2000, J. Med. Chem. 43:1135–42). It should be understood that the term "FK506 derivative" covers at least this kind of FK506 derivatives in the context of binding complementary mutant FKBP. Furthermore, FK506 derivatives can also be those structurally similar but not identical compounds which have essentially the same function as FK506.

"Reporter moiety" as used herein means a feature that can be detected by certain means. For example, one routine assay for detection is achieved by western blot using antibody specific for a protein feature. Alternatively, the reporter moiety or a reporter moiety-containing moiety may be capable of capable exhibiting an intended detectable function. Particularly, the function may be suppressed or inhibited before a certain event occurs (such as cleavage of the reporter moiety from the Cub-domain in a split ubiquitin system) and the suppression or inhibition may be abolished after such event occurs. For example, without limitation, a transcription reporter moiety may be rendered non-functional when it is attached to a Cub moiety that is tethered to a membrane outside the nucleus of a target cell. It may become functional after cleavage of the reporter moiety from the Cub-moiety when it can freely translocate to the nucleus to exert its transcription activation/suppression function, which activity is in turn detectable by measuring the activity of a functionally linked reporter gene.

As used herein, the terms "gene", "recombinant gene" and "gene construct" refer to a nucleic acid comprising an open reading frame encoding a polypeptide, including both exon and (optionally) intron sequences. The term "intron" refers to a DNA sequence present in a given gene which is not translated into protein and is generally found between exons.

The term "high affinity" as used herein means strong binding affinity between molecules with a dissociation Constance $K_D$ of no greater than 1 μM. In a preferred case, the $K_D$ is less than 100 nM, 10 nM, 1 nM, 100 pM, or even 10 pM or less. In a most preferred embodiment, the two molecules can be covalently linked (KD is essentially 0).

"Homology" or "identity" or "similarity" refers to sequence similarity between two peptides or between two nucleic acid molecules, with identity being a more strict comparison. Homology and identity can each be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences. An "unrelated" or "non-homologous" sequence shares less than 40% identity, though preferably less than 25% identity with another sequence.

The term "interact" as used herein is meant to include all interactions (e.g. biochemical, chemical, or biophysical interactions) between molecules, such as protein-protein, protein-nucleic acid, nucleic acid-nucleic acid, protein-small molecule, nucleic acid-small molecule or small molecule-small molecule interactions.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject polypeptides preferably includes no more than 10 kilobases (kb) of nucleic acid sequence which naturally immediately flanks the gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

"Kit" as used herein means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

"Instruction(s)" as used herein means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

"Library" as used herein generally means a multiplicity of member components constituting the library which member components individually differ with respect to at least one property, for example, a chemical compound library. Particularly, as will be apparent to skilled artisan, "library" means a plurality of nucleic acids/polynucleotides, preferably in the form of vectors comprising functional elements (promoter, transcription factor binding sites, enhancer, etc.) necessary for expression of polypeptides, either in vitro or in vivo, which are functionally linked to coding sequences for polypeptides. The vector can be a plasmid or a viral-based vector suitable for expression in prokaryotes or eukaryotes or both, preferably for expression in mammalian cells. There should also be at least one, preferably multiple pairs of cloning sites for insertion of coding sequences into the library, and for subsequent recovery or cloning of those coding sequences. The cloning sites can be restriction endonuclease recognition sequences, or other recombination based recognition sequences such as loxP sequences for Cre recombinase, or the Gateway system (Life Technologies, Inc.) as described in U.S. Pat. No. 5,888,732, the contents of which is incorporated by reference herein. Coding sequences for polypeptides can be cDNA, genomic DNA fragments, or random/semi-random polynucleotides. The methods for cDNA or genomic DNA library construction are well-known in the art, which can be found in a number of commonly used laboratory molecular biology manuals (see below).

The term "modulation" as used herein refers to both upregulation (i.e., activation or stimulation, e.g., by agonizing or potentiating) and down-regulation (i.e. inhibition or suppression e.g., by antagonizing, decreasing or inhibiting) of an activity.

The term "mutation" or "mutated" as it refers to a gene or nucleic acid means an allelic or modified form of a gene or nucleic acid, which exhibits a different nucleotide sequence and/or an altered physical or chemical property as compared to the wild-type gene or nucleic acid. Generally, the mutation could alter the regulatory sequence of a gene without affecting the polypeptide sequence encoded by the wild-type gene. But more commonly, a mutated gene or nucleic acid will either completely lose the ability to encode a polypeptide (null mutation) or encode a polypeptide with an altered property, including a polypeptide with reduced or enhanced biological activity, a polypeptide with novel biological activity, or a polypeptide that interferes with the function of the corresponding wild-type polypeptide. Alternatively, a mutation may take advantage of the degeneracy of the genetic code, by replacing a triplet codon by a different triplet codon that nevertheless encodes the same amino acid as the wild-type triplet codon. Such replacement may, for example, lead to increased stability of the gene or nucleic acid under certain conditions. Furthermore, a mutation may comprise a nucleotide change in a single position of the gene or nucleic acid, or in several positions, or deletions or additions of nucleotides in one or several positions.

The term "reduced-associating mutant" as used herein means a mutant polypeptide that exhibits reduced affinity for its normal binding partner. For example, a reduced-associating mutant of the ubiquitin N-terminus (Nux) is a polypeptide that exhibits reduced affinity for its normal binding partner—the C-terminal half of ubiquitin (Cub), to the point that it will show reduced association or not associate with a wild-type Cub and form a "quasi-wild-type ubiquitin" without the supplemented binding affinity between two polypeptides fused to Nux and Cub, respectively. In a preferred embodiment of the invention, such mutations in Nux are certain missense mutations introduced to either the $3^{rd}$ or the $13^{th}$ amino acid residue of the wild-type ubiquitin. Different missense mutations at these positions may differentially affect the affinity/association between Nux and Cub, thereby providing different sensitivity of the assay as disclosed by the instant invention. These missense point mutations can be routinely introduced into cloned genes using standard molecular biology protocols, such as site-directed mutagenesis using PCR.

As used herein, the term "nucleic acid," in its broadest sense, refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or anti-sense) and double-stranded polynucleotides.

Specifically, "nucleic acid(s)" may refer to polynucleotides that contain information required for transcription and/or translation of polypeptides encoded by the polynucleotides. These include, but are not limited to, plasmids comprising transcription signals (e.g. transcription factor binding sites, promoters and/or enhancers) functionally linked to downstream coding sequences for polypeptides, genomic DNA fragments comprising transcription signals (e.g. transcription factor binding sites, promoters and/or enhancers) functionally linked to downstream coding sequences for polypeptides, cDNA fragments (linear or circular) comprising transcription signals (e.g. transcription factor binding sites, promoters and/or enhancers) functionally linked to downstream coding sequences for polypeptides, or RNA molecules comprising functional elements for translation either in vitro or in vivo or both, which are functionally linked to sequences encoding polypeptides. These polynucleotides should also be understood to include, as equivalents, analogs of either RNA or DNA made from nucleotide analogs, and, as applicable to the embodiment being described, single (sense or anti-sense) and double-stranded polynucleotides. These polynucleotides can be in an isolated form, e.g. an isolated vector, or included into the episome or the genome of a cell.

As used herein, the term "promoter" means a DNA sequence that regulates expression of a selected DNA sequence operably linked to the promoter, and which effects expression of the selected DNA sequence in cells. The term encompasses "tissue specific" promoters, i.e. promoters, which effect expression of the selected DNA sequence only in specific cells (e.g. cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e. expression levels can be controlled).

The terms "protein", "polypeptide" and "peptide" are used interchangeably herein when referring to a natural or recombinant gene product or fragment thereof which is not a nucleic acid.

The term "recombinant protein" refers to a polypeptide which is produced by recombinant DNA techniques, wherein generally, DNA encoding a polypeptide is inserted into a suitable expression vector which is in turn used to transform a host cell to produce the polypeptide encoded by said DNA. This polypeptide may be one that is naturally expressed by the host cell, or it may be heterologous to the host cell, or the host cell may have been engineered to have lost the capability to express the polypeptide which is otherwise expressed in wild type forms of the host cell. The polypeptide may also be a fusion polypeptide. Moreover, the phrase "derived from", with respect to a recombinant gene, is meant to include within the meaning of "recombinant protein" those proteins having an amino acid sequence of a native polypeptide, or an amino acid sequence similar thereto which is generated by mutations, including substitutions, deletions and truncation, of a naturally occurring form of the polypeptide.

"Small molecule" as used herein, is meant to refer to a composition or compound, which has a molecular weight of less than about 5 kD and most preferably less than about 4 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be potentially screened with methods of the invention by linking such chemicals to a common ligand as used in the instant invention.

"Transcription" is a generic term used throughout the specification to refer to a process of synthesizing RNA molecules according to their corresponding DNA template sequences, which may include initiation signals, enhancers, and promoters that induce or control transcription of protein coding sequences with which they are operably linked. "Transcriptional repressor," as used herein, refers to any of various polypeptides of prokaryotic or eukaryotic origin, or which are synthetic artificial chimeric constructs, capable of repression either alone or in conjunction with other polypeptides and which repress transcription in either an active or a passive manner. It will also be understood that the transcription of a recombinant gene can be under the control of transcriptional regulatory sequences which are the same or which are different from those sequences which control transcription of the naturally-occurring forms of the recombinant gene, or its components.

"Translation" as used herein is a generic term used to describe the synthesis of protein or polypeptide on a template, such as messenger RNA (mRNA). It is the making of a protein/polypeptide sequence by translating the genetic code of an mRNA molecule associated with a ribosome. The whole process can be performed in vivo inside a cell using protein translation machinery of the cell, or be performed in vitro using cell-free systems, such as reticulocyte lysates or any other equivalents. The RNA template for translation may be separately provided either directly as RNA or indirectly as the product of transcription from a provided DNA template, such as a plasmid.

"Translationally providing" means providing a polypeptide/protein by way of translation. As defined above, translation is a process that can be done in vivo inside a cell using protein translation machinery of the cell, or be performed in vitro using cell-free systems, such as reticulocyte lysates or any other equivalents. The RNA template for translation may be separately provided either directly as RNA or indirectly as the product of transcription from a provided DNA template, such as a plasmid. The template DNA can be introduced into a host/target cell by a variety of standard molecular biology procedures, such as transformation, transfection, mating or cell fusion, or can be provided to an in vitro translation reaction directly.

The terms "transfection" and "transformation" are used interchangeably herein to denominate the introduction of a nucleic acid, e.g., without limitation, via an expression vector, into a recipient cell.

The term "treating" as used herein is intended to encompass curing as well as ameliorating at least one symptom of the condition or disease.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked may be referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of vectors which serve equivalent functions and which are known or become known in the art subsequently hereto.

The "ubiquitins" are a class of proteins found in all eukaryotic cells. The ubiquitin polypeptide is characterized by a carboxy-terminal glycine residue that is activated by ATP to a high-energy thiol-ester intermediate in a reaction catalyzed by a ubiquitin-activating enzyme (E1). The activated ubiquitin is transferred to a substrate polypeptide via an isopeptide bond between the activated carboxy-terminus of ubiquitin and the epsilon-amino group of (a) lysine residue(s) in the protein substrate. This transfer requires the action of ubiquitin conjugating enzymes such as E2 and, in some instances, E3 activities. The ubiquitin modified substrate is thereby altered in biological function, and, in some instances, becomes a substrate for components of the ubiquitin-dependent proteolytic machinery which includes both UBP enzymes as well as proteolytic proteins which are subunits of the proteasome. As used herein, the term "ubiquitin" includes within its scope all known as well as unidentified eukaryotic ubiquitin homologs of vertebrate or invertebrate origin which can be classified as equivalents of human ubiquitin. Examples of ubiquitin polypeptides as referred to herein include the human ubiquitin polypeptide which is encoded by the human ubiquitin encoding nucleic acid sequence (GenBank Accession Numbers: U49869, X04803). Equivalent ubiquitin polypeptide encoding nucleotide sequences are understood to include those sequences that differ by one or more nucleotide substitutions, additions or deletions, such as allelic variants; as well as sequences which differ from the nucleotide sequence encoding the human ubiquitin coding sequence due to the degeneracy of the genetic code. Another example of a ubiquitin polypeptide as referred to herein is murine ubiquitin which is encoded by the murine ubiquitin encoding nucleic acid sequence (GenBank Accession Number: X51730). It will be readily apparent to the person skilled in the art how to modify the methods and reagents provided by the present invention to the use of ubiquitin polypeptides other than human ubiquitin.

The term "ubiquitin-like protein" as used herein refers to a group of naturally occurring proteins, not otherwise describable as ubiquitin equivalents, but which nonetheless show strong amino acid homology to human ubiquitin. As used herein this term includes the polypeptides NEDD8, UBL1, NPVAC, and NPVOC. These "ubiquitin-like proteins" are at least over 40% identical in sequence to the human ubiquitin polypeptide and contain a pair of carboxy-terminal glycine residues which function in the activation and transfer of ubiquitin to target substrates as described supra.

As used herein, the term "ubiquitin-related protein" as used herein refers to a group of naturally occurring proteins, not otherwise describable as ubiquitin equivalents, but which nonetheless show some relatively low degree (<40% identity) of amino acid homology to human ubiquitin. These "ubiquitin-related" proteins include human Ubiquitin Cross-Reactive Protein (UCRP, 36% identical to huUb, Accession No. P05161), FUBI (36% identical to huUb, GenBank Accession No. AA449261), and Sentrin/Sumo/Pic1 (20% identical to huUb, GenBank Accession No. U83117). The term "ubiquitin-related protein" as used herein further pertains to polypeptides possessing a carboxy-terminal pair of glycine residues and which function as protein tags through activation of the carboxy-terminal glycine residue and subsequent transfer to a protein substrate.

The term "ubiquitin-homologous protein" as used herein refers to a group of naturally occurring proteins, not otherwise describable as ubiquitin equivalents or ubiquitin-like or ubiquitin-related proteins, which appear functionally distinct from ubiquitin in their ability to act as protein tags, but which nonetheless show some degree of homology to human ubiquitin (34–41% identity). These "ubiquitin-homologous proteins" include RAD23A (36% identical to huUb, SWISS-PROT. Accession No. P54725), RAD23B (34% identical to huUb, SWISS-PROT. Accession No. P54727), DSK2 (41% identical to huUb, GenBank Accession No. L40587), and GDX (41% identical to huUb, GenBank Accession No. J03589). The term "ubiquitin-homologous protein" as used herein is further meant to signify a class of ubiquitin homologous polypeptides whose similarity to ubiquitin does not include glycine residues in the carboxy-terminal and penultimate residue positions. Said proteins appear functionally distinct from ubiquitin, as well as ubiquitin-like and ubiquitin-related polypeptides, in that, consistent with their lack of a conserved carboxy-terminal glycine for use in an activation reaction, they have not been demonstrated to serve as tags to other proteins by covalent linkage.

The term "ubiquitin conjugation machinery" as used herein refers to a group of proteins which function in the ATP-dependent activation and transfer of ubiquitin to substrate proteins. The term thus encompasses: E1 enzymes, which transform the carboxy-terminal glycine of ubiquitin into a high energy thiol intermediate by an ATP-dependent reaction; E2 enzymes (the UBC genes), which transform the E1-S~Ubiquitin activated conjugate into an E2-S~Ubiquitin intermediate which acts as a ubiquitin donor to a substrate, another ubiquitin moiety (in a poly-ubiquitination reaction), or an E3; and the E3 enzymes (or ubiquitin ligases) which facilitate the transfer of an activated ubiquitin molecule from an E2 to a substrate molecule or to another ubiquitin moiety as part of a polyubiquitin chain. The term "ubiquitin conjugation machinery", as used herein, is further meant to include all known members of these groups as well as those members which have yet to be discovered or characterized but which are sufficiently related by homology to known ubiquitin conjugation enzymes so as to allow an individual skilled in the art to readily identify it as a member of this group. The term as used herein is meant to include novel ubiquitin activating enzymes which have yet to be discovered as well as those which function in the activation and conjugation of ubiquitin-like or ubiquitin-related polypeptides to their substrates and to poly-ubiquitin-like or poly-ubiquitin-related protein chains.

The term "ubiquitin-dependent proteolytic machinery" as used herein refers to proteolytic enzymes which function in the biochemical pathways of ubiquitin, ubiquitin-like, and ubiquitin-related proteins. Such proteolytic enzymes include the ubiquitin C-terminal hydrolases, which hydrolyze the linkage between the carboxy-terminal glycine residue of ubiquitin and various adducts; UBPs, which hydrolyze the glycine76-lysine48 linkage between cross-linked ubiquitin moieties in poly-ubiquitin conjugates; as well as other enzymes which function in the removal of ubiquitin conjugates from ubiquitinated substrates (generally termed "deubiquitinating enzymes"). The aforementioned protease activities function in the removal of ubiquitin units from a ubiquitinated substrate following or during uibiquitin-dependent degradation as well as in certain proofreading functions in which free ubiquitin polypeptides are removed from incorrectly ubiquitinated proteins. The term "ubiquitin-dependent proteolytic machinery" as used herein is also meant to encompass the proteolytic subunits of the proteasome (including human proteasome subunits C2, C3, C5, C8, and C9). The term "ubiquitin-dependent proteolytic machinery" as used herein thus encompasses two classes of proteases: the deubiquitinating enzymes and the proteasome subunits. The protease functions of the proteasome subunits are not known to occur outside the context of the assembled proteasome, however independent functioning of these polypeptides has not been excluded.

The term "kinase" as used herein refers to an enzyme that transfers a phosphate group from a nucleoside triphosphate to another molecule. Preferably, the kinase is selected from the following list: AMP-PK (AMP-activated protein kinase, acetyl-CoA carboxylase kinase-3, HMG-CoA reductase kinase, hormone-sensitive lipase kinase), ACK2 (acetyl-CoA carboxylase kinase-2), AFK (actin-fragmin kinase), APL-A1 (Aplysia Californica cAMP-dependent PK 1), APL-A2 (Aplysia Californica cAMP-dependent PK 2), CAK (Cdk-activating kinase), CAMII (=CaM-II), beta-ARK1 (beta-adrenergic receptor kinase 1=GRK2), beta-ARK2 (beta-adrenergic receptor kinase 2=GRK3), c-Ab1 (cellular Ab1), c-Raf (cellular Raf), c-Src (cellular Src), Cdk (cyclin dependent kinase), cdc2 (cell division cycle protein kinase), CK (casein kinase), CK-I or CKI (casein kinase I), CK-II or CKII (casein kinase II), CTD kinase ((RNA polymerase II) carboxy-terminal domain kinase), CaM-I (calmodulin-dependent protein kinase I), CaM-II (calmodulin-dependent protein kinase II, calmodulin-dependent multiprotein kinase, CaM-MPK), CaM-III (calmodulin-dependent protein kinase III, EF-2 kinase), DNA-PK (DNA-dependent protein kinase), ds-DNA kinase (double-stranded DNA-activated protein kinase), ds-RNA kinase (double stranded RNA-activated protein kinase, p68 kinase), EGF-R or EGFR (epidermal growth factor receptor), ERK (extracellular signal regulated kinase=MAPK), ERT PK (growth factor-regulated kinase), FAK (focal adhesion kinase), GRK1 (G protein-coupled receptor kinase 1=RK), GRK2 (G protein-coupled receptor kinase 2=beta-ARK1), GRK3 (G protein-coupled receptor kinase 3=beta-ARK2), GRK4 (G protein-coupled receptor kinase 4), GRK5 (G protein-coupled receptor kinase 5), GRK6 (G protein-coupled receptor kinase 5), GSK1 (glycogen synthase kinase 1=PKA), GSK2 (glycogen synthase kinase 2=PHK), GSK3 (glycogen synthase kinase 3), GSK4 (glycogen synthase kinase 4), GSK5 (glycogen synthase kinase 5=CKII), HI-HK (growth-associated HI histone kinase (MPF), cdc2+/CDC28 protein kinase) H4-PK (histone-H4-specific, protease activated protein kinase), H4-PK-I (histone H4 kinase I), H4-PK-II (histone H4 kinase II), HCR (heme-controlled repressor, heme-regulated eIF-2-alpha kinase), HKII (histone kinase II), INS-R or INSR (insulin receptor), Jak1 (Janus protein-tyrosine kinase 1), Jak2 (Janus protein-tyrosine kinase 2), LCK/FYN (LYMPHOCYTE-SPECIFIC PROTEIN TYROSINE KINASE P56LCK), MAPK (mitogen-activated protein kinase (MAP kinase)=ERK), MAPKAPK-1 (MAP kinase-activated protein kinase 1=S6K-II), MAPKAPK-2 (MAP kinase-activated protein kinase 2), MEK (MAP, Erk kinase, MAP kinase kinase), MFPK (multifunctional protein kinase), MHCK (myosin heavy chain kinase), MLCK (myosin light chain kinase), p135tyk2 (135 kD tyk2 tyrosine-protein kinase), p34cdc2 (34 kD cell division cycle protein kinase), p42cdc2 (42 kD cell division cycle protein kinase), p42mapk (42 kD MAP kinase isoform), p44 mpk (44 kD meiosis-activated myelin basic protein kinase=ERK1), p60-src (tyrosin-protein kinase src), p74raf-1 (74 kDa protein kinase Raf isoform), PDGF-R or PDGFR (platelet-derived growth factor receptor), PHK (phosphorylase kinase), PI-3 kinase (phosphatidylinositol 3' kinase), PKA (cAMP-dependent protein kinase, protein kinase A), PKC (protein kinase C), PKG (cGMP-dependent protein kinase), PRK1 (lipid-activated PKC-related kinase), Raf (protein kinase Rat), RK (rhodopsin kinase=GRK1), RS kinase (nuclear envelope-bound protein kinase), S6K (S6 kinase), S6K-II (S6-kinase 2=MAPKAPK-1), v-Src (viral Src).

The term to "bind to or inhibit a kinase" refers to the ability of certain compounds to bind to kinases with high affinity, and the further property of certain compounds to lower the activity of a kinase. The "or" therein is not meant exclusive, i.e. a compound may both bind to a kinase and inhibit it, or it may only bind, or it may only inhibit such kinase, as the case may be.

3. In-vitro Uses of the Molecules of the Present Invention

The hybrid ligands of the present invention may be used advantageously in in vitro pull-down experiments. For example, they may be used in a method to identify a ligand which binds to a given polypeptide P2. To this purpose, one, or a library of, hybrid ligand(s) of the general structure R1-Y—R2 as further substantiated above could be synthesized by one of the methods given below, wherein R1 is chosen to bind specifically to a known polypeptide P1, and R2 is a one, or a collection of, candidate ligand(s) to be screened for binding to P2. P1 may then be immobilized on a matrix, and the matrix incubated with solutions containing the one, or a library of, hybrid ligand(s) R1-Y—R2, preferably in a manner that allows a resolution of different members of the library if several are to be employed. Subsequently, the matrix is incubated with a solution containing P2, wherein P2 may be labelled for easy detection, such that binding of P2 to a ligand R2 with high affinity for P2 may occur. Finally, P2 immobilized to the matrix through binding to a ligand R2 with high affinity for P2 is detected, and the corresponding hybrid ligand may be isolated for further analysis.

In such embodiment, the matrix may, for example, be chosen to be a collection of beads, a particulate resin, a gel, a porous membrane or a solid surface, for example a glass surface. Usually, the immobilization of P1 on the matrix surface will be performed in batch mode. The method of choice for immobilization of P1 on the surface will depend on P1 and the choice of matrix. Preferably, a covalent bond is created between P1 and the matrix surface; where the binding between P1 and the matrix is non-covalent, the matrix should be chosen such as to maximize the affinity of P1 for binding to the matrix. For example, the surface may have been pre-treated such that it displays sulfhydryl groups, which may be reacted with cystein groups on P1 to form disulfide bridges. Another convenient method is the use of matrices with imidazolyl-carbamate groups on their surface (e.g. Reacti-gel, Pierce Biotechnology, Rockford, Ill., USA, Cat. # 20259). Many other methods to immobilize proteins on surfaces are known to the skilled person, and may be applied where appropriate; see, for example, Hermanson, G. T., Bioconjugate Techniques (1996), Academic Press, San Diego, Calif., USA.

Where the matrix is chosen to be a collection of beads or a particulate resin, after the immoblization of P1 in batch mode the batch will preferably be divided up into fractions, and each fraction may then be treated with a different hybrid linker R1-Y—R2, differing only in R2, for example in different wells of a microtiter plate. When the hybrid ligands have bound to the matrix via the association of R1 to P1, a sample containg the polypeptide P2 is added and allowed to bind. This may be performed keeping the beads or resin particles with the different hybrid ligands separated. Alternatively, if a suitable separation technique is available, the beads or resin particles may be pooled before exposure to P2; subsequent separation can, for example, be performed by using a fluorescently labelled P2, and, for example, sorting fluorescent from non-fluorescent beads on a fluorescence assisted sorter.

Where a gel, membrane or solid surface is chosen as a matrix, after preferably uniform immobilization of P1 on the matrix, the library of hybrid ligands, if several are employed, is preferably distributed on the matrix in a spatially resolved format, i.e. in a dotted grid where at every location on the matrix, there is only one hybrid ligand, or only one pool of hybrid ligands. Preferably, such a grid is addressable, and/or the identity of the hybrid ligands present at a given location on the matrix is known. The matrix is then incubated with a solution containing the polypeptide P2, such that P2 may bind to any R2 with affinity for P2. After washing away unbound P2, bound P2 may be detected in situ or after dissociation from the matrix, for example by detecting the presence of a fluorescent or enzymatically active tag present on P2, or by reacting the matrix with a labelled antibody with affinity for P2, or by methods such as surface plasmon resonance or mass spectrometry, or by other methods to detect the presence of a polypeptide well known to the skilled person.

Alternatively, the hybrid ligands of the invention may be used in a method to identify a polypeptide P2 which binds to a given small molecule ligand R2. Such a method will be almost identical to the methods described in the preceding paragraphs, except that only one hybrid ligand R1-Y—R2 is synthesized and incubated with the matrix pretreated with P1, and the matrix with the immobilized complexes P1::R1-Y—R2 is incubated with a sample containing one or a plurality of candidate binding partner/interactor polypeptide(s) P2, either in pools or separately if several are employed. Such a sample could, for example, be a cell extract. After eluting unbound P2, bound P2 may be detected as described in the previous paragraph. In order to identify a P2 that is detected as binding to the immobilized P1::R1-Y—R2 complex, it may be dissociated from the matrix and isolated by any known method, for example by competitive displacement using isolated R2 or another polypeptide known to bind strongly to R2, or denaturation of peptides by drastic pH change or addition of other denaturing agents such as 6 M guanidine-HCl, 2 M urea, or 10 mM DTT. The identification of P2 is conveniently carried out by mass spectrometry, either of isolated P2, or after degradation of the polypeptides on the matrix, for example by incubating the matrix with a solution containing trypsin. Other methods to identify polypeptides are known to the skilled person and may be equally used, such as amino acid sequencing WO 93/08278, WO 98/37186, WO 01/14539 and WO 02/22826 describe biological systems for the investigation of protein-protein interactions which may be used in such a manner with the hybrid ligands and methods of the present invention. These documents provide nucleic acids and nucleic acid libraries to identify polypeptides that bind to a molecule of interest. These nucleic acids encode fusion polypeptides, comprising the polypeptide to be tested for interaction with the molecule of interest, and a second domain which is capable to bind to a certain nucleic acid sequence motif with high affinity, or even covalently as described in WO 98/37186, WO 01/14539 and WO 02/22826. The vector for the expression of the fusion polypeptides is designed to comprise the nucleic acid sequence motif which the nucleic acid binding domain of the fusion polypeptides binds to. Therefore, when this vector is introduced into cells and the polypeptide is expressed, it will bind to the vector which encodes itself, forming a polypeptide-nucleic acid-complex. These complexes may be isolated from the cells used for their expression, and applied to a screening assay which identifies polypeptides that bind to a hybrid ligand of the invention.

To this end, at least one hybrid ligand R1-Y—R2 as detailed above is synthesized, as well as a library of vectors encoding DNA-binding fusion polypeptides. The construction of variegated libraries is detailed below, further guidance is given, for example, in WO 93/08278, WO 98/37186, WO 01/14539 and WO 02/22826, which are incorporated herein by reference. These vectors are introduced into suitable host cells, preferably mammalian cells if post-translational modifications of polypeptides need be incorporated, and the cells propagated to the desired quantity.

Subsequently, the host cells may be lysed and the polypeptide-DNA complexes separated from cellular debris; optionally, further purification steps may be performed, such as centrifugation or gel filtration. The library of polypeptide-DNA complexes may then be incubated in solution with the hybrid ligand(s) directly and subsequently passed over a matrix with immobilized P1 on its surface as described above, or incubated with a matrix which has been pre-treated with the hybrid ligand. Alternatively, host cells may be treated with the hybrid ligand, then lysed, and the lysates incubated with or passed over the P1-bearing matrix, optionally after one or more purification steps.

After washing away unbound complexes, those complexes that did establish binding to the hybrid ligand may be recovered from the matrix as described above, and the DNA isolated for sequencing to identify P2. Alternatively, the binding of the DNA to the surface via the DNA-binding domain of P2 may be abolished, for example by denaturing the DNA, and only the DNA encoding P2 may be isolated and sequenced. For example, the plasmid encoding P2 may contain restriction sites flanking the binding site of the DNA binding domain fused to P2, allowing the elution and isolation of a linear DNA fragment after treatment of the complexes with restriction enzymes. Alternatively, a protease may be used to cleave the P2 fusion protein, or the P2 fusion protein may be denatured, for example by treatment with SDS or mercaptoethanol, and the DNA eluted from the matrix.

DNA isolated from the matrix will usually be amplified by PCR before sequencing. However, the part of the plasmid encoding P2 may be directly amplified on the matrix using appropriate primers, and the PCR product used for sequencing. Sequencing will usually be carried out by well established methods, such as Dideoxy-mediated sequencing using T7-DNA-Polymerase or Klenow-Polymerase or Taq-Polymerase, Cycle-Sequencing using Taq-Polymerase or Chemical Sequencing (Maxam-Gilbert sequencing), but other methods may be used, even those developed subsequently hereto.

Either way, this method directly yields genetic information on the identity of polypeptides which bind R2, which greatly facilitates the identification of P2. DNA sequencing is cheaper, faster and less cumbersome when trying to obtain polypeptide sequence information than most methods that employ the polypeptide itself. Example 4 herein exemplifies the use of such method as contemplated herein, using non-covalent bonding between the gene product of lacI, the lac repressor, to the lac operon DNA sequence on the plasmid. However, other combinations of DNA motif and DNA binding polypeptide may be used and are within the scope of the present invention, including combinations wherein the binding between the DNA binding domain and the DNA motif is covalent, and specifically those described in WO 98/37186, WO 01/14539 and WO 02/22826. More specifically, the DNA binding protein may be a nucleic acid modification (NAM) protein, which covalently attaches to an enzyme attachment sequence (EAS). Suitable NAM proteins include, but are not limited to, Rep proteins, specifically Rep68 and Rep78 proteins, of adeno-associated viruses, NS1 and H-1 proteins of parvovirus, bacteriophage phi-29 terminal proteins and the 55 Kd adenovirus proteins, and fragments and derivatives thereof which retain the respective DNA binding activity, although homologues of these proteins from other viruses may also be employed. Suitable EAS for use with these DNA binding proteins may be taken from the literature, e.g. WO 98/37186, WO 01/14539 and WO 02/22826.

In the above methods, R1 preferably represents a first ligand selected from: steroid, retinoic acid, beta-lactam antibiotic, cannabinoid, FK506, FK506 derivative, rapamycin, tetracycline, methotrexate, novobiocin, maltose, glutathione, vitamin D, dexamethasone, estrogen, progesterone, cortisone, testosterone, 2,4-diaminopteridine derivative or cyclosporin, or a derivative thereof with minor modifications.

P1 may be chosen to be a fusion polypeptide, comprising at least two domains which are not found in combination in nature.

Such fusion polypeptide P1 may comprise one domain chosen from the group consisting of: β-lactamase, a steroid receptor, retinoic acid receptor, cannabinoid receptor, FKB 12, Tet-R, DHER, GyrB, maltose binding protein, glutathione-S-transferase, vitamin D receptor, glucocorticoid receptor, estrogen receptor, progesterone receptor, testosterone receptor, or a fragment thereof retaining the binding capacity to its respective ligand, and a second domain comprising a tag which allows the immobilization of said fusion protein on a matrix. Such tag may be chosen from the group consisting of: strep tag, FLAG tag, his$_6$-tag, CBD tag, E-tag, GFP tag, GST tag, haemagglutinin tag, Myc tag, T7 tag, Tag 100, V5 tag, Calmodulin binding peptide tag, S tag, Intein/chitin binding domain tag, Xpress tag, thioredoxin tag or VSV tag.

4. Transcriptional and Other Reporter Systems

According to another embodiment of the invention, a reporter system is used to detect the proximity of two polypeptides P1 and P2 (as defined above) when a small molecule compound is present so that either the small molecule compound or one of the polypeptides can be identified and further characterized.

The following sections will describe a variety of reporter systems that can be used in the invention. It will be readily apparent to the skilled artisan that the immediate invention may also be used in conjunction with other reporter systems, even those that are developed in the future.

4.1 Split Ubiquitin Reporter Systems

In part, the invention is based upon the finding that even transient interactions can be detected using a novel split ubiquitin based polypeptide association selection method. The split ubiquitin method has been used to demonstrate, for example, the association of Sec63p with various other yeast membrane proteins which traffic through the endoplasmic reticulum (ER) and the Golgi apparatus or are targeted to the plasma membrane.

The invention is understood to encompass modifications and extensions of the above described examples as follows.

The invention provides a fusion protein comprising P1-Cub-Z-RM polypeptide, where P1 is a first polypeptide, Cub is a C-terminal sub-domain of ubiquitin, Z is an amino acid residue and RM is a reporter moiety wherein the fusion protein is cleavable by a ubiquitin-specific protease in the presence of an interacting wild-type or mutant form of the Nub sub-domain of ubiquitin fused to a second polypeptide P2 (P2-Nux fusion) and results in the release of the reporter moiety. Depending on the identity of residue Z, the released RM may be stable if Z is Met and unstable if Z is a non-methionine amino-terminal amino acid, thus the activity of said reporter moiety can be changed before and/or after said release. The affinity between the Cub and Nub may be modulated by introducing point mutations (for example, at residues 3 or 13 or both positions) into Nub so that Cub and Nub (or its derivative mutant forms "Nux") can not interact with each other without the presence of other stabilizing forces such as the one provided by interaction between P1 and P2, in this case indirectly, through a compound ligand. It should be understood that due to the symmetric nature of the system, the designation of P1/P2 and R1/R2 is arbitrary. The reporter moiety of these fusion proteins may be a variety of proteins including, but not limited to: a negative selectable marker, a positive selectable marker, a metabolic marker, a transcription factor, and a fluorescent marker. In preferred applications, the reporter is a selectable marker which is capable of both positive and negative selection such as URA3, HygTk, Tkneo, TKBSD, PACTK, HygCoda, Codaneo, CodaBSD, and PACCoda. Other reporters include LYS2, HIS3 and mammalian GPT. The reporter moiety may also be a fluorescent marker, a transcription factor, e.g. PLV (Stagljar et al., PNAS, 1998, 95:5187–92), or DHFR.

The invention uses peptide libraries expressed as fusion proteins. Such peptide libraries may be synthetic, natural, random, biased-random, constrained, non-constrained and combinatorial peptide libraries. In certain instances, the peptide libraries are provided by expression of nucleic acid construct(s) encoding the polypeptides. The DNA libraries may be cDNA, random, biased-random, synthetic, genomic or oligonucleotide nucleic acid construct(s) encoding polypeptides.

The invention further provides a method of detecting the binding of a chemical compound to a protein comprising: providing a first protein as a first polypeptide fusion comprising the structure P1-Cub-Z-RM polypeptide, where P1 is a first polypeptide, Cub is a C-terminal sub-domain of ubiquitin, Z is an amino acid residue and RM is a reporter moiety; providing a second fusion protein as a second polypeptide fusion comprising the structure P2-Nux where P2 is a second polypeptide and Nux is a wild-type or mutant form of an amino-terminal sub-domain of ubiquitin; providing a chemical compound of the general formula R1-Y—R2 wherein R1 is a known ligand for P1, R2 is a potential ligand for P2, and Y is a linker sequence; allowing the chemical compound to come into close proximity with the first polypeptide fusion and the second polypeptide fusion under conditions wherein if R2 interacts with P2, and cleavage of the first fusion protein results in release of the reporter moiety having the amino-terminal amino acid residue Z; providing conditions that allow the detection of activity of the reporter moiety wherein the presence or absence of a detectable signal from the reporter moiety indicates that the chemical compound R2 binds P2. It should be understood that due to the symmetric nature of the system, the designation of P1/P2 and R1/R2 is arbitrary and either P1 or P2 can be fused to Cub-Z-RM. Similarly, in the PI-Nux fusion protein, it should be understood that, unless specifically specified, P1-Nux refers to either of the two possible configurations of the fusion protein, namely P1-Nux (N-terminal fusion) or Nux-P 1 (C-terminal fusion). In addition, P1-Cub-Z-RM is understood to encompass all possible configurations of the fusion protein as long as it is in an order wherein Cub-Z is closer to the N-terminus of the fusion protein than RM (for example, P1-Cub-Z-RM, Cub-Z-P1-RM, and Cub-Z-RM-PI are all possible configurations).

In a preferred embodiment, P1 and R1 are known to interact with each other while either the ligand binding to known protein P2 or protein P2 binding to known ligand R2 can be identified and further characterized.

This method of the invention may be performed in an in vitro or an in vivo format. The in vivo formats may utilize a host cell such as a eukaryotic cell. Suitable eukaryotic cells include mammalian cells including human, mouse, rat, and hamster cells; vertebrate cells including zebra fish cells; invertebrate cells including Drosophila and nematode cells; and fungal cells including S. pombe and S. cerevisiae cells. In preferred in vivo embodiments of the method of the invention, the reporter moiety is a positive selectable marker. The reporter may also be a negative selectable marker. The marker may be a metabolic marker, a transcription factor, both a positive and negative selectable marker, a fluorescent marker, a transcription factor, or DHFR. The method provides for the use of various amino acid residues to be engineered to the presumptive amino terminus of the reporter or selectable marker protein. In one embodiment, this amino acid is arginine, however it may also be an other non-methionine amino acid—e.g. lysine or histidine. In another embodiments, Z can be methionine or other stable amino acids in a given environment (see below).

The method of the invention uses first and/or second polypeptides, P1 and/or P2 which may be supplied as synthetic, natural, random, biased-random, constrained, non-constrained and combinatorial peptide libraries. These libraries may be provided by expression of nucleic acid construct(s) encoding said first and/or second polypeptides. The method of the invention also uses a fusion protein comprising P2 and Nux, wherein the Nux is fused to the N-terminus of the second polypeptide P2 or to the C-terminus of the second polypeptide P2.

The method of the invention provides chemical compound R1-Y—R2, which may be supplied as synthetic or natural or other chemical compound libraries.

4.1.1 Selectable Markers

The principle set up of the current split ubiquitin protein sensor technology employs two yeast/*E. coli* shuttle vectors coding for the "bait-Cub-Reporter" and the "Nub-prey" fusion proteins, where Nub and Cub stand for the respective N- and C-terminal halves of the ubiquitin monomer (Johnsson & Varshavsky, 1994, Proc. Natl. Acad. Sci. U.S.A. 91:10340–10344).

Upon interaction between bait and prey through a chemical compound R1-Y—R2, the ubiquitin halves are brought into close contact and re-associate to form a unit that is sufficiently well recognized by UBPs (ubiquitin-specific-proteases). This recognition event leads to proteolytic cleavage and subsequent release of the C-terminally fused reporter.

In a typical 3-hybrid approach re-association of the ubiquitin halves with subsequent release of the reporter would rely on a small molecule-protein interaction, rather than protein-protein interaction. The bait construct would employ a "receptor-Cub-reporter" (P1-Cub-RM) fusion. Similarly to the split ubiquitin protein sensor technology, the "Receptor-Cub-reporter" and the Nub-prey constructs are expressed from 2 separate shuttle vectors. The small molecule to be investigated is fused to a common functional group that binds to the "receptor". The receptor may be DHFR (dehydrofolate reductase). Here, DHFR functions as receptor for the common functional group methotrexate (Mtx). Mtx or its derivatives with a similar functional group (such as 2,4-diaminopteridine) will be fused to various small molecules with numerous different linker molecules. The small molecule itself will be analyzed for its interaction with proteins present in a Nub-prey library. Interaction of the compound with a prey will lead to bridging of R-Cub-DHFR::Mtx-small molecule::prey-Nub, thereby bringing Cub and Nub (or Nux) into close contact, leading to release of the reporter moiety RM.

The reporter moiety may trigger any sort of detectable change, i.e. may rely on detection of proteolytic splice products by gel electrophoresis and/or western blot analysis, enzymatic or fluorescence readout, nutritional complementation, or other forms of transcriptional readout.

The reporter moiety may be a transcription factor tethered to a cellular membrane preventing entry into the nucleus and transcriptional activation. Only upon re-association of the ubiquitin halves after compound-protein interaction, the reporter moiety will be released and translocate into the nucleus where transcription of a reporter gene may be activated. Reporter genes may be enzymes, fluorescent markers or nutritional markers (e.g. lacZ, green fluorescent protein GFP/ yeast codon optimized red fluorescent protein yRFP, HISIURA) (Stagljar et al. (1998) Proc. Natl. Acad. Sci. U.S.A., 95: 5187–92).

The invention uses negative selectable marker genes or "selectable reporters" which can be used in a eukaryotic host cell, preferably a yeast or a mammalian cell, or a prokaryotic cell, and which can be selected against under appropriate conditions. In preferred embodiments, the selectable reporter is provided as a fusion polypeptide with a carboxy- or C-terminal sub-domain of ubiquitin (or Cub) and is altered so as to encode a non-methionine amino acid residue at the junction with the Cub. The non-methionine amino acid residue is preferably an amino acid which is recognized by the N-end rule ubiquitin protease system (e.g. an arginine, lysine histidine, phenylalanine, tryptophan, tyrosine, leucine or isoleucine residue) and which, when present at the amino-terminal end of the negative selectable marker, targets the negative selectable marker for rapid proteolytic degradation.

A preferred example of a selectable marker gene for use in yeast is the URA3 gene which can be both selected for (positive selection) by growing ura3 auxotrophic yeast strains in the absence of uracil, and selected against (negative selection) by growing cells on media containing 5-fluoroorotic acid (5-FOA) (see Boeke, et al. (1987) Methods Enzymol 154: 164–75). The concentration of 5-FOA can be optimized by titration so as to maximally select for cells in which the URA3 reporter is, for example, inactivated by proteolytic degradation to some preferred extent. For example, relatively high concentrations of 5-FOA can be used which allow only cells expressing very low steady-state levels of URA3 reporter to survive. Such cells will correspond to those in which the first and second ubiquitin sub-domain fusion proteins have a relatively high affinity for one another, resulting in efficient reassembly of the Nub and Cub fragments and a correspondingly efficient release of the Z-URA3 labilized marker. In contrast, lower concentrations of 5-FOA can be used to select for protein binding partners with relatively weak affinities for one another. In addition, proline can be used in the media as a nitrogen source to make the cells hypersensitive to the toxic affects of the 5-FOA (McCusker & Davis (1991) Yeast 7: 607–8). Accordingly, proline concentrations, as well as 5-FOA concentrations can be titrated so as to obtain an optimal selection for URA3 reporter deficient cells. Therefore the use of URA3 as a negative selectable marker allows a broad range of selective stringencies which can be adapted to minimize false positive background noise and/or to optimize selection for high affinity binding interactions. Other negative selectable markers which operate in yeast and which can be adapted to the method of the invention are included within the scope of the invention.

Numerous selectable markers which operate in mammalian cells are known in the art and can be adapted to the method of the invention so as to allow direct negative selection of interacting proteins in mammalian cells. Examples of mammalian negative selectable markers include Thymidine kinase (Tk) (Wigler et al. (1977) Cell 11: 223–32; Borrelli et al. (1988) Proc. Natl. Acad. Sci. USA 85: 7572–76) of the Herpes Simplex virus, the human gene for hypoxanthine phosphoriboxyl transferase (HPRT) (Lester et al. (1980) Somatic Cell Genet. 6: 241–59; Albertini et al. (1985) Nature 316: 369–71) and Cytidine deaminase (codA) from E. coli (Mullen et al. (1992) Proc. Natl. Acad. Sci. USA 89: 33–37; Wei and Huber (1996) J. Biol. Chem. 271: 3812–16). For example: the Tk gene can be selected against using Gancyclovir (GANC) (e.g. using a 1 µM concentration) and codA gene can be selected against using 5-Fluor Cytidin (5-FIC) (e.g. using a 0.1–1.0 mg/ml concentration). In addition, certain chimeric selectable markers have been reported (Karreman (1998) Gene 218: 57–61) in which a functional mammalian negative selectable marker is fused to a functional mammalian positive selectable marker such as Hygromycin resistance ($Hyg^R$, neomycin resistance ($neo^R$), puromycin resistance ($PAC^R$) or Blasticidin S resistance ($BlaS^R$). These produce various Tk-based positive/negative selectable markers for mammalian cells such as HygTk, Tkneo, TKBSD, and PACTK, as well as various codA-based positive/negative selectable markers for mammalian cells such as HygCoda, Codaneo, CodaBSD, and PACCoda. Tk-neo reporters which incorporate luciferase, green fluorescent protein and/or beta-galactosidase have also been recently reported (Strathdee et al. (2000) BioTechniques 28: 210–14). These vectors have the advantage of allowing ready screening of the "positive" marker/reporter by fluorescent and/or immunofluorescent microscopy. The use of such positive/negative selectable markers affords the advantages mentioned above for URA3 as a reporter in yeast, inasmuch as they allow mammalian cells to be assessed by both positive and negative selection methods for the expression and relative steady-state level of the reporter fusion. Other advantages of these mammalian reporter and selectable marker constructs will be apparent to the skilled artisan.

4.1.2 Components of N-End Rule Proteolytic Pathway

The "N-end rule" system for proteolytic degradation is a particular branch of the ubiquitin-mediated proteolytic pathway present in eukaryotic cells (Bachmair et al. (1986) Science 234: 179–86). This system operates to degrade a cellular polypeptide at a rate dependent upon the amino-terminal amino acid residue of that polypeptide. Protein translation ordinarily initiates with an ATG methionine codon and so most polypeptides have an amino-terminal methionine residue and are typically relatively stable in vivo. For example, in the yeast S. cerevisiae, a beta-galactosidase polypeptide with a methionine amino terminus has a half-life of >20 hours (Varshavsky (1992) Cell 725–35). Under certain circumstances, however, polypeptides possessing a non-methionine amino-terminal residue can be created. For example, when an endoprotease hydrolyzes and thus cleaves a unique polypeptide bond (A-B) internal to a polypeptide, it results in the release of two separate polypeptides—one of which possesses an amino-terminal amino acid, Z, which may not be methionine. For example, the endoprotease ubiquitin-specific protease, which is a preferred component of the present invention, will cleave a polypeptide bond carboxy-terminal to the final glycine residue (codon 76), regardless of what the next codon is. In the normal function of the cell, this-specific protease serves to cleave a polyubiquitin precursor into individual ubiquitin units. However it can also be used to generate a target polypeptide with virtually any amino-terminal residue by merely fusing the target polypeptide in-frame to a codon corresponding to the desired amino-terminal amino acid (Z), which codon, in turn, is fused downstream of ubiquitin (typically contiguous with ubiquitin Gly codon 76). The resulting target gene chimera construct, has the general formula Ubiquitin-Z-Target. Preferred target constructs further comprise an epitope tag (Ep) so that the resulting target gene chimera construct has the general formula Ubiquitin-Z-Ep-target, which results in the eventual production of a polypeptide of the general formula Z-Ep-Target. Constitutively active ubiquitin-specific protease activities present in eucaryotic cells will result in the endoproteolytic processing of the Ubiquitin-Z-Target polypeptide into ubiquitin and Z-Target entities. The Z-Target polypeptide is further acted upon by the components of the N-end rule system as described below. If the Target polypeptide is a negative selection marker (NSM) and if Z is an amino acid residue (such as arg) which potentiates rapid degradation by the N-end rule system, then cells expressing intact Ubiquitin-Z-NSM can be selected against while cells in which the fusion is clipped into a relatively labile Z-NSM polypeptide can be selected for.

It has been determined, with reasonable reliability, the relative effect of a given amino-terminal residue, Z, upon target polypeptide stability. For example, when all 20 possible amino-terminal amino acid residues were tested to determine their effect on the stability of beta-galactosidase (utilizing a ubiquitin-Z-beta-galactosidase chimeric fusion)

in *Saccharomyces cerevisiae*, drastic differences were discovered (see Varshavsky (1992) Cell 69: 725–35). For example when Z was met, cys, ala, ser, thr, gly, val, or pro, the resulting polypeptide was very stable (half-life of >20 hours). When Z was tyr, ile, glu, or gln, the resulting polypeptide possessed moderate protein stability (half-life of 10–30 minutes). In contrast, the residues arg, lys phe, leu, trp, his, asp, and asn, all conferred low stability on the beta-galactosidase polypeptide (half-life of <3 minutes). The residue arginine (arg), when located at the amino terminus of a polypeptide, appears to generally confer the lowest stability. Thus, chimeric constructs and corresponding fusion polypeptides employing an arg residue at the position Z, described above, are generally preferred embodiments of the present invention.

The above described experiments establishing the relative half-lives conferred by each of the 20 possible amino terminal residues form the basis of the N-end rule. The N-end rule system components are those gene products which act to bring about the rapid proteolysis of polypeptides possessing amino-terminal residues which confer instability. The N-end rule system for proteolysis in eukaryotes appears to be a part of the general ubiquitin-dependent proteolytic system pathways possessed by apparently all eucaryotic cells. Briefly, this system involves the covalent tagging of a target polypeptide on one or more lysine residues by a ubiquitin polypeptide marker (to form a target(lys)-epsilon amino-gly(76) Ubiquitin covalent bond). Additional ubiquitin moieties may be subsequently conjugated to the target polypeptide and the resulting "ubiquitinated" target polypeptide is then subject to complete proteolytic destruction by a large (26S) multiprotein complex known as the proteasome. The enzymes which conjugate the ubiquitin moieties to the targeted protein include E2 and E3 (or ubiquitin ligase) functions. The E2 and E3 enzymes are thought to possess most of the specificity for ubiquitin dependent proteolytic processes.

A key component of the N-end rule proteolytic pathway in yeast is UBR1 (Bartel, et al. (1990) EMBO J. 9: 3179–89), a gene which encodes an E3 like function which appears to recognize polypeptides possessing susceptible amino terminal residues and thereby facilitates ubiquitination of such polypeptides (Dohmen et al. (1991) Proc. Natl. Acad. Sci. USA 88: 7351–55). Accordingly UBR1 can be used as a regulatable N-end rule component which is the effector of proteolytic degradation of the target gene polypeptide. The UBR1 gene has now been cloned from a mammalian organism (Kwon et al. (1998) Proc. Natl. Acad. Sci. USA 95: 7893–903) as well as from yeast. Thus the construction of a UBR1 mouse cell line knockout is imminent and so control of the instability of Z-Reporter fusions can-be further manipulated by controlling the level of UBR1 expressed.

The UBR1 gene is particularly central to some aspects of the present invention because it can be selectively used in conjunction with any of the above described non-methionine "Z" amino-terminal destabilizing residues including: the most destabilizing—arg; strongly destabilizing residues—such as lys phe, leu, trp, his, asp, and asn; and moderately destabilizing residues—such as tyr, ile, glu, or gln. Indeed, it is an object of certain embodiments the present invention to provide a means, where desired, to not completely shut-off a negative selectable marker's function, but merely to attenuate it to some set degree. This can be achieved using the method of the present invention in any of a number of ways. For example, a moderately destabilizing amino-terminal residue (Z=tyr, ile, glu, or gln) can be deployed on the target polypeptide reporter—resulting in a less rapid removal of the target polypeptide pool.

Other N-end rule components for use in the present invention include *S. cerevisiae* UBC2 (RAD6), which encodes an E2 ubiquitin conjugating function which cooperates with the UBR1—encoded N-end rule E3 to promote multiubiquitination and subsequent degradation of N-end rule substrates (Dohmen et al. (1991) Proc. Natl. Acad. Sci. USA 88: 7351–55). Thus N-end rule directed proteolysis will not occur in the absence of either UBR1 or UBC2. This allows either gene to be used as the inducible "effector of targeted proteolysis" by methods of the present invention. Indeed, a target gene polypeptide possessing an N-end rule destabilizing amino-terminal amino acid (such as arg) will be stable until expression of either the UBR1 (E3) or the UBC2 (E2) is induced from the cognate inducible promoter construct.

Both UBR1 and UBC2 can be used in conjunction with any of the above described "Z" amino-terminal destabilizing residues including: the most destabilizing—arg; strongly destabilizing residues—such as lys phe, leu, trp, his, asp, and asn; and moderately destabilizing residues—such as tyr, ile, glu, or gln. Still other alternative embodiments of the N-end rule component of the present invention are components of the N-end rule system which affect only a subset of the destabilizing residues. For example, the NTAI deamidase (Baker and Varshavsky (1995) J Biol Chem 270: 12065–74) functions to deaminate amino-terminal asn or gln residues (to form polypeptides with asp or glu amino-terminal residues respectively). Yeast strains harboring ntal null alleles are unable to degrade N-end rule substrates that bear amino-terminal asn or gln residues. Thus, the NTA1 gene is an alternative embodiment of the N-end rule component of the present invention, but is used preferably in conjunction with a target gene polypeptide (Z-target), in which Z is either asn or gln. Similarly the ATE1 transferase (Balzi et al. (1990) J. Biol Chem 265: 7464–71) is an enzyme which acts to transfer the arg moiety from a tRNA~Arg activated tRNA to amino-terminal glu or asp bearing polypeptides. The resulting arg-glu-polypeptide and arg-asp-polypeptide products are then susceptible to the E2/E3—mediated N-end rule dependent proteolytic processes described above. Thus, the ATE1 transferase is an alternative embodiment of the N-end rule component of the present invention, but its use is preferably tied to target gene polypeptides (Z-target), in which Z is asp, glu, asn or gln. Polypeptides bearing the latter two amino-terminal residues are first converted to polypeptides bearing one of the former tow amino-terminal residues by NTA1 deamidase function described above.

It is important to note here that, as is the case for the repressor which is made subject to induction by an inducible promoter, the N-end rule component must be available as a clone so that it can be put under the control of an inducible promoter (using standard subcloning methods known in the art). This can be achieved by first introducing genetically engineered copies of the inducible repressor and the inducible N-end rule component constructs, and subsequently deleting the normal chromosomal copies of these genes from the host by "knockout" methods. Such methods, we note here are well developed in the art—particularly in the case of both the yeast *Saccharomyces cerevisiae* and the mammal mouse. More convenient, however, is the availability of "knock-in" technology which allows the existing chromosomal copy of the gene to be modified to so that its native promoter is deleted and an inducible promoter is inserted in a single step.

4.1.3 Ubiquitin Polypeptide Sequences

A complete and detailed description of the Cub and Nub constructs which can be used in the method of the present invention is given in U.S. Pat. Nos. 5,503,977 and 5,585,245. A background to the molecular biology of the ubiquitin proteolytic system in general, and the N-end rule system and ubiquitin sensor association assay is presumed of the skilled artisan seeking to practice the present invention. Briefly, ubiquitin (Ub) is a 76-residue, single-domain protein whose covalent coupling to other proteins yields branched Ub-protein conjugates and plays a role in a number of cellular processes, primarily through routes that involve protein degradation. Unlike the branched Ub conjugates, which are formed posttranslationally, linear Ub adducts are the translational products of natural or engineered Ub fusions. It has been shown that, in eukaryotes, newly formed Ub fusions are rapidly cleaved at the Ub-polypeptide junction by Ub-specific proteases (UBPs). In the yeast *Saccharomyces cerevisiae*, there are at least five species of UBP. Recent work has shown that the cleavage of a Ub fusion by UBPs requires the folded conformation of Ub, because little or no cleavage is observed with fusions whose Ub moiety was conformationally destabilized by single-residue replacements or a deletion distant from the site of cleavage by UBPs.

The present invention relies in part upon the previously described split ubiquitin protein sensor system (see U.S. Pat. Nos. 5,503,977 & 5,585,245 and WO 02/12902). Briefly, it has been demonstrated that an N-terminal ubiquitin sub-domain and a C-terminal ubiquitin sub-domain, the latter bearing a reporter extension at its C-terminus, when coexpressed in the same cell by recombinant DNA techniques as distinct entities, have the ability to associate, reconstituting a ubiquitin molecule which is recognized, and cleaved, by ubiquitin-specific processing proteases which are present in all eukaryotic cells. This reconstituted ubiquitin molecule, which is recognized by ubiquitin-specific proteases, is referred to herein as a quasi-native ubiquitin moiety. As disclosed herein, ubiquitin-specific proteases recognize the folded conformation of ubiquitin. Remarkably, ubiquitin-specific proteases retained their cleavage activity and specificity of recognition of the ubiquitin moiety that had been reconstituted from two unlinked ubiquitin sub-domains.

Ubiquitin is a 76-residue, single-domain protein comprising two sub-domains which are relevant to the present invention—the N-terminal sub-domain and the C-terminal sub-domain. The ubiquitin protein has been studied extensively and the DNA sequence encoding ubiquitin has been published (Ozkaynak et al., EMBO J. 6: 1429 (1987)). The N-terminal sub-domain (Nub), as referred to herein, is that portion of the native ubiquitin molecule which folds into the only alpha-helix of ubiquitin interacting with two beta-strands. Generally speaking, this sub-domain comprises amino acid residues from about residue number 1 to about residue number 36.

The C-terminal sub-domain of ubiquitin (Cub), as referred to herein, is that portion of the ubiquitin which is not a portion of the N-terminal sub-domain defined in the preceding paragraph. Generally speaking, this sub-domain comprises amino acid residues from about 37 to about 76. It should be recognized that by using only routine experimentation it will be possible to define with precision the minimum requirements at both ends of the N-terminal sub-domain and the C-terminal sub-domain which are necessary to be useful in connection with the present invention.

It is important to note that the Nub refers, in preferred embodiments of the invention, to the amino-terminal ubiquitin sub-domain unit which has been mutated so as to decrease its binding affinity, thereby making the Cub/Nub association dependent upon the binding of a second protein pair fused to the Cub and Nub subunits. Suitable forms of Nub are described below and still others are readily available to the skilled artisan by routine mutation and screening methods.

In order to study the interaction between a hybrid ligand and a pair of ligand binding domains, one member of the pair is fused to the N-terminal sub-domain of ubiquitin and the other member of the pair is fused to the C-terminal sub-domain of ubiquitin. Since the members of the specific-binding pair (linked to sub-domains of ubiquitin) have an affinity for the hybrid ligand, this affinity increases the "effective" (local) concentration of the N-terminal and C-terminal sub-domains of ubiquitin, thereby promoting the reconstitution of a quasi-native ubiquitin moiety. For convenience, the term "quasi-native ubiquitin moiety" will be used herein to denote a moiety recognizable as a substrate by ubiquitin-specific proteases. In light of the fact that the N-terminal and C-terminal sub-domains of ubiquitin associate to form a quasi-native ubiquitin moiety even in the absence of fusion of the two sub-domains to individual-members of the ligand binding domain pair, a further requirement may be imposed in certain embodiments of the present invention in order to increase the resolving capacity of the method for studying such interactions. This further preferred requirement is that the N-terminal sub-domain of ubiquitin may be mutation ally altered to reduce its ability to produce, through association with Cub, a quasi-native ubiquitin moiety. It will be recognized by one of skill in the art that the binding interaction studies described herein are carried out under conditions appropriate for protein/ligand interaction. Such conditions are provided in vivo (i.e., under physiological conditions inside living cells) or in vitro, when parameters such as temperature, pH and salt concentration are controlled in a manner intended to mimic physiological conditions.

The mutational alteration of an amino-terminal ubiquitin sub-domain for use with the instant invention is preferably a point mutation. In light of the fact that it is essential that the reconstituted ubiquitin moiety must "look and feel" like native ubiquitin to a ubiquitin-specific protease, mutational alterations which would be expected to grossly affect the structure of the sub-domain bearing the mutation are to be avoided. A number of ubiquitin-specific proteases have been reported, and the nucleic acid sequences encoding such proteases are also known (see e.g., Tobias et al., J. Biol. Chem. 266: 12021 (1991); Baker et al., J. Biol. Chem. 267: 23364 (1992)). It should be added that all of the at least five ubiquitin-specific proteases in the yeast *S. cerevisiae* require a folded conformation of ubiquitin for its recognition as a substrate. Extensive deletions within the N— sub-domain of ubiquitin are an example of the type of mutational alteration which would be expected to grossly affect sub-domain structure and, therefore, are examples of types of mutational alterations which should be avoided.

In light of this consideration, the preferred mutational alteration within the Nub subunit is a mutation in which an amino acid substitution is effected. For example, the substitution of an amino acid having chemical properties similar to the substituted amino acid (e.g., a conservative substitution) is preferred. Specifically, the desired mild perturbation of ubiquitin sub-domain interaction is achieved by substituting a chemically similar amino acid residue which differs primarily in the size of its side chain. Such a steric perturbation is expected to introduce a desired (mild) conformational destabilization of a ubiquitin sub-domain. The goal is to reduce the affinity of the N-terminal and C-terminal sub-domains for one another, not necessarily to eliminate this affinity.

For example, the mutational alteration may be introduced into the N-terminal sub-domain of ubiquitin. More specifically, a first neutral amino acid residue may be replaced with a second neutral amino acid having a side chain which differs in size from the first neutral amino acid residue side chain to achieve the desired decrease in affinity. For example, the first neutral amino acid residue isoleucine (either residue 3 or 13 of wild-type ubiquitin) may be replaced with a neutral amino acids which has a side chain which differs in size from isoleucine such as glycine, alanine or valine (see Johnsson & Varshavsky, 1994, Proc. Natl. Acad. Sci. U.S.A. 91:10340–10344, the entire contents of which are hereby incorporated by reference).

A wide variety of fusion construct combinations can be used in the methods of this invention. One strict requirement which applies to all N- and C-terminal fusion construct combinations is that the C-terminal sub-domain must bear an amino acid (e.g., peptide, polypeptide or protein) extension. This requirement is based on the fact that the detection of interaction between two proteins of interest linked to two sub-domains of ubiquitin is achieved through cleavage after the C-terminal residue of the quasi-native ubiquitin moiety, with the formation of a free reporter protein (or peptide) that had previously been linked to a C-terminal sub-domain of ubiquitin. Ubiquitin-specific proteases cleave a linear ubiquitin fusion between the C-terminal residue of ubiquitin and the N-terminal residue of the ubiquitin fusion partner, but they do not cleave an otherwise identical fusion whose ubiquitin moiety is conformationally perturbed. In particular, they do not recognize as a substrate a C-terminal sub-domain of ubiquitin linked to a "downstream" reporter sequence, unless this C-terminal sub-domain associates with an N-terminal sub-domain of ubiquitin to yield a quasi-native ubiquitin moiety.

Furthermore, the characteristics of the C-terminal amino acid extension of the C-terminal ubiquitin sub-domain must be such that the products of the cleaved fusion protein are distinguishable from the uncleaved fusion protein. In practice, this is generally accomplished by monitoring a physical property or activity of the C-terminal extension which is cleaved free from the C-terminal ubiquitin moiety. It is generally a property of the free C-terminal extension that is monitored as an indication that a quasi-native ubiquitin has formed, because monitoring of the quasi-native ubiquitin moiety directly is difficult in eukaryotic cells due to the presence of native ubiquitin. While unnecessary for the practice of the present invention, it would of course be appropriate to monitor directly the presence of the quasi-native ubiquitin as well, provided that this monitoring could be carried out in the absence of interference from native ubiquitin (for example, in prokaryotic cells, which naturally lack ubiquitin).

The size of the C-terminal extension which is released following cleavage of the quasi-native ubiquitin moiety within a reporter fusion by a ubiquitin-specific protease is a particularly convenient characteristic in light of the fact that it is relatively easy to monitor changes in size using, for example, electrophoretic methods. For instance, if the C-terminal reporter extension has a molecular weight of about 20 kD, the cleavage products will be distinguishable from the non-cleaved quasi-native ubiquitin moiety by virtue of the appearance of a previously absent reporter-specific 20 kD band following cleavage of the reporter fusion.

In light of the fact that the cleavage can take place, for example, in crude cell extracts or in vivo, it is generally not possible to monitor such changes in molecular weight of cleavage products by simply staining an electrophoretogram with a dye that stains proteins nonspecifically, because there are too many proteins in the mixture to analyze in this manner. One preferred method of analysis is immunoblotting. This is a conventional analytical method wherein the cleavage products are separated electrophoretically, generally in a polyacrylamide gel matrix, and subsequently transferred to a charged solid support (e.g., nitrocellulose or a charged nylon membrane). An antibody which binds to the reporter of the ubiquitin-specific protease cleavage products is then employed to detect the transferred cleavage products using routine methods for detection of the bound antibody.

Another useful method is immunoprecipitation of either a reporter-containing fusion to C-terminal sub-domains of ubiquitin or the free reporter (liberated through the cleavage by ubiquitin-specific proteases upon reconstitution of a quasi-native ubiquitin moiety) with an antibody to the reporter. The proteins to be immunoprecipitated are first labeled in vivo with a radioactive amino acid such as $^{35}$S-methionine, using methods routine in the art. A cell extract is then prepared, and reporter-containing proteins are precipitated from the extract using an anti-reporter antibody. The immunoprecipitated proteins are fractionated by electrophoresis in a polyacrylamide gel, followed by detection of radioactive protein species by autoradiography or fluorography.

A preferred experimental design is to extend the C-terminal sub-domain of ubiquitin with a peptide containing an epitope foreign to the system in which the assay is being carried out. It is also preferable to design the experiment so that the C-terminal reporter extension of the C-terminal sub-domain of ubiquitin is sufficiently large, i.e., easily detectable by the electrophoretic system employed. In this preferred embodiment, the C-terminal reporter extension of the C-terminal sub-domain should be viewed as a molecular weight marker. The characteristics of the extension other than its molecular weight and immunological reactivity are not of particular significance. It will be recognized, therefore, that this C-terminal extension can represent an amalgam comprising virtually any amino acid sequence combination fused to an epitope for which a specifically binding antibody is available. For example, the C-terminal extension of the C-terminal ubiquitin sub-domain may be a combination of the "ha" epitope fused to mouse DHFR (an antibody to the "HA" epitope is readily available).

Aside from the molecular weight of the C-terminal amino acid extension of the C-terminal ubiquitin sub-domain, other characteristics can also be monitored in order to detect cleavage of a quasi-native ubiquitin moiety. For example, the enzymatic activity of some proteins can be abolished by extending their N-termini. Such a "reporter" enzyme, which, in its native form, exhibits an enzymatic activity that is abolished when the enzyme is N-terminally extended, can also serve as the C-terminal reporter linked to the C-terminal ubiquitin sub-domain.

In this detection scheme, when the reporter is present as a fusion to the C-terminal ubiquitin sub-domain, the reporter protein is inactive. However, if the C-terminal ubiquitin sub-domain and the N-terminal ubiquitin sub-domain associate to reconstitute a quasi-native ubiquitin moiety in the presence of a ubiquitin-specific protease, the reporter protein will be released, with the concomitant restoration of its enzymatic activity.

In preferred embodiments, the reporter protein is a eukaryotic negative selectable marker (NSM) which has been engineered to be processed and released as an N-end rule-labile Z-NSM fusion following ubiquitin-specific protease proteolytic cleavage. The negative selectable markers (NSMs) for use in the invention are described elsewhere. The advantage of using an Z-NSM fusion is that interaction of the specific binding pair can be directly selected for (as opposed to screened for) by virtue of the fact that only cells in which Z-NSM has been released will survive negative selection.

The target gene reporter (negative selectable marker) must be fused downstream of a codon which encodes an N-end rule susceptible residue (Z, as described above) and this residue, in term, must be fused in-frame to the carboxy-terminus of a ubiquitin coding sequence (generally the carboxy-terminus of a C-terminal ubiquitin sub-domain (Cub) which corresponds to gly76 of intact ubiquitin). The reason for constructing this extensive chimeric gene construct is to take advantage of the ability of constitutive ubiquitin proteases to cleave any peptide bond which is carboxy-terminal to gly76 of an intact ubiquitin unit. This ubiquitin-specific protease normally functions to process poly-ubiquitin chains (the translational product of the tandem ubiquitin encoding sequences of eucaryotic genomes) into discrete (normally 76 aa) ubiquitin moieties which are used in ubiquitin-system pathways. In the method of the present invention, the ubiquitin-specific proteases serve as a convenient means to generate target gene polypeptides bearing specific amino-terminal residues (Z). Nonetheless, it is understood that other alternatives to mammalian or yeast ubiquitin exist which can function in the method of the present invention. Such ubiquitin equivalents include, for example, ubiquitin mutants, ubiquitin-like proteins, ubiquitin-related proteins, and ubiquitin-homologous proteins. For example, ubiquitin-like proteins such as NEDD8, UBL1, FUBI, and UCRP, as well as analogous ubiquitin-related proteins such as SUMO/Sentrin/Pic1 may be used as ubiquitin equivalents in the method of the invention. Other proteins related to ubiqutin, but which are somewhat less homologous to it, include ubiquitin-homologous proteins such as Rad23 and Dsk2 whose similarity to ubiquitin does not include the presence of a carboxyl-terminal pair of glycines. These ubiquitin-like proteins share the common features of being related to ubiquitin by amino acid sequence homology and, with the apparent exception of the ubiquitin homologous proteins, of being covalently transferred to cellular protein targets post-translationally.

Indeed, in some embodiments the intended scope of the immediate invention encompasses any means known in the art by which a target polypeptide bearing an N-end rule susceptible residue (Z=arg, lys, his, leu, phe, try, ile, trp, asn, gln, asp, or glu) can be generated. General methods for engineering such N-end residues into ubiquitin-reporter chimera expression vectors are well known in the art (e.g. the "fusion PCR" method; see Karreman (1988) BioTechniques 24: 736–42).

The summary description in the preceding paragraph does not discuss certain important experimental considerations. For example, for two interacting proteins, P1 (fused to Nub) and P2 (fused to Cub) the following additional considerations are included within the scope of the invention. In light of its role as an affinity component, it will be recognized that P1 can be fused to the N-terminus or the C-terminus of the N-terminal ubiquitin sub-domain. Similarly, P2 can be fused to the N-terminus or the C-terminus of the C-terminal ubiquitin sub-domain. If P2 is fused to the C-terminus of the C-terminal ubiquitin sub-domain, it will be removed by cleavage by the ubiquitin-specific protease, providing that the ubiquitin sub-domains associate to form a quasi-native ubiquitin moiety. Consistent with the summary description in the preceding paragraph, if the P2 moiety is fused to the C-terminus of the C-terminal ubiquitin sub-domain, it may also be used as a reporter for detecting reconstitution of a quasi-native ubiquitin moiety. Furthermore, the position of P2 within the C-terminal reporter-containing region of the fusion is not a critical consideration.

4.1.4 Detection of Cleavage of the Reporter Moiety

The most straight forward way to detect cleavage of the reporter moiety is by detecting the presence of the cleaved "free-RM". One routine assay for that type of detection is achieved by Western blot using an antibody specific for the RM. No additional activity of the RM is required as long as it is reasonably stable. For that reason, a Met shall be present at the N-terminus of the cleaved RM. Alternatively, if the N-terminus of the cleaved RM has a non-stabilizing amino acid and the free-RM form will therefore be degraded, a detection of the un-cleaved RM linked to Cub will also be able to assess the degree of cleavage which has occurred. To obviate the need of an antibody for each particular RM, an epitope tag (such as HA, myc, or any other routinely used tags against which commercially available antibodies may exist) may be fused to the RM at a proper location, such as the C-terminus. Western blot is well-known in the art and can be found in a number of laboratory manuals.

If the RM has an enzymatic activity that is only present when the RM is cleaved off the Cub-RM fusion, degree of cleavage can also be indirectly determined by assaying for the enzymatic activity of the free RM. For example, some kinases my be inactive when fused to an N-terminal inhibitory domain and become activated after removing the inhibitory domain. Such kinases can be used as a RM for this embodiment of the invention. A Met shall preferably form the N-terminus of the free-RM.

Similarly, if a RM is enzymatically inactivated/degraded when it is cleaved off the fusion, an assay of the enzymatic activity can also be used to determine the degree of cleavage. For that assay, a non-Met amino acid is preferably the first amino acid of the cleaved RM.

Other activities of the RM may be useful for detecting cleavage. For example, if the RM is a fluorescent protein, then the cleaved RM may be degraded by UBP if the first amino acid is non-Met. Changes in fluorescent strength can be measured to indicate the degree of cleavage.

If the RM is a transcription factor (e.g. PLV, Stagljar et al. (1998) Proc. Natl. Acad. Sci. U.S.A., 95: 5187–92), cleaved RM may now relocate to the nucleus and be available for transcriptional activation of a reporter gene, the activity of which in turn serves as an indicator of the degree of cleavage. If the un-cleaved RM is able to serve as a transcription factor, then the overall level of transcription is expected to drop if the cleaved free-RM is unstable as determined by N-end rule.

The above exemplary detection methods are for illustration purpose only. A skilled artisan shall be able to envision equivalent methods of these examples, and thus, those equivalent methods are also within the scope of the instant invention.

4.2 Other Reporter Systems

According to the invention, a transcription based reporter system can be used to detect whether P1 and P2 are within close range of each other. A typical transcription-based reporter system is yeast two-hybrid system, which is well-known in the art (see below). In that respect, P1 and P2 are both synthesized as fusion proteins, one fused to a DNA binding domain, the other fused to a transcription activation domain. The DNA binding domain will bind to the promoter region of a reporter gene. If P1 and P2 are with close range of each other (via binding to R1-Y—R2), then the transcription activation domain will be able to activate the transcription of a reporter gene, which will facilitate the identification of either the test protein or the test small chemical compound. Due to the symmetric nature of the system, there shall be no limitation as to whether P1 or P2 is fused to the DNA binding domain or the transcription activation domain. In addition, both P1 and P2 can be synthesized as either N- or C-terminal fusion proteins.

Detailed description of various components of yeast two hybrid system can be readily found elsewhere. For example, *The Yeast Two-Hybrid System* (*Advances in Molecular Biology*), Ed. Paul L. Bartel and Stanley Fields, Oxford University Press, 1997, is a book devoted solely to the yeast two-hybrid system. Pioneers in the field provide detailed protocols, practical advice on troubleshooting, and suggestions for future development. In addition, they illustrate how to construct an activation domain hybrid library, how to identify mutations that disrupt an interaction, and how to use the system in mammalian cells. Chapter topics include characterizing hormone/receptor complexes; identifying peptide ligands; and analyzing interactions mediated by protein modifications. Equally valuable two-hybrid techniques and variations can also be found in *Yeast hybrid technologies* (Zhu, L., and Hannon, G. J., Eds., Biotechniques Press, Westborough, Mass., USA, 2000). A third book, *Two-Hybrid Systems: Methods and Protocols* (*Methods in Molecular Biology Vol. 177*), Ed. Paul MacDonald, Humana Press, 2001, provides some recent updates to the field of yeast two-hybrid assay.

Other version of yeast two-hybrid systems are also described. For example, the reverse yeast two-hybrid system is described in U.S. Pat. Nos. 5,955,280 and 5,965,368, the contents of which are incorporated herein in their entirety. These patents disclosed methods for identifying molecular interactions (e.g., protein/protein, protein/DNA, protein/RNA, or RNA/RNA interactions), all of which employ selection and counter-selection and at least two hybrid molecules. Similar to the conventional yeast two-hybrid system, reverse two-hybrid systems also involve molecules which interact to reconstitute a transcription factor and direct expression of a reporter gene, the expression of which is then assayed. Also disclosed by these patents are genetic constructs which are useful in practicing the methods of the invention.

Licitra and Liu (WO 97/41255, and U.S. Pat. No. 5,928, 868) also described a "three hybrid screen assay" in which the basic yeast two-hybrid assay system is implemented. The significant difference is: instead of depending on the interaction between a so-called "bait" and a so-called "prey" protein, the transcription of the reporter gene is conditioned on the proximity of the two proteins, each of which can bind specifically to one of the two moieties of a small hybrid ligand. The small hybrid ligand constitute the "third" component of the hybrid assay system. In that system, one known moiety of the hybrid ligand will bind to the "bait" protein, while the interaction between the other moiety and the "prey" protein can be exploited to screen for either a protein that can bind a known moiety, or a small moiety (pharmaceutical compound or drug) that can bind a known protein target.

Bartel and Fields summarize many different approaches/variations of the available two-hybrid systems in The yeast-two-hybrid system (Bartel, P. L., and Fields, S., Eds., Oxford University Press, New York, N.Y., USA, 1997). Equally valuable two-hybrid techniques and variations can also be found in Yeast hybrid technologies (Zhu, L., and Hannon, G. J., Eds., Biotechniques Press, Westborough, Mass., USA, 2000). Further systems include WO 9602561, a two hybrid system using conformationally constrained proteins as one of the hybrids; EP 0646644, a periplasmic membrane bound interaction system; WO 98/25947, a prokaryotic two-hybrid system using *E. coli* and other cells; and WO 98/07845, an interaction trap system or "ITS" which is derived using recombinantly engineered prokaryotic cells. WO 98/34120 describes a strategy for designing and implementing protein-fragment complementation assays (PCAs) to detect biomolecular interactions in vivo and in vitro—the DHFR protein interaction screening system. The design, implementation and broad applications of this strategy are illustrated with a large number of enzymes with particular detail provided for the example of murine dihydrofolate reductase (DHFR). Fusion peptides consisting of N and C-terminal fragments of murine DHFR fused to GCN4 leucine zipper sequences were coexpressed in *Escherichia coli* grown in minimal medium, where the endogenous DHFR activity was inhibited with trimethoprim. Coexpression of the complementary fusion products restored colony formation. Survival only occurred when both DHFR fragments were present and contained leucine-zipper forming sequences, demonstrating that reconstitution of enzyme activity requires assistance of leucine zipper formation. DHFR fragment-interface point mutants of increasing severity (Ile to Val, Ala and Gly) resulted in a sequential increase in *E. coli* doubling times illustrating the successful DHFR fragment reassembly rather that non-specific interactions between fragments. This assay could be used to study equilibrium and kinetic aspects of molecular interactions including protein-protein, protein-DNA, protein-RNA, protein-carbohydrate and protein-small molecule interactions, for screening cDNA libraries for binding of a target protein with unknown proteins or libraries of small organic molecules for biological activity. The selection and design criteria applied here is developed for numerous examples of clonal selection, colorometric, fluorometric and other assays based on enzymes whose products can be measured. The development of such assay systems is shown to be simple, and provides for a diverse set of protein fragment complementation applications. WO 98/39483 shows methods for identifying nucleic acid sequences that affect a cellular phenotype. The method uses a reporter gene whose level of expression correlates with the phenotype in conjunction with a method or device for measuring the level of reporter expression. WO 98/44350 discloses an enzyme complementation assay in which methods and compositions for detecting molecular interactions, particularly protein-protein interactions, are provided. The invention allows detection of such interactions in living cells or in vitro. Detection of molecular interactions in living cells is not limited to the nuclear compartment, but can be accomplished in the cytoplasm, cell surface, organelles, or between these entities. In one embodiment, the method utilizes novel compositions comprising fusion proteins between the molecules of interest and two or more inactive, weakly-complementing β-galactosidase mutants. Association between the molecules of interest brings the complementing β-galactosidase mutants into proximity so that complementation occurs and active β-galactosidase is produced. The active β-galactosidase may be detected by methods well-known in the art.

A further similar assay was disclosed in WO 99/28746 and related application WO01/73108; this assay was designed to perform specifically in bacterial expression systems, and it relies on the activation, rather than functional complementation, of an enzymatic activity by the spatial proximity of two fragments induced by an interaction of a molecule of interest with a test substance each fused or bound to one of the fragments. Van Ostade et al., J. Interf. Cytok. Res. (2000), 20, 79–87, WO0/06722 and WO 01/90188 collectively suggest a bioassay for ligands that signal through receptor clustering, called MAPPIT. Specifically, the invention relates to a recombinant receptor, comprising an extracellular ligand-binding domain and a cytoplasmic domain that comprises a heterologous bait polypeptide, which receptor is activated by binding of a ligand to said ligand binding domain and by binding of a prey polypeptide to said heterologous bait peptide. The invention also relates to a method to detect compound-compound binding using said recombinant receptor. WO 94/18317, WO 96/13613, WO 99/41258 (Schreiber, methods to induce a biological event by compound induced dimerization), and Ghosh et al., J. Am. Chem. Soc., 2000, 122: 5658–9 (reconstitution of fluorescence from a split green fluorescent protein).

Systems for studying protein-protein interactions in mammalian cells have also be described. For example, Fearon et al. (Karyoplasmic interaction selection strategy: A general strategy to detect protein-protein interactions in mammalian cells, Proc. Natl. Acad. Sci. USA 89: 7958–7962, 1992) describe a strategy and reagents for study of protein-protein interactions in mammalian cells, termed the karyoplasmic interaction selection strategy (KISS). With this strategy, specific protein-protein interactions are identified by reconstitution of the functional activity of the yeast transcriptional activator GAL4 and the resultant transcription of a GAL4-regulated reporter gene. Reconstitution of GAL4 function results from specific interaction between two fusion proteins: one contains the DNA-binding domain of GAL4; the other contains a transcriptional activation domain. Transcription of the reporter gene occurs if the two fusion proteins can form a complex that reconstitutes the DNA-binding and transcriptional activation functions of GAL4. Using the KISS system, Fearon et al. demonstrate specific interactions for sequences from three different pairs of proteins that complex in the cytoplasm. In addition, they demonstrate that reporter genes encoding cell surface or drug-resistance markers can be specifically activated as a result of protein-protein interactions. With these selectable markers, the KISS system can be used to screen specialized cDNA libraries to identify novel protein interactions.

In an extension of the work of Michnick et al. (WO 98/34120) and Rossi et al. (WO 98/44350), Wehrman et al., Proc. Natl. Acad. Sci. U.S.A. (2002), 99:3469–3474 recently described an enzyme complementation assay employing α-197 and ω-198 fragments of a class A β-lactamase. The β-lactamases are small, monomeric enzymes that can be expressed both in prokaryotes and eukaryotes, including mammalian cells. Particularly in the latter, where no constitutive expression of β-lactamases is present, this resulted in a highly sensitive system with low background. A similar system was also recently described in WO 01/94617 and in Galarneau et al., Nat. Biotech. (2002), 20:619–622. Surprisingly, these systems are equally well suited to be used in a three hybrid mode using the hybrid ligands and methods of the present invention. Thereby, a method to determine whether a polypeptide P2 and a small molecule R2 are able to bind each other is created.

Such an embodiment will preferably comprise the use of eukaryotic cells, more preferably mammalian cells, although in certain cases bacterial cells, fungal cells, plant cells or insect cells may be preferred and are not excluded. In order to obtain good signal-to-noise ratios, the host cell type of choice should not contain constitutively expressed β-lactamases. The β-lactamase fragments may be taken from a class A β-lactamase, but may also be taken from another class, and the fragments may comprise amino acid substitutions, additions or deletions compared to the wild type protein. For example, Wehrman et al., Proc. Natl. Acad. Sci. U.S.A. (2002), 99:3469–3474 have shown that the addition of a Asn-Gly-Arg tripeptide to the carboxy terminal end of the α-197 fragment produced a profound enhancement of the activity of the reconstituted enzyme.

For this assay, the protein P2 for which a small molecule interactor is sought, or a library of proteins where an interacting partner is sought for a small molecule ligand R2, is cloned into an expression vector in frame with one of the β-lactamase fragments, the polypeptide known to interact with R1, e.g. DHFR where R1 is methotrexate, is cloned into an expression vector in frame with the second of the β-lactamase fragments. Any type of expression vector may in principle be used, such as, for example, a plasmid, cosmid, phage vector or artificial chromosome, and the choice will depend on the host cell type to be employed. For example, for expression in mammalian cells, a retroviral vector may be applied generating stably transfected cells; in other instances, it may be advantageous to transfect only transiently. The vectors preferably further carry a selectable marker, for example an antibiotic resistance or auxotrophic marker, which are preferably different for the two vectors encoding the two different β-lactamase fragments. After construction, the vectors are introduced into the host cells by a method to be chosen depending on the host cell type, such as electroporation, lipofection, rendering cells chemically competent by heat shock or treatment with bivalent cations, packaging of DNA or RNA into viral or phage particles and subsequent transduction of host cells or with ballistic methods ("gene gun").

After introduction of the vectors encoding the β-lactamase fragments into host cells, the host cells are preferably grown under conditions conducive to growth only for cells containing both selectable markers encoded by the two β-lactamase fragment encoding vectors. For example, without limitation, if one of the vectors encodes a hygromycin resistance, the other a HIS3 marker, then the host cells will be cultured in a medium containing hygromycin but lacking histidine.

Ultimately, the host cells, or their progeny, are treated with the hybrid ligand, or hybrid ligands, and the activity of the β-lactamase is assayed in the cells in the presence of the hybrid ligand(s). This step may be carried out on whole cells, but it may also prove advantageous to permeabilize or lyse the cells before addition of the hybrid ligand(s) and/or the β-lactamase substrate. The choice of the β-lactamase substrate will in part depend on the host cell system, and the desired method of detection. Numerous suitable substrates are known to the skilled person, such as nitrocefin (detection of absorbance of visible light) or CCF2/AM (detection of fluorescence). The β-lactam antibiotics could be used for a growth inhibition assay when host cells are bacteria.

A skilled artisan shall be able to identify the suitable two-hybrid system components for use with the instant invention without undue experimentation. These will include, but are not limited to expression vectors for reporter systems and their assay/detection methods, expression vectors for expression of fusion proteins comprising the two moieties collectively constituting the reporter system and P1/P2, respectively. In certain embodiments, P2 is from a polypeptide library or libraries, so the vector chosen for the expression of the P2 fusion shall be appropriate for library construction. A skilled artisan shall be able to utilize any of the technologies/methods described above, or combination thereof, or modification thereof, to practice the instant invention. The contents of all these references are incorporated by reference herein.

4.3 Reporter Genes

In a reporter system based on the transcriptional activation of a reporter gene, one has to choose a reporter gene appropriate for the host cell type and assay format envisaged. The host cell of choice needs to provide the appropriate transcriptional machinery, the choice of reporter gene will depend on the method chosen to detect and potentially quantify the transcription of the reporter gene, for example, by Western Blot, calorimetric or fluorimetric methods or a growth inhibition assay on selective or counterselective media, or a cell surface marker.

A wide range of reporter genes suitable for use in the methods of the present invention will be known to the skilled artisan, and he will be readily able to chose the appropriate reporter gene for a given assay format. Such reporter gene may be a positive selectable marker gene which can be selected for under appropriate conditions. In principle, any non-redundant gene in a synthetic pathway that is essential to the survival of the cell can be used for the construction of an auxotrophic positive selectable marker, but frequently used such makers include, without limitation, HIS3, LYS2, LEU2, TRP2, ADE2. Usually, a cell line is constructed that is deficient in the marker gene, and that can only grow on media supplemented with the corresponding metabolic product, i.e. histidine, lysine, leucine, tryptophane or adenine. When used for selection, a desirable phenotype, i.e. expression of a desired recombinant gene, is linked to the expression of the gene the cell is deficient in. Other positive selectable markers include antibiotic resistance markers, e.g. Hygromycin resistance (HygR), neomycin resistance (neoR), puromycin resistance (PACR) or Blasticidin S resistance (BlaSR), or any other antibiotic resistance marker. Here, expression of a desired recombinant gene is linked to the expression of the antibiotic resistance marker by transforming cells with gene constructs comprising both the desired recombinant gene and a recombinant form of the antibiotic resistance marker gene. Selection is then carried out on media containing the antibiotic, e.g. Hygromycin, neomycin, puromycin or Blasticidin S.

In addition, the reporter gene may encode a detectable protein that, upon transcriptional activation of said reporter gene, allows host cells to be visually differentiated from host cells in which said reporter gene has not been activated. Such a detectable protein is preferably encoded by at least one of the genes lacZ, gfp, yfp, bfp, cat, luxAB, HPRT or a cell surface marker gene. Other similar genes exist and the person skilled in the art will readily identify other such genes that can be employed according to this embodiment.

WO 98/25947 describes a prokaryotic two-hybrid assay system, which also provides details about bacterial reporter genes that can be used with the instant invention. The contents of WO 98/25947 are incorporated by reference herein. Selectable markers for use in bacterial cells include antibiotic resistance markers, e.g. bla (beta-lactamase resistance gene), cam (chloramphenicol acetyl transferase gene) or kan (kanamycin phosphoryl transferase gene), luminescence markers such as gfp, color inducing markers, for example lacZ, auxotrophic markers (any amino acid biosynthesis gene) and heavy metal resistance markers. Further selectable markers may be found in: *Escherichia coli and Salmonella: Cellular and molecular biology, Second edition*, F. C. Neidhardt, et al. (Edrs.), 1996. ASM Press, Washington, D.C., USA Furthermore, negative selectable reporter genes which can be used in a cell, and which can be selected against under appropriate conditions, may be employed. In preferred applications, the reporter is a selectable marker which is capable of both positive and negative selection. For example, the reporter gene may be chosen from the list of URA3, HIS3, LYS2, HygTk, Tkneo, TKBSD, PACTK, HygCoda, Codaneo, CodaBSD, PACCoda, Tk, codA, and GPT2. The reporter moiety may also be TRP1, CYH2, CANI, HPRT.

A preferred example of a negative selectable marker gene for use in yeast is the URA3 gene which can be both selected for (positive selection) by growing ura3 auxotrophic yeast strains in the absence of uracil, and selected against (negatively selection) by growing cells on media containing 5-fluoroorotic acid (5-FOA) (Boeke, et al., 1987, Methods Enzymol 154: 164–75). The concentration of 5-FOA can be optimized by titration so as to maximally select for cells in which the URA3 reporter is inactivated by proteolytic degradation to some preferred extent. For example, relatively high concentrations of 5-FOA can be used which allow only cells expressing very low steady-state levels of URA3 reporter to survive. In contrast, lower concentrations of 5-FOA can be used to select for binding partners with relatively weak affinities for one another. In addition, proline can be used in the media as a nitrogen source to make the cells hypersensitive to the toxic affects of the 5-FOA (Mc-Cusker & Davis (1991) Yeast 7: 607–8). Accordingly, proline concentrations, as well as 5-FOA concentrations can be titrated so as to obtain an optimal selection for URA3 reporter deficient cells. Therefore the use of URA3 as a negative selectable marker allows a broad range of selective stringencies which can be adapted to minimize false positive background noise and/or to optimize selection for high affinity binding interactions. Other negative selectable markers which can be adapted to the methods of the invention are included within the scope of the invention.

Another example of a negative selectable marker gene for use in yeast is the TRP1 gene which can be both selected for (positive selection) by growing trp1 auxotrophic yeast strains in the absence of tryptophan, and selected against (negatively selection) by growing cells on media containing 5-fluoroanthranilic acid (5-FAA) (Toyn et al., 2000, Yeast, 16: 553–560).

Two other negative selectable marker genes for the use in yeast are CYH2 and CAN1 both of which can be selected against (negative selection) by growing cells on media containing cycloheximide or canavanine (*The Yeast Two-Hybrid System* (*Advances in Molecular Biology*), Ed. Paul L. Bartel and Stanley Fields, Oxford University Press, 1997).

Counter-selectable markers for use in bacteria include sacB (*B. subtilis* gene encoding levansucrase that converts sucrose to levans, which is harmful to the bacteria), rpsL (strA) (Encodes the ribosomal subunit protein (S12) target of streptomycin), tetA$^R$ (Confers resistance to tetracycline but sensitivity to lipophilic compounds, e.g. fusaric and quinalic acids), phe$^S$ (Encodes the subunits of Phe-tRNA synthetase, which renders bacteria sensitive to p-chlorophenylalanine, a phenylalanine analog), thyA Encodes thymidilate synthetase, which confers sensitivity to trimethoprim and related compounds, lacY (Encodes lactose permease, which renders bacteria sensitive to t-o-nitrophenyl—D-galactopyranoside), gata-1 (Encodes a zinc finger DNA-binding protein which inhibits the initiation of bacterial replication), ccdB (Encodes a cell-killing protein which is a potent poison of bacterial gyrase). Further counter-selectable markers may be found in: *Escherichia coli and Salmonella: Cellular and molecular biology*, Second edition, F. C. Neidhardt, et al. (Edrs.), 1996. ASM Press, Washington, D.C., USA Numerous selectable markers which operate in mammalian cells are known in the art and can be adapted to the method of the invention so as to allow direct negative selection of interacting proteins in mammalian cells. Examples of mammalian negative selectable markers include Thymidine kinase (Tk) (Wigler et al., 1977, Cell 11: 223–32; Borrelli et al., 1988, Proc. Natl. Acad. Sci. USA 85: 7572–76) of the Herpes Simplex virus, the human gene for hypoxanthine phosphoriboxyl transferase (HPRT) (Lester et al., 1980, Somatic Cell Genet. 6: 241–59; Albertini et al., 1985, Nature 316: 369–71) and Cytidine deaminase (codA) from *E. coli* (Mullen et al., 1992, Proc. Natl. Acad. Sci. USA 89: 33–37; Wei and Huber, 1996, J. Biol. Chem. 271: 3812–16). For example: the Tk gene can be selected against using Gancyclovir (GANC) (e.g. using a 11M concentration) and codA gene can be selected against using 5-Fluor Cytidin (5-FIC) (e.g. using a 0.1–1.0 mg/ml concentration). In addition, certain chimeric selectable markers have been reported (Karreman, 1998, Gene 218: 57–61) in which a functional mammalian negative selectable marker is fused to a functional mammalian positive selectable marker such as Hygromycin resistance ($Hyg^R$, neomycin resistance ($neo^R$), puromycin resistance ($PAC^R$) or Blasticidin S resistance ($BlaS^R$). These produce various Tk-based positive/negative selectable markers for mammalian cells such as HygTk, Tkneo, TKBSD, and PACTk, as well as various codA-based positive/negative selectable markers for mammalian cells such as HygCoda, Codaneo, CodaBSD, and PACCoda. Tk-neo reporters which incorporate luciferase, green fluorescent protein and/or beta-galactosidase have also been recently reported (Strathdee et al., 2000, BioTechniques 28: 210–14). These vectors have the advantage of allowing ready screening of the "positive" marker/reporter by fluorescent and/or immunofluorescent microscopy. The use of such positive/negative selectable markers affords the advantages mentioned above for URA3 as a reporter in yeast, inasmuch as they allow mammalian cells to be assessed by both positive and negative selection methods for the expression and relative steady-state level of the reporter fusion. For example, Rojo-Niersbach et al reported the use of GPT2 (Guanine Phosphoryl Transferase 2) in mammalian cells as a basis for the selection of protein interactions (Biochem. J. 348: 585–590, 2000).

The above listing of genes suitable for use as reporter genes in the methods of the present invention is not meant to be exhaustive nor limiting. The skilled artisan may know other or become aware of newly discovered or developed systems suitable for use as reporter genes in the methods of the present invention. The scope of the present invention is meant to include their use.

4.4 The Halo Growth Assay

A halo growth assay may be used in several embodiments of the present invention. Generally, this type of assay provides for the qualitative determination of the effect of different concentrations of a compound on cellular growth. In essence, a halo growth assay comprises the distribution of a dilute solution of the cells under investigation on an agar plate, followed by the placement of a drop of a solution containing the compound under investigation on a predetermined spot on the agar (for example the middle of a petri dish). Subsequently, the agar plate is cultured under conditions conducive to cellular growth, and growth is assessed a predetermined time later. During this time, the compound will diffuse through the agar, forming a concentration gradient with its highest concentration at the point of application, radially declining outwards from this point. If the agar is prepared to sustain cellular growth, and the compound has no effect, a uniform cell carpet should be found. Conversely, if the agar is prepared to stifle cellular growth, for example agar lacking a component essential for cellular growth, and the compound has no effect, no cell growth should appear. If the compound has a toxic effect on the cells, no change should be seen with growth-stifling agar, but on growth-sustaining agar, a circular area (Halo) without growth should appear on growth-sustaining agar around the point of application, growth gradually declining inwards to this point. Where a compound has a beneficial effect on growth, such as complementing the lack of an essential component in a growth stifling agar, a circular Halo of growth should appear around the point of application, growth gradually declining outwards from this point. Such halo assays will be familiar to a skilled artisan. However, alternative methods fulfilling the same needs may be used equivalently.

In certain embodiments of the invention, it may be advantageous to conduct large numbers of such assays for a single experiment, preferably greater than about 10, 100, 1 000 or more than 10 000 assays. Such numbers of assays may be assisted through the use of petri or agar dishes of around 70, 300, 480 or greater than 500 $cm^2$ surface area on to which the cells and hybrid ligand/compounds of the invention are placed. Indeed, to maximise throughput and minimise the cost of performing a single such assay, it is preferable to reduce the scale of the assay. Minimised assays may for example, be conducted using microtitre plate of preferably 96, 384, 1536 or more than 1536 wells. Alternatively, such assays may be conducted on solid growth agar where the cells and hybrid ligand/compounds are placed at high numbers or densities. For example, around 10, 100, 1 000 or more than 10 000 separate assays may be conducted on one or more petri or agar dishes, wherein one particular assay is separated from another assay by a distance of about 1, 3, 10 or more than 30 mm. In certain embodiments, it is advantageous that the assays are placed in a regular pattern so that subsequent analysis of growth can be more readily conducted by eye or machine vision. Such numbers, densities or patterns of assays may be formed by a number of methods, as will be apparent to a person skilled in the art. For example, 8, 12 or 16-way multi channel pipettes or 96384-well replicators (Genetix) may be used. Alternatively, if high throughout or accuracy is desired, an automated device may be employed. Many suitable automated devices will be known to the skilled artisan and included with out limitation automated pipetting units with 1, 2, 4, 8, 12, 96 or more than 96 pipetteing tips such as sold by several manufacturers including the MultiProbe II or MultiTrack (Packard), Hamillton, Quadra 96 or 384 (Tomtec), CyBio etc. Other automated devices that accurately transfer large numbers of small amounts of biologically active materials my also be employed. For example, gridding robots such as the Qbot (Genetix, UK), BioGrid (BioRobotics, UK) or those described in Maier et al 1997 (in Automation for genome characterisation. Ed T J Beuelsdijk. J Wiley New York) may be employed.

4.5 The Fluorescence Detection Growth Assay

A growth assay which can be performed in a microtiter plate format is advantageous. For example, MTPs can be easily handled in large numbers, use relatively little material per assay and hence large numbers of assays may be conducted using standard laboratory automation. We developed such an assay based on the principle that cells growing in suspension consume oxygen from the surrounding medium. However, using this principle is not meant as limiting the scope of the invention, as the skilled person will be able to appreciate other methods of assessing the growth of cells in microtiter plates.

With an integrated oxygen sensor built into the bottom of the plate, the OxoPlate (PreSens Precision Sensing GmbH, Regensburg, Germany) is able to measure the oxygen concentration in the solution in each well of a 96 well plate in near-real time (response time <30 s). The measurement is based on the fluorescence emission of two dyes in a sensor on the bottom of each well, one of which can be quenched be by oxygen, while the fluorescence of the second dye is unaffected by oxygen, and is used as an internal reference. Both dyes have equal excitation (540 nm), but different Stokes shifts and emission wavelengths (quenchable dye: 590 nm, unquenchable dye: 650 nm). The ratio of the emissions at 650 nm and 590 nm ($I_{quenchable}/I_{unquenchable}$) is taken as a measure of oxygen concentration. When the oxygen partial pressure in the solution in the well is reduced, the emission intensity of the dye that can be quenched by oxygen will rise, while the emission intensity of the second dye will remain constant. Using such internal reference makes this assay independent of many potential error sources, such as instability of the optical system. It also obviates the need for separate calibration wells, and hence all 96 wells of a 96 well plate can be used for samples. This method uses a plate reader which can read from the bottom of a microtiter plate, and can measure in dual kinetic mode, i.e. taking several measurement at two different wavelengths. Suitable readers will be well known to a person skilled in the art and include without limitation the Perkin Elmer Wallac Victor2 V 1420 multilabel HTS counter (Perkin Elmer, Wellesley, Mass., USA).

When suitable cells are seeded into the wells of an OxoPlate in a medium conducive to growth, logarithmic cell growth will occur, oxygen will be used up and the oxygen partial pressure may become limiting. As the level of oxygen diminishes further, cell growth could become hampered, until the oxygen partial pressure reaches near-zero at which point cell growth may cease. This growth pattern is reflected in a sigmoidal curve of the fluorescence emission intensity ratio of the two dyes. Conversely, if the medium in a well stifles growth, no oxygen will be used, and the measurements of the fluorescence emission intensity ratio yield a constant line near the value for medium without cells.

5. Hybrid Small Molecules

Yeast three hybrid assays using hybrid ligand compounds different from those of the present invention are known in the art (See, for example: Crabtree et al. WO 9418317; Schreiber et al. WO 9613613; Holt et al. WO 9606097; Licitra and Liu WO 9741255; Bergmann et al., J. Steroid Biochem. Molec. Biol. 1994, 49:139–52; Lin et al., J. Am. Chem. Soc. 2000, 122:4247–8). However, the hybrid ligand compounds according to the present invention possess advantageous properties setting them distinctly apart from those described in the prior art. For example, Lin et al. used a metadibenzothioester as linker between R1 and R2, conferring rigidity, lipophilicity and low water solubility to their Mtx-mdbt-Dex hybrid ligand compound. In order to pass cell membranes, a certain lipophilicity is desirable. However, in order to get to the membrane, such compound first has to cross an aequeous compartment by diffusion. If its water solubility is too low, too little compound can reach the membrane and exert its effect inside the cell.

5.1 Linker Sequences

In certain embodiments, any chemical linker Y (including synthetic polypeptides, see below) can be used to link R1 to R2, provided that the presence of the linker sequence will not significantly interfere with the reporter system when P1 binds to R1 and P2 binds to R2. In addition, the presence of the linker should not overly adversely affect the affinities between P1 and R1 or between P2 and R2.

As such, in order to confirm the suitability of a given hybrid ligand as a dimerizing compound of general structure R1-Y—R2 for the uses proposed herein, it may be helpful to characterize the binding properties of such hybrid ligand to its binding partners P1 and P2, in as far as these are known, and to possibly compare these binding characteristics with those of the unlinked compounds R1 and R2, respectively. Preferably, the hybrid ligand should exhibit binding properties similar to the binding properties of the unlinked compounds. However, the molecular weight increase brought about by the linking, as well as steric and electronic effects caused by the attachment of the linker to a functional group of the unlinked compounds may alter the binding characteristics. Therefore, while not being essential, it is preferable to perform such characterization on a newly synthesized hybrid ligand. This, however, should not be interpreted as limiting the scope of the invention.

The affinity of hybrid ligands to their corresponding binding partners may be determined, for example, using a BIACORE™ assay system (Biacore AB, Uppsala, SE). Other systems yielding a qualitatively similar result, for example, those developed by Affinity Sensors (Cambridge, UK), will be readily apparent to those skilled in the art. Furthermore, other interaction methodologies that measure the binding affinities between a hybrid ligand and its binding proteins may be employed.

Linker moieties (Y), need not contain essential elements for binding to the P1 and/or P2 proteins, and for certain embodiments of the present invention may be selected from a very broad range of structural types. Preferred moieties include $C_2$–$C_{20}$ alkyl, aryl, or dialkylaryl structures where alkyl and25 aryl are defined as above. Linker moieties may be conveniently joined to monomers R1 and R2 through functional groups such as ethers, amides, ureas, carbamates, and esters; or through alkyl-alkyl, alkyl-aryl, or aryl-aryl carbon-carbon bonds. Furthermore, linker moieties may be optimized (e.g., by modification of chain length and/or substituents) to enhance pharmacokinetic properties of the multimerizing agent. Holt et al. (WO 9606097) and Kathryn et al. (J. Steroid Biochem. Molec. Biol., 49: 139–152) describe a number of linker moieties that can be used to construct the hybrid ligands of the instant invention (R1-Y—R2), the contents of these references are incorporated by reference herein.

In other embodiments, linker sequences are specifically designed so that increased solubility and enhanced permeability results. This is important since the components of the hybrid molecule, R1 and R2, are organic molecules with potentially low water solubility. By linking two small molecules, the molecular weight is obviously increased, potentially further decreasing the water solubility and diffusion coefficient. By designing a linker that increases solubility and enhances permeability of the hybrid, the available R1-Y—R2 hybrid in solution and ultimately inside the cell is effectively increased, so that significantly higher sensitivity of the whole system can be achieved. In one embodiment, from 2 to 25 repeats of polyethylenglycol (PEG) groups of the general formula $CH_2XCH_2$ can be used, wherein X represents O, S, SO, or $SO_2$. The number of repeats is preferably in the range of 3–25, 5–25, 9–25, 2–15, 3–15, 5–15 or 9–15, and more specifically is preferably 25, 20, 15, 10, 9, 8, 7, 6, 5, 4, or 2. In a most preferred embodiment, three polyethylenglycol groups are used as linker which offer significantly better solubility and membrane permeability (see example 7 and GPC 285937 below). In other cases where an even more strongly increased solubility and/or membrane permeability is desired, five repeats may be used. Furthermore, it should be understood that modifications of the side-chains of the linker can be easily achieved without adversely affecting the solubility, membrane permeability, and/or overall biological activity of the compound, and therefore, such derivative linker sequence units are also within the scope of the invention.

Below are presented several examples for hybrid molecules as envisaged by the present invention. $(CH_2XCH_2)_n$-groups, wherein X represents O, n=3 or 5, were employed for these examples, without limitation. Increasing the length of the linker sequence appears to increase the effectiveness of the compound in at least some three-hybrid assays, which is most likely due to the increased solubility or membrane permeability or flexibility of the molecule, or a combination thereof. For example, the n-octanol-water partition coefficient (clogP) of the compound Mtx-mdbt-Dex is predicted by structure based calculations using the program Kowwin (Syracuse Research Corporation) to be 3.62, and it's water solubility to lie in the range of 0.00035 mg/l, while clogP for GPC 285937, identical with Mtx-mdbt-Dex except for the replaced linker, is estimated by the same method to be −1.71, and its solubility as 0.13 mg/l, corresponding to a factor of approximately 300 in increased solubility.

Structure of Mtx-mdbt-Dex (R1=Methothrexate, R2=Dexamethasone, Y=metadibenzothioester)

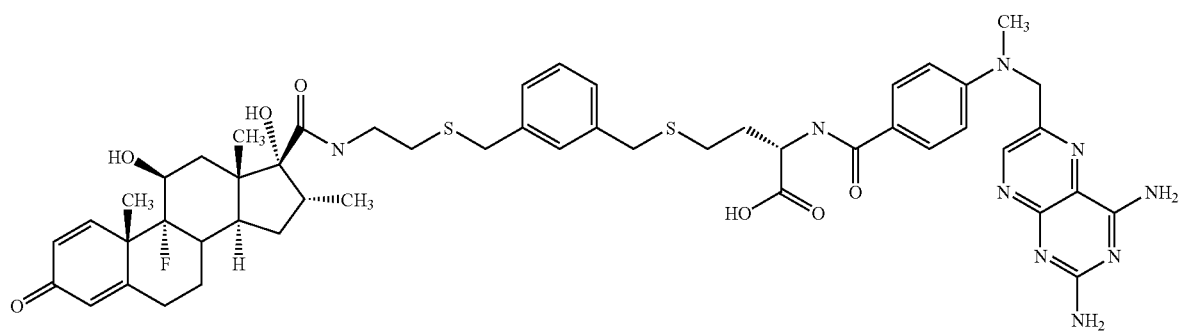

Structure of GPC 285937 (R1=Methothrexate, R2=Dexamethasone, Y=$(CH_2—CH_2—O)_3$)

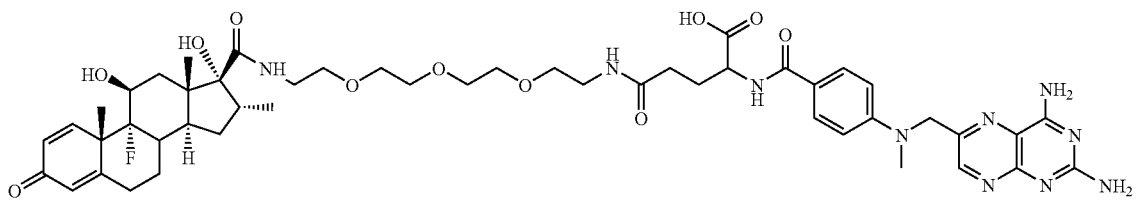

4-(N-{2-[2-(2-{2-[((2S, 11S,15S,17S, 1R, 13R, 14R)-1-fluoro-14,17-dihydroxy-2,13,15-trimethyl-5-oxotetracyclo[8.7.0.0<2,7>0.0<11,15>]heptadeca-3,6-dien-14-yl) carbonylamino]ethoxy}ethoxy)ethoxy] ethyl}carbamoyl)-2-[(4-{[(2,4-diaminopteridin-6-yl) methyl]methylamino}phenyl)carbonylamino]butanoic acid Structure of GPC 285985 (R1=Methothrexate, Y=(CH$_2$—CH$_2$—O)$_3$, R2 is an active CDK2-inhibitor)

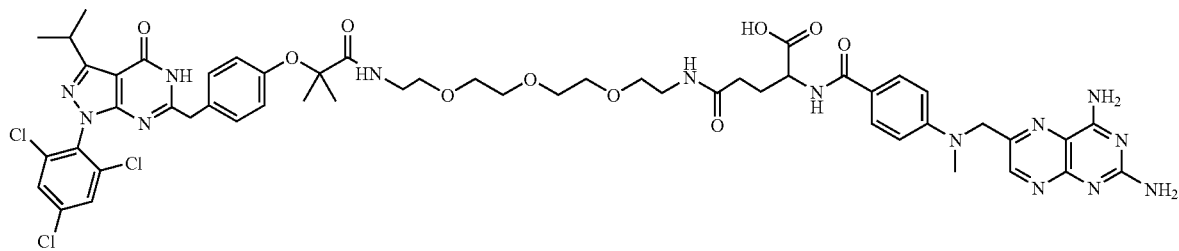

2-[(4-{[(2,4-diaminopteridin-6-yl)methyl]methylamino [phenyl)carbonylamion[no]-4-(N-{2-[2-(2-{2-[2-methyl-2-(4-{[3-(methylethyl)-4-oxo-1-(2,4,6-trichlorophenyl) (5-hydropyrazolo[5,4-d]pyrimidin-6-yl)] methyl}phenoxy)propanoylamino]ethoxy}ethoxy) ethoxy]ethyl}carbamoyl)butanoic acid Structure of GPC 285993 (R1=Methothrexate, Y=(CH$_2$—CH$_2$—O)$_3$, R2 is inactive as CDK2-inhibitor)

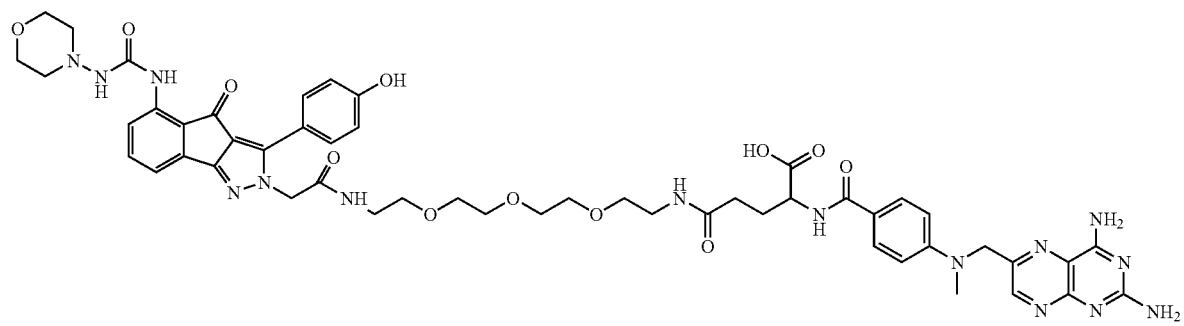

2-[(4-{[(2,4-diaminopteridin-6-yl)methyl] methylamino}phenyl)carbonylamino]-4-{N-[2-(2-{2-[2-(2-{3-(4-hydroxyphenyl)-5-[(morpholin-4-ylamino)carbonylamino]-4-oxoindeno[3,2-c]pyrazol-2-yl}acetylamino)ethoxy]ethoxy}ethoxy)ethyl] carbamoyl}butanoic acid Structure of GPC 286004 (R1=Methothrexate, Y=(CH$_2$—CH$_2$—O)$_3$, R2 is an active CDK2-inhibitor)

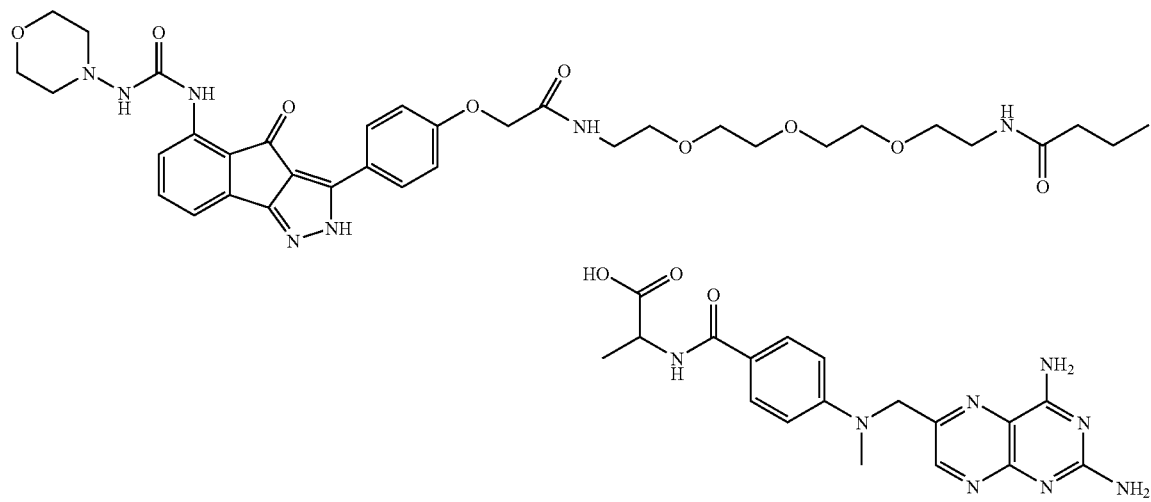

2-[(4-{[(2,4-diaminopteridin-6-yl)methyl]methylamino}phenyl)carbonylamino]-4-(N-{2-[2-(2-{2-[2-(4-{5-[(N-morpholin-4-ylcarbamoyl)amino]-4-oxoindeno[3,2-c]pyrazol-3-yl}phenoxy)acetylamino]ethoxy}ethoxy)ethoxy]ethyl}carbamoyl)butanoic acid Structure of GPC 286026 (R1=Methothrexate, Y=(CH$_2$—CH$_2$—O)$_5$, R2 is an active CDK2-inhibitor)

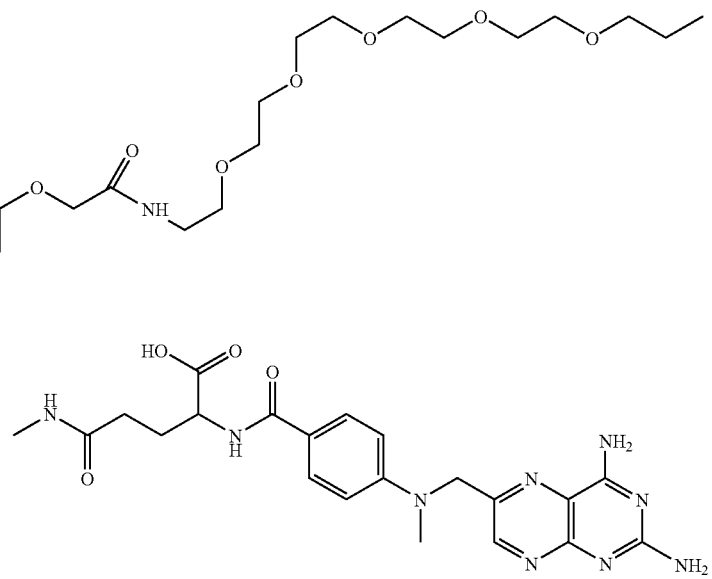

2-[(4-{[(2,4-diaminoptedin-6-yl)methyl]methylamino]phenyl)carbonylamino]-4-{N-[2-(2-{2-[2-(2-{2-[2-(4-{5-[(N-morpholin-4-ylcarbamoyl)amino]-4-oxoindeno[3,2-c]pyrazol-3-yl}phenoxy)acetylamino]ethoxy}ethoxy)ethoxy]ethoxy}ethoxy)ethyl]carbamoyl}butanoic acid In a preferred embodiment, more than one hybrid small molecule is employed for screening, wherein R1 and/or R2 are linked via the same linker sequence but using different reaction groups in such a way so that the relative orientation of R1 and R2 can be adjusted. This is useful in optimization of an effective compound ligand since certain orientations might overcome or at least alleviate potential steric hinderances that serve to weaken the interaction between the ligand and its protein binding partner.

The structures of the hybrid small molecules shown above are by no means to be understood as limiting the scope of the present invention.

5.2. High Affinity Ligands/Ligand Binding Proteins

According to the invention, two pairs of polypeptide/small chemical compound interactions have to be present for the three-hybrid system to activate a reporter system. One pair of interaction is between a known ligand and its known polypeptide binding partner. This essentially serves as an "adaptor" to create a R2::P2 interaction interface, and to provide the necessary second element of the reporter system, RS2. Therefore, the stronger the P1::R1 interaction, the better the overall performance of the system.

There are at least two categories of P1::R1 interactions available for this purpose: covalent and non-covalent interactions. Covalent interactions are almost always stronger. For example, certain enzymes and their suicide inhibitors or suicide substrates can be exploited to constitute such covalent interaction pairs. Suicide inhibitors or suicide substrates bind to their prospective enzymes with high specificity and affinity. Once bound, a chemical reaction occurs, physically linking the inhibitor/substrate to the enzyme, usually at its active site, thereby irreversibly inactivates the enzyme. If such enzyme is used as P1 and its suicide inhibitor/substrate used as R1 in the three-hybrid system, a covalent link between P1-R1 can be established. For example, beta-lactamase may covalently bind suicide inhibitors such as beta-lactam antibiotics. However, there are only limited selections of these enzyme—substrate/inhibitor pairs, particularly when the substrate/inhibitor needs to be connected to another small compound R2 via a linker yet still retains solubility and membrane permeability in vivo.

On the other hand, non-covalent P1::R1 interactions are more versatile. There are many known high affinity ligand-receptor interactions that can be employed in the three-hybrid system. For example, FK506 and FKBP (FK506 Binding Protein), FK506 and Rapamycin, biotin and streptavidin, DHFR and methotroxate (Mtx), glucocorticoid receptor and Dexamethasone (Dex), etc, represent binding pairs with affinities high enough to be potentially suitable as ligand receptor binding pairs. The DHFR-Mtx interaction offers pM affinity, and therefore is much better than FK506-FKBP interaction.

Any of a number of ligand/ligand binding protein pairs known in the art may be utilized. For example, the steroid molecule, dexamethasone, which binds the glucocorticoid receptor with high affinity may be employed. Dexamethasone is modular in nature; it can be covalently linked to another small molecule such as biotin without losing its affinity for the glucocorticoid receptor- The use of steroids such as dexamethasone is advantageous in that these molecules are highly membrane permeable and are small in size. The method of the invention may utilize other steroid molecules as well as small molecules other than steroids as ligand R1. Other ligands such as cyclosporin (M.W. 1200) may also be used where the target or receptor to which the ligand is bound has been identified in the art. As another example, the small molecule FK506 (M.W. 850) which binds an FK binding protein (FKBP), and modified derivatives of FK506 (i.e. "bump" modified compounds) which bind to modified FK binding proteins (i.e. FKBP mutants which compensate for-such "bump" modifications) are also adaptable for use as ligand/ligand-binding proteins of the invention (see e.g. U.S. Pat. No. 6,054,436, the contents of which are incorporated herein by reference).

Table 1 provides a list of ligands and ligand-binding pairs which are known in the art and adaptable to the compositions and methods of the invention. Particularly preferred ligand/ligand-binding protein pairs have strong binding affinities as reflected in low dissociation constants (e.g., methotrexate/DHFR at 52 pM; or dexamethasone/glucocorticoid receptor at 86 nM).

TABLE 1

List of Some High Affinity Ligand/Ligand Binding Proteins

| Ligand | Molecular weight (D) | Ligand Binding Protein | Affinity |
|---|---|---|---|
| Biotin | (244) | Avidin | 80 fM |
| Ni | (59) | 6 X His | 0.8 µM |
| Rapamycin | (914) | FKB12 | 12 µM |
| FK506 | (804) | FKB12 | 12 µM |
| Methotrexate | (454) | DHFR | 52 pM |
| Tetracyclin | (444) | Tet-R | 24 nM |
| Dexamathasone | (392) | Glucocorticoid receptor | 86 nM |
| Glutathione | (307) | Glutathione-S-Transferase | 24 µM |
| Maltose | (342) | Maltose Binding Protein | 40 nM |
| Novobiotin | (612) | GyrB | 123 µM |

In general, virtually any ligand/ligand-binding protein pair with sufficient affinity may be adapted to the compositions and methods of the invention. Particularly preferred embodiments utilize ligand binding proteins which are known to function efficiently intracellularly. For example, steroid receptors occur intracellularly and bind with high affinities to their cognate steroid hormones under intracellular physiological conditions. Examples of such steroid receptors include the human estrogen receptor (e.g. GenBank Accession No. NM_000125), which is found in estrogen-sensitive animal cells, and human glucocorticoid receptor protein (e.g. GenBank Accession No. NM_004491), which is found in cells responsive to glucocorticoid hormones-Other steroids with suitable receptors for use in the invention include testosterone, progesterone, and cortisone.

It should be understood that the above mentioned ligands shall also include those derivatives and equivalents that share close structural relationship to those ligands. To illustrate, Mtx only uses its 2,4-diaminopteridine double-ring structure to bind DHFR. Therefore, 2,4-diaminopteridine shall be considered a derivative of Mtx that is also within the scope of the invention. A "derivative" generally shares the effective moiety with the original compound but may also have other non-essential structural elements for a given activity.

Still other preferred ligands for use in the invention are known in the art and may be adapted to the methods and compositions of the invention by skilled artisan without undue experimentation. For example, other preferred ligands which could be adapted to the invention include fat-soluble vitamins with cognate receptors such as Vitamin D and its various forms such as $D_1$, $D_2$ (9, 10-secoergosta-5, 7, 10 (19), 22-tetraen-3-ol), $D_3$ (9, 10-secocholeta-5, 7, 10(19)-trien-3-ol) and $D_4$ (9, 10-secoergosta-5, 7, 10(19)-trien-3-ol). Vitamin $D_3$ binds with affinity to the human nuclear vitamin D receptor protein (e.g. GenBank Accession No. NM_000376; see also Haussler et al. (1995) Bone 17: 33S-38S) and this ligand/ligand-binding protein pair may be adapted to the invention. Still other ligands with cognate ligand-binding proteins that may be adapted to the invention include thyroid hormone and retinoic acid. DeWolf and Brett ((2000) Pharmacol Rev. 52: 207–36) provides a summary of many useful ligand-binding proteins with cognate ligands including: biotin-binding proteins, lipid-binding protein, periplasmic binding proteins, lectins, serum albumins, immunoglobulins, various inactivated enzymes, insect pheromone binding proteins, odorant-binding proteins, immunosuppressant-binding proteins, phosphate- and sulfate-binding protein.

In addition, steroid, retinoic acid, beta-lactam antibiotic, cannabinoid, nucleic acid, polypeptide, FK506, FK506 derivatives, rapamycin, tetracycline, methotrexate, 2,4-diaminopteridine, novobiocin, maltose, glutathione, biotin, vitamin D, dexamethasone, estrogen, progesterone, cortisone, testosterone, niche, cyelosporin and their natural or synthesized binding partners are all possible for use in the instant invention as a component of the above described high affinity ligand/ligand binding pair. In all those compounds mentioned above, it should be understood that basically equivalent compounds with only minor structural variations can also be used.

On the other hand, a user-specified second ligand need to be linked to the above-described ligand to form a compound ligand. At least the following chemical groups and those basically equivalent compounds with only minor structural variations can be used as such user-specified ligands: a peptide, a nucleic acid, a carbohydrate, a polysaccharide, a lipid, a prostaglandin, an acyl halide, an alcohol, an aldehyde, an alkane, an alkene, an alkyne, an alkyl, an alkyl halide, an alkaloid, an amine, an aromatic hydrocarbon, a sulfonate ester, a carboxylate acid, an aryl halide, an ester, a phenol, an ether, a nitrile, a carboxylic acid anhydride, an amide, a quaternary ammonium salt, an imine, an enamine, an amine oxide, a cyanohydrin, an organocadmium, an aldol, an organometallic, an aromatic hydrocarbon, a nucleoside, a nucleotide. For example, in a recent publication (U.S. Pat. No. 6,326,155), a method is described that aids in selecting a ligand for a given target molecule.

6. Libraries and Screening Methods 6.1 Variegated Peptide Display

One aspect of the invention provides a method to identify polypeptides that bind to a given small molecule/chemical compound. The polypeptides are usually provided in the form of a variegated library, which can contain different number of members, preferably from 2 to 10 members, or 10 to 500 members, 500 to 10,000 members or more than 10,000 members. The library can be a nucleic acid library (mRNA, cDNA, genomic DNA, EST, YAC, p1 clones, BAC/PAC libraries, etc.) which encodes polypeptides. Depending on the specific embodiments of the screens used (for example, split-ubiquitin based hybrid system or transcription based yeast hybrid system), the nucleic acid library is usually constructed in vectors suitable for the chosen embodiment, using art-recognized techniques.

The variegated peptide libraries of the subject method can be generated by any of a number of methods, and, though not limited by, preferably exploit recent trends in the preparation of chemical libraries. The library can be prepared, for example, by either synthetic or biosynthetic approaches. As used herein, "variegated" refers to the fact that a population of peptides is characterized by having a peptide sequence which differ from one member of the library to the next. For example, in a given peptide library of N amino acids in length, the total number of different peptide sequences in the library is given by the product of $(X_1 * X_2 * \ldots X_i)$, where each $X_i$ represents the number of different amino acid residues occurring at position X of the peptide. In a preferred embodiment of the present invention, the peptide display collectively produces a peptide library including at least 96 to $10^7$ different peptides, so that diverse peptides may be simultaneously assayed for the ability to interact with the small molecule/chemical compound.

The polypeptide libraries can be prescreened for interactions with the small molecule/chemical compound, for example using a phage display method. Peptide libraries are systems which simultaneously display, in a form which permits interaction with a target molecule, a highly diverse and numerous collection of peptides. These peptides may be presented in solution (Houghten (1992) Biotechniques 13:412–421), or on beads (Lam (1991) Nature 354:82–84), chips (Fodor (1993) Nature 364:555–556), bacteria (Ladner U.S. Pat. No. 5,223,409), spores (Ladner U.S. Pat. No. 5,223,409), plasmids (Cull et al. (1992) Proc Natl Acad Sci USA 89:1865–1869) or on phage (Scott and Smith (1990) Science 249:386–390; Devlin (1990) Science 249:404–406; Cwirla et al. (1990) Proc. Natl. Acad. Sci. 87:6378–6382; Felici (1991) J. Mol. Biol. 222:301–310; and Ladner U.S. Pat. No. 5,223,409).

In one embodiment, the peptide library is derived to express a combinatorial library of peptides which are not based on any known sequence, nor derived from cDNA. That is, the sequences of the library are largely random. It will be evident that the peptides of the library may range in size from dipeptides to large proteins.

In another embodiment, the peptide library is derived to express a combinatorial library of peptides which are based at least in part on a known polypeptide sequence or a portion thereof (not a cDNA library). That is, the sequences of the library is semi-random, being derived by combinatorial mutagenesis of a known sequence(s). See, for example, Ladner et al. PCT publication WO 9002909; Garrard et al., PCT publication WO 9209690; Marks et al. (1992) J. Biol. Chem. 267:16007–16010; Griffiths et al. (1993) EMBO J. 12:725–734; Clackson et al. (1991) Nature 352:624–628; and Barbas et al. (1992) PNAS 89:4457–4461. Accordingly, polypeptide(s) which are known ligands for a target molecule can be mutagenized by standard techniques to derive a variegated library of polypeptide sequences which can further be screened for binding partners including agonists and/or antagonists.

In still another embodiment, the combinatorial polypeptides are produced from a cDNA library, a genomic DNA library. The source of DNA can be of human, non-human mammalian, fish, amphibium, insect, worm, yeast, plant, or bacteria.

Depending on size, the combinatorial peptides of the library can be generated as is, or can be incorporated into larger fusion proteins, such as library-reporter system fusions. The fusion protein may also provide, for example, stability against degradation or denaturation, as well as a secretion signal if secreted, or the reporter function necessary for screens. In an exemplary embodiment, the polypeptide library is provided as part of thioredoxin fusion proteins (see, for example, U.S. Pat. Nos. 5,270,181 and 5,292,646; and PCT publication WO9402502). The combinatorial peptide can be attached on the terminus of the thioredoxin protein, or, for short peptide libraries, inserted into the so-called active loop. In another preferred embodiment, the fusion protein library can be provided as a fusion to either the Cub or Nux domain of the split ubiquitin sensor proteins (see below). In another preferred embodiment, the fusion protein library can be provided as a fusion to either the DNA binding domain or the transcription activation domain of the transcription based yeast three-hybrid system.

In preferred embodiments, the combinatorial polypeptides are in the range of 3–1000 amino acids in length, more preferably at least 5–500, and even more preferably at least 3–100, 5–50, 10, 13, 15, 20 or 25 amino acid residues in length. Preferably, the polypeptides of the library are of uniform length. It will be understood that the length of the combinatorial peptide does not reflect any extraneous sequences which may be present in order to facilitate expression, e.g., such as signal sequences or invariant portions of a fusion protein.

Regardless of the nature of the peptide libraries, the same peptide libraries can also be provided as nucleic acid libraries encoding such peptide libraries. These nucleic acid libraries can be provided in suitable vectors for expression in various systems, including, but are not limited to mammalian, insect, yeast and bacteria expression systems. A skilled artisan shall be able to determine the appropriate vectors to use for various expression systems.

6.1.1 Biosynthetic Peptide Libraries

The harnessing of biological systems for the generation of peptide diversity is now a well established technique which can be exploited to generate the peptide libraries of the subject method. The source of diversity is the combinatorial chemical synthesis of mixtures of oligonucleotides. Oligonucleotide synthesis is a well-characterized chemistry that allows tight control of the composition of the mixtures created. Degenerate DNA sequences produced are subsequently placed into an appropriate genetic context for expression as peptides.

There are two principal ways in which to prepare the required degenerate mixture. In one method, the DNAs are synthesized a base at a time. When variation is desired at a base position dictated by the genetic code a suitable mixture of nucleotides is reacted with the nascent DNA, rather than the pure nucleotide reagent of conventional polynucleotide synthesis. The second method provides more exact control over the amino acid variation. First, trinucleotide reagents are prepared, each trinucleotide being a codon of one (and only one) of the amino acids to be featured in the peptide library. When a particular variable residue is to be synthesized, a mixture is made of the appropriate trinucleotides and reacted with the nascent DNA. Once the necessary "degenerate" DNA is complete, it must be joined with the DNA sequences necessary to assure the expression of the peptide, as discussed in more detail below, and the complete DNA construct must be introduced into the cell.

Whatever the method may be for generating diversity at the codon level, chemical synthesis of a degenerate gene sequence can be carried out in an automatic DNA synthesizer, and the synthetic genes can then be ligated into an appropriate gene or vector for expression. The purpose of a degenerate set of genes is to provide, in one mixture, all of the sequences encoding the desired set of potential test peptide sequences. The synthesis of degenerate oligonucleotides is well known in the art (see for example, Narang, SA (1983) Tetrahedron 39:3; Itakura et al. (1981) Recombinant DNA, Proc $3^{rd}$ Cleveland Sympos. Macromolecules, ed. AG Walton, Amsterdam: Elsevier pp273–289; Itakura et al. (1984) Annu. Rev. Biochem. 53:323; Itakura et al. (1984) Science 198:1056; Ike et al. (1983) Nucleic Acid Res.

11:477. Such techniques have been employed in the directed evolution of other proteins (see, for example, Scott et al. (1990) Science 249 :386–390; Roberts et al. (1992) PNAS 89 :2429–2433; Devlin et al. (1990) Science 249 : 404–406; Cwirla et al. (1990) PNAS 87: 6378–6382; as well as U.S. Pat. Nos. 5,223,409, 5,198,346, and 5,096,815).

Because the number of different peptides one can create by this combination approach can be huge, and because the expectation is that peptides with the appropriate structural characteristics to serve as ligands for a given target protein will be rare in the total population of the library, the need for methods capable of conveniently screening large numbers of clones is apparent. Several strategies for selecting peptide ligands from the library have been described in the art and are applicable to certain embodiments of the present method.

The number of possible peptides for a given library may, in certain instances, exceed $10^{12}$. To sample as many combinations as possible depends, in part, on the ability to recover large numbers of transformants. For phage with plasmid-like forms (as filamentous phage), electrotransformation provides an efficiency comparable to that of phage-transfection with in vitro packaging, in addition to a very high capacity for DNA input. This allows large amounts of vector DNA to be used to obtain very large numbers of transformants. The method described by Dower et al. (1988) Nucleic Acids Res., 16:6127–6145, for example, may be used to transform fd-tet derived recombinants at the rate of about $10^7$ transformants/μg of ligated vector into *E. coli* (such as strain MC1061), and libraries may be constructed in fd-tet B1 of up to about $3 \times 10^8$ members or more. Increasing DNA input and making modifications to the cloning protocol within the ability of the skilled artisan may produce increases of greater than about 10-fold in the recovery of transformants, providing libraries of up to $10^{10}$ or more recombinants.

6.1.2 Synthetic Peptide Libraries

In contrast to the recombinant methods, in vitro chemical synthesis provides a method for generating libraries of compounds, without the use of living organisms, that can be screened for ability to bind to a target molecule. Although in vitro methods have been used for quite some time in the pharmaceutical industry to identify potential drugs, recently developed methods have focused on rapidly and efficiently generating and screening large numbers of compounds and are particularly amenable to generating peptide libraries for use in the subject method.

One particularly useful features of the synthetic peptide library is that it can be used to supply libraries of R2 to be coupled to R1-Y, in order to make the hybrid ligand. This can be used to screen for a synthetic polypeptide that can bind a user-specified polypeptide. For example, the synthetic polypeptide can be a potential peptide inhibitor of a user-specified enzyme or transcription factor, etc. Such screens can be a prescreen of large number of random polypeptides in an in vitro high-throughput setting, so that primary positive peptides can be selected, and its variants encoded by a nucleic acid library further screened in an in vivo embodiment.

Another use for the synthetic peptide library is to generate libraries of short peptide linkers to be inserted between R1 and R2 ligands. This is particularly useful since an optimal linker sequence may be generated for a particular R1-R2 pair, so that the final hybrid ligand may possess the optimal chemical and/or structural characteristics such as solubility, membrane permeability, etc.

Both uses require coupling of a synthetic polypeptide, using knowledge well-known in the art (such as the ones described below or elsewhere), to another molecule (linker Y or ligands R1 and R2), which may be peptide or non-peptide in nature.

The various approaches to simultaneous preparation and analysis of large numbers of synthetic peptides (herein "multiple peptide synthesis" or "MPS") each rely on the fundamental concept of synthesis on a solid support introduced by Merrifield in 1963 (Merrifield, R. B. (1963) J Am Chem Soc 85:2149–2154; and references cited in section I above). Generally, these techniques are not dependent on the protecting group or activation chemistry employed, although most workers today avoid Merrifield's original tBoc/Bzl strategy in favor of the more mild Fmoc/tBu chemistry and efficient hydroxybenzotriazole-based coupling agents. Many types of solid matrices have been successfully used in MPS, and yields of individual peptides synthesized vary widely with the technique adopted (e.g., nanomoles to millimoles).

6.1.2.1 Multipin Synthesis

One form that the peptide library of the subject method can take is the multipin library format. Briefly, Geysen and co-workers (Geysen et al. (1984) PNAS 81:3998–4002) introduced a method for generating peptide by a parallel synthesis on polyacrylic acid-grated polyethylene pins arrayed in the microtitre plate format. In the original experiments, about 50 mmol of a single peptide sequence was covalently linked to the spherical head of each pin, and interactions of each peptide with receptor or antibody could be determined in a direct binding assay. The Geysen technique can be used to synthesize and screen thousands of peptides per week using the multipin method, and the tethered peptides may be reused in many assays. In subsequent work, the level of peptide loading on individual pins has been increased to as much as 2 μmol/pin by grafting greater amounts of functionalized acrylate derivatives to detachable pin heads, and the size of the peptide library has been increased (Valerio et al. (1993) Int J Pept Protein Res 42:1–9). Appropriate linker moieties have also been appended to the pins so that the peptides may be cleaved from the supports after synthesis for assessment of purity and evaluation in competition binding or functional bioassays (Bray et al. (1990) Tetrahedron Lett 31:5811–5814; Valerio et al. (1991) Anal Biochem 197:168–177; Bray et al. (1991) Tetrahedron Lett 32:6163–6166).

More recent applications of the multipin method of MPS have taken advantage of the cleavable linker strategy to prepare soluble peptides (Maeji et al. (1990) J Immunol Methods 134:23–33; Gammon et al. (1991) J Exp Med 173:609–617; Mutch et al. (1991) Pept Res 4:132–137).

6.1.2.2 Divide-Couple-Recombine

In yet another embodiment, a variegated library of peptides can provide on a set of beads utilizing the strategy of divide-couple-recombine (see, e.g., Houghten (1985) PNAS 82:5131–5135; and U.S. Pat. Nos. 4,631,211; 5,440,016; 5,480,971). Briefly, as the name implies, at each synthesis step where degeneracy is introduced into the library, the beads are divided into as many separate groups to correspond to the number of different amino acid residues to be added that position, the different residues coupled in separate reactions, and the beads recombined into one pool for the next step.

In one embodiment, the divide-couple-recombine strategy can be carried out using the so-called "tea bag" MPS method first developed by Houghten, peptide synthesis occurs on resin that is sealed inside porous polypropylene bags (Houghten et al. (1986) PNAS 82:5131–5135). Amino acids are coupled to the resins by placing the bags in solutions of the appropriate individual activated monomers, while all common steps such as resin washing and amino group deprotection are performed simultaneously in one reaction vessel. At the end of the synthesis, each bag contains a single peptide sequence, and the peptides may be liberated from the resins using a multiple cleavage apparatus (Houghten et al. (1986) Int J Pept Protein Res 27:673–678). This technique offers advantages of considerable synthetic flexibility and has been partially automated (Beck-Sickinger et al. (1991) Pept Res 4:88–94). Moreover, soluble peptides of greater than 15 amino acids in length can be produced in sufficient quantities (>0.5 mmol) for purification and complete characterization if desired.

Multiple peptide synthesis using the tea-bag approach is useful for the production of a peptide library, albeit of limited size, for screening the present method, as is illustrated by its use in a range of molecular recognition problems including antibody epitope analysis (Houghten et al. (1986) PNAS 82:5131–5135), peptide hormone structure-function studies (Beck-Sickinger et al. (1990) Int J Pept Protein Res 36:522–530; Beck-Sickinger et al. (1990) Eur J Biochem 194:449–456), and protein conformational mapping (Zimmerman et al. (1991) Eur J Biochem 200:519–528).

An exemplary synthesis of a set of mixed peptides having equimolar amounts of the twenty natural amino acid residues is as follows. Aliquots of five grams (4.65 mmols) of p-methylbenzhydrylamine hydrochloride resin (MBHA) are placed into twenty porous polypropylene bags. These bags are placed into a common container and washed with 1.0 liter of $CH_2Cl_2$ three times (three minutes each time), then again washed three times (three minutes each time) with 1.0 liter of 5 percent $DIEA/CH_2Cl_2$ (DIEA=diisopropylethylamine; $CH_2Cl_2$=DCM). The bags are then rinsed with DCM and placed into separate reaction vessels each containing 50 ml (0.56 M) of the respective t-BOC-amino acid/DCM. N,N-Diisopropylcarbodiimide (DIPCDI; 25 ml; 1.12 M) is added to each container, as a coupling agent. Twenty amino acid derivatives are separately coupled to the resin in 50/50 (v/v) DMF/DCM. After one hour of vigorous shaking, Gisen's picric acid test (Gisen (1972) Anal. Chem. Acta 58:248–249) is performed to determine the completeness of the coupling reaction. On confirming completeness of reaction, all of the resin packets are then washed with 1.5 liters of DMF and washed two more times with 1.5 liters of $CH_2Cl2$. After rinsing, the resins are removed from their separate packets and admixed together to form a pool in a common bag. The resulting resin mixture is then dried and weighed, divided again into 20 equal portions (aliquots), and placed into 20 further polypropylene bags (enclosed).

In a common reaction vessel the following steps are carried out: (1) deprotection is carried out on the enclosed aliquots for thirty minutes with 1.5 liters of 55% TFA/DCM; and 2) neutralization is carried out with three washes of 1.5 liters each of 5% DIEA/DCM. Each bag is placed in a separate solution of activated t-BOC-amino acid derivative and the coupling reaction carried out to completion as before. All coupling reactions are monitored using the above quantitative picric acid assay.

Next, the bags are opened and the resulting t-BOC-protected dipeptide resins are mixed together to form a pool, aliquots are made from the pool, the aliquots are enclosed, deprotected and further reactions are carried out. This process can be repeated any number of times yielding at each step an equimolar representation of the desired number of amino acid residues in the peptide chain. The principal process steps are conveniently referred to as a divide-couple-recombine synthesis.

After a desired number of such couplings and mixtures are carried out, the polypropylene bags are kept separated to here provide the twenty sets having the amino-terminal residue as the single, predetermined residue, with, for example, positions 2–4 being occupied by equimolar amounts of the twenty residues. To prepare sets having the single, predetermined amino acid residue at other than the amino-terminus, the contents of the bags are not mixed after adding a residue at the desired, predetermined position. Rather, the contents of each of the twenty bags are separated into 20 aliquots, deprotected and then separately reacted with the twenty amino acid derivatives. The contents of each set of twenty bags thus produced are thereafter mixed and treated as before-described until the desired oligopeptide length is achieved.

6.1.2.3 Multiple Peptide Synthesis through Coupling of Amino Acid Mixtures

Simultaneous coupling of mixtures of activated amino acids to a single resin support has been used as a multiple peptide synthesis strategy on several occasions (Geysen et al. (1986) Mol Immunol 23 :709–715; Tjoeng et al. (1990) Int J Pept Protein Res 35 :141–146; Rutter et al. (1991) U.S. Pat. No. 5,010,175; Birkett et al. (1991) Anal Biochem 196:137–143; Petithory et al. (1991) PNAS 88:11510–11514) and can have applications in the subject method. For example, four to seven analogs of the magainin 2 and angiotensinogen peptides were successfully synthesized and resolved in one HPLC purification after coupling a mixture of amino acids at a single position in each sequence (Tjoeng et al. (1990) Int J Pept Protein Res 35 : 141–146). This approach has also been used to prepare degenerate peptide mixtures for defining the substrate specificity of endoproteolytic enzymes (Birkett et al. (1991) Anal Biochem 196:137–143; Petithory et al. (1991) PNAS 88:11510–11514). In these experiments a series of amino acids was substituted at a single position within the substrate sequence. After proteolysis, Edman degradation was used to quantitate the yield of each amino acid component in the hydrolysis product and hence to evaluate the relative kcat/Kn values for each substrate in the mixture.

However, it is noted that the operational simplicity of synthesizing many peptides by coupling monomer mixtures is offset by the difficulty in controlling the composition of the products. The product distribution reflects the individual; rate constants for the competing coupling reactions, with activated derivatives of sterically hindered residues such as valine or isoleucine adding at a significantly slower rate than glycine or alanine for example. The nature of the resin-bound component of the acylation reaction also influences the addition rate, and the relative rate constants for the formation of 400 dipeptides form the 20 genetically coded amino acids have been determined by Rutter and Santi (Rutter et al. (1991) U.S. Pat. No. 5,010,175). These reaction rates can be used to guide the selection of appropriate relative concentrations of amino acids in the mixture to favor more closely equimolar coupling yields.

6.1.2.4 Multiple Peptide Synthesis on Nontraditional Solid Supports

The search for innovative methods of multiple peptide synthesis has led to the investigation of alternative polymeric supports to the polystyrene-divinylbenzene matrix originally popularized by Merrifield. Cellulose, either in the form of paper disks (Blankemeyer-Menge et al. (1988) Tetrahedron Lett 29–5871–5874; Frank et al. (1988) Tetrahedron 44 :6031–6040; Eichler et al. (1989) Collect Czech Chem Commun 54:1746–1752; Frank, R. (1993) Bioorg Med Chem Lett 3:425–430) or cotton fragments (Eichler et al. (1991) Pept Res 4 :296–307; Schmidt et al. (1993) Bioorg Med Chem Lett 3:441–446) has been successfully functionalized for peptide synthesis. Typical loadings attained with cellulose paper range from 1 to 3 mmol/cm$^2$, and HPLC analysis of material cleaved from these supports indicates a reasonable quality for the synthesized peptides. Alternatively, peptides may be synthesized on cellulose sheets via non-cleavable linkers and then used in ELISA-based binding studies (Frank, R. (1992) Tetrahedron 48:9217–9232). The porous, polar nature of this support may help suppress unwanted nonspecific protein binding effects. By controlling the volume of activated amino acids and other reagents spotted on the paper, the number of peptides synthesized at discrete locations on the support can be readily varied. In one convenient configuration spots are made in an 8×12 microtiter plate format. Frank has used this technique to map the dominant epitopes of an antiserum raised against a human cytomegalovirus protein, following the overlapping peptide screening (Pepscan) strategy of Geysen (Frank, R. (1992) Tetrahedron 48:9217–9232). Other membrane-like supports that may be used for multiple solid-phase synthesis include polystyrene-grafted polyethylene films (Berg et al. (1989) J Am Chem Soc 111:8024–8026).

6.1.2.5 Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) Annu Rep Med Chem 26:271–280; Fodor, S.P.A. (1991) Science 251: 767; Pirrung et al. (1992) U.S. Pat. No. 5,143,854; Jacobs et al. (1994) Trends Biotechnol 12:19–26). The technique combines two well-developed technologies: solid-phase peptide synthesis chemistry and photolithography. The high coupling yields of Merrifield chemistry allow efficient peptide synthesis, and the spatial resolution of photolithography affords miniaturization. The merging of these two technologies is done through the use of photolabile amino protecting groups in the Merrifield synthetic procedure.

The key points of this technology are illustrated in Gallop et al. (1994) J Med Chem 37:1233–1251. A synthesis substrate is prepared for amino acid coupling through the covalent attachment of photolabile nitroveratryloxycarbonyl (NVOC) protected amino linkers. Light is used to selectively activate a specified region of the synthesis support for coupling. Removal of the photolabile protecting groups by lights (deprotection) results in activation of selected areas. After activation, the first of a set of amino acids, each bearing a photolabile protecting group on the amino terminus, is exposed to the entire surface. Amino acid coupling only occurs in regions that were addressed by light in the preceding step. The solution of amino acid is removed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed. The target protein can be labeled with a fluorescent reporter group to facilitate the identification of specific interactions with individual members of the matrix.

In a light-directed chemical synthesis, the products depend on the pattern of illumination and on the order of addition of reactants. By varying the lithographic patterns, many different sets of test peptides can be synthesized in the same number of steps; this leads to the generated of many different masking strategies.

6.1.2.6 Encoded Combinatorial Libraries

In yet another embodiment, the subject method utilizes a peptide library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries above, where activity derives from expressed peptides, but the structures of the active peptides are deduced from the corresponding genomic DNA sequence. The first encoding of synthetic combinatorial libraries employed DNA as the code. Two forms of encoding have been reported: encoding with sequenceable bio-oligomers (e.g., oligonucleotides and peptides), and binary encoding with non-sequenceable tags.

6.1.2.6.1 Tagging with Sequenceable Bio-Oligomers

The principle of using oligonucleotides to encode combinatorial synthetic libraries was described in 1992 (Brenner et al. (1992) PNAS 89:5381–5383), and an example of such a library appeared the following year (Needles et al. (1993) PNAS 90:10700–10704). A combinatorial library of nominally 7$^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected NH2 groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following the such techniques, the peptide libraries can be derived for use in the subject method and screened using the D-enantiomer of the target protein.

It is noted that an alternative approach useful for generating nucleotide-encoded synthetic peptide libraries employs a branched linker containing selectively protected OH and NH2 groups (Nielsen et al. (1993) J Am Chem Soc 115:9812–9813; and Nielsen et al. (1994) Methods Compan Methods Enzymol 6:361–371). This approach requires that equimolar quantities of test peptide and tag co-exist, though this may be a potential complication in assessing biological activity, especially with nucleic acid based targets.

The use of oligonucleotide tags permits exquisitely sensitive tag analysis. Even so, the method requires careful choice of orthogonal sets of protecting groups required for alternating co-synthesis of the tag and the library member. Furthermore, the chemical liability of the tag, particularly the phosphate and sugar anomeric linkages, may limit the choice of reagents and conditions that can be employed for the synthesis on non-oligomeric libraries. In preferred embodiments, the libraries employ linkers permitting selective detachment of the test peptide library member for bioassay, in part (as described infra) because assays employing beads limit the choice of targets, and in part because the tags are potentially susceptible to biodegradation.

Peptides themselves have been employed as tagging molecules for combinatorial libraries. Two exemplary approaches are described in the art, both of which employ branched linkers to solid phase upon which coding and ligand strands are alternately elaborated. In the first approach (Kerr J M et al. (1993) J Am Chem Soc 115: 2529–2531), orthogonality in synthesis is achieved by employing acid-labile protection for the coding strand and base-labile protection for the ligand strand.

In an alternative approach (Nikolaiev et al. (1993) Pept Res 6:161–170), branched linkers are employed so that the coding unit and the test peptide are both attached to the same functional group on the resin. In one embodiment, a linker can be placed between the branch point and the bead so that cleavage releases a molecule containing both code and ligand (Ptek et al. (1991) Tetrahedron Lett 32:3891–3894). In another embodiment, the linker can be placed so that the test peptide can be selectively separated from the bead, leaving the code behind. This last construct is particularly valuable because it permits screening of the test peptide without potential interference, or biodegradation, of the coding groups. Examples in the art of independent cleavage and sequencing of peptide library members and their corresponding tags has confirmed that the tags can accurately predict the peptide structure.

It is noted that peptide tags are more resistant to decomposition during ligand synthesis than are oligonucleotide tags, but they must be employed in molar ratios nearly equal to those of the ligand on typical 130 mm beads in order to be successfully sequenced. As with oligonucleotide encoding, the use of peptides as tags requires complex protection/deprotection chemistries.

6.1.2.6.2 Non-Sequenceable Tagging: Binary Encoding

An alternative form of encoding the test peptide library employs a set of non-sequenceable electrophoric tagging molecules that are used as a binary code (Ohlmeyer et al. (1993) PNAS 90:10922–10926). Exemplary tags are haloaromatic alkyl ethers that are detectable as their tetramethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode 240 (e.g., upwards of 1012) different molecules. In the original report (Ohlmeyer et al., supra) the tags were bound to about 1% of the available amine groups of a peptide library via a photocleavable O-nitrobenzyl linker. This approach is convenient when preparing combinatorial libraries of peptides or other amine-containing molecules. A more versatile system has, however, been developed that permits encoding of essentially any combinatorial library. Here, the ligand is attached to the solid support via the photocleavable linker and the tag is attached through a catechol ether linker via carbene insertion into the bead matrix (Nestler et al. (1994) J Org Chem 59:4723–4724). This orthogonal attachment strategy permits the selective detachment of library members for bioassay in solution and subsequent decoding by ECGC after oxidative detachment of the tag sets.

Binary encoding with electrophoric tags has been particularly useful in defining selective interactions of substrates with synthetic receptors (Borchardt et al. (1994) J Am Chem Soc 116:373–374), and model systems for understanding the binding and catalysis of biomolecules. Even using detailed molecular modeling, the identification of the selectivity preferences for synthetic receptors has required the manual synthesis of dozens of potential substrates. The use of encoded libraries makes it possible to rapidly examine all the members of a potential binding set. The use of binary-encoded libraries has made the determination of binding selectivities so facile that structural selectivity has been reported for four novel synthetic macrobicyclic and tricyclic receptors in a single communication (Wennemers et al. (1995) J Org Chem 60:1108–1109; and Yoon et al. (1994) Tetrahedron Lett 35:8557–8560) using the encoded library mentioned above. Similar facility in defining specificity of interaction would be expected for many other biomolecules.

Although the several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) PNAS 92:6027–6031) and provide guidance for generating the subject peptide library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, ligands are partially detached and transferred to assay plates; third, a bioassay identifies the active wells; fourth, the corresponding beads are rearrayed singly into new microtiter plates; fifth, single active compounds are identified; and sixth, the structures are decoded.

The above approach was employed in screening for carbonic anhydrase (CA) binding and identified compounds which exhibited nanomolar affinities for CA. Unlike sequenceable tagging, a large number of structures can be rapidly decoded from binary-encoded libraries (a single ECGC apparatus can decode 50 structures per day). Thus, binary-encoded libraries can be used for the rapid analysis of structure-activity relationships and optimization of both potency and selectivity of an active series. The synthesis and screening of large unbiased binary encoded peptide libraries for lead identification, followed by preparation and analysis of smaller focused libraries for lead optimization, offers a particularly powerful approach to drug discovery using the subject method.

6.1.3 Nucleic Acid Libraries

In another embodiment, the library is comprised of a variegated pool of nucleic acids, e.g. single or double-stranded DNA or an RNA. A variety of techniques are known in the art for generating screenable nucleic acid libraries which may be exploited in the present invention. The libraries that can be used with the instant invention include libraries generated from: synthetic oligonucleotides, cDNA sequence, bacterial genomic DNA fragments, and eukaryotic genomic DNA fragments.

In particular, many of the techniques described above for synthetic peptide libraries can be used to generate nucleic acid libraries of a variety of formats. For example, divide-couple-recombine techniques can be used in conjugation with standard nucleic acid synthesis techniques to generate bead immobilized nucleic acid libraries.

In another embodiment, solution libraries of nucleic acids can be generated which rely on PCR techniques to amplify for sequencing those nucleic acid molecules which selectively bind the screening target. By such techniques, libraries approaching $10^{15}$ different nucleotide sequences have been generated in solution (see, for example, Bartel and Szostak (1993) Science 261: 1411–1418; Bock et al. (1992) Nature 355: 564; Ellington et al. (1992) Nature 355: 850–852; and Oliphant et al. (1989) Mol Cell Biol 9: 2944–2949).

According to one embodiment of the subject method, the SELEX (systematic evolution of ligands by exponential enrichment) is employed with the enantiomeric screening target. See, for example, Tuerk et al. (1990) Science 249: 505–510 for a review of SELEX. Briefly, in the first step of these experiments on a pool of variant nucleic acid sequences is created, e.g. as a random or semi-random library. In general, an invariant 3' and (optionally) 5' primer sequence are provided for use with PCR anchors or for permitting subcloning. The nucleic acid library is applied to screening a target, and nucleic acids which selectively bind (or otherwise act on the target) are isolated from the pool. The isolates are amplified by PCR and subcloned into, for example, phagemids. The phagemids are then transfected into bacterial cells, and individual isolates can be obtained and the sequence of the nucleic acid cloned from the screening pool can be determined.

When RNA is the test ligand, the RNA library can be directly synthesized by standard organic chemistry, or can be provided by in vitro translation as described by Tuerk et al., supra. Likewise, RNA isolated by binding to the screening target can be reverse transcribed and the resulting cDNA subcloned and sequenced as above.

Isolation of mRNA for cDNA synthesis and isolation of genomic DNA, either of prokaryotic or eukaryotic origin, are well-known in the art of molecular biology. Many standard laboratory manuals such as *Current Protocols in Molecular Biology*, John Wiley & Sons, N.Y. (1989 or later editions), or *Molecular Cloning: A Laboratory Manual*, Cold Spring Harbor press (1989 or later editions) have detailed description of these subjects. In addition, many companies offer commercial kits specifically designed for such purposes.

6.2 Small Molecule Libraries

Recent trends in the search for novel pharmacological agents have focused on the preparation of chemical libraries. Peptide libraries are described above. Nucleic acid libraries (including cDNA, genomic DNA and EST libraries) are well-known in the art. Saccharide libraries and their synthesis using combinatory chemistry have been described in WO 9816536 and its related applications. However, the field of combinatorial chemistry has also provided large numbers of non-polymeric, small organic molecule libraries which can be employed in the subject method.

Exemplary combinatorial libraries include benzodiazepines, peptoids, biaryls and hydantoins. In general, the same techniques described above for the various formats of chemically synthesized peptide libraries may also be used to generate and (optionally) encode synthetic non-peptide libraries.

6.3 Selecting Compounds from the Library

As with the diversity contemplated for the compound library and form in which the compound library is provided, the subject method is envisaged to identify hybrid ligands with the general formula of R1-Y—R2 which interacts with a polypeptide screening target or to identify inhibitors or antagonists of a certain interaction. In most embodiments, the screening programs test libraries of compounds/hybrid ligands suitable for high throughput analysis in order to maximize the number of compounds surveyed in a given period of time. However, as a general rule, the screening portion of the subject method involves contacting the screening target with the compound library and isolating those compounds from the library which interact with the screening target or causing a desired effect. Such interaction between the test compound/hybrid ligands and the screening target may be detected, for example, based on the change of status of any one of the suitable reporter system as described in section 3, or modulation of an enzymatic/catalytic activity of the screening target (for example, when the binding of a hybrid ligand for its potential dimerizable target is tested). The efficacy of the test compounds can be assessed by generating dose response curves from data obtained using various concentrations of the test compound. Moreover, a control assay can also be performed to provide a baseline for comparison.

In one embodiment, the variegated compound library is subjected to affinity enrichment in order to select for compounds which bind a preselected screening target. The term "affinity separation" or "affinity enrichment" includes, but is not limited to (1) affinity chromatography utilizing immobilizing screening targets, (2) precipitation using screening targets, (3) fluorescence activated cell sorting where the compound library is so amenable, (4) agglutination, and (5) plaque lifts. In each embodiment, the library of compounds are ultimately separated based on the ability of a particular compound to bind a screening target of interest. See, for example, the Ladner et al. U.S. Pat. No. 5,223,409; the Kang et al. International Publication No. WO 9218619; the Dower et al. International Publication No. WO 9117271; the Winter et al. International Publication WO 9220791; the Markland et al. International Publication No. WO 9215679; the Breitling et al. International Publication WO 9301288; the McCafferty et al. International Publication No. WO 9201047; the Garrard et al. International Publication No. WO 9209690; and the Ladner et al. International Publication No. WO 9002809.

It will be apparent that, in addition to utilizing binding as the separation criteria, compound libraries can be fractionated based on other activities of the target molecule, such as modulation of catalytic activity or certain biochemical properties.

In one embodiment, binding between a chemical compound and a target polypeptide can be measured by the activity of the reporter system as described above. For example, if a ubiquitin based reporter system is used for the detection, depending on the identity of the residue Z (the first amino acid of the cleaved reporter moiety), the detection could either be the presence of some activity of the reporter moiety (if Z is stabilizing amino acid like methionine) or the absence of certain activity of the reporter moiety (if Z is a destabilizing non-methionine amino acid). The activity to be detected could be transcription activity, fluorescence, enzymatic activity, or any other biological or biochemical activity described above. If a transcription based reporter system is used for the detection, transcription activity of the reporter moiety can be monitored to screen for the compound or the polypeptide binding to their target. Those skilled in the art will readily appreciate and recognize other appropriate methods suitable for those screens.

7. Nucleic Acids

The invention provides nucleic acids, including certain genes and homologs thereof, and portions thereof. Preferred nucleic acids have a sequence at least about 60%, 61%,62%, 63%, 64%, 65%, 66%, 67%, 68%, 69%; 70%, 71%, 72%, 73%, 74%, 75%, 76%, 77%, 78%, 79%, 80%, and more preferably 85% homologous and more preferably 90% and more preferably 95% and even more preferably at least 99% homologous with a nucleotide sequence of a particular gene or complement thereof of the nucleic acid. It is understood that other equivalent nucleic acids include those which encode polypeptides having functions analogous to those described in the instant invention using illustrative examples. Nucleic acids at least 90%, more preferably 95%, and most preferably at least about 98–99% identical with a nucleic sequence represented in one of these sequences or complement thereof are of course also within the scope of the invention.

The invention also pertains to isolated nucleic acids comprising a nucleotide sequence encoding certain polypeptides, variants and/or equivalents of such nucleic acids. The term equivalent is understood to include nucleotide sequences encoding functionally equivalent polypeptides or functionally equivalent peptides having an activity of a protein such as described herein.

Equivalent nucleotide sequences will include sequences that differ by one or more nucleotide substitution, addition or deletion, such as allelic variants; and will, therefore, include sequences that differ from the nucleotide sequence of the invention due to the degeneracy of the genetic code.

Regardless of species, particularly preferred nucleic acids of the invention encode polypeptides that are at least 60%, 65%, 70%, 72%, 74%, 76%, 78%, 80%, 90%, or 95% similar or identical to an amino acid sequence of the invention. For example, such nucleic acids can comprise about 50, 60, 70, 80, 90, or 100 base pairs. Also within the scope of the invention, are nucleic acid molecules for use as probes/primer or antisense molecules (i.e. noncoding nucleic acid molecules), which can comprise at least about 6, 12, 20, 30, 50, 60, 70, 80, 90 or 100 base pairs in length.

Another aspect of the invention provides a nucleic acid which hybridizes under stringent conditions to a nucleic acid of the invention. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–6.3.6 or in *Molecular Cloning: A Laboratory Manual*, Cold Spring Harbor press (1989). For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, at about 22° C., to high stringency conditions at about 65° C. Both temperature and salt may be varied, or temperature and salt concentration may be held constant while the other variable is changed.

Nucleic acids having a sequence that differs from the nucleotide sequences provided by the invention, or complement thereof due to degeneracy in the genetic code are also within the scope of the invention. Such nucleic acids encode functionally equivalent peptides but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of an htrb polypeptide. However, it is expected that DNA sequence polymorphisms that do lead to changes in the amino acid sequences of the subject polypeptides will exist among mammals. One skilled in the art will appreciate that these variations in one or more nucleotides (e.g., up to about 3–5% of the nucleotides) of the nucleic acids encoding polypeptides may exist among individuals of a given species due to natural allelic variation.

7.1 Probes and Primers

The nucleotide sequences determined from the cloning of genes from prokaryotic or eukaryotic organisms will further allow for the generation of probes and primers designed for use in identifying and/or cloning other homologs from other species. For instance, the present invention also provides a probe/primer comprising a substantially purified oligonucleotide, which oligonucleotide comprises a region of nucleotide sequence that hybridizes under stringent conditions to at least approximately 12, preferably 25, more preferably 40, 50 or 75 consecutive nucleotides of sense or anti-sense sequence of the invention.

In preferred embodiments, the primers are designed so as to optimize specificity and avoid secondary structures which affect the efficiency of priming. Optimized PCR primers of the present invention are designed so that "upstream" and "downstream" primers have approximately equal melting temperatures such as can be estimated using the formulae: Tm (° C.)=81.5−16.6(log[Na$^+$])+0.41(%G+C)−0.63(% formamide)−(600/length), for long polynucleotides; or Tm (° C.)=2(A+T)+4(G+C), for polynucleotides comprising less than 20 bases. Optimized primers may also be designed by using various programs, such as "Primer3" provided by the Whitehead Institute for Biomedical Research.

7.2. Vectors of the Invention

The invention further provides certain plasmids and vectors which encode certain polypeptide products either in vitro or in vivo. The host cell may be any prokaryotic or eukaryotic cell. Thus, a nucleotide sequence derived from the cloning of a mammalian pre-mRNA, encoding all or a selected portion of the full-length pre-mRNA, can be used to produce a recombinant form of the pre-mRNA or other RNA sequence of interest via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial) cells, are standard procedures well known in the art.

Vectors that allow expression of a nucleic acid in a cell are referred to as expression vectors. Typically, expression vectors used for expressing an RNA affinity substrate of the invention encode a ribonucleoprotein assembly sequence and an affinity tag sequence which contains a nucleic acid encoding an RNA binding protein binding site, operably linked to at least one transcriptional regulatory sequence. Regulatory sequences are art-recognized. Transcriptional regulatory sequences are described in Goeddel; Gene Expression Technology: Methods in Enzymology 185, Academic Press, San Diego, Calif. (1990).

Suitable vectors for the expression of the RNA affinity substrate include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YBP52, pYES2, and YRP17 are cloning and expression vehicles useful in the introduction of genetic constructs into *S. cerevisiae* (see, for example, Broach et al. (1983) in Experimental Manipulation of Gene Expression, ed. M. Inouye Academic Press, p. 83, incorporated by reference herein). These vectors can replicate in *E. coli* due to the presence of the pBR322 ori, and in *S. cerevisiae* due to the replication determinant of the yeast 2 micron plasmid. In addition, drug resistance markets such as ampicillin can be used.

The preferred expression vectors contain both prokaryotic promoter sequences, such as a T7 promoter or an SP6 promoter so that synthetic RNA affinity substrates can be generated in vitro using standard methodologies. The various methods employed in the preparation of the plasmids and transformation of host organisms are well known in the art. Fox other suitable expression systems for both prokaryotic and eukaryotic cells, as well as general recombinant procedures, see Molecular Cloning A Laboratory Manual, $2^{nd}$ Ed., ed. By Sambrook, Fritsch and Maniatis (Cold Spring Harbor Laboratory Press: 1989).

In some instances, it may be desirable to express a recombinant polypeptide by the use of a baculovirus expression system. Examples of such baculovirus expression systems include pVL-derived vectors (such as pVL1392, pVL1393 and pVL941), pAcUW-derived vectors (such as pAeUVf1), and pBlueBac-derived vectors (such as the-β-gal containing pBlueBac III).

When it is desirable to express only a portion of a protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) J. Bacteriol. 169:751–757) and *Salmonella typhimurium* and its ire vitro activity has been demonstrated on recombinant proteins (Miller et al. (1987) PNAS 84:2718–1722). Therefore, removal of an N-terminal methionine, if desired, can be achieved either in vivo by expressing polypeptides in a host which produces MAP (e.g., *E. coli* ox CM89 or *S. cerevisiae*), or in vitro by use of purified MAP (e.g., procedure of Miller et al., supra).

Moreover, the gene constructs of the present invention can also be used as part of a gene therapy protocol to deliver nucleic acids encoding either an agonistic or antagonistic form of one of the subject ribonucloprotein complexes. Thus, another aspect of the invention features expression vectors for in vivo or in vitro transfection and expression of a polypeptide in particular cell types so as to reconstitute the function of, or alternatively, abrogate the function of a ribonucleoprotein complex in a tissue. Thus could be desirable, for example, when the naturally-occurring form of the protein is misexpressed or the natural protein is mutated and less active.

8. Polypeptides of the Present Invention

The present invention provides methods to identify polypeptides that interact with a given ligand. Polypeptides identified through such methods can be produced in large quantity using any art-recognized methods, either as a purified polypeptide, or as a purified fusion polypeptide with other polypeptides. All forms of polypeptides can be formulated, with an acceptable pharmaceutical excipient, into a pharmaceutical composition using any art-recognized methods.

Such a purified polypeptide will be isolated from, or otherwise substantially free of other cellular proteins. The term "substantially free of other cellular proteins" (also referred to herein as "contaminating proteins") or "substantially pure or purified preparations" are defined as encompassing preparations of polypeptides having less than about 20% (by dry weight) contaminating protein, and preferably having less than about 5% contaminating protein. Functional forms of the subject polypeptides can be prepared, for the first time, as purified preparations by using a cloned gene as described herein.

Preferred subject polypeptides have an amino acid sequence which is at least about 60%, 65%, 66%, 67%, 68%, 69%, 70%, 71%, 72%, 73%, 74%, 75%, 76%, 77%, 78%, 79%, 80%, 85%, 90%, or 95% identical or homologous to an amino acid sequence. Even more preferred subject polypeptides comprise an amino acid sequence of at least 10, 20, 30, or 50 residues which is at least about 70, 80, 90, 95, 97, 98, or 99% homologous or identical to an amino acid sequence. Such proteins can be recombinant proteins, and can be, e.g., produced in vitro from nucleic acids comprising a nucleotide sequence identified by the methods of the invention or homologs thereof. For example, recombinant polypeptides preferred by the present invention can be encoded by a nucleic acid, which is at least 85% homologous and more preferably 90% homologous and most preferably 95% homologous with a nucleotide sequence identified by the methods of the invention- Polypeptides which are encoded by a nucleic acid that is at least about 98–99% homologous with the sequence identified by the methods of the invention are also within the scope of the invention.

The scope of the invention also includes isoforms of the subject polypeptides encoded by splice variants. Such isoforms may have identical or different biological activities. Such isoforms may arise, for example, by alternative splicing of one or more gene transcripts.

Full length proteins or fragments corresponding to one or more particular motifs and/or domains or to arbitrary sizes, for example, at least 5, 10, 20, 25, 50, 75 and 100, amino acids in length are within the scope of the present invention.

For example, isolated polypeptides can be encoded by all or a portion of a nucleic acid sequence. Isolated peptidyl portions of proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a subject polypeptide may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") protein.

A polypeptide can be a membrane bound form or a soluble form. A preferred soluble polypeptide is a polypeptide which does not contain a hydrophobic signal sequence domain. Such proteins can be created by genetic engineering by methods known in the art. The solubility of a recombinant polypeptide may be increased by deletion of hydrophobic domains, such as predicted transmembrane domains, of the wild type protein.

In general, polypeptides referred to herein as having an activity (e.g., are "bioactive") of a protein are defined as polypeptides which include an amino acid sequence encoded by all or a portion of the nucleic acid sequences and which mimic or antagonize all or a portion of the biological/biochemical activities of a naturally occurring protein. Examples of such biological activity include a region of conserved structure referred to as the conserved domain.

Other biological activities of the subject proteins will be reasonably apparent to those skilled in the art. According to the present invention, a polypeptide has biological activity if it is a specific agonist or antagonist of a naturally-occurring form of an protein.

In addition to utilizing fusion proteins to enhance immunogenicity, it is widely appreciated that fusion proteins can also facilitate the expression of proteins, and accordingly, can be used in the expression of the polypeptides of the present invention. For example, polypeptides can be generated as glutathione-S-transferase (GST-fusion) proteins. Such GST-fusion proteins can enable easy purification of the polypeptide, as for example by the rise of glutathione-derivatized matrices (see, for example, Current Protocols in Molecular Biology, eds, Ausubel et al. (N.Y.: John Wiley & Sons, 1991)). Additionally, fusion of polypeptides to small epitope tags, such as the FLAG or hemagluttinin tag sequences, can be used to simplify immunological purification of the resulting recombinant polypeptide or to facilitate immunological detection in a cell or tissue sample. Fusion to the green fluorescent protein, and recombinant versions thereof which are known in the art and available commercially, may further be used to localize polypeptides within living cells and tissue.

The subject polypeptides may be produced by any method known in the art. For example, a host cell transfected with a nucleic acid vector directing expression of a nucleotide sequence encoding the subject polypeptides can be cultured under appropriate conditions to allow expression of the peptide to occur. Suitable media for cell culture are well known in the art. The recombinant polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In, a preferred embodiment, the recombinant polypeptide is a fusion protein containing a domain which facilitates its purification, such as GST fusion protein.

Moreover, it will be generally appreciated that, under certain circumstances, it may be advantageous to provide homologs of one of the subject polypeptides which function in a limited capacity as one of either an agonist (mimetic) or an antagonist in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of proteins.

Homologs of each of the subject proteins can be generated by mutagenesis, such as by discrete point mutation(s), or by truncation. For instance, mutation can give rise to homologs which retain substantially the same, or merely a subset, of the biological activity of the polypeptide from which it was derived. Alternatively, antagonistic forms of the protein can be generated which are able to inhibit the function of the naturally occurring form of the protein, such as by competitively binding to an receptor.

The recombinant polypeptides of the present invention also include homologs of the wild-type proteins, such as versions of those protein which are resistant to proteolytic cleavage, as for example, due to mutations which alter ubiquitination or other enzymatic targeting associated with the protein.

Polypeptides may also be chemically modified to create derivatives by forming covalent or aggregate conjugates with other chemical moieties, such as glycosyl groups, lipids, phosphate, acetyl groups and the like. Covalent derivatives of proteins can be prepared by linking the chemical moieties to functional groups on amino acid sidechains of the protein or at the N-terminus or at the C-terminus of the polypeptide.

Modification of the structure of the subject polypeptides can be for such purposes as enhancing therapeutic or prophylactic efficacy, stability (e-g., ex vivo shelf life and resistance to proteolytic degradation), or post-translational modifications (e.g., to alter phosphorylation pattern of protein). Such modified peptides, when designed to retain at least one activity of the naturally-occurring form of the protein, or to produce specific antagonists thereof, are considered functional equivalents of the polypeptides described in more detail herein. Such modified peptides can be produced, for instance, by amino acid substitution, deletion, or addition. The substitutional variant may be a substituted conserved amino acid or a substituted non-conserved amino acid.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine, histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, $2^{nd}$ ed., Ed by L. Stryer, WFT Freeman and Co.: 1981). Whether a change in the amino acid sequence of a peptide results in a functional homolog (e.g., functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates the generation of sets of combinatorial mutants of the subject polypeptides as well as truncation mutants, and is especially useful for identifying potential variant sequences (e.g., homologs). The purpose of screening such combinatorial libraries is to generate, for example, novel homologs which can act as either agonists or antagonist, or alternatively, possess novel activities all together. Thus, combinatorially-derived homologs can be generated to have an increased potency relative to a naturally occurring form of the protein.

In one embodiment, the variegated library of variants is generated by combinatorial mutagenesis at the nucleic acid level, and is encoded by a variegated gene library. For instance, a mixture of synthetic oligonucleotides can be enzymatically ligated into gene sequences such that the degenerate set of potential sequences are expressible as individual polypeptides, or alternatively, as a set of larger fusion proteins (e.g., for phage display) containing the set of sequences therein.

There are many ways by which such libraries of potential homologs can be generated from a degenerate oligonucleotide sequence. Chemical synthesis of a degenerate gene sequence can be carried out in an automatic DNA synthesizer, and the synthetic genes then ligated into all appropriate expression vector. The purpose of a degenerate set of genes is to provide, in one mixture, all of the sequences encoding the desired set of potential sequences. The synthesis of degenerate oligonucleotides is well known in the art (see for example, Narang, SA (1983) Tetrahedron 39:3; Itakura et al. (1981) Recombinant DNA, Proc 3d Cleveland Sympos. Macromolecules, ed: AG Walton, Amsterdam: Elsevier pp 273–289; Itakura et al. (1984) Annu. Rev. Biochem. 53:323; Itakura et al. (1984) Science 198 :1056; Ike et al. (1983) Nucleic Acid Res. 11:477. Such techniques have been employed in the directed evolution of other proteins (see, for example, Scott et al. (1990) Science 249 :386–390; Roberts et al. (1992) PNAS 89 :2429–2433; Devlin et al. (1990) Science 249 : 404–406; Cwirla et al. (1990) PNAS 87: 6378–6382; as well as U.S. Pat. Nos. 5,223,409, 5,198,346, and 5,096,815).

Likewise, a library of coding sequence fragments can be provided for any clone in order to generate a variegated population of fragments for screening and subsequent selection of bioactive fragments. A variety of techniques are known in the art for generating such 1 ibrary, including chemical synthesis. In one embodiment, a library of coding sequence fragments can be generated by (i) treating a double stranded PCR fragment of an coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

The invention also provides for reduction of the proteins to generate mimetics, e.g., peptide or non-peptide agents, such as small molecules, which are able to disrupt binding of a subject polypeptide with a molecule, e.g. target peptide. Thus, such mutagenic techniques as described above are also useful to map the determinants of the proteins which participate in protein-protein interactions involved in, for example, binding of the subject polypeptide to a target peptide. To illustrate, the critical residues of a subject polypeptide which are involved in molecular recognition of its receptor can be determined and used to generate derived peptidomimetics or small molecules which competitively inhibit binding of the authentic protein with that moiety. By employing, for example, scanning mutagenesis to map the amino acid residues of the subject proteins which are involved in binding other proteins, peptidomimetic compounds can be generated which mimic those residues of the protein which facilitate the interaction. Such mimetics may then be used to interfere with the normal function of an protein. For instance, non-hydrolyzable peptide analogs of such residues can be generated using benzodiazepine (e.g., see Freidinger et al. In Peptides: Chemistry and Biology, G.R-Marshall ed., ESCOM- Publisher: Leiden, Netherlands, 1988), azepine (e.g., see Huffman et al. in Peptides: Chemistry and Biology, G. R. Marshall ed., ESCOM Publisher. Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methyleue pseudopeptides (Ewenson et al. (1986) J Med Chem 29:295; and Ewenson et al. in Peptides: Structure and Function (Proceedings of the American Peptide Symposium) Pierce Chemical Co, Rockland, Ill., 1985), b-tum dipeptide cores (Nagai et al. (1985) tetrahedron Lett 26:647; and Sato et al. (1986) 3 Chem Soc Perkin Trans 1:1231), and b-aminoalcohols (Gordon et al. (1985) Biochem Biophys Res Com:munl26:419; and Dann et al. (1986) Biochem Biophys Res Commun 134:71).

9. Kits

The invention further provides kits for creating hybrid ligands which include a user-specified chemical ligand. The compound or agent can be packaged in a suitable container. The kit can further comprise instructions for using the kit to isolate binding proteins for the user-specified ligand of the hybrid ligand.

One aspect of the invention provides a kit comprising a polynucleotide encoding at least one ligand binding domain and a functional domain heterologous to the ligand binding domain which by itself is not capable of inducing or allowing the detection of a detectable event, but which is capable of inducing or allowing the detection of a detectable event when brought into proximity of a second functional domain, further comprising instructions 1) to synthesize a hybrid ligand of general structure R1-Y—R2, and 2) to test the binding between the hybrid ligand and the ligand binding domain, wherein one of R1 and R2 binds to or inhibits a kinase.

Another aspect of the invention provides a kit comprising a polynucleotide encoding at least one ligand binding domain and a functional domain heterologous to the ligand binding domain which by itself is not capable of inducing or allowing the detection of a detectable event, but which is capable of inducing or allowing the detection of a detectable event when brought into proximity of a second functional domain, further comprising instructions 1) to synthesize a hybrid ligand of general structure R1-Y—R2, and 2) to test the binding between the hybrid ligand and the ligand binding domain, wherein Y is of the general structure ($CH_2$—X—$CH_2$)$_n$, where X represents O, S, SO, or $SO_2$, and n is an integer from 2 to 25.

Another aspect of the invention provides a kit comprising a polynucleotide encoding at least one ligand binding domain and a functional domain heterologous to the ligand binding domain which by itself is not capable of inducing or allowing the detection of a detectable event, but which is capable of inducing or allowing the detection of a detectable event when brought into proximity of a second functional domain, further comprising instructions 1) to synthesize a hybrid ligand of general structure R1-Y—R2, and 2) to test the binding between the hybrid ligand and the ligand binding domain, wherein the functional domain is Cub or Nux.

Another aspect of the invention provides a kit comprising: 1) a compound of general structure R1-Y-L, wherein Y is of the general structure $(CH_2-X-CH_2)_n$ and L is a chemical group that is easily substituted by a different chemical group, and 2) instructions to use the compound for the synthesis of a hybrid ligand R1-Y—R2 where R1 is different from R2, and at least one of R1 and R2 is not a peptide.

10. Business Methods

Other aspects of the invention provides for certain methods of doing business. In particular, practicing the methods of the invention may identify certain hybrid ligands, inhibitors and polypeptides. This technical step, when combined with one of more additional steps provides for novel approaches to conduct a pharmaceutical, agrochemical, biotechnological or preferable a life-science business. For example, such compositions identified by the method of the invention may be tested for efficacy as therapeutics in a variety of disease models, the potential therapeutic compositions then tested for toxicity and other safety-profiling before formulating, packaging and subsequently marketing the resulting formulation for the treatment of disease. Alternatively, the rights to develop and market such formulations or to conduct such steps may be licensed to a third party for consideration. In certain other aspects of the invention, the hybrid ligands, inhibitors and polypeptides thus identified may have utility in the form of information that can be provided to a third party for consideration such that an improved understanding of the function or side effects of said hybrid ligands, inhibitors and polypeptides in a biological or therapeutic context.

By way of example, a particular preferably method of doing business comprises:

(i) the identification of polypeptides binding to a hybrid ligand of general formula R1-Y—R2, wherein Y is of the general structure $(CH_2-X-CH_2)_n$, R1 is different from R2, and at least one of R1 and R2 is not a peptide, X=O, S, SO or $SO_2$, and wherein said polypeptides were previously not known to bind to such hybrid ligand, and (ii) providing access to data, nucleic acids or polypeptides obtained from such identification to another party for consideration.

EXAMPLES

The present invention is further illustrated by the following examples which should not be construed as limiting in any way. One skilled in the art, having read the specification and examples herein, will readily appreciate the possibility of numerous modifications, substitutions, combinations, permutations and improvements to the methods and compositions of the invention as herein disclosed. Such modifications, substitutions, combinations, permutations and improvements are considered to be part of the present invention. The contents of all cited references (including literature references, issued patents, published patent applications as cited throughout this application) are hereby expressly incorporated by reference.

It will be clear to any skilled person that the biological systems described herein are complex. The adaptation of the methods expressly exemplified herein below to similar systems as described above may involve a reasonable amount of experimentation, e.g. the adaptation of cell lines, construction of vectors, titration of concentrations, chemical modification of molecular species etc. In light of the complex nature of the systems contemplated herein, such experimentation cannot be called undue, but will form a regular part of the establishment of such methods in any laboratory. The skilled person will find sufficient guidance herein, and in the references cited as well as in standard textbooks, to carry out modifications as necessary.

The practice of the present invention will employ, unless otherwise indicated, conventional techniques of chemistry, cell biology, cell culture, molecular biology, microbiology and recombinant DNA, which are within the skill of the art. Such techniques are explained fully in the literature. See, for example, *Molecular Cloning: A Laboratory Manual, $2^{nd}$ Ed.*, ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al.; U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987).

The split ubiquitin technique was used to detect protein interactions in vivo or in vitro. It is generally useful for all kinds of protein-protein interactions, but is particularly useful in cases when conventional yeast two-hybrid assay is problematic, i.e. membrane and cytosolic proteins, transcriptional activators or repressors, etc.

Example 1

Compound Synthesis

The following is a description of the synthesis of the hybrid ligands used herein. However, this description is to be understood as exemplary in nature, and shall in no way limit the scope of the compounds according to the immediate invention. The person skilled in the art will be readily able to envisage other synthetic routes to compounds as provided by the present invention. For example, without limitation, the building blocks $H_2N-CH_2-(CH_2-O-CH_2-O-)_n-CH_2-N_3$ with n=3, 6 and 12 are available from commercial sources (Toronto Research Chemicals Inc., Toronto, Calif.; Fluka, Buchs, CH) and can be employed for the synthesis of compounds of the general structure R1-Y—R2 with $Y=(-CH_2-O-CH_2)_n$, for example, without limitation, by a synthesis strategy as used below in the synthesis of GPC 285937 following Scheme 2 (See FIG. 1B).

In the compounds used herein, a methotrexate-moiety is linked over 2 or more polyethylenglycol moieties as a linker to dexamethasone (GPC 285937), or to compounds known to bind to or inhibit CDKs. These potential or known CDK inhibitors (CDKi) may be linked to methotrexate via a linker in an orientation that preserves their activity towards inhibition of CDKs (GPC 285985, $IC_{50}$ for CDK2 is approx. 180 nM), or in an orientation which abolishes this activity (GPC 285993, $IC_{50}>10$ μM). For comparison to previous results using methotrexate linked to other compounds in a three hybrid assay (Lin et al., J. Am. Chem. Soc. 2000, 122: 4247–8), a hybrid ligand of methotrexate-linker-dexamethasone that uses a metadibenzothioester as linker (Mtx-mdbt-Dex) was employed. For the establishment of the effect of varying exclusively the linker, two hybrid ligands were synthesized wherein methotrexate is linked to a compound with CDK inhibiting activity via a linker containing 3 (GPC 286004) or 5 (GPC 286026) polyethylenglycol units.

Except where explicitly stated, all chemical reactants and solvents used are available commercially from vendors the skilled artisan is well familiar with, for example Sigma-Aldrich (St. Louis, Mo., USA) and its subsidiaries.

Synthesis of GPC 285937 following Scheme I (See FIG. 1A)

Synthesis of tert-butyl (2R)-4-[N-(2-(2-[2-(2-azidoethoxy)ethoxy]ethoxy}ethyl)carbamoyl]-2-[(fluoren-9-ylmethoxy)carbonylamino]butanoate (3).

Fmoc-Glutamic acid a-tert-butyl ester (2.15 g, 5.1 mmol) was dissolved in 10 ml dimethyl formamide (DMF) and 1-amino-11-azido-3,6,9-trioxaundecane (1.0 g, 4.6 mmol) was added in 10 ml DMF. To this solution O-Benzotriazole-N,N,N'N'-tetramethyl-uronium-hexafluorophosphate (HBTU) (2.3 g, 6 mmol) and diisoproylethylamine (DIEA) (1.75 ml, 10 mmol) were added and the reaction stirred at room temperature for 2 hours. The reaction mixture was diluted with 100 ml ethyl acetate and the organic layer was washed with saturated sodium bicarbonate, 10% citric acid, and brine, and then dried over magnesium sulfate and concentrated to a brown oil. The crude product (compound 3) was purified by flash silica chromatography (2% MeOH in EtOAc) to yield a light brown oil, 2.3 g, 3.7 mmol, 80%.

Synthesis of tert-butyl (2R)-2-amino-4-[N-(2-t2-[2-(2-azidoethoxy)ethoxy]ethoxy}ethyl) carbamoyl]butanoate (4).

Compound 3 (2.7 g, 4.3 mmol) was dissolved in 30 ml methylene chloride and 30 ml diethylamine was added. The reaction mixture was stirred at room temperature for 2 h, and then concentrated to an oil under reduced pressure. The residue was dissolved with diethyl ether and ethyl acetate (ca. 50 ml ea.) and extracted with 10% citric acid. The aqueous layer was neutralized to pH13 with 10N NaOH and extracted with ethyl acetate. The organic layer was washed with brine, dried over magnesium sulfate and concentrated under reduced pressure to give 1.6 g of a brown oil, 4.0 mmol, 92% (compound 4).

Synthesis of tert-butyl (2R)-4-[N-(2-{(2-[2-(2-azidoethoxy)ethoxy]ethoxy}ethyl)carbamoyl]-2-[(4-{[(2,4-diaminopteridin-6-yl)methyl]methylamino}phenyl)carbonylamino]butanoate (6)

Compound 4 (140 mg, 0.35 mmol) and pteroic acid (compound 5) were dissolved together in 5 ml DMF and benzotriazole-1-yl-oxy-tris-pyrrolidino-phosphonium hexafluorophosphate (PyBop) (0.26 g, 0.50 mmol) was added as a solid followed by DIEA (0.3 ml, 1.7 mmol). The reaction mixture was stirred at room temperature overnight, diluted with 30 ml ethyl acetate and the organic layer was washed with 1N NaOH, brine, and then dried over magnesium sulfate and concentrated under reduced pressure to give a brown oil. The crude product was purified by reverse-phase (C8) HPLC to give 0.155 g of a yellow oil, approximately 70% pure (compound 6). The yield was 0.15 mmol, 43%.

Synthesis of tert-butyl (2R)-4-[N-(2-{(2-[2-(2-aminoethoxy)ethoxy]ethoxy}ethyl)carbamoyl]-2-[(4-{[(2,4-diaminopteridin-6-yl)methyl]methylamino}phenyl)carbonylamino]butanoate (7)

Compound 6 (0.155 g 70% pure, 0.15 mmol) was dissolved in 3 ml of tetrahydrofuran and 200 ml of water was added followed by triphenylphosphine (130 mg, 0.5 mmol). The reaction mixture was stirred at room temperature for 16 hours, diluted with 20 ml diethyl ether and the organic layer extracted with 10% citric acid. Aqueous layer was neutralized to pH 12 with ION NaOH and extracted with ethyl acetate. The organic layer was washed with brine, dried over magnesium sulfate and concentrated under reduced pressure to yield an oil. The crude product was purified by reverse-phase (C8) HPLC to give 16 mg of a yellow oil, 0.022 mmol, 15% (compound 7).

Synthesis of 4-((2,4-diamino-6-pteridinylmethyl)methylamino)benzoyl-L-Gln(11-(9-fluoro-11b,17-dihydroxy-16a-methyl-3-oxoandrosta-1,4-diene-17b-carboxamido)-3,6,9-trioxoundecyl) (9, GPC 285937)

9-fluoro-11b, 17-dihydroxy-16a-methyl-3-oxoandrosta-1, 4-diene-17b-carboxylic acid (compound 8) 12 mg, 0.032 mmol) and compound 7 (15 mg, 0.021 mmol) were combined in 0.5 ml DMF and PyBop (20 mg, 0.038 mmol) was added followed by 0.017 ml DIEA (0.1 mmol). The reaction mixture was stirred at room temperature for 16 hours and then diluted with 10 ml ethyl acetate. The organic layer was washed with 0.2 N NaOH and brine, and then concentrated under reduced pressure to give an oil. This oil was dissolved in 2 ml 1:1 TFA:$CH_2Cl_2$ and let stand for 1 hour. The solvent was removed under reduced pressure and the residue was purified by reverse-phase (C8) HPLC to give 2.8 mg of product, 0.0028 mmol, 13% (compound 9).

Figure 1B:
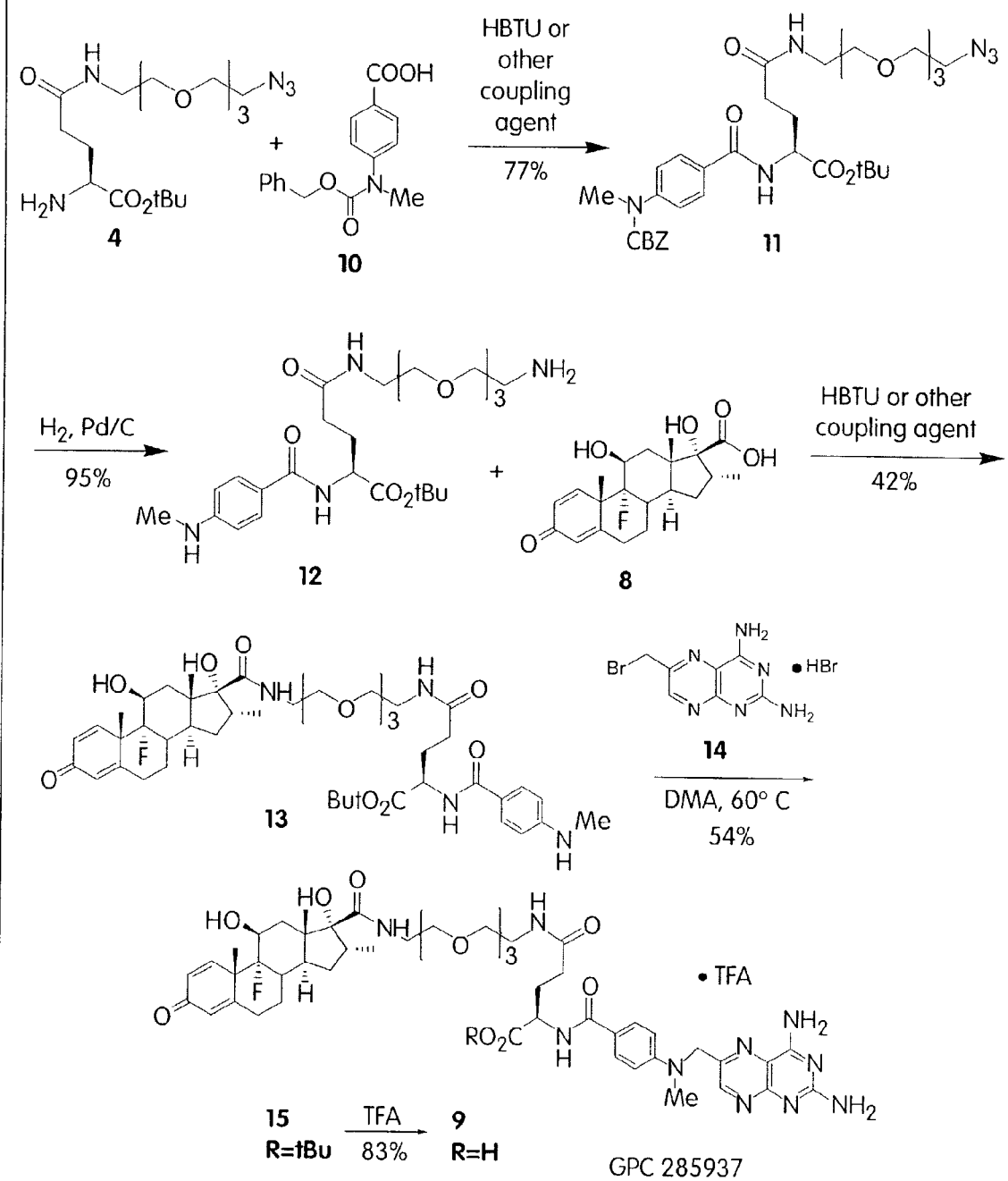

Synthesis of GPC 285937 following Scheme 2 (See FIG 1B)

Synthesis of tert-butyl (2S)-4-[N-(2-{2-[2-(2-azidoethoxy)ethoxy]ethoxy}ethyl)carbamoyl]-2-({4-[N-methyl(phenylmethoxy)carbonylamino]phenyl}carbonylamino)butanoate (11)

Compound 4 (0.81 g, 2.0 mmol) and 4-carboxybenzylmethylaminobenzoic acid (compound 10) (0.61 g, 2.1 mmol) were dissolved in 10 ml DMF. To this solution, HBTU (1.0 g, 2.6 mmol) was added as a solid followed by DIEA (0.8 ml, 4.6 mmol). The reaction mixture was stirred overnight at room temperature, diluted with ethyl acetate and the organic layer was washed with 0.5N NaOH, brine, dried over magnesium sulfate and concentrated under reduced pressure to give a brown oil. The crude product was purified by flash silica chromatography (5% MeOH in EtOAc) to yield a brown oil (1.03 g, 1.5 mmol, 77%, compound 11).

Synthesis of tert-butyl (2S)-4-[N-(2-{2-[2-(2-aminoethoxy)ethoxy]ethoxy}ethyl)carbamoyl]-2-({4-[N-methyl(phenylmethoxy)carbonylamino]phenyl}carbonylamino)butanoate (12)

Compound 11 (1.0 g, 1.49 mmol) was dissolved in 50 ml MeOH and 130 mg 10% Pd/C added. The reaction mixture was shaken under 40 psi hydrogen for 16 hours, the catalyst was filtered off, and the filtrate was concentrated under reduced pressure to give 0.75 g (1.47 mmol, 98%) of a colorless oil (compound 12).

Synthesis of 4-methylaminobenzoyl-L-Gln(11-(9-fluoro-11b, 17-dihydroxy-16a-methyl-3-oxoandrosta-1,4-diene-17b-carboxamido)-3,6,9-trioxoundecyl) tert-butyl ester (13)

Compound 12 (0.75 g, 1.47 mmol) was dissolved in DMF with 9-fluoro-11b, 17-dihydroxy-16a-methyl-3-oxoandrosta-1,4-diene-17b-carboxylic acid (8) (0.60 g, 1.6 mmol) and to this solution HBTU was added (0.75 g, 2 mmol) followed by DIEA (0.35 ml, 2 mmol). The reaction mixture was stirred overnight at room temperature, diluted with ethyl acetate, and the organic layer was washed with saturated sodium bicarbonate, brine, and concentrated under reduced pressure to give an orange oil. The crude product was purified by flash silica chromatography (10% MeOH in EtOAc) to yield 0.54 g of a white foam (0.62 mmol, 42%, compound 13).

Synthesis of 2,4-diamino-6-(bromomethyl)pteridine hydrobromide (14)

Synthesis of 2,4-diamino-6-(bromomethyl)pteridine hydrobromide (compound 14) was carried out in two steps individually described in the literature (Taghavi and Pfleiderer, Tetrahedron Lett., 1997, 38:6835–36; Taylor and Portnoy, J. Org. Chem., 1973, 38:806).

Synthesis of 4-((2,4-diamino-6-pteridinylmethyl)methylamino)benzoyl-L-Gln(11-(9-fluoro-11b, 17-dihydroxy-16a-methyl-3-oxoandrosta-1,4-diene-17b-carboxamido)-3, 6,9-trioxoundecyl) tert-butyl ester (15)

Compound 13 (0.54 g, 0.62 mmol) and 0.41 g compound 14 (1.2 mmol) were combined in 8 ml dimethylacetamide and heated to 60° C. for 6 hours. Diethyl ether (100 ml) was added and a precipitate formed. The supernatant was decanted off and the residue was purified by silica chromatography (1:10:89, saturated $NH_4OH:MeOH:CH_2Cl_2$) to yield 0.35 g of a yellow solid (0.33 mmol, 54%, compound 15).

Synthesis of 4-((2,4-diamino-6-pteridinylmethyl)methylamino)benzoyl-L-Gln(11-(9-fluoro-11b,17-dihydroxy-16a-methyl-3-oxoandrosta-1,4-diene-17b-carboxamido)-3,6,9-trioxoundecyl) (9, GPC 285937)

Compound 15 (0.35 g, 0.33 mmol) was dissolved in 20 ml (1:1:8:10, $H_2O:Me_2S:CH_2Cl_2:TFA$) and the reaction was stirred for 1 hour at room temperature. The solvent was removed under reduced pressure and the residue was dissolved in MeOH and purified by reverse-phase (C8) HPLC. The fractions containing product were concentrated to a minimal volume and then lyophilized to give 0.30 g of a yellow solid (0.27 mmol, 83%).

Figure 1C:
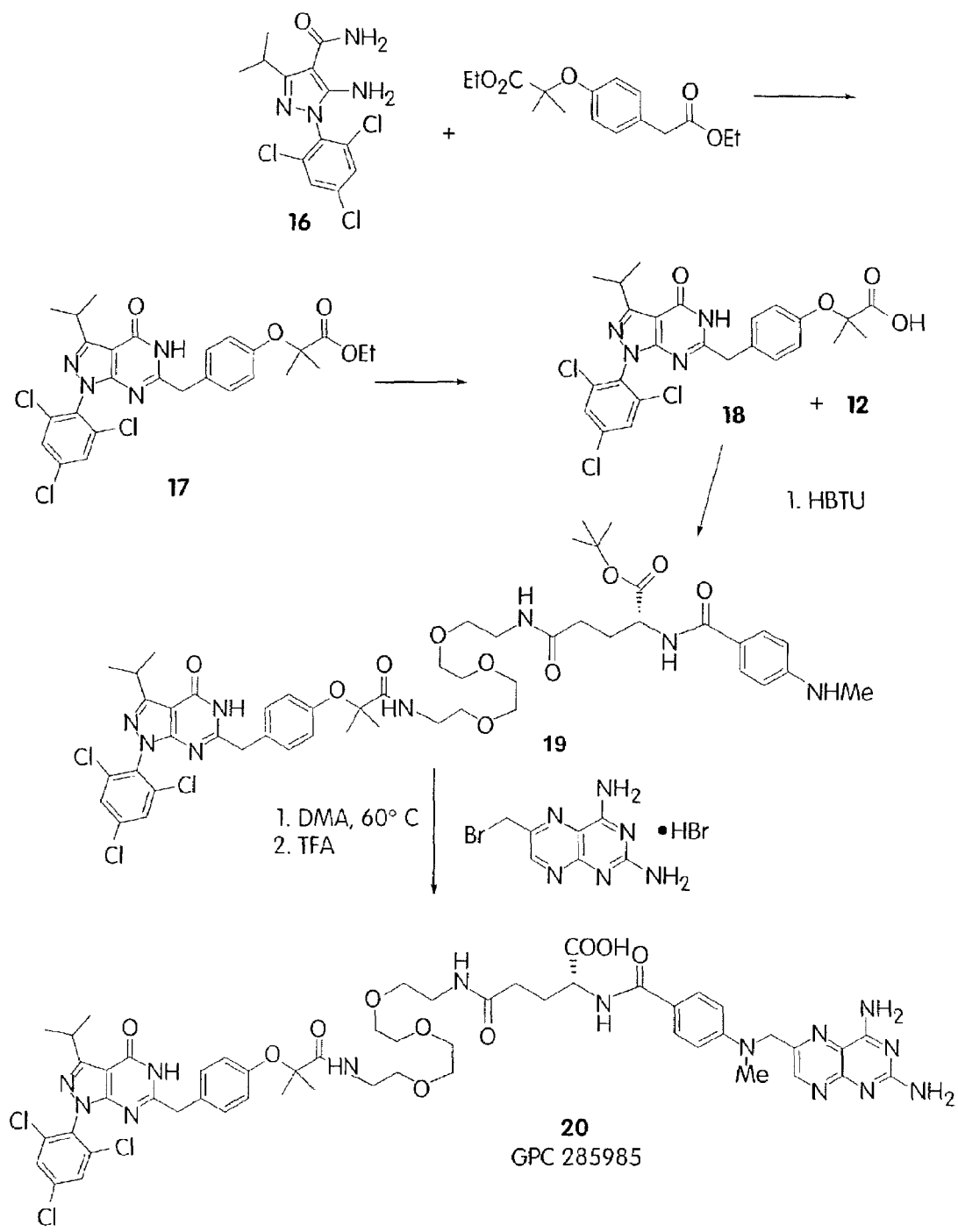

Synthesis of GPC 285985 following Scheme 3 (See FIG. 1C)

Synthesis of Ethyl 2-methyl-2-(4-{[3-(methylethyl)-4-oxo-1-(2,4,6-trichlorophenyl)(5-hydropyrazolo[5,4-d]pyrimidin-6-yl)]methyl}phenoxy) propanoate (17)

Compound 16 (2.5 g, 7.2 mmol) and ethyl 2-{4-[(ethoxycarbonyl)methyl]phenoxy}-2-methylpropanoate (4.5 g, 15.3 mmol) were dissolved in 15 ml of ethanol and 5.8 ml of a 2.66M solution of sodium ethoxide in ethanol (15.3 mmol) was added. The reaction mixture was heated to reflux for 5 hours, cooled to room temperature and let stand overnight. The reaction mixture was then diluted with ethyl acetate and washed with water and brine, dried over magnesium sulfate, filtered and concentrated to 1.6 g (2.8 mmol, 38%) of a beige solid (compound 17).

Synthesis of 2-methyl-2-(4-{[3-(methylethyl)-4-oxo-1- (2,4,6-trichlorophenyl)(5-hydropyrazolo[5,4-d]pyrimidin-6-yl)]methyl}phenoxy)propanoic acid (18)

Compound 16 (1.6 g, 2.8 mmol) was dissolved in 30 ml dioxane, 10 ml methanol and treated with 5 ml (5 mmol) of 1N NaOH. The reaction was stirred at room temperature overnight, then diluted with ethyl acetate and washed with 1N HCl and then brine. The organic layer was dried over magnesium sulfate, filtered and concentrated to a solid (1.4 g, 2.5 mmol, 91%, compound 18).

Synthesis of Tert-Butyl (2R)-2-{[4-(methylamino)phenyl] carbonylamino}-4-(N-{2-[2-(2-{2-[2-methyl-2-(4-{([3-(methylethyl)-4-oxo-1-(2,4,6-trichlorophenyl)(5-hydropyrazolo[5,4-d]pyrimidin-6-yl)]methyl}phenoxy)propanoylamino]ethoxy}ethoxy)ethyl}carbamoyl)butanoate (19)

Compound 18 (0.70 g, 1.3 mmol) and compound 12 (0.63 g, 1.2 mmol) were dissolved in dimethyl formamide and HBTU (0.75 g, 2 mmol) was added followed by diisopropylethylamine (0.5 ml, 2.9 mmol). The reaction mixture was stirred at room temperature for 3 days, diluted with ethyl acetate and then washed with 0.5N NaOH and brine. The organic layer was dried over magnesium sulfate, filtered and concentrated to an oil which was purified by flash silica chromatography (5 to 10% MeOH/EtOAc) to give 430 mg (0.41 mmol, 34%) of brown foam (compound 19).

Synthesis of (2R)-2-[4-{[(2,4-diaminopteridin-6-yl)methyl] methylamino}phenyl) carbonylamino]-4-(N-{2-[2(2-{2-[2-methyl-2-(4-{[3-(methylethyl)-4-oxo-1-(2,4,6-trichlorophenyl)(5-hydropyrazolo[5,4-d]pyrimidin-6-yl)] methyl}phenoxy)propanoylamino]ethoxy}ethoxy)ethoxy] ethyl}carbamoyl)butanoic Acid (20, GPC 285985)

Compound 19 (0.43 g, 0.41 mmol) was dissolved in 10 ml dimethyl acetamide and 0,27 g compound 14 (0.80 mmol) was added to the reaction mixture as a solid. The reaction mixture was heated to 60° C. for 5 hours, then let cool to room temperature and 100 ml diethyl ether added. The supernatant was decanted off leaving a dark brown residue which was taken up in 10 ml of a cleavage cocktail (10:10: 1:1 $TFA:CH_2Cl_2: Me_2S: H_2O$) and stirred for one hour. Solvent removed under reduced pressure, and the residue was purified by RPHPLC. Fractions containing the product were combined, concentrated to a small volume and lyophilized to yield a yellow solid (101 mg, 0.086 mmol, 21%, compound 20).

Figure 1D:
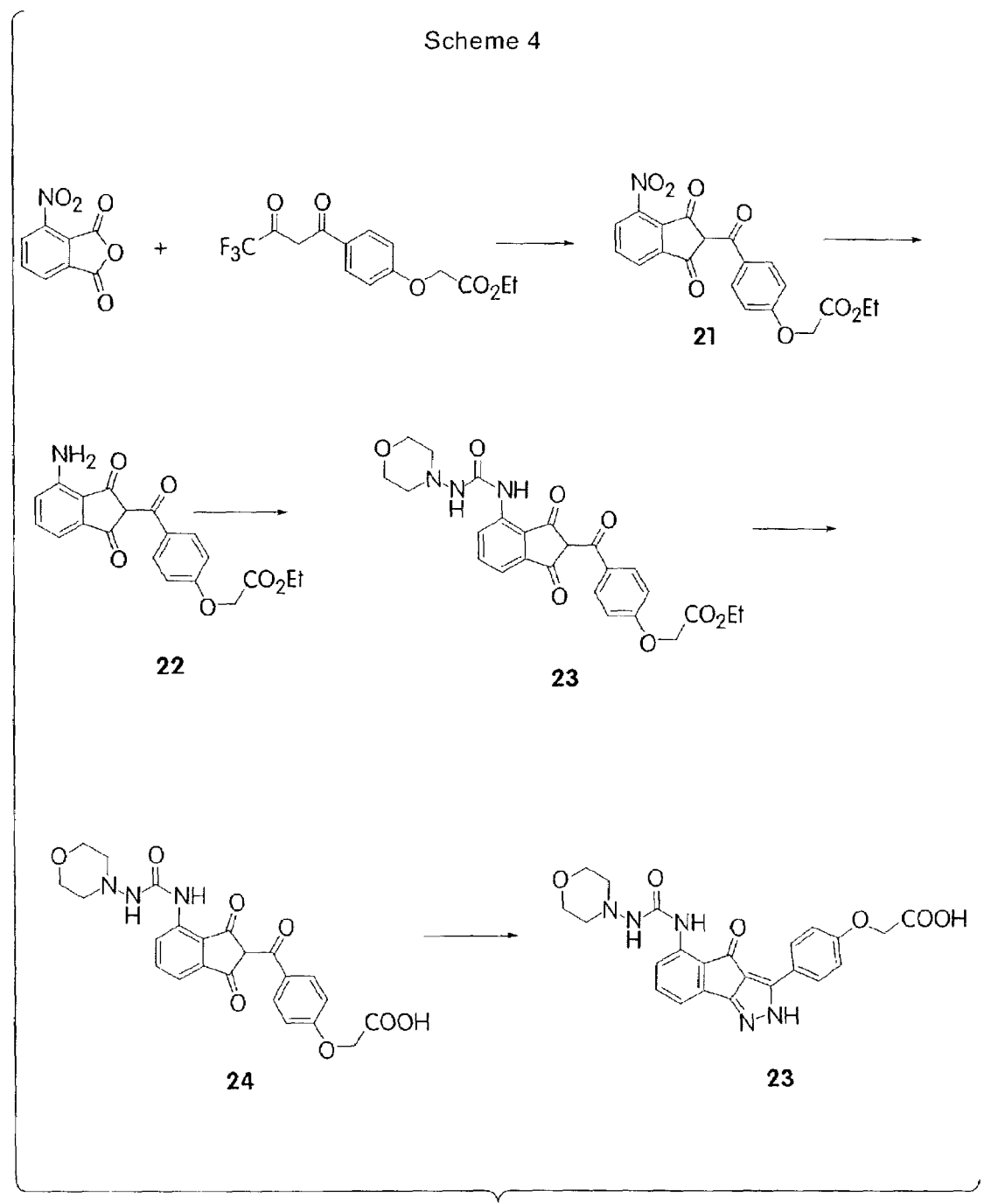
Figure 1E:
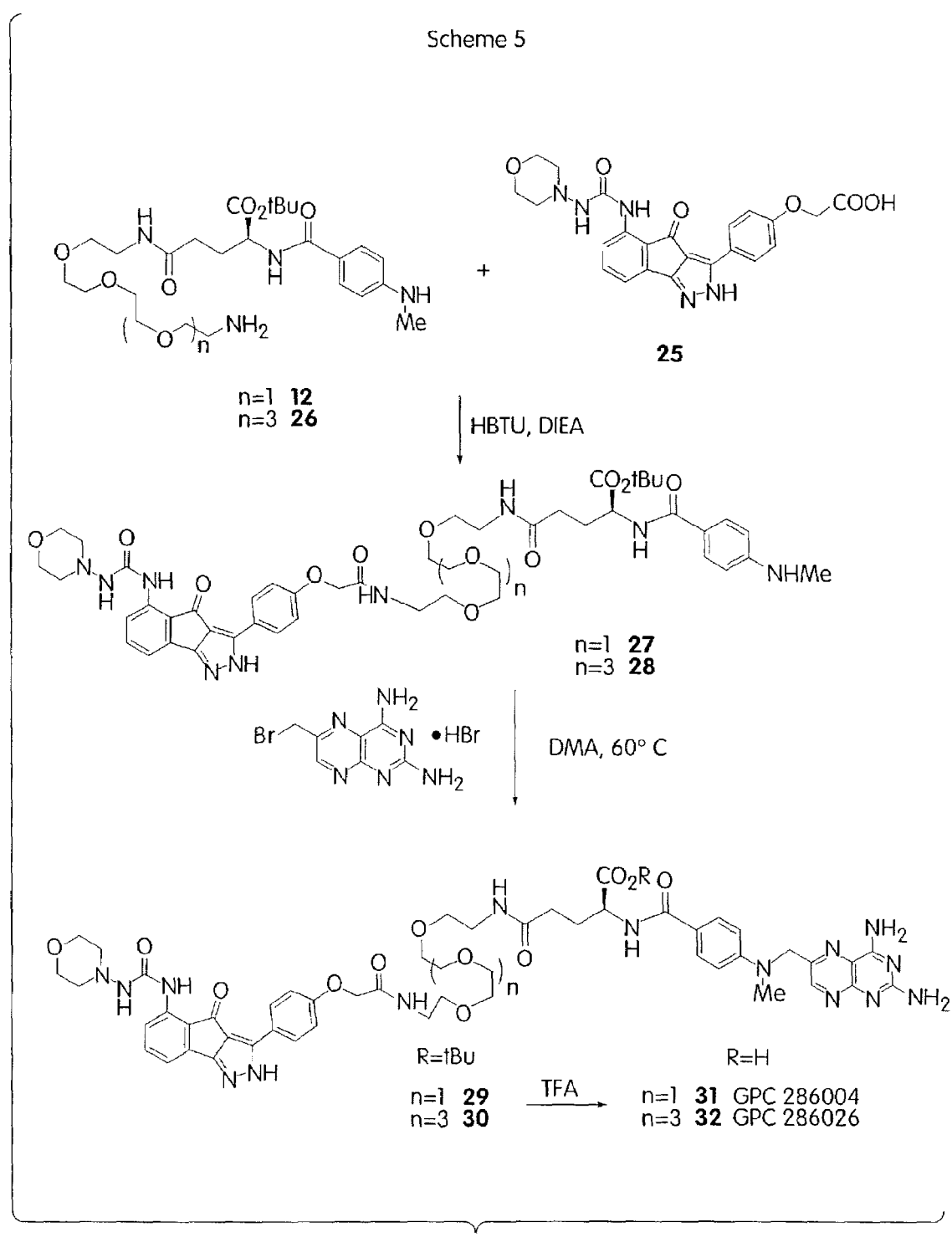

Synthesis of GPC 286004 and GPC 286026 following Schemes 4 and 5 (See FIGS. 1D and 1E)

Synthesis of Ethyl 2-{4-[(4-nitro-1,3-dioxo-2-hydrocyclopenta[3,4-a]benzen-2-yl)carbonyl]phenoxy}acetate (21)

Ethyl 2-[4-(4,4,4-trifluoro-3-oxobutanoyl)phenoxy]acetate (31.9 g, 0.1 mol) was combined with 19.3 g (0.1 mol) 3-nitrophthallic anhydride and 57 ml (0.6 mol) of acetic anhydride added. The slushy suspension was stirred at 0° C. and 28 ml (0.2 mol) triethyl amine added. The reaction mixture became homogenous and red and was stirred at room temperature overnight at which time 600 ml 1N HCl added. The resulting tacky suspension was stirred for 2 hours and the precipitate became a granular solid which was filtered off, resuspended in 200 ml ethanol, heated to reflux and then cooled to 0° C. A yellow solid was filtered off, washed with ethanol (3×40 ml) and dried to 12.7 g, 32 mmol, 32% yield (compound 21).

Synthesis of Ethyl 2-{4-[(4-amino-1,3-dioxo-2-hydrocyclopenta[3,4-a]benzen-2-yl)carbonyl]phenoxy}acetate (22)

Compound 21 (12.7 g, 32 mmol) was partially dissolved in 600 ml ethyl acetate and 1.5 g of 10% Pd/C added. The reaction was stirred under a balloon of $H_2$ overnight. The balloon was recharged with $H_2$ and stirred for 24 hours more. The reaction was filtered through celite with the help of THF and $CH_2Cl_2$ to dissolve the product, and the filtrate was concentrated to 10.7 g (29.1 mmol, 91%) of solid (compound 22).

Synthesis of ethyl 2-[4-({4-[(morpholin-4-ylamino)carbonylamino]-1,3-dioxo-2-hydrocyclopenta[3,4-a]benzen-2-yl}carbonyl)phenoxy]acetate (23)

Compound 22 (6.4 g, 17.4 mmol) was combined in acetonitrile with 4-nitrophenyl morpholine-4-carboxylate (containing 1 eq. triethyl ammonium chloride impurity) (8.0 g, 19.8 mmol) and dimethylaminopyridine (0.20 g, 1.6 mmol) was added. The suspension was heated to reflux for 3 hours, cooled to 0° C. and a yellow solid filtered off. This solid was washed with a minimum of cold acetonitrile, and dried to 6.7 g, 13.5 mmol, 78% (compound 23).

Synthesis of 2-[4-({4-[(morpholin-4-ylamino)carbonylamino]-1,3-dioxo-2-hydrocyclopenta[3,4-a]benzen-2-yl)carbonyl)phenoxy]acetic Acid (24)

Compound 23 (6.7 g, 13.5 mmol) was dissolved in 200 ml dioxane and 20 ml (20 mmol) 1N NaOH added. The reaction mixture was stirred for one hour. The white suspension was diluted with 1 l ethyl acetate and washed with 1N HCl and brine. The organic layer was dried over magnesium sulfate, filtered and concentrated to a yellow solid (6.3 g, 13.5 mmol, 100%, compound 24).

Synthesis of 2-(4-(5-[(morpholin-4-ylamino)carbonylamino]-4-oxoindeno[3,2-c]pyrazol-3-yl}phenoxy)acetic Acid (25)

Compound 24 (6.5 g, 13.5 mmol) was dissolved in 200 ml THF, 100 ml DMSO and treated with 4 g (80 mmol) hydrazine hydrate and 190 mg, (1 mmol) p-toluenesulfonic acid hydrate. The reaction mixture was heated to 60° C. for 5 hours, let cool to room temperature and 600 ml Et$_2$O added. The resulting suspension was then filtered, the precipitate washed with 1N HCl and dried under vacuum to yield 4.0 g (8.6 mmol, 64%) of yellow solid (compound 25).

Synthesis of tert-butyl (2S)-4-(N-{2-[2-(2-{2-[2-(2-aminoethoxy)ethoxy]ethoxy}ethoxy)ethoxy]ethyl}carbamoyl)-2-{[4-(methylamino)phenyl]carbonylamino}butanoate (26)

Compound 26 was synthesized by an analogous procedure as employed for compound 12, but using 1-amino-17-azido-3,6,9,12,15-pentaoxaheptadecane instead of 1-amino-11-azido-3,6,9-trioxaundecane in the first step of synthesis.

Synthesis of tert-butyl (2S)-2-{[4-(methylamino)phenyl]carbonylamino}-4-(N-{2-[2-(2-{2-[2-(4-{5-[(N-morpholin-4-ylcarbamoyl)amino]-4-oxoindeno[3,2-c]pyrazol-3-yl}phenoxy)acetylamino]ethoxy}ethoxy)ethoxy]ethyl}carbamoyl)butanoate (27)

Compound 12 (0.71 g, 1.4 mmol) and compound 25 (0.57 g, 1.2 mmol) were dissolved in 10 ml DMF and HBTU (0.8 g, 2.1 mmol) was added as a solid followed by DIEA (0.52 ml, 3 mmol). The reaction mixture was stirred at room temperature for 3 days, diluted with EtOAc and the organic phase washed with saturated NaHCO$_3$. The aqueous layer was back extracted with EtOAc twice and the combined organic layers dried over MgSO$_4$, filtered and concentrated to an oil. This oil was purified by flash silica chromatography (2 to 5% MeOH/EtOAc) to give an orange oil (0.50 g, 0.52 mmol, 44%, compound 27).

Synthesis of tert-butyl (2S)-2-{[4-(methylamino)phenyl]carbonylamino}-4-{N-[2-(2-{2-[2-(2-{2-[2-(4-{5-[(N-morpholin-4-ylcarbamoyl)amino]-4-oxoindeno[3,2-c]pyrazol-3-yl}phenoxy)acetylamino]ethoxy}ethoxy)ethoxy]ethoxy)ethyl]carbamoyl}butanoate (28)

Compound 25 (0.60 g, 1 mmol) and compound 26 (0.46 g, 1 mmol) were dissolved in 10 ml DMF and HBTU (0.7 g, 1.8 mmol) was added as a solid followed by DIEA (1.0 ml, 5.7 mmol). The reaction mixture was stirred at room temperature overnight, diluted with EtOAc and the organic phase washed with 0.5N NaOH, brine, dried over MgSO$_4$, filtered and concentrated to an oil. This oil was purified by flash silica chromatography (10 to 20% MeOH/EtOAc) to give a yellow foam (0.65 g, 0.62 mmol, 62%, compound 28).

Synthesis of tert-butyl (2S)-2-[(4-{[(2,4-diaminopteridin-6-yl)methyl]methylamino}phenyl) carbonylamino]-4-{N-[2-(2-{2-[2-(2-{4-[5-(methoxycarbonylamino)-4-oxoindeno[3,2-c]pyrazol-3-yl]phenoxy}acetylamino)ethoxy]ethoxy}ethoxy)ethyl]carbamoyl}butanoate (29)

Compound 27 (0.50 g, 0.52 mmol) was dissolved in dimethylacetamide and 0,33 g of compound 14 (1.0 mmol) was added to the reaction mixture as a solid. The reaction mixture was heated to 60° C. for 6 hours, then let cool to room temperature and 80 ml diethyl ether added. The supernantant was decanted off leaving a dark brown residue, which was purified by flash silica chromatography (5 to 10% MeOH/CH$_2$Cl$_2$ then 5 to 10% MeOH/CH$_2$Cl$_2$ w/1% NH$_4$OH) to give 0.33 g (0.29 mmol, 56%) of a yellow solid (compound 29).

Synthesis of Tert-butyl (2S)-2-[(4-{[(2,4-diaminopteridin-6-yl)methy]methylamino}phenyl) carbonylamino]-4-{N-[2-(2-{2-[2-(2-{2-[2-(4-{5-[(morpholin-4-ylamino)carbonylamino]-4-oxoindeno[3,2-c]pyrazol-3-yl}phenoxy)acetylamino]ethoxy}ethoxy)ethoxy]ethoxy}ethoxy) ethyl]carbamoyl}butanoate (30)

Compound 28 (0.65 g, 0.62 mmol) was dissolved in dimethylacetamide and 0,4 g of compound 14 (1.2 mmol) was added to the reaction mixture as a solid. The reaction mixture was heated to 60° C. for 6 hours, then let cool to room temperature and 80 ml diethyl ether added and let stand for 3 days. The supernantant was decanted off leaving a dark brown residue, which was purified by flash silica chromatography (5 to 10% MeOH/CH$_2$Cl$_2$ then 5 to 10% MeOH/CH$_2$Cl$_2$ w/1% NH$_4$OH) to give 0.45 g (0.37 mmol, 60%) of a yellow solid (compound 30).

Synthesis of (2S)-2-[(4-{[(2,4-diaminopteridin-6-yl)methyl]methylamino}phenyl)carbonyl-amino]-4-{N-[2-(2-{2-[2-{(4-[5-(methoxy-carbonyl-amino)-4-oxoindeno[3,2-c]pyrazol-3-yl]phenoxy}acetylamino)ethoxy]ethoxy}ethoxy)ethyl]carbamoy}butanoic Acid (31, GPC 286004)

Compound 29 (0.33 g, 0.29 mmol) was treated with 20 ml of a cleavage cocktail (10:10:1:1 TFA:CH$_2$Cl$_2$: Me$_2$S: H$_2$O). After one hour, solvent removed and the residue purified by RPHPLC. Fractions containing the product were combined, concentrated to a small volume and lyophilized to yield a yellow solid (0.19 g, 0.18 mmol, 61%, compound 31).

Synthesis of (2S)-2-[(4-{[(2,4-diaminopteridin-6-yl)methyl]methylamino}phenyl)carbonyl-amino]-4-{N-[2-(2-{2-[2-(2-{2-[2-(4-{5-[(morpholin-4-ylamino)carbonylamino]-4-oxoindeno [3,2-c]pyrazol-3-yl}phenoxy)acetylamino]ethoxy}ethoxy)ethoxy]ethoxy}ethoxy)ethyl]carbamoyl}butanoic Acid (32, GPC286026)

Compound 30 (0.45 g, 0.37 mmol) was treated with 20 ml of a cleavage cocktail (10:10:1:1 TFA:CH$_2$Cl$_2$: Me$_2$S: H$_2$O). After one hour, the solvent was removed and the residue purified by RPHPLC. Fractions containing the product were combined, concentrated to a small volume and lyophilized to yield a yellow solid (0.23 g, 0.18 mmol, 49%, compound 32).

Figure 1F:
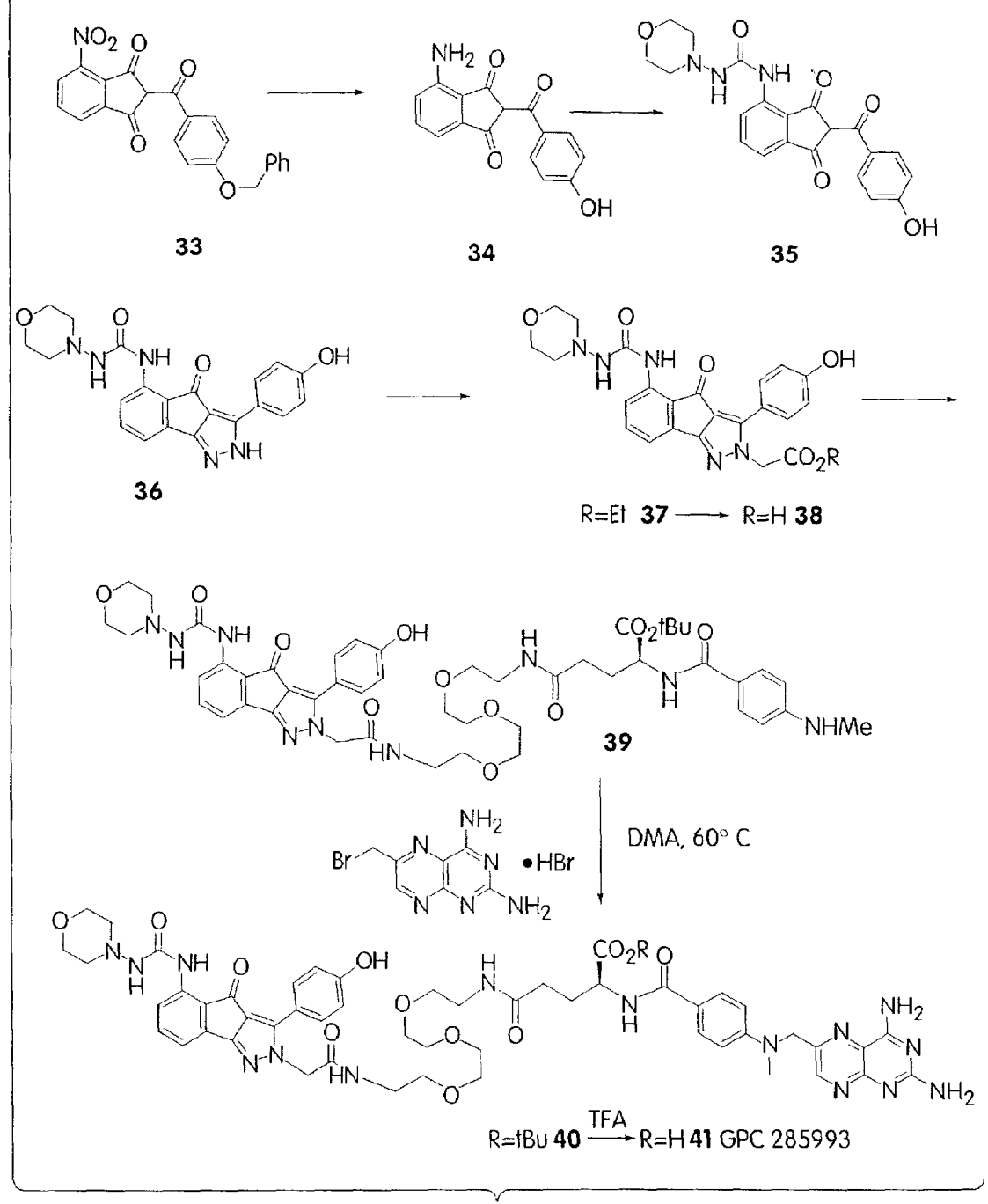

Synthesis of GPC 285993 following Scheme 6 (See FIG. 1F)

Synthesis of 1-(4-Benzyloxy-phenyl)-4,4,4-trifluoro-butane-1,3-dione

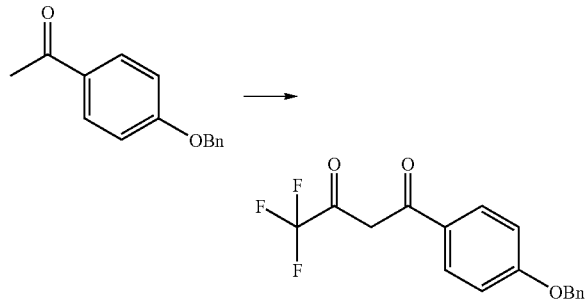

45.2 g 1-(4-Benzyloxy-phenyl) ethanone (200 mmol) was taken up in THF (250 mL) and treated with $CF_3CO_2Et$ (30 ml, 250 mmol). The solution was cooled to 0° C. and treated with 2.66 M NaOEt (94 ml, 250 mmol) solution over 1 h. The ice bath was removed and the solution was stirred at room temperature for 4 h. The reaction was poured into 1N HCl (1000 ml) and extracted with EtOAc (1500 ml). The organic layer was washed with brine, dried and evaporated to yield 64.2 g 1-(4-Benzyloxy-phenyl)-4,4,4-trifluoro-butane-1,3-dione (200 mmol, 100% yield).

Synthesis of 4-nitro-2-[(4-hydroxyphenyl)carbonyl]-2-hydrocyclopenta[1,2-a]benzene-1,3-dione (33)

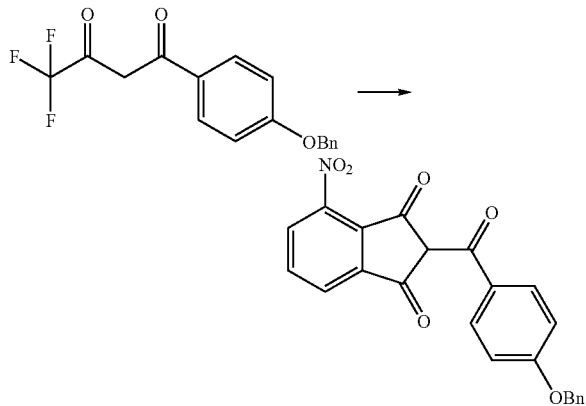

64 g 1-(4-Benzyloxy-phenyl)-4,4,4-trifluoro-butane-1,3-dione (200 mmol) was suspended in $Ac_2O$ (114 mL, 1.2 mol) and treated with 3-nitropthalic anhydride (28.6 g, 200 mmol). The suspension was cooled to 0° C. and treated slowly with $Et_3N$ (56 ml, 400 mmol). The reaction was stirred at room temperature for 16 h, then poured into ice/3N HCl (500 ml) and stirred vigorously for 1 h. The precipitate was filtered and washed with water. The precipitate was suspended in boiling ethanol (450 ml) for 10 min, then cooled to 0° C. for 2 h and filtered. The solid was washed with cold ethanol and dried under vacuum to yield 34 g (72 mmol, 36% yield, compound 33).

Synthesis of 4-amino-2-[(4-hydroxyphenyl)carbonyl]-2-hydrocyclopenta[1,2-a]benzene-1,3-dione (34)

Compound 33 (32.1 g, 67.6 mmol) was dissolved in 1500 ml EtOAc and 3.2 g 10% Pd/C added. The reaction mixture was stirred under an atmosphere (balloon) of $H_2$ for 3 days. Methanol was added to aid dissolution and the reaction mixture was filtered through celite. The filtrate was concentrated to 19 g (67 mmol, 100%) of an orange solid (compound 34).

Synthesis of N-{2-[(4-hydroxyphenyl)carbonyl]-1,3-dioxo(2-hydrocyclopenta[2,1-b]benzen-4-yl)}(morpholin-4-ylamino)carboxamide (35)

Compound 34 (10.0 g, 35.3 mmol) was dissolved in acetonitrile with 4-nitrophenyl morpholine4-carboxylate (containing 1 eq. triethyl ammonium chloride impurity) (13.0 g, 32.1 mmol) and dimethylaminopyridine (0.60 g, 5.4 mmol) was added. The reaction mixture was heated to reflux for 3 hours, cooled to room temperature and a pale green solid filtered off and dried to 7.5 g (18.3 mmol, 57%, compound 35).

Synthesis of N-[3-(4-hydroxyphenyl)-4-oxoindeno[3,2-c]pyrazol-5-yl](morpholin-4-ylamino)carboxamide (36)

Compound 35 (7.5 g, 18.3 mmol) was suspended in 200 ml THF and hydrazine hydrate (4.5 g, 90 mmol) was added followed by p-toluenesulfonic acid hydrate (340 mg, 1.8 mmol). The reaction mixture was heated to reflux overnight (homogenous solution), let cool to room temperature and a precipitate formed, which was filtered off to give 1.2 g of product. The filtrate was concentrated to a solid, suspended in EtOAc and filtered. This solid was purified by flash silica chromatography (5 to 10% MeOH/EtOAc) to give 2.2 g more of product. The combined yield was 3.3 g, 8.4 mmol, 46% (compound 36).

Synthesis of Ethyl 2-{(3-(4-hydroxyphenyl)-5-[(morpholin-4-ylamino)carbonylamino]-4-oxoindeno[3,2-c]pyrazol-2-yl} acetate (37)

Compound 36 (2.2 g, 5.6 mmol) was dissolved in 50 ml acetone, 10 ml THF, and 10 ml DMF and $Cs_2CO_3$ (1.8 g, 5.6 mmol) was added followed by ethyl bromoacetate (0.93 g, 5.6 mmol). The reaction mixture was stirred for 2 hours, diluted with ethyl acetate, and the organic layer washed with 1N HCl, brine, dried over $MgSO_4$, filtered and concentrated to a yellow solid. The solid was purified by flash silica chromatography (2 to 3 to 4% $MeOH/CH_2Cl_2$) to give 1.2 g (2.4 mmol, 44%) of a yellow solid (compound 37).

Synthesis of 2-{3-(4-hydroxyphenyl)-5-[(morpholin-4-ylamino)carbonylamino]-4-oxoindeno[3,2-c]pyrazol-2-yl}acetic Acid (38)

Compound 37 (1.2 g, 2.4 mmol) was dissolved in 60 ml 3:2:1; dioxane:ethanol:DMSO and 12 ml 0.5 N NaOH added and the reaction became red. The reaction mixture was stirred at room temperature for one hour, diluted with EtOAc and washed with 1N HCl. The aqueous layer was back extracted once with ethyl acetate and the combined organic layers dried over MgSO4 and concentrated to an orange solid. The solid was triturated with 10 ml MeOH/100 ml $Et_2O$, filtered off and dried to a solid (1.1 g, 2.4 mmol, 100%, compound 38).

Synthesis of Tert-Butyl (2S)-4-{N-[2-(2-{2-[2-(2-{3-(4-hydroxyphenyl)-5-[(N-morpholin-4-ylcarbamoyl)amino]-4-oxoindeno[3,2-c]pyrazol-2-yl}acetylamino)ethoxy]ethoxy}ethoxy) ethyl]carbamoyl}-2-{[4-(methylamino)phenyl]carbonylamino}butanoate (39)

Compound 38 (0.52 g, 1.1 mmol) and compound 12 (0.55 g, 1.1 mmol) were dissolved in DMF and HBTU (0.8 g, 2.1 mmol) was added as a solid followed by DIEA (0.52 ml, 3 mmol). The reaction mixture was stirred at room temperature overnight, diluted with EtOAc and the organic phase washed with saturated $NaHCO_3$, brine, dried over $MgSO_4$, filtered and concentrated to an oil. This oil was purified by flash silica chromatography (1 to 2 to 3 to 4 to 5% MeOH/CH$_2$Cl$_2$) to give a yellow foam (0.45 g, 0.47 mmol, 43%, compound 39).

Synthesis of tert-butyl (2S)-2-[(4-{[(2,4-diaminopteridin-6-yl)methyl]methylamino}phenyl carbonylamino]-4-{N-[2-(2-{2-[2-(2-{3-(4-hydroxyphenyl)-5-[(N-morpholin-4-yl-carbamoyl) amino]-4-oxoindeno[3,2-c]pyrazol-2-yl}acetylamino)ethoxy]ethoxy}ethoxy)ethyl]carbamoyl}butanoate (40)

Compound 39 (0.45 g, 047 mmol) was dissolved in 8 ml dimethylacetamide and 0,2 g compound 14 (0.60 mmol) was added to the reaction mixture as a solid. The reaction mixture was heated to 60° C. for 6 hours, then let cool to room temperature and diethyl ether added. The supernantant was decanted off leaving a dark brown residue, which was purified by flash silica chromatography (5 to 10% MeOH/CH$_2$Cl$_2$ then 5 to 10% MeOH/CH$_2$Cl$_2$ w/1% NH$_4$OH) to give 0.32 g (0.27 mmol, 56%) of yellow solid (compound 40).

Synthesis of (2S)-2-[(4-{[(2,4-diaminopteridin-6-yl)methyl]methylamino}phenyl) carbonylamino]-4-{(N-[2-(2-{(2-[2-(2-{3-(4-hydroxyphenyl)-5-[(N-morpholin-4-ylcarbamoyl) amino]-4-oxoindeno[3,2-c]pyrazol-2-yl}acetylamino) ethoxy]ethoxy}ethoxy) ethyl]carbamoyl}butanoic Acid (41, GPC 285993)

Compound 40 (0.30 g, 0.27 mmol) was treated with 20 ml of a cleavage cocktail (10:10:1:1 TFA:CH$_2$Cl$_2$: Me$_2$S: H$_2$O). After one hour, solvent removed and the residue purified by RPHPLC. Fractions containing the product were combined, concentrated to a small volume and lyophilized to yield a yellow solid (78 mg, 0.073 mmol, 27%, compound 41).

Synthesis of Mtx-(CH$_2$—O—CH$_2$)$_5$-Purvalanol B (42) according to Scheme 7 (See FIG. 1G)

Purvalanol B was synthesized following the methods described in Chang et al. & Schultz (1999), Chem. Biol. 6:361–375. Purvalanol B (0.35 g, 0.8 mmol) and (S)-4-{2-[2-(2-{2-[2-(2-Amino-ethoxy)-ethoxy]-ethoxy}-ethoxy)-ethoxy]-ethylcarbamoyl}-2-(4-methylamino-benzoylamino)-butyric acid tert-butyl ester (0.54 g, 0.9 mmol) were mixed in 2 ml of dimethyl acetamide (DMA) to which was added diisopropylethylamine (0.31 g, 2.4 mmol) and HBTU (0.36 g, 1.0 mmol). The reaction mixture was stirred overnight, the resulting solution diluted with 8 ml ethyl acetate and washed with saturated aqueous NaHCO$_3$ and brine. The organic layer was separated, dried with anhydrous magnesium sulfate, filtered and concentrated. The crude product was purified via silica gel chromatography eluting with 5% MeOH/1% NH$_4$OH/94% CH$_2$Cl$_2$ to give 0.48 g of compound 43 (60% yield)

Compound 43 (0.48 g, 0.48 mmol) and 6-Bromomethyl-pteridine-2,4-diamine hydrobromide (0.32 g, 0.96 mmol) were combined in DMA and heated to 60° C. for 4 hours. The reaction vessel was allowed to cool, the mixture diluted with diethyl ether and washed with saturated aqueous NaHCO$_3$ and brine. Organic layer separated, dried with anhydrous magnesium sulfate, filtered and concentrated. Crude product purified via silica gel chromatography eluting with 10% MeOH/2% NH$_4$OH/84% CH$_2$Cl$_2$ to give 0.29 g of compound 44 (50% yield.)

Compound 44 (0.29 g, 0.24 mmol) was placed in a mixture of 4.5 ml trifluoroacetic acid, 4.5 ml methylene chloride, 0.5 ml water and 0.5 ml dimethylsulfide at room temperature and stirred for 30 minutes. The solution was then concentrated and the residue diluted with 20 ml of a 1:1 acetonitrile/water mixture. The solution was purified via preparative HPLC to give 69.3 mg of compound 42 after lyophilization.

Example 2

Measurement of Affinities of Hybrid Ligands for Selected Binding Proteins

To demonstrate the characterization of affinity between hybrid ligands and proteins they bind to, we analyzed the binding of GPC 285985 to its expected binding partners DHFR and CDK2/E (cyclin dependent kinase 2/cyclin E complex). The analysis was performed on a BIACORE 2000 SPR-Biosensor (Biacore, Uppsala, Sweden) at 22° C. using a running buffer containing 20 mM HEPES (pH 7.4), 150 mM NaCl, 1 mM DTT and 0.005% Tween20 (protein grade, Calbiochem). Vector pQE40 (Qiagen, Hilden, Germany), comprising the gene encoding DHFR fused to a his$_6$-tag, was transformed into E. coli and the His$_6$-DHFR fusion protein purified following manufacturers protocols. His$_6$-DHFR was subsequently coupled at pH 4.6 to the dextrane-surface of a CM5 sensor-chip (Biacore, Uppsala, Sweden; research grade) according to manufacturers instructions. The loading density reached 1100 RU (Resonance Units). A 10 µM solution of GPC 285985 was allowed to pass over the DHFR-loaded chip surface for 5 minutes at a flow rate of 30 µl/min, followed by 5 minutes of running buffer at the same flow rate. A profile for adsorption and desorption of GPC 285985 on DHFR was obtained and stored. Non-specific binding of GPC 285985 was assessed using a CM5-surface with deactivated COOH-groups. The resulting sensorgram (not shown) demonstrated specific and high affinity binding of the hybrid ligand to the DHFR-coated surface.

In order to characterize the binding of GPC 285985 to other proteins, the CM5-DHFR surface was first loaded with GPC 285985 by passing a 10 µM solution of GPC 285985 over the chip surface for 5 minutes at a flow rate of 10 µl/min Then, CDK2/E complex, for example purified from baculovirus infected cells expressing CDK2 and Cyclin E (Sarcevic et al., J. Biol. Chem., 1997 272:33327–37), was diluted in running buffer to obtain eight distinct protein concentrations ranging from 6 nM to 750 nM, which were then each allowed to pass over the sensor surface consecutively for 5 min each, followed by 5 min of running buffer at the same flow rate. The association and dissociation of the CDK2/E complex onto the CM5-DHFR::GPC 285985-loaded chip surface was measured at a flow rate of 301 µl/min After each association/dissociation experiment, the chip was regenerated to remove bound protein by two consecutive injections of 3 M guanidinium-hydrochloride (20 sec, 30 µl/min) before the next sample was loaded. Non-specific binding was assessed using a CM5-surface loaded with DHFR only.

The data were analyzed using the Bioevaluation software version 3.1 (Biacore AB, Uppsala, SE). The curves were normalized to the injection start, and the non-specific binding to the DHFR-loaded control surface and the background line drift resulting from desorption of GPC 285985 from the CM5-DHFR during the 10 min run were subtracted. The association and dissociation rates were determined separately or globally using a Langmuir 1:1 binding model as provided by the Bioevaluation software 3.1. The affinities (KD) were calculated using the equation:

$$K_D = k_{diss}/k_{ass}$$

Figure 2:
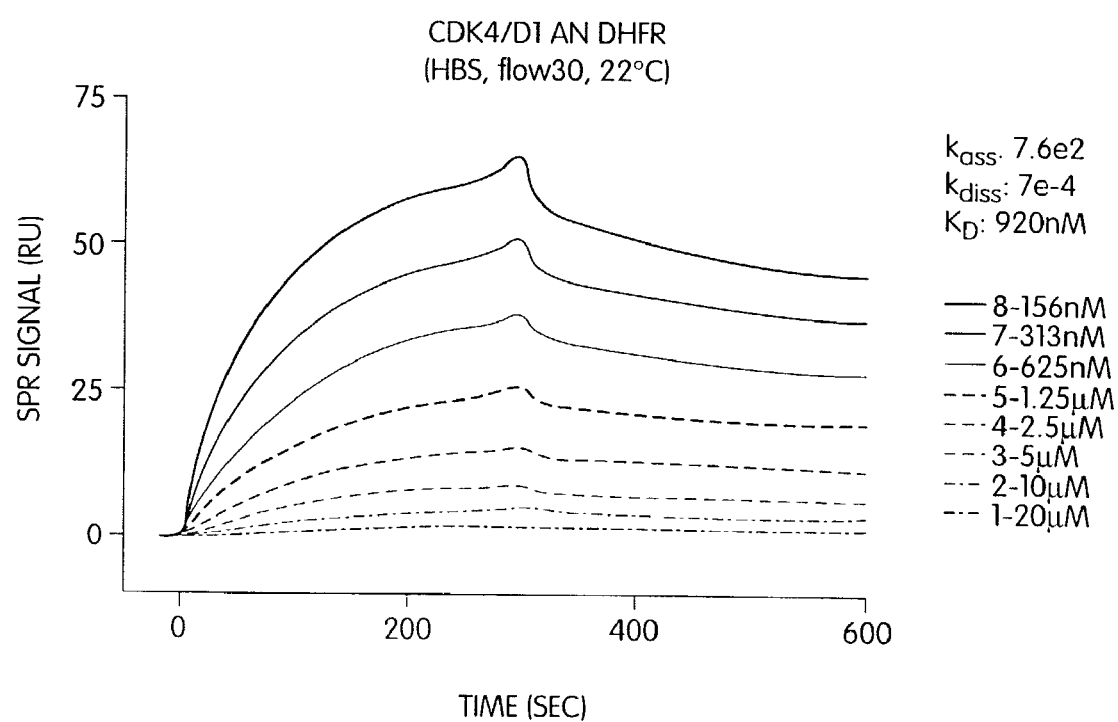
FIG. 2. Sensorgram and subsequent determination of dissociation constant K$_D$ for binding of the complex Cyclin Dependent Kinase (CDK) 4/Cyclin D1 (CDK4/D1) to a Methotrexate-based hybrid ligand using a Biacore 2000-SPR Biosensor. DHFR was covalently coupled to the surface of an SPR chip and the hybrid ligand (GPC 285985) was allowed to bind. Subsequently, solutions of different concentrations of the CDK4/D1 complex (shown by different curves) were pumped over the chip surface for 300 sec, followed by running buffer to monitor dissociation. The binding characteristics of methotrexate to DHFR were taken into account to estimate k$_{ass}$ and k$_{diss}$ of the hybrid ligand to CDK4/D1 and the K$_D$ calculated.
Figure 3A:
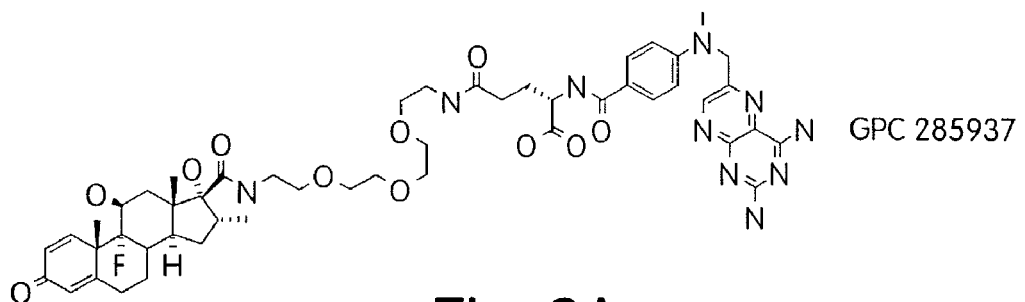
FIGS. 3A–3C. Structural representations of GPC 285937, GPC 285985 and GPC 285993.
Figure 3B:
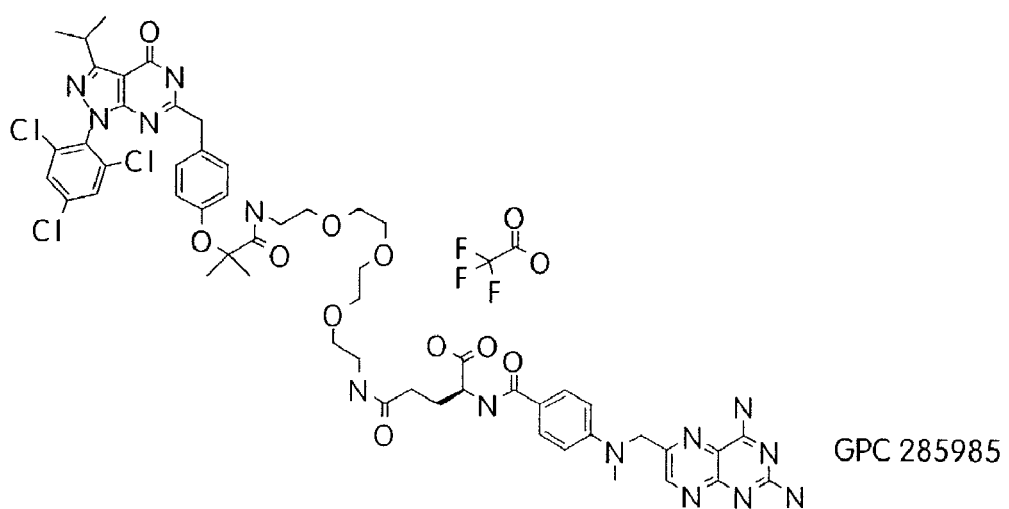
Figure 3C:
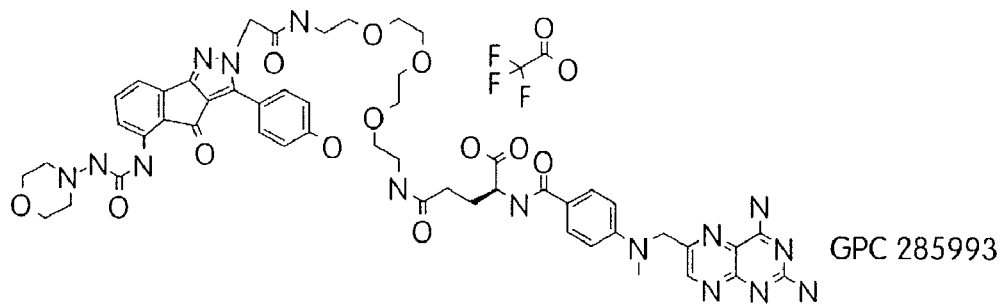

This association/disassociation experiment gave a K$_D$ of 8.0 nM for the binding of GPC 285985 to CDK2, confirming the high specificity of the hybrid ligand GPC 285985 for CDK2. FIG. 2 shows as an example the results of an analogous association/dissociation experiments obtained for the binding of CDK4/D1 to the CM5-DHFR::GPC 285985-loaded chip. The $K_D$ for the binding of GPC 285985 to the CDK4/D1 complex was calculated from these data as 920 nM. This confirms the expected results of strong binding of GPC 285985 to DHFR and CDK2, but weak binding to the closely related kinase CDK4. The CDK4/CyclinD1 complex was purified for example from baculovirus infected cells expressing (Konstantinidis et al., J. Biol. Chem., 1998, 273:26506–15).

Example 3

Pull Down of Polypeptides which Interact with a Hybrid Ligand of the Invention

To show the usefulness of the hybrid ligands of the invention for so called "pull-down" experiments, a method was devised where the hybrid ligand was incubated with strep-tagged DHFR and cell lysates, complexes subsequently pulled down using a Streptactin-coated resin, unbound proteins washed out and the bound proteins eluted by competitive displacement of the hybrid ligand. Therein, in terms of the present invention, DHFR and Methotrexate represents P1 and R1, respectively, the known protein-ligand combination, the linker Y is represented by a —($CH_2$—O—$CH_2$)$_5$-group, R2, the small molecule for which interactors are sought is purvalanol B, and the P2 are effectively a protein library, namely cellular extracts obtained from cultured Jurkat cells. The hybrid ligand as provided by the present invention, MTX-($CH_2$—O—$CH_2$)$_5$-purvalanol B was synthesized as described in Example 1 above.

The assay described here somewhat follows the concepts developed in Knockaert et al. (2000), Chem. Bio. 7:411–422. Therein, purvalanol B, an inhibitor of CDK1/cyclinB, was immobilized on an agarose matrix and incubated with cellular extracts to identify polypeptides selectively binding to purvalanol B.

Pull Down of DHFR-Hybrid Ligand-Interactor Complexes Using Streptactin Coated Resin To construct a vector expressing a strep-tagged DHFR, the vector pQE-40 (Qiagen, Hilden, Germany), which encodes a his$_6$-DHFR fusion protein, under the expression-control of lac 0, upstream of a multiple cloning site comprising BglII and HindIII restriction sites, was digested to completion with BglII and HindIII (New England Biolabs, Beverly, Mass., USA) following manufacturer's protocols, and purification was performed using a HiSpeed Tip and QiaPrecipitator (Qiagen, Hilden, Germany) according to manufacturer's instructions.

50 µl each of 1 µM solutions of the 5'-phosphorylated oligonucleotides ON284 and ON285 of sequences The two fragments were combined and ligated using the Quick Ligation Kit (New England Biolabs, Beverly, Mass., USA) according to manufacturer's instructions. The purified vector was transfected into E. coli strain JM1O9 (Genotype: el4-(McrA-) recAl endAl gyrA96 thi-1 hsdR17(rK– mK+) supE44 relA1 Δ(lac-proAB) [F' traD36 proAB lacI$^q$Z ΔM15]) (Stratagene, Amsterdam, Netherlands), over-expressing the lacI repressor, by electroporation using standard procedures. Transformants were cultured overnight under vigorous shaking at 200 rpm, 37° C. in LB medium supplemented with 100 µg/ml ampicillin (LBAmp). This preculture was adjusted with fresh LBAmp to an A600 nm=0.1, expression was induced by adding isopropyl-PD-thiogalactoside (IPTG) to a concentration of 1 mM, and the bacteria were allowed to grow for an additional 4 h. Cells were harvested by 15 min centrifugation at 4500×g at 4° C. The resulting cell pellets were stored at –20° C.

1 g of frozen cell pellets was re-suspended in 20 ml lysis-buffer (100 mM Tris, pH 8 containing 1 mg/ml lysozyme, 2 µg/ml avidin, 10,000-fold diluted benzonase and protease inhibitors (P 2714, Sigma, Taufkirchen)) and sonicated for 10 min (pulse: 10 sec on; 10 sec off) at 4° C. The crude extract was cleared by centrifugation at 10.000×g for 20 min to remove cell debris and the strep-tagged protein products isolated using Strep-tactin Macroprep (IBA GmbH, Gottingen, Germany) affinity chromatography columns according to manufacturer's instructions.

Jurkat cells (DSMZ-Deutsche Sammlung von Mikroorganismen und Zellkulturen GmbH, Braunschweig, Germany; Cat. # ACC282) were cultured in 90% RPMI 1640 (Invitrogen, Carlsbad, Calif., USA, Cat. # 42401042)+10% FBS (BioWhittaker, Verviers, Belgium, Cat. # US14-501 F)+2 mM L-glutamine (Invitrogen, Carlsbad, Calif., USA, Cat. #25030024), seed out after thawing at about $1×10^6$ cells/ml, split ratio of about 1:2 to 1:3 every 2–3 days; incubation at 37° C. with 5% $CO_2$). $2,5×10^7$ cells were harvested upon attaining a cell density of approximately $1.5×10^6$ cells/ml, pelleted at 300 g for 6 min at room temperature, and the pellet washed once with ice cold Dulbecco's PBS (PAA Laboratories, Linz, Austria, Cat. # H15-002). The pellet was re-suspended in 1 ml lysis buffer: 150 mM NaCl, 15 mM $MgCl_2$ (Merck, Darmstadt, Germany, Cat. # 1.06404.1000 and 1.05833.0250), 5 mM EDTA, 5% Glycerol (Serva, Heidelberg, Germany, Cat, # 11280 and 23176), 50 mM HEPES, pH 7.5, 1% Triton X-100, 1 mM DTT, 5 mM NaF, 1/10 protease inhibitor cocktail and phosphatase inhibitor cocktail II (Sigma-Aldrich, St. Louis, Mo., USA, Cat. # H9897, T8787, D0632, S7920, P2714 and P5726). Cells were lysed at 4° C. for 20 min. After centrifugation for 15 min at 4° C. and 16.000×g to remove cell debris, the pellet was discarded and the supernatant stored at –80° C. for further use.

Strep-tactin Macroprep resin (IBA GmbH, Gottingen, Germany) was also used as the matrix resin for the pull-

```
ON284  5'-GAT CTT GGA GCC ACC CGC AGT TCG AAA AAT A-3'  (SEQ. ID No. 1)

ON285  5'-AGC TTA TTT TTC GAA CTG CGG GTG GCT CCA A-3'  (SEQ. ID No. 2)
``` were combined and annealed by heating to 80° C. for 10 min and then cooling continuously to 30° C. over 20 min. After annealing, the double stranded fragment possesses ends suitable for recombination with the BglII and HindIII restriction ends of the linearized fragment of pQE40, and, when ligated, encodes a strep tag fused in frame to the his$_6$-DHFR fusion protein of pQE40.

down methods. The matrix was equilibrated with 30 volumes of chilled equilibration buffer (100 mM Tris buffer, pH 8) for 30 min, the buffer decanted, and a slurry was prepared by combining equal volumes of the wet resin and equilibration buffer.

25 µl of his$_6$-DHFR-Strep, 1 mg/ml, were preincubated on ice with 0.625 µl 20 mM NADPH and 1.25 µl 1 mM solution of the hybrid ligand MTX-(CH$_2$—O—CH$_2$)$_3$-purvalanol B for 15 min. Then 180 µl of Jurkat cell lysate, corresponding to lysate from 4.5×10$^6$ cells, was added. After 1 hour incubation at 4° C. under tilt rotation 50 µl of the Streptactin-resin slurry were supplemented and again incubated for 1 hour at 4° C. under tilt rotation. The resin was allowed to settle, the supernatant removed carefully using a pipet, and the remaining resin washed with 4×1 ml of ice-cold wash buffer (100 mM Tris, pH 8, 500 mM NaCl).

In order to elute the complexes bound to the resin, the resin is incubated 3 times with 36 µl of elution buffer (100 mM Tris, pH 8, 5 mM biotin) for 10 min by resuspending the matrix several times, allowing the matrix to settle, and removing the supernatant carefully using a pipet. The supernatant fractions and the used resin were stored at −80° C. for further analysis.

For the identification of proteins that had bound to MTX-(CH$_2$—O—CH$_2$)$_3$-purvalanol B, the supernatant fractions were digested with trypsin, analysed by LC-mass spectrometry (LC: Altimate NanoLC, Dionex, Sunnyvale, Calif., USA; MS: Esquire 3000, Bruker Daltonics, Billerica, Mass., USA) and the results compared to a peptide fragment library. Essentially, the results presented in Knockaert et al. (2000), Chem. Bio. 7:411–422, were confirmed, as CDKl/cyclin B, CDK2/cyclin A, CDK5/p25, CK1 (mammalian), Erkl, Erk2, S6 kinase (p7orsk) and CaM kinase II were identified.

Example 4

Pull-Down of Polypeptides Bound to the DNA Encoding them which Interact with a Hybrid Ligand of the Invention While pull-down experiments represent a useful method to isolate polypeptides binding to or interacting with a molecule of interest, the direct identification of polypeptides, for example using mass spectrometry or amino acid sequencing, is more cumbersome and less reliable than DNA sequencing. WO 93/08278, WO 98/37186, WO 01/14539 and WO 02/22826 present methods which combine the relative ease of pull-down methods in isolating molecular species interacting with a given target molecule with the convenience of DNA sequencing for the identification of polypeptide interactors.

In order to demonstrate the applicability of the methods shown in WO 93/08278, WO 98/37186, WO 01/14539 and WO 02/22826 to the hybrid ligands of the present invention, we devised an experimental protocol wherein a cDNA-library is expressed as a library of fusion proteins comprising a DNA-binding domain. The vectors encoding the library of fusion proteins each comprise the corresponding DNA-motif which the DNA-binding domain binds to. When expressed in a suitable host, the fusion proteins will bind to the vectors encoding them, and the complexes may be isolated and used for panning. For the panning of interaction partners for the hybrid ligands of the invention of general structure R1-Y—R2, the known interactor for R1, P1, is immobilized on a matrix, and the hybrid ligand is added such that it will be attached to the matrix via its binding to P1. Subsequently, the DNA-polypeptide complexes are added and unbound complexes are washed away. Finally, the DNA is isolated from the complexes and sequenced.

Construction of Plasmids pMC3 and pMC520

The bacterial strains used are E. coli K12 strains MC1061 (araD139 Δ(araABC-leu)7696 thr ΔlacX74_galU galK hsd.R mcrB rpsL(strA) thi), ARI20 (F' lac$^+$ pro$^+$ lacIq18 lacIam74//Δ (lac-pro) thi rpsL(strA) recA::cat), and XL1-Blue (F' proAB lacIq lacZΔM15 Tn10// recA1 endA1 gyrA96 thi hsdR17 supE44 re1A1 lac), and E. coli B strain ARI 161 (ion-11, su1A1, hsdR17, Δ(ompT-fepC), ΔclpA319::kan). AR1161 is a protease deficient strain and serves to minimize proteolysis of the peptides in the library, which would reduce the available diversity for panning. Mutations known to reduce proteolysis include degP, Ion, htpR, ompT, and clpA,P.

The library plasmid pMC5 is constructed in several steps using plasmid pBAD18 as the starting plasmid. Plasmid pBAD18 contains the araB promoter followed by a polylinker and a terminator under the control of the positive/negative regulator AraC, also specified by the plasmid. Plasmid pBAD18 also contains a modified plasmid pBR322 origin and the bla gene to permit replication and selection in E. coli, as well as the phage M13 intragenic region to permit rescue of single-stranded DNA for sequencing.

The lacI gene is modified for cloning into plasmid pBAD18 using the GeneAmp® PCR amplification kit (Perkin-Elmer Cetus Instruments) with oligonucleotides ON-286 and ON-287, shown below:

```
ON-286 5'-GCG GGC TAG CTA ACT AAT GGA GGA TAC ATA AAT    (SEQ. ID No. 3)
         GAA ACC AGT AAC GTT ATA CG-3'

ON-287 5'-CGT TCC GAG CTC ACT GCC CGC TCT CGA GTC GGG    (SEQ. ID No. 4)
         AAA CCT GTC GTG C-3'.
```

The amplification reaction is carried out according to the manufacturer's instructions, except for the use of Vent™ DNA polymerase (New England Biolabs, Beverly, Mass., USA). ON-286 contains a nonhomologous 5' region that adds an NheI site, a consensus ribosome binding site (see Gold and Stormo, 1990, Methods in Enzymology (Goeddel, ed., Boston: Academic Press), pp. 89–103, incorporated herein by reference), and changes the initiation codon of lacI from GTG to ATG. ON-287 changes codons 356 and 357 of lacI to an XhoI site through two silent mutations, and adds a SacI site after the lacI stop codon. The sequence of the PCR product is confirmed by sequencing.

Cloning of the NheI, SacI digested amplification product into plasmid pBAD18 produced vector pJS100. Two lacO$_s$ sequences are added to this vector, with their centers spaced 326 bp apart, by amplifying an unrelated sequence (the human D2 dopamine receptor gene; see: England et al., 1991, FEBS Lett. 279:87–90, incorporated herein by reference), with oligonucleotides ON-295 and ON-296, shown below:

```
ON-295  5'-CCT CCA TAT GAA TTG TGA GCG CTC ACA ATT CGG    (SEQ. ID No.5)
        TAC AGC CCC ATC CCA CCC-3'

ON-296  5'-CGC CAT CGA TCA ATT GTG AGC GCT CAC AAT TCA    (SEQ. ID No. 6)
        GGA TGT GTG TGA TGA AGA-3'
```

ON-295 adds an NdeI site and a lacO$_s$ sequence at one end of the amplified fragment, and ON-296 adds a ClaI site and lacO$_s$ at the other end. Cloning of the NdeI to ClaI fragment into pJS100 produced plasmid pJS102.

Plasmid pMC3, encoding the dynorphin B-tailed lac repressor, is constructed by cloning complementary oligonucleotides ON-312 and ON-313 to replace the XhoI to XbaI fragment at the 3' end of lacI in pJS102. These oligonucleotides add sequence encoding a five amino acid spacer (GADGA (SEQ. ID No. 7)) and dynorphin B (YGG-FLRRQFKVVT (SEQ. ID No. 8)) to the end of the wild-type lacI sequence, introduce an SfiI site in the sequence encoding the spacer, and are shown below:

The 3'-phosphorylated oligonucleotides ON 369 and ON 370 are synthesized to possess the sequences

```
ON 369:  5'-AGC AGC AGC AGC-3'      (SEQ. ID No. 14)
ON 370   5'-GCT GCT GCT GCT CGT-3'  (SEQ. ID No. 15)
```

When annealed and ligated to the cDNA library, these oligonucleotides create an end compatible with the SfiI-restriction fragment of vector pMC5.

400 pmol of each oligonucleotide are annealed in 25 µl reaction buffer (10 mM Tris, pH 7.4, 1 mM EDTA, 100 mM NaCl), by heating to 65° C. for 10 min and cooling for 30

```
ON-312  5'-TCG AGA GCG GGC AGG GGG CCG ACG GGG CCT ACG    (SEQ. ID No. 9)

GTG GTT TCC TGC GTC GTC AGT TCA AAG TTG TAA CCT

AAT-3'

ON-313  5'-CTA GAT TAG GTT ACA ACT TTG AAC TGA CGA CGC    (SEQ. ID No. 10)

AGG AAA CCA CCG TAG GCC CCG TCG GCC CCC TGC CCG

CTC-3'
```

The library plasmid pMC5 is constructed by cloning complementary oligonucleotides ON-335 and ON-336 to replace the SfiI to HindIII dynorphin B segment of pMC3. Oligonucleotides ON-335 and ON-336 are shown below:

```
                                                    (SEQ. ID No. 11)
ON-335   5'-GGG CCT AAT TAA TTA-3'

(SEQ. ID No. 12)
ON-336   5'-AGC TTA ATT AAT TAG GCC CCG T-3'
```

Plasmid pMC3 is available in strain ARI161 from the American Type culture Collection under the accession number ATCC No. 68818.

Construction of a cDNA Library in Vector pMC5

To construct a library of plasmids encoding the DNA-binding lac repressor fused to a library of polypeptides, a cDNA library is generated from poly A+ RNA isolated from human fetal brain (hFB) (Clontech, CAT# 6525-1) essentially using a commercially available protocol and reagents (Superscript, Invitrogen, Carlsbad, Calif., USA, CAT. NO. 18248-013) but employing oligo-dT primers for first-strand synthesis as follows:

min to room temperature, and ligated to the cDNA-library by standard procedures. The vector pMC5 is digested to completion with SfiI and HindIII, the cDNA library only with HindIII, and the vector backbone and the cDNA digestion products are isolated by 4 rounds of washing with TE buffer (10 mM Tris, pH 8.0, 1 mM EDTA) in a Centricon 100 microconcentrator (Amicon) by the manufacturer's instructions, followed by phenol extraction and ethanol precipitation. The digested library is added to 64 µg of digested pMC5 in a 3.2 ml ligation reaction containing 5% PEG, 3200 units of HindIII, 194 Weiss units of T4 ligase (New England Biolabs, Beverly, Mass., USA), 1 mM ATP, 20 mM Tris, pH 7.5, 10 mM MgCl$_2$, 0.1 mM EDTA, 50 µg/ml BSA, and 2 mM DTT. The reaction is split equally into 8 tubes and incubated overnight at 15° C.

After ethanol precipitation, 1/16 of the ligated DNA (4 µg) is introduced into MC1061 (80 µl) by electroporation (Dower et al., 1988, Nucl. Acids Res. 16:6127–6145, incorporated herein by reference), to yield 5.5×10$^8$ independent transformants. The library is amplified approximately 1000-fold in 1 liter of LB/100 µg/ml ampicillin by growth of the transformants at 37° C. to an A$_{600}$ of 1. The cells containing the library are concentrated by centrifugation at 5500×g for

```
TT2-A:  5'TTT TGT ACA TCT AGA TCG CGA AAG CTT CTT TTT TTT    (SEQ. ID No. 13)
        TTT TTT TV-3'
``` with V being A, G, or C at equal molar ratio. This primer introduces a HindIII restriction site.

6 min, washed once in ice-cold 50 mM Tris (pH 7.6), 10 mM EDTA, 100 mM KCl, followed by a wash in ice-cold 10 mM Tris, 0.1 mM EDTA, 100 mM KCl. The final pellet is resuspended in 16 ml of HEG buffer (35 mM HEPES/KOH, pH 7.5, 0.1 mM EDTA, 100 mM Na Glutamate), distributed into 19 tubes of 1.0 ml each, frozen on dry ice, and stored at −70° C.

Panning the Library

Vector pQE40 (Qiagen, Hilden, Germany), comprising the gene encoding DHFR fused to a his6-tag, is transformed into E. coli strain JM109 and the $His_6$-DHFR fusion protein isolated and purified as described above (see Example 3). $His_6$-DHFR is subsequently coupled to HIS-Select HS Nickel coated microtiter plates (Sigma, Cat. No. S 5688) according to manufacturers instructions using a volume of 150 μl/well at a concentration of 1,5 μg/ml $His_6$-DHFR fusion protein in PBS (Sigma, Cat. No. P 3813) at pH 7.0 for 4 h at room temperature. Wells are washed 3 times with PBS containing 0,05% Tween 20 (Sigma, Cat. No. P 3563), followed by incubation with 100 μl] of a 10 uM solution of GPC 285985 in PBS, pH 7.0, containing 0,5 mM NADPH, for 1 h at room temperature, or with 0,5 mM NADPH PBS for control wells.

One aliquot (1.0 ml) of the library prepared in Example 2 is thawed on ice and added to 9 ml of lysis buffer (35 mM HEPES adjusted to pH 7.5 with KOH, 0.1 mM EDTA, 100 mM Na glutamate, 5% glycerol, 0.3 mg/ml BSA, 1 mM DTT, and 0.1 mM PMSF). Lysozyme is added (0.3 ml at 10 mg/ml in HEG), and the mixture is incubated on ice for 1 hr.

The cellular debris is removed by centrifugation of the lysate at 20,000×g for 15 min, and the supernatant is concentrated by centrifugation in a Centriprep® 100 concentrator (Amicon) at 500×g for 40 min The concentrated supernatant (about 0.5 ml) is washed with 10 ml of HEG buffer and centrifuged as before. A sample (5%) of the total lysate is removed to determine the pre-panned input of plasmid complexes.

An alternate method for partially purifying and concentrating the lysate is as follows. About 2.0 ml of the frozen cells in HEG are thawed on ice, and then 8 ml of lysis buffer without Na glutamate (high ionic strength inhibits lysozyme; DTT is optional) are added to the cells, and the mixture is incubated on ice for 1 hr. The cellular debris is removed from the lysate by centrifugation at 20,000×g for 15 min, and the supernatant is loaded onto a Sephacryl® S-400 High Resolution (Pharmacia) gel-filtration column (22 mm×250 mm). The plasmid-fusion protein complexes elute in the void volume. The void volume (30 ml) is concentrated with two Centriprep® 100 concentrators, as described above. After adjusting the Na glutamate concentration of the concentrate, one carries out the remainder of the procedure in the same manner as with the first method.

195 μl of the concentrated lysate are adjusted to 0,5 mM NADPH by adding 5 μl of 20 mM NADPH in PBS, and the solution is added to a DHFR-GPC 285985 treated well of a HIS-Select HS Nickel coated microtiter plate, another 200 μl of this solution is added to a control well lacking GPC 285985. After incubating the lysates in the wells at 30° C. for 1 hr. with shaking, the wells are washed three times with 200 μl of cold HEG/O. 1% BSA and then three times with HEG. The plasmids are dissociated from the wells by phenol extraction, and after adding 20 pg of glycogen 35 (Boehringer Mannheim), the DNA is precipitated with an equal volume of isopropanol. The pellet is washed with 75% ethanol, and the DNA is resuspended in 4 μl of $H_2O$. Strain MC 1061 is transformed using 2 μl each of the DNA solutions to permit counts of recovered plasmids and amplification of the selected plasmids. Optionally, additional rounds of panning may be added.

ELISA Analysis of the Library

An ELISA is used to test MC1061 transformants from the panning for GPC 285985-specific ligands. The ELISA is performed in a 96-well plate (Beckman). Single colonies of transformants obtained from panning are grown overnight in LB/100 μg/ml ampicillin at 37° C. The overnight cultures are diluted ⅒ in 3 ml LB/100 μg/ml ampicillin and grown 1 hr. The expression of the lac repressor-peptide fusions is induced by the addition of arabinose to a final concentration of 0.2%.

The cells are lysed as described above in 1 ml of lysis buffer plus lysozyme and stored at −70° C. Thawed crude lysate is added to each of 2 wells (1.00 μl/well), and the plate is incubated at 37° C. After 45 min, 100 μl of 1% BSA in PES (10 mM NaPO4, pH 7.4, 120 mM NaCl, and 2.7 mM KCl) are added for an additional 15 min at 37° C., followed by 3 washes with PBS/0.05% Tween 20. Each well then is blocked with 1% BSA in PES (200 μl/well) for 30 min at 37° C., and the wells are washed as before.

GPC 285985 (100 μl of a 10 μM solution in PBS/0.1% BSA) is added to each well, the plate is incubated at room temperature for 1 hr., and then each well is washed as before. $His_6$-DHFR fusion protein is prepared as described above, and 150 μl/well at a concentration of 1,5 μg/ml $His_6$-DHFR fusion protein in PBS/0.1% BSA is added to the wells and incubated for 2 h at 37° C., followed by 3 washes with 150 μl PBS/0.1% BSA. Bound $His_6$-DHFR fusion protein is detected using an anti-His6 antibody coupled to horseradish peroxidase (RGS-His HRP Conjugate Kit, Qiagen, Hilden, Cat. # 34450) following manufacturers instructions. To determine the structure of the peptide ligands obtained by the present method, plasmids from both ELISA positive and ELISA negative colonies obtained after panning are sequenced. Double stranded plasmid DNA, isolated from strain XL1-Blue, is sequenced using Sequenase@ (US Biochemicals) according to the instructions supplied by the manufacturer.

Example 5

Construction of Genetic Constructs and Yeast Strains for a Yeast Three Hybrid Experiment Employing a Transcriptional-Based Interaction System A yeast three hybrid experiment employing a transcriptional-based interaction system was demonstrated by utilizing a yeast strain comprising three genetic constructs: a first construct encoding a fusion protein comprising a DNA-binding domain (BD) and a first protein or peptide (P1) able to specifically bind the first ligand R1 of the envisaged hybrid ligand R1-Y—R2; a second construct encoding a fusion protein comprising a transcriptional activation domain (AD) and a second protein or peptide, or a library of second proteins or peptides, (P2) able or suspected to bind the second ligand R2 of said envisaged hybrid ligand; a third construct comprising a reporter gene under the transcriptional control of a promoter comprising the genetic sequence the BD is able to bind to, wherein the AD must be capable of initiating the transcription of the reporter gene when brought in spatial proximity of the promoter via bridging interaction of the hybrid ligand between the BD-comprising fusion protein and the AD-comprising fusion protein.

Two plasmids were constructed: the first plasmid containing a fragment encoding the bacterial LexA binding domain for expression as a fusion with a first protein; the second plasmid containing a fragment encoding the yeast GAL4 transcriptional activation domain for expression as a fusion with a second protein. These plasmids were transformed into yeast cells deficient in the endogenous HIS3 locus but comprising a genetic construct combining a recombinant his3 gene with a promoter containing the LexA binding sequence. Since methotrexate was chosen as the first ligand R1 in the present investigations, the sequence encoding the LexA BD was fused to the gene encoding E. coli dihydrofolate reductase (folA). The sequence encoding the GAL4 transcriptional activation domain was fused either to the gene encoding the dexamethasone-binding rat glucocorticoid receptor gr2, the genes for human cdk2 (hcdk2) or cdk4 (hcdk4) or to a library of genes from a human brain cDNA library, depending on the choice of R2.

Yeast strain L40 (Invitrogen, Carlsbad, Calif., USA,; MATa, his3-A200, trp1-901, leu2-3,112, ade2, LYS2::(1ex-Aop)$_4$—HIS3, URA3::(1exAop)$_8$-LacZ, ga180) was chosen for the experiments in yeasts described herein. However, other suitable yeast strains, or even other cell types, such as bacteria, insect cells, plant cells or mammalian cells may be chosen for the methods of the invention, provided, the cells comprise a reporter system that allows a detectable readout that is conditional on the formation of a trimeric complex of the hybrid ligand together with the first and second fusion proteins.

For the DNA binding domain-fusion plasmid, the E. coli folA (dihydrofolate reductase, DHFR) coding sequence was PCR amplified from a genomic library (Clonetech, Cat. No.: XL4001AB) using primers CR89 and CR 90

```
CR 89   5'-GGG GTC GAC ATG ATC AGT CTG ATT GCG GCG TTA     (SEQ. ID No. 16)
        GCG-3'

CR 90   5'-GGG GGC GGC CGC TTA CCG CCG CTC CAG AAT CTC     (SEQ. ID No.
                                                          17).
        AAA G-3'
```

The sequence of the PCR product was confirmed by sequencing. The PCR product was digested with SalI and NotI, and the resulting 479 bp fragment was subcloned into pBTM118c containing TRP1 as a selectable marker in yeast (see Wanker et al., WO 99/31509), resulting in the construct pBTM 118c-DHFR.

For the activation domain fusion-plasmid comprising the rat glucocorticoid receptor, a gene fragment encoding amino acids 524–795 of the rat glucocorticoid receptor was PCR amplified from a rat brain cDNA library (Life Technologies, Cat. No. 10653-012) using primers CR91 and CR92:

```
CR91  5'-GGG GTC GAC ATG GGT GGT GGT GGT GGT GGT GCA      (SEQ. ID No. 18)
         GGA GTC TCA CAA GAC-3'

CR92  5'-GGG GGC GGC CGC TTT TTG ATG AAA CAG AAG-3'.      (SEQ. ID No. 19)
```

The sequence of the PCR product was confirmed by sequencing. The PCR product was digested with SalI and NotI, and the resulting 813 bp fragment was subcloned into pGAD426c containing LEU2 as a selectable marker in yeast (Wanker et al., WO 99/31509). Subsequently, amino acids F620 and C656 of GR2 were replaced with Ser and Gly respectively to increase the affinity of GR2 for dexamethasone (Chakraborti et al., 1991, J. Biol. Chem., 266: 22075–22078), using a site-directed mutagenesis PCR reaction. Mutagenesis was performed employing the "Quick-Change Site directed mutagenesis kit" (Stratagene, Amsterdam, Netherlands) according to manufacturers protocols. The presence of these mutations was confirmed by sequencing. The resulting construct was designated pGAD426c-GR2.

For the activation domain fusion comprising hcdk2, the cDNA encoding hCDK2 was amplified from the human placenta MATCHMAKER cDNA library (C!ontech, Cat# HL4025AH, Heidelberg, Germany) by PCR using primers CR92 and CR93

```
                                                (SEQ. ID No. 20)
CR92    5'-GGG TCG ACG CAT GGA GAA CTT CC-3'

(SEQ. ID No. 21)
CR93    5'-GGG CGG CCG CTC AGA GTC GAA G-3'.
```

Similarly, hcdk4 cDNA was amplified by PCR using primers CR94 and CR95:

```
                                                (SEQ. ID No. 22)
CR94    5'-GGG TCG ACG CAT GGC TAC CTC TCG-3'

(SEQ. ID No. 23)
CR95    5'-GGGCGGCCGCTCAGGCTGTATTCAGC-3'.
```

The sequences of the PCR products were confirmed by sequencing. After digestion of the PCR products with SalI and NotI, the resulting 894 bp (CDK2) and 909 bp (CDK4) fragments were individually subcloned into pGAD426c, and the sequences of the clones verified by DNA sequencing. The resulting constructs were termed pGAD426c-hCDK2 and pGAD426c-hCDK4, respectively.

Figures 17A, 17B:
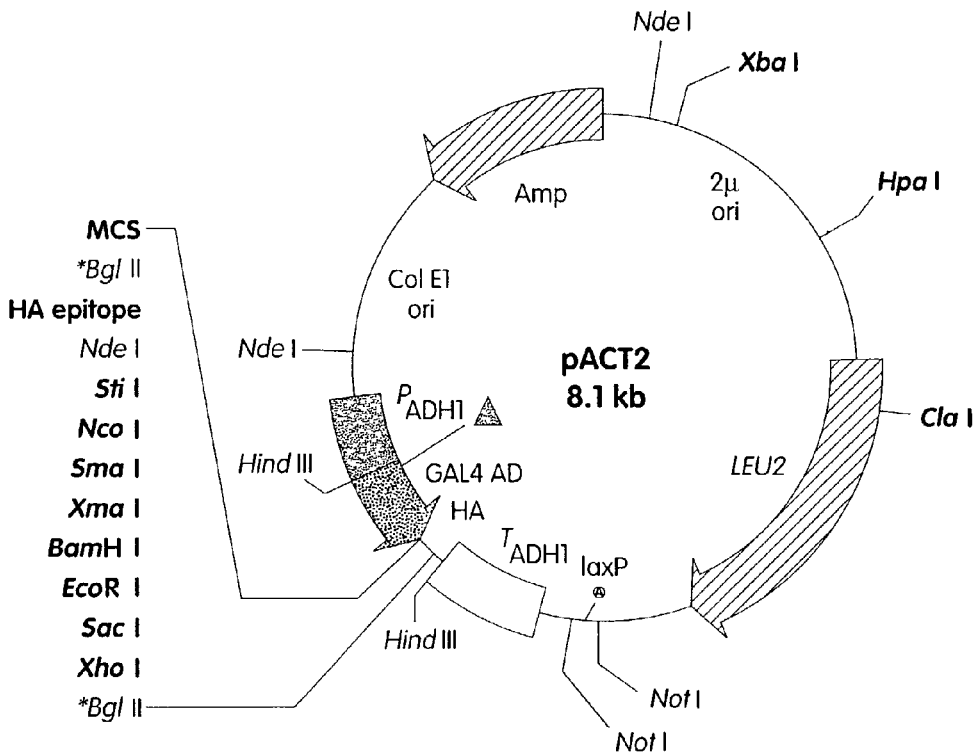
FIGS. 17A and 17B. Description of plasmid pACT2; a human fetal brain cDNA library was obtained commercially from Clontech that was cloned in this vector and used subsequently in screening experiments. a. A vector map. b. A restriction map and multiple cloning site (SEQ ID NO: 41).

A library of human fetal brain cDNA's fused to the gene encoding the GAL4 activation domain cloned into vector pACT2 (Clontech, Cat. No.: HY4004AH; see FIG. 17) bearing LEU2 as a yeast selectable marker was used as purchased for clone selection experiments in yeast as described in Example 10.

Example 6

The Halo Growth Assay

A halo growth assay was conducted to test the dimerizing capacity of hybrid ligands of the invention. FIG. 4 a. shows a halo growth in a petri dish spotted with GPC 285937. Dimerization of the LexA-DNA Binding Domain (LexA-BD)—DHFR and GAL4-transcription activation domain (GAL4-AD)GR2 fusion proteins in the presence of GPC 285937 in the L40 yeast strain caused transcription of the His3 reporter gene. This transcriptional expression of HIS3 enabled the yeast cells to overcome the lack of histidine in the medium, leading to cell growth in the area to which sufficient GPC 285937 had diffused from the center of the dish. Conversely, no visible growth appears in the control dish spotted with DMSO only shown in FIG. 4b.

To conduct the halo assay, plasmids pGAD426c-GR2 and pBTM118c-DHFR were co-transformed into the yeast strain L40 using standard yeast methods (Burke at al., Methods in yeast genetics: A Cold Spring Harbor Laboratory course manual; Cold Spring Harbor Laboratory Press, 2000). Transformants receiving both plasmids were selected on media lacking trp and leu. Individual colonies were then inoculated and incubated in liquid SD-medium for 24 hrs. The cultures were diluted to a density of $10^6$ cells/ml and 100 µl were plated on a 10 cm petri dish containing SD medium lacking trp, leu and his. 1 µl of a 1 mM solution of GPC 285937 dissolved in DMSO or 1 µl of DMSO as control was spotted in the center of each petri dish. The growth of yeast cells was determined after 2 days of growth at 30° C.

Example 7

The Fluorescence Detection Growth Assay

To demonstrate the suitability of the fluorescence detection growth assay employing the PreSens Precision Sensing GmbH (Regensburg, Germany) OxoPlate, an experiment analogous to Example 4 was performed. Yeast cells were transformed with the plasmid encoding the DHFR-LexA DNA binding domain fusion protein and either the plasmid encoding hCDK2 or hCDK4 fused to the GAL4 activation domain. Cells of the resulting strain were seeded into wells of an Oxoplate and exposed to one of four conditions: 1) SD medium lacking leu and trp (positive control); 2) SD medium lacking leu, trp and his (negative control); 3) SD medium lacking leu, trp and his and supplemented with a range of concentrations (1 mM to 4 µM) of GPC 285985, a compound known to bind strongly to DHFR and hCDK2, but only weakly to hCDK4; 4) SD medium lacking leu, trp and his and supplemented with 1 mM GPC 285993, a compound known to bind strongly to DHFR, but not to hCDK2 or hCDK4 (compound selectivity control).

Figure 8:
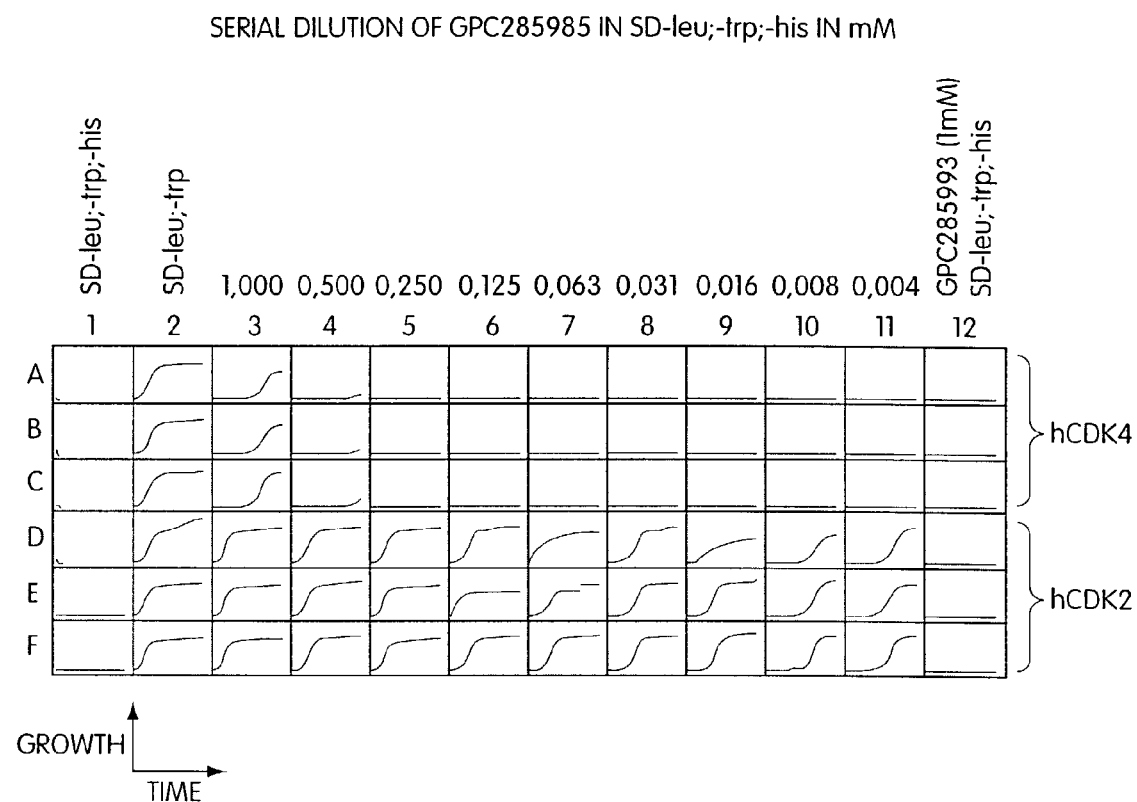
FIG. 8. Growth curves of yeast cultures exposed to different concentrations of the hybrid ligand GPC 285985 in medium lacking histidine as measured by oxygen consumption using an OxoPlate (PreSens, Germany). Yeast cultures expressing the CDK2 fusion protein show typical growth curves over time. In contrast, yeast cultures expressing a CDK4 fusion protein only show growth at the high concentrations of the hybrid ligand, confirming the specificity of the hybrid ligand to CDK2.

The results obtained in this experiment are represented in FIG. 8, and as expected, no oxygen consumption due to growth of cells was observed in the negative controls or the compound selectivity controls. In contrast, growth was observed in the positive controls and in the cells transformed with the construct encoding the hCDK2 fusion protein at all concentrations of GPC 285985, albeit growth onset was slightly delayed at the lowest concentrations of GPC 285985. Cells transformed with the construct encoding the hCDK4 fusion protein grew only when exposed to a high concentration (1 mM) of GPC 285985, further confirming the specificity of binding of this hybrid ligand compound to hCDK2.

The fluorescent assay was conducted as follows: First, cells of yeast strain L40 were co-transformed with pBTM 118c-DHFR and one of either pGAD426c-hCDK2 or pGAD426c-hCDK4 using standard techniques (Burke at al., Methods in yeast genetics: A Cold Spring Harbor Laboratory course manual; Cold Spring Harbor Laboratory Press, 2000). Transformants containing both plasmids were selected on SD medium lacking trp and leu, and individual colonies were inoculated in liquid SD-medium and incubated for 48 hrs at 30° C. Second, cells were precipitated and washed with sterile water 3 times, the cell number adjusted to a density of $10^8$ cells/ml and 50 µl transferred to each well of an OxoPlate F96 (PreSens Precision Sensing GmbH, Regensburg). 150 µl of a solution representing one of four conditions was added: 1) SD-medium lacking leu, trp and his (wells A11-F1, negative control); 2) SD -leu, -trp (wells A2-F2, positive control), 3) SD-medium lacking leu, trp and his supplemented with the compound GPC 285985 at concentrations of 1 mM, 0,5 mM, 0,25 mM. 125 µM, 63 µM, 31 µM, 16 µM, 8 µM or 4 µM (wells A3-F11); 4) SD-medium lacking leu, trp and his supplemented with 1 mM of the control compound GPC 285993 (A12-F12, compound selectivity control). Third, oxygen consumption of growing yeast cells was monitored as a function of the ratio of fluorescent emissions of a first fluorescent dye that was quenchable by oxygen (emission at 590 nm) and a second dye unquenchable by oxygen (emission at 640 nm). This ratio of fluorescence was monitored over 18 hours in 20 min intervals at 30° C. using a Perkin Elmer Wallac Victor2 V 1420 multilabel HTS counter (Perkin Elmer, Wellesley, Mass., USA) with an excitation setting of 540 nm and an emission setting of 590/640 nm (dual kinetic mode).

Example 8

Testing of Hybrid Ligand Compounds for Effects not Related to Dimerization

Effects of hybrid ligand compounds independent of their dimerizing action on the cells used for an assay may invalidate results from assays employing these compounds. Such effects may be, for example, toxicity or growth promotion via routes other than lack of, or induced production of, leucine, tryptophane and/or histidine in the assays described above. Therefore, the in vivo effect of the hybrid ligands was determined in a halo growth assay as described in Example 4, but using empty (i.e. not containing the subcloned gr gene and hence lacking a second ligand P2 to bind R2) pGAD426c instead of pGAD426c-GR. 1 µl each of a dilution series of the hybrid ligands (10 mM to 1 µM in DMSO) were used for spotting in the center of petri dishes prepared to contain either medium lacking trp and leu, or trp, leu and his and plated with L40 yeast cells containing the plasmids pGAD426c and pBTM118c-DHFR. Growth was monitored after two days of incubation at 30° C. Cells are expected to grow irrespective of concentration of the hybrid ligand compound on media lacking only trp and leu, while no growth should appear on media lacking trp, leu and his. This expected behaviour was observed with all hybrid ligand compounds used herein at all concentrations tested.

Example 9

Improved Functionality of the Dimerizing Hybrid Ligands of the Present Invention Over the State of the Art To compare Mtx-mdbt-Dex (Lin et al., J. Am. Chem. Soc. 2000, 122:4247–8) with Mtx-(ethylenglycol)$_3$-Dex (GPC 285937) in a yeast three hybrid assay, we first prepared dilutions of both compounds in liquid SD medium lacking his, trp and leu, in a concentration range from 1 mM to 1 µM by adding the appropriate amount of compound dissolved in DMSO to the medium. Second, L40 yeast cells were transformed with plasmids pBTM 118c-DHFR and pGAD426c-GR2 and inoculated into the media containing the compounds in different amounts at a density of 0.1 OD$_{595}$. Growth was monitored for 48 hours by measuring OD$_{595}$ on a Perkin Elmer Wallac Victor2 V 1420 multilabel HTS counter (Perkin Elmer, Wellesley, Mass., USA). It appeared that the yeast strain grew in a window of between 25 to 400

μM showing optimum growth at 100 μM GPC 285937 (Data not shown). However, at these concentrations, Mtx-mdbt-Dex showed severe precipitation in the medium (See FIG. 5). This precipitation may cause the compound to be less bio-available and hence growth of yeast cells in the presence of this compound to be impaired.

The functional advantages of a hybrid ligand of the invention; Mtx-(ethylenglycol)$_3$-Dex (GPC 285937) over the prior-art compound Mtx-mdbt-Dex was further shown in a halo assay as follows. First, L40 yeast strain was transformed with plasmids pBTM118c-DHFR and pGAD426c-GR2 and transformants containing both plasmids were selected on media lacking trp and leu. Second, individual colonies were inoculated in liquid SD-medium and incubated for 24 hrs. The cell cultures were diluted to a density of 106 cell/ml and 100 μl were plated on a 10 cm petri dish containing SD medium lacking trp, leu and his. Third, 1 μl of a 1 mM solution of GPC 285937 (three ethylenglycol units as linker) or Mtx-mdbt-Dex (metadibenzothioester as a linker) dissolved in DMSO was spotted in the center of each petri dish. The growth of yeast cells was determined after 2 days of growth at 30° C.

Figure 6:
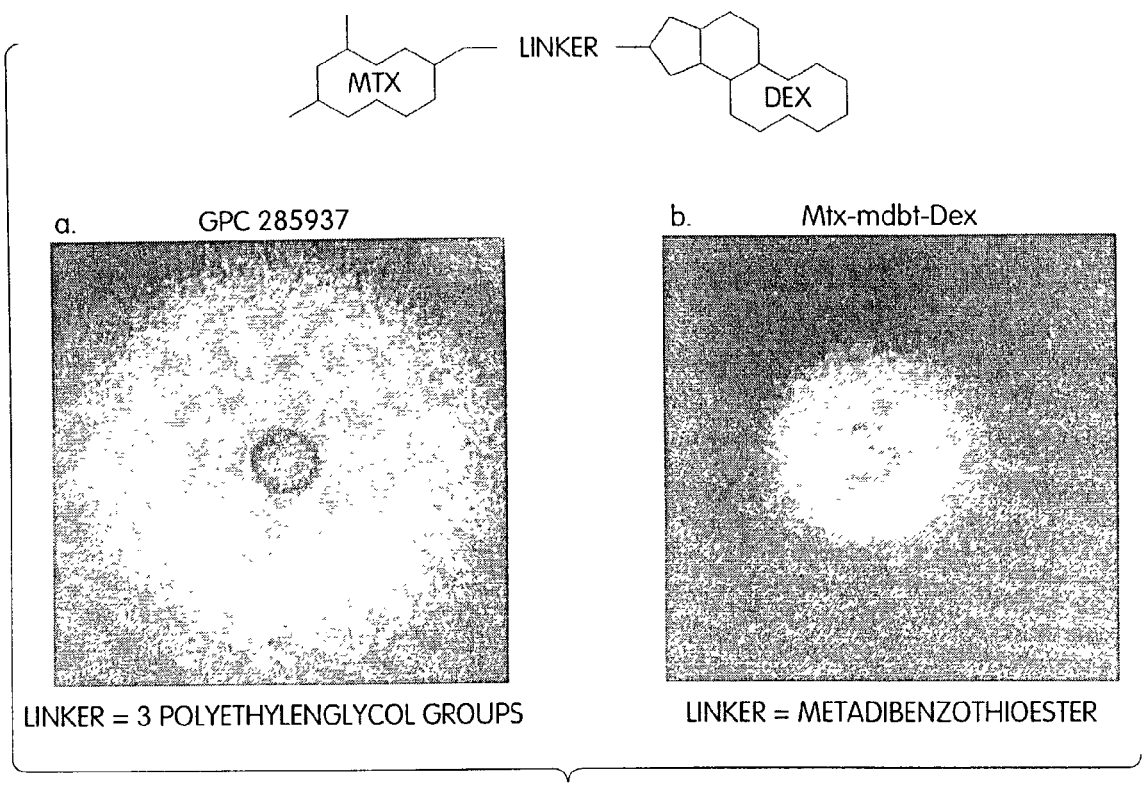
FIG. 6. Influence of different linker moieties of hybrid ligands and their biological effects. A hybrid ligand of the invention (GPC 285937) employs 3 ethylenglycol (EG) groups as a linker, which offers improved superiority over the metadibenzothioester linker present in the prior art hybrid ligand Mtx-mdbt-Dex by promoting better overall growth of the colony.

FIG. 6 a. shows the growth halo that developed around the point of application of GPC 285937, while FIG. 6b displays the same result for Mtx-mdbt-Dex. The growth halo of yeast cells receiving Mtx-mdbt-Dex was much smaller than that of the hybrid ligand of the invention, further demonstrating the superiority of the latter.

Figure 7A:
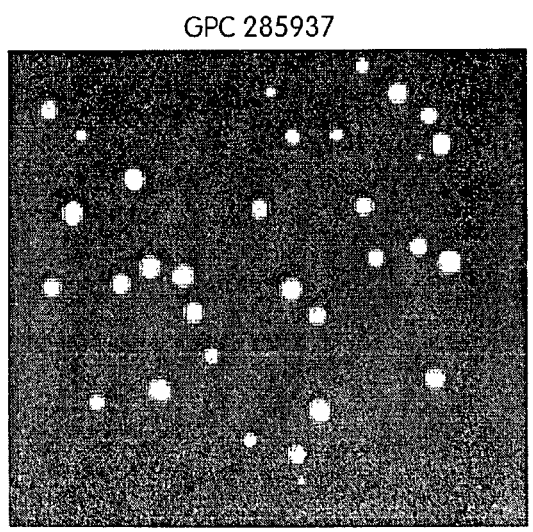
FIGS. 7A and 7B. Difference in growth of yeast colonies on screening plates in the presence of either GPC 285937 or Mtx-mdbt-Dex. Colonies growing on media with Mtx-mdbt-Dex were hardly detectable, whereas clones grew visibly better on media containing GPC 285937.
Figure 7B:
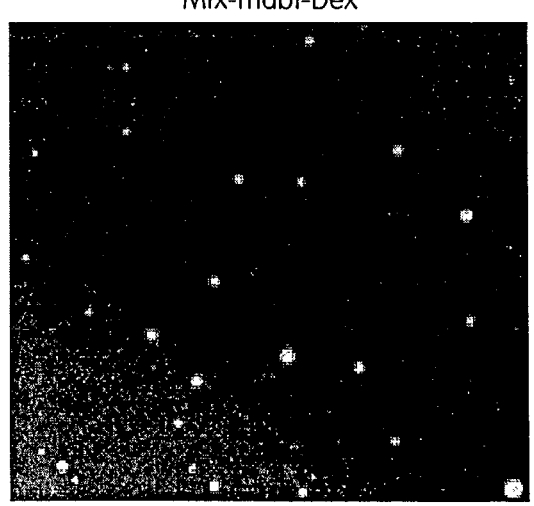

A hybrid ligand of the invention also showed significant improvement over the prior art hybrid ligand under conditions appropriate to library screening of yeast cells. The yeast strain L40 was cotransformed with the plasmids pBTM 118c-DHFR and pGAD426c-GR2. Transformants containing both plasmids were selected on media lacking trp and leu, and individual colonies were inoculated in liquid SD-medium and incubated for 24 hrs. These cell cultures were diluted to a density of $10^4$ cell/ml and $2 \times 10^4$ cells were plated on 22×22 cm plates containing yeast synthetic agar medium lacking his, trp and leu but containing 200 μM GPC 285937 or Mtx-mdbt-Dex. Growth of individual colonies was monitored after 48 h at 30° C. Colonies growing on SD-media with Mtx-mdbt-Dex were hardly detectable, whereas clones visibly grew better on media containing GPC 285937, a hybrid ligand of the invention (FIG. 7).

Example 10

Figure 16A:
FIGS. 16A and 16B. Effects of linker length (number of PEG repeats in the linker) on functionality as measured by biological activity in a three-hybrid halo assay. Yeast halo growth was only seen in cells in the presence of GPC 286026 (5 PEG units as a linker) but not in the presence of GPC 286004 (3 PEG units as linker).
Figure 16B:

Advantages of Different Embodiments of the Dimerizing Hybrid Ligands of the Present Invention For certain small molecules, particular physiochemical properties such as solubility may require a particular choice of linker to be used in order to generate particularly advantageous hybrid ligands of the general structure R1-Y—R2. For example, the bioavailability and, hence, biological activity may be further enhanced by adding additional (—CH2-X-CH2) repeats to the linker Y. This was the rationale behind the synthesis of the hyrbid ligands GPC 286004 (comprising an (ethylenglycol)$_3$ linker and GPC 286026 comprising an (ethylenglycol)$_5$ linker. Plasmid pGAD426c-hCDK2 was cotransformed with pBTM118c-DHFR into the yeast strain L40. Transformants containing both plasmids were selected on media lacking trp and leu, and individual colonies were inoculated in liquid SD-medium and incubated for 24 hrs. These cultures were diluted 1:10 and 20 μl of the diluted culture was spotted in duplicate on a 10 cm petri dish containing SD medium that lacks trp, leu and his. 1 μl of a 1 mM solution of GPC 286004 or GPC 286026 dissolved in DMSO was spotted in the center of each spot. The growth of yeast cells was determined after 3 days of growth at 30° C. The results of this halo assay show that after 3 days on medium lacking leu, trp and his, halo growth was only seen in the presence of GPC 286026 (five ethylenglycol units as linker; FIG. 16b.) but not in the presence of GPC 286004 (three ethylenglycol units as linker; FIG. 16 a.), This demonstrated the superior suitability of the (ethylenglycol)$_5$ linker group over the (ethylenglycol)$_3$ linker group when linking these two particular compounds to form a hybrid ligand.

Example 11

Methods of Testing a Polypeptide for Binding to a User-Specified Ligand: a Three-Hybrid Assay System Based on a Reporter System Using Transcriptional Activation In certain embodiments, the methods of the invention are used to test polypeptides for their ability to bind to a user-specified ligand. To demonstrate this concept, we first designed a three-hybrid experiment using a small-molecule compound to distinguish between two polypeptides. The first polypeptide was known to bind with high affinity to the small-molecule compound, while the second was known to bind to the small-molecule compound only weakly. For this purpose, said small-molecule compound was integrated into a hybrid ligand of the invention, and used in a three hybrid screen with a transcriptional-based interaction system.

Figure 10:
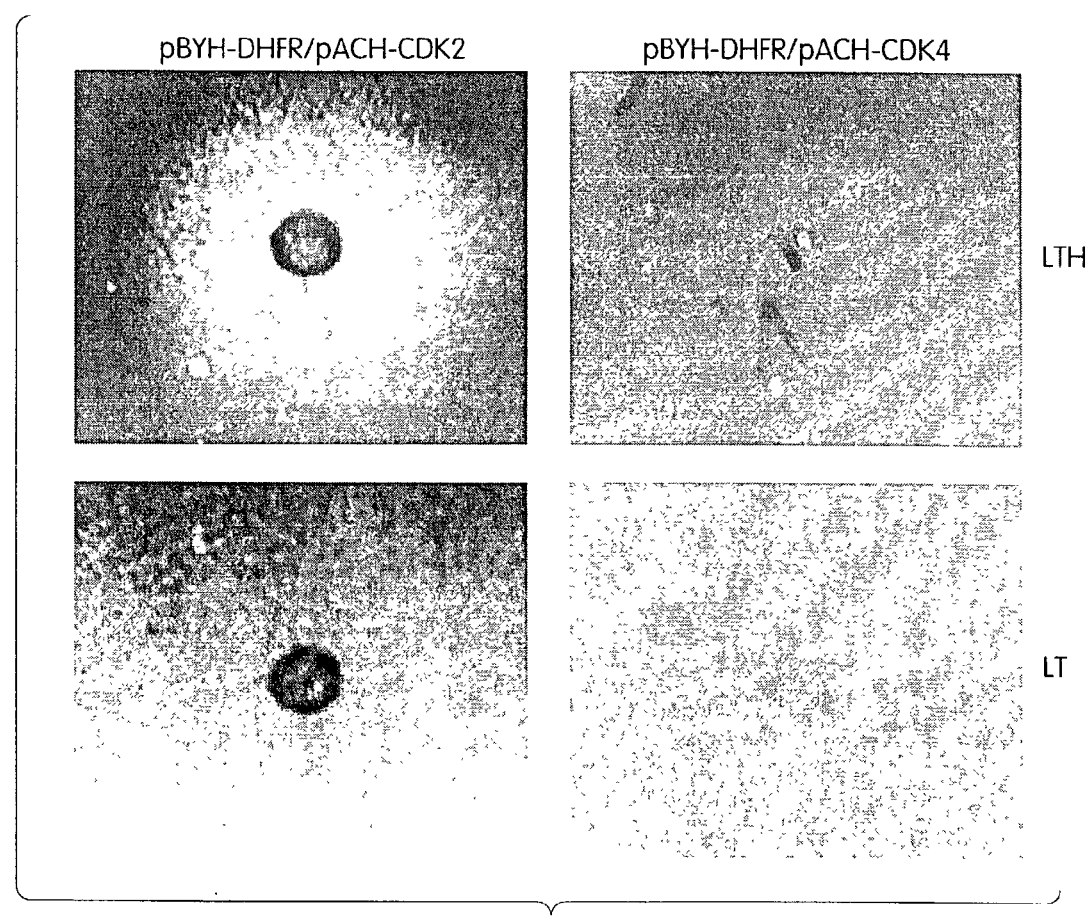
FIG. 10. A test of the hybrid ligand GPC 285985 using a yeast three-hybrid system in a halo assay. The top row shows the growth of cells transformed with pBTM118c-DHRF and either pGAD426c-hCDK2 (top left) or pGAD426c-hCDK4 (top right) after two days on medium lacking trp, leu and his following the addition of 1 µl of a 1 mM DMSO solution GPC 285985. The bottom row shows growth after two days on medium lacking trp and leu his following the addition of GPC 285985. On the medium lacking histidine, only cells transformed with pGAD426c-hCDK2 display detectable growth, while on medium lacking only trp and leu, both pGAD426c-hCDK2 (bottom left) and pGAD426c-hCDK4 (bottom right) transformed cells form dense populations.
Figure 11:
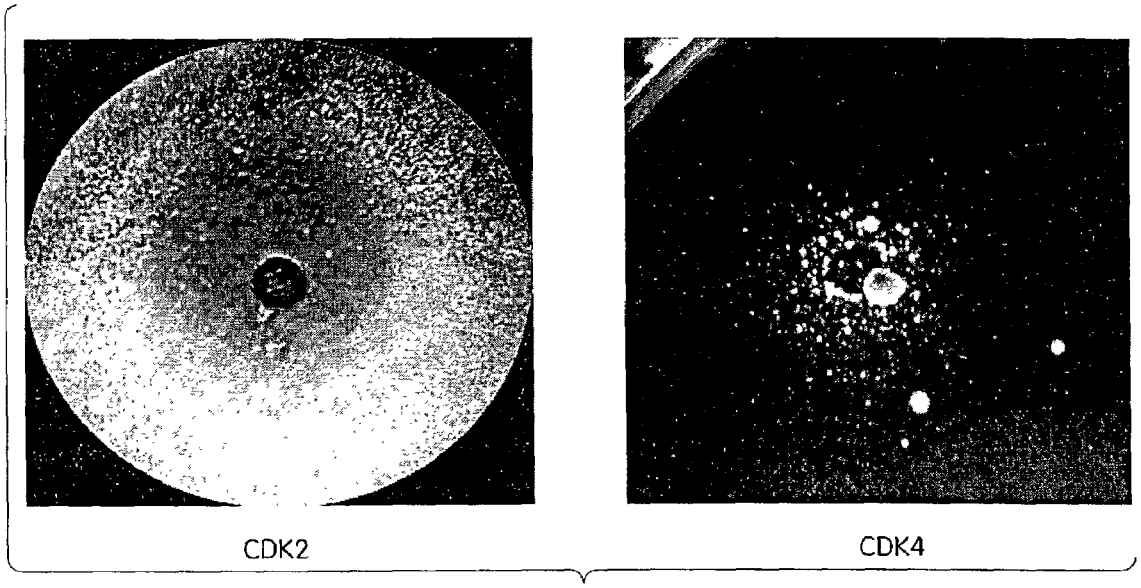
FIG. 11. Weak interactions can be detected after longer periods of growth. In an experiment analogous to the experiment shown in FIG. 10, cells transformed with pBTM 118c-DHRF and either pGAD426c-hCDK2 (left panel) or pGAD526c-hCDK4 (right panel) were incubated for six days at 30° C. on medium lacking trp, leu and his after addition of 1 µl of a 1 mM solution of GPC 285985 dissolved in DMSO to the center of each petri dish. After this incubation time the low affinity interaction (900 μM) between CDK4 and GPC 285985 was able to allow weak but detectable growth. In contrast, cells expressing the CDK2 fusion protein formed dense populations under the same conditions.

A hydropyrazolo-pyrimidine-moiety was developed by GPC as a selective inhibitor of hCDK2. It binds with high affinity to hCDK2 but only weakly to hCDK4 as can be determined for example using a method analogous to Example 4. When linked via a (—CH$_2$—O—CH$_2$)$_3$-linker to Methotrexate (GPC 285985), the resulting hybrid ligand should be expected to bind to and bridge a combination of BD-DHFR and hCDK2-AD fusion proteins, and consequently activate a lexA-controlled reporter gene. However, the same hybrid ligand should not be able to bind to and bridge the combination of BD-DHFR and hCDK4-AD fusion proteins when used at working concentrations. To test this hypothesis, cells of yeast strain L40 were co-transfected with pBTM 118c-DHFR and either pGAD426c-hCDK2 or pGAD426c-hCDK4 as appropriate. Transformants receiving both plasmids were selected on media lacking trp and leu, and individual colonies were inoculated in liquid SD-medium and incubated for 24 hrs. These two yeast strain cultures were diluted to a density of 106 cell/ml and 100 μl of each diluted culture were plated on a 10 cm petri dish containing SD medium lacking trp, leu, and also on a 10 cm petri dish containing SD medium lacking trp, leu and his. 1 μl of a 1 mM solution of GPC 285985 dissolved in DMSO or 1 μl DMSO as a control was spotted in the center of each petri dish. The growth of yeast cells was determined after 2 days of growth at 30° C. (FIG. 10) where growth was seen on medium lacking leu, trp and his only for cells containing pGAD426c-hCDK2. After 6 days, cells containing pGAD426c-hCDK2 had completely overgrown the petri dish, while very minimal growth was observed in cells containing pGAD426c-hCDK4 (FIG. 11). This is consistent with the relative affinities of GPC 285985 for hCDK2 and hCDK4, and demonstrates a method of testing the ability of a polypeptide to bind to a user-specified ligand.

Example 12

Methods of Identifying a Polypeptide that Binds to a User-Specified Ligand: a Three-Hybrid Assay System Based on a Transcriptional-Based Interaction System To demonstrate the suitability of certain methods of the invention for the identification of polypeptides that bind to a user-specified ligand from large collections of candidate polypeptides, a genetic screen was carried out using three hybrid molecules: first, GPC 285985, a hybrid ligand of the invention; second, a BD-DHFR fusion protein able to bind to the methotrexate moiety in GPC 285985 and bind to the lexA promoter; third, a library of human fetal brain cDNA's fused to the GAL4-AD. As a negative control, an alternative hybrid hybrid ligand comprising a small molecule linked to methotrexate via a (—$CH_2$—O—$CH_2$)$_3$-linker so as to be unable to bind to hCDK2 (GPC 285993) was used to confirm compound specific growth.

The 3-hybrid screen of the invention was conducted as follows. First, cells from yeast strain L40 were transformed with pBTM 118c-DHFR, and transformants receiving the plasmid were selected on synthetic medium lacking tryptophan. Second, individual colonies were regrown in liquid media, rendered competent and the L40 cells containing pBTM118c-DHFR were transformed with a human fetal brain cDNA library cloned in vector pACT2 (Clontech, Cat. No: HY4004AH). $1 \times 10^7$ individual colonies were selected on 60 22×22 cm SD agar plates lacking trp and leu. After three days of growth at 30° C. the colonies were washed off the plates, mixed and frozen in small aliquots. $2 \times 10^6$ cells were plated on each of 18 SD plates containing media lacking trp, leu and his but containing 20 μM of GPC 285985 and incubated for 2–5 days. A total of 2811 colonies appeared and were picked into 384 well microtiter plates containing SD medium lacking trp and leu. All clones were tested in a high-throughput halo assay against GPC 285985 dissolved in DMSO as growth promoter, or GPC 285993 dissolved in DMSO, or pure DMSO (LTH) as negative control. This halo assay was analogous to that described in Example 4 except that multiple different assays (between 10 and 1000) were tested in singular or replicate on 22×22 cm agar trays containing appropriate growth media. Test and control yeast strains, or test and control hybrid ligands/compounds were deposited on the agar in a regular pattern (between 3 and 50 mm spacing) using a standard laboratory pipetting robot (Multiprobe II, Packard, US). FIG. 12 shows an example of the analysis performed. Clones that were able to grow on spotting with GPC 285993 or DMSO alone were discarded. Around 102 clones showed growth only on spotting with GPC 285985. These clones were recovered and identified by DNA sequencing and comprised cDNA clones representing hcdk2 genes as well as other genes.

Figure 13:
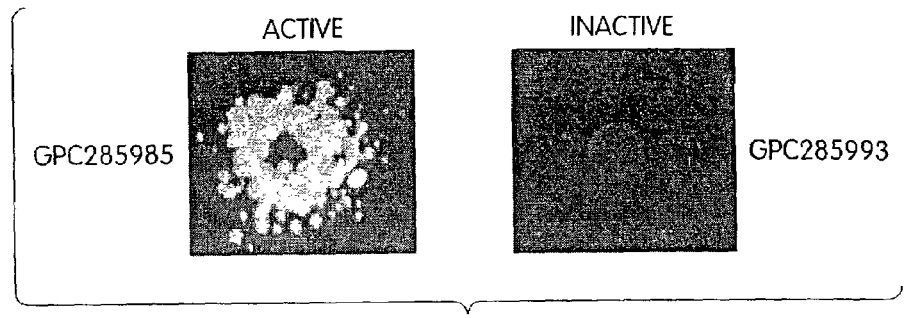
FIG. 13. An isolated plasmid coding for protein GPC761 expressed as a fusion protein with GAL4 AD (isolated from a three-hybrid genetic screen) was co-transformed with pBTM118c-DHFR into yeast strain L40. A halo assay was conducted to validate and further characterize and investigate the structure activity relationship between the interaction between this protein and the hybrid ligand used for the initial screen. Only hybrid ligand comprising the active CDK2 inhibitor GPC 285985 (left panel) allowed growth of cells on medium lacking trp, leu and his, while the structural variant GPC 285993 (which does not bind to CDK2) was ineffective at promoting growth in this assay and hence did not bind to protein GPC761.

To validate the compound specificity of the interaction between genes isolated in the above screen, the genes were recloned, and the halo assay repeated. One unknown gene (denominated GPC-761) was isolated four times in the screen described above. One of the isolated plasmids coding for this gene in vector pACT2 was co-transformed with pBTM 118c-DHFR into the yeast strain L40 and a halo assay conducted against GPC 285985 or GPC 285993 (dissolved in DMSO) or 1 μl DMSO as a control. FIG. 13 demonstrates compound-specific growth of the clone containing GPC-761. Equivalent results were also seen for such validation tests conducted using the hcdk2 genes identified from the above screen.

Substitution at the Nitrogen in 2-position of the 4-oxoindeno[3,2-c]pyrazol group as in GPC 285993 had been proven to abolish all activity towards CDK2 in this substance class (data not shown). The binding of GPC-761 to GPC 285985 but not to the n-substituted equivalent GPC 285993 is similar in characteristic to that of CDK2 binding to these compounds. This demonstrates, that the methods provided herein are able to identify a polypeptide binding to a user-specified ligand from a large pool of polypeptides without prior knowledge of the polypeptide.

Example 13

A 3-Hybrid Assay Using Mammalian Cells

Mammalian cells may possess distinct advantages for performing the three hybrid assay. They may exhibit better compound intake and may allow detection of interactions that would not be seen in heterologous host cells due to their ability to provide machinery/environment for correct folding and/or post-translational modifications that may be required for certain interactions.

Figure 14A:
FIGS. 14A–14C. The performance of the hybrid ligands of the invention in mammalian cells was tested as described in example 11. The CAT reporter gene is activate as shown by the presence of a colored precipitate in the positive control (FIG. 14A). Cells expressing the DHFR and GR2 fusions incubated with the respective dimerizing hybrid ligand GPC 285937 (FIG. 14B) also show a colored precipitate, but not where GPC 285937 is missing (FIG. 14C).
Figure 14B:
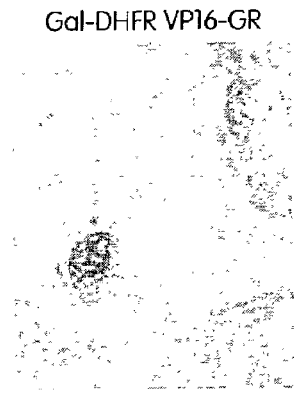
Figure 14C:
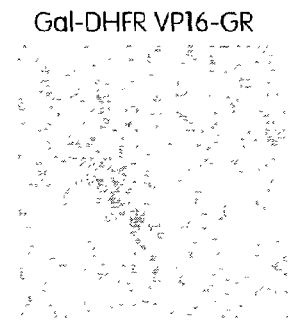
Figure 15:
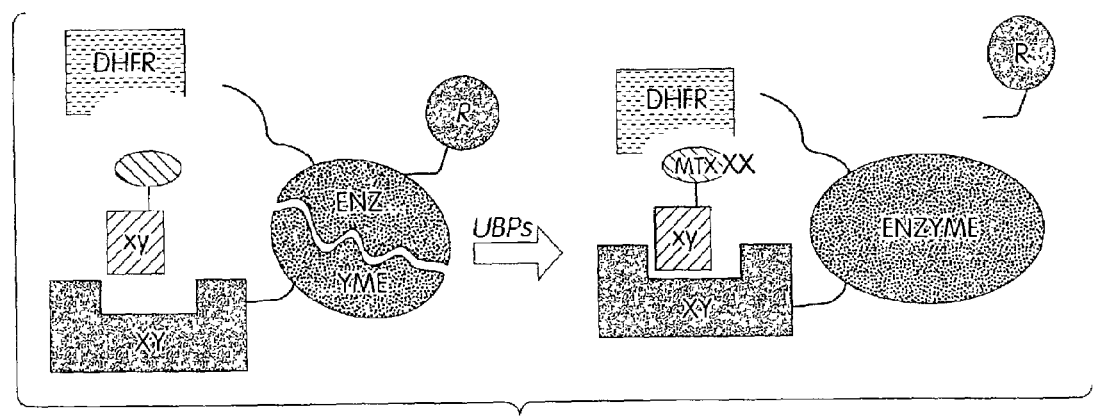
FIG. 15. Three-hybrid assay system based on Spit ubiquitin protein sensor technology. Two fusion proteins are constructed, one consisting of the N-terminal half of ubiquitin (Nub) and a prey protein (XY), and the other consisting of the C-terminal half of ubiquitin (Cub), a bait protein (DHFR) and the reporter moiety (R). Association of prey and bait via mutual binding to the hybrid small molecule mtx-xy reconstitutes a quasi-native ubiquitin structure (UBI) recognized by the ubiquitin specific protease (UBPs), whereby the reporter moiety is cleaved from the fusion protein. The cleavage of the reporter moiety from the fusion protein can be detected by several techniques, e.g., without limitation, Western Blot, cleavage or destabilization of the reporter via N-end rule considerations (R having a non-methionine amino acid at its N-terminus) or by providing a transcription factor as R and allowing for its translocation into the nucleus.

To test the performance of the dimerizing hybrid ligands and methods of the invention in mammalian cells, the activation of a CAT reporter gene using the Mammalian Matchmaker System (Clontech, Cat. No.: K1602-1) was tested. For this purpose, DHFR was cloned into vector pM (Clontech) and GR2 into the vector pVP16 (Clontech) using analogous methods as described in Example 3; the resulting vectors are termed pM-DHFR and pVP 16-GR2. Standard HeLa cells were transfected with pM3-VP16 and pG5CAT (positive control) or pM-DHFR, pVP16-GR2, and pG5CAT. 24 hours after transfection the medium was exchanged for medium to which 100 μl/100 ml medium of a 100 μM solution of GPC 285937 in DMSO was added (FIG. 14A,B) or medium containing the same amount of DMSO (FIG. 14C). 24 hours later the CAT activity was visualized using the CAT staining set (Roche, Cat. No. 1836358). A colored precipitate was clearly seen in the positive control (FIG. 14A) and in the cells expressing the DHFR and GR2 fusions incubated with GPC 285937 (FIG. 14B), but no coloured precipitate was seen in the DMSO control (FIG. 14C).

This shows, that the methods of the invention may be transferred to a cell system other than yeast.

Example 14

Figure 1:
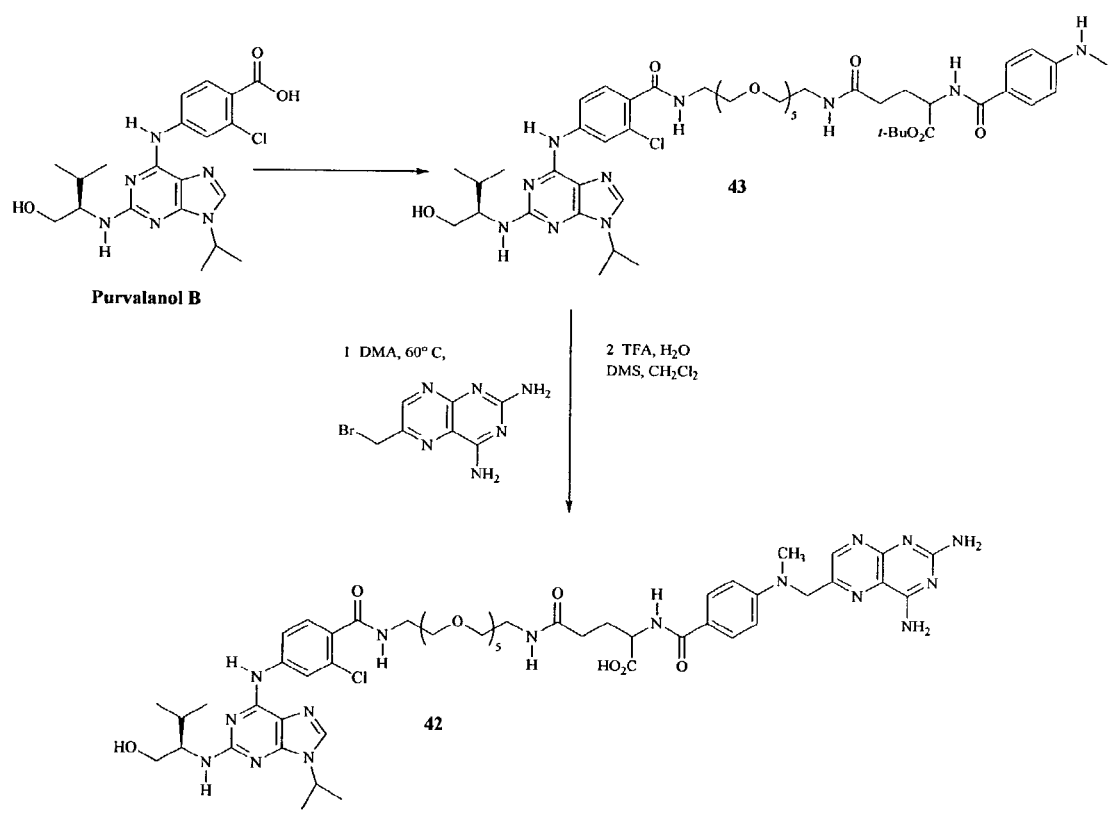

Methods of Identifying a Ligand for a User-Specified Peptide: a Three-Hybrid Assay System Based on Transcriptional-Based Interaction System In certain applications, it is advantageous to have methods at hand that can identify a small molecule from a pool or library of small molecules that is able to bind to a certain first polypeptide P1 of interest. To this end, a library of small molecules R1 may be prepared by well established methods of, for example, combinatorial chemistry, or other methods known to the skilled artisan, and subsequently coupled to a second ligand R2 known to bind to a second polypeptide P2 via a (—$CH_2$—X—$CH_2$)$_n$-linker to form a library of R1(—$CH_2$—X—$CH_2$)$_n$—R2 hybrid ligand compounds. Alternatively, a library of R1(—$CH_2$—X—$CH_2$)$_n$—R2 hybrid ligand compounds may be prepared de novo, using steps such as those given in Schemes 1–4 in FIG. 1. However, this is not meant to limit the scope of the invention to said schemes. Rather, the skilled artisan will, depending on the intended application choose from the large variety of known chemical reactions those best suited to generate the library fitting his needs.

If, for example, without limitation, R2 is chosen to be methotrexate, the library of hybrid ligand compounds can be used in the following screen: The coding sequence for P1 is amplified from a suitable library or sample known to contain this sequence using primers chosen to be specific for P1, digested, and subcloned into vector pGAD426c, to give pGAD426c-P1. Cells from yeast strain L40 are co-transformed with pBTM118c-DHFR and pGAD426c-P1. Transformants receiving the plasmid are selected on synthetic medium lacking tryptophan and leucine, and individual colonies are regrown in liquid medium. Microtiter plates are prepared to contain individual or pooled members of the library of hybrid ligand compounds at an appropriate concentration (which may be between 10 mM and 0.1 nM) in reporter and detection on Western Blots, yeast strain L40 is used in experiments where PLV-induced transcription of HIS3 is used as readout.

Figure 9:
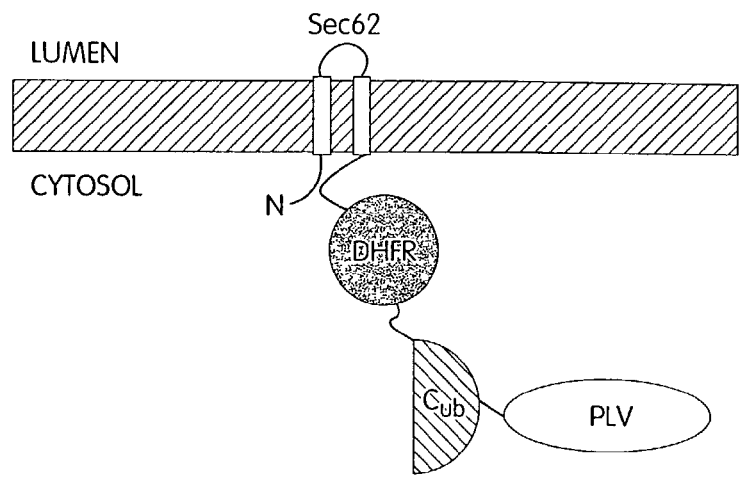
FIG. 9. A representation of the fusion protein Sec62-DHFR-Cub-PLV attached to the membrane of endoplasmic reticulum (ER). Whilst tethered to the membrane, the PLV transcription factor is unable to activate a reporter gene. However, on cleavage of the Cub-PLV following the formation of a quasi-native ubiquitin molecule, the cleaved PLV reporter moiety is able to shuttle to the nucleus and activate an appropriate reporter gene.

The plasmid PSDHFR-Cub-PLV, encoding a fusion protein (FIG. 9) comprising Sec62 which facilitates membrane anchoring, DHFR (dihydrofolate reductase), Cub, the C-terminal part of ubiquitin and PLV (chimeric transcription factor: proteinA::lexA::VP16) is constructed as follows. First, an *E. coli* folA' (DHFR) fragment is PCR amplified from an *E. coli* genomic DNA library (Clontech, Cat# XL4001AB), using primers CR96 and CR97:

```
CR96 5'-GGG GGT CGA CAT GAT CAG TCT GAT TGC GGC GTT AGC G-3'    (SEQ. ID No. 24)

CR97 5'-GGG GGC GGC CGC TTA CCG CCG CTC CAG AAT CTC AAA G-3'.   (SEQ. ID No. 25)
```

SD medium lacking leu, trp and his. Approximately $1 \times 10^4$, preferably $1 \times 10^5$, more preferably $1 \times 10^6$, or most preferably $1 \times 10^7$ cells cotransformed with pGAD426c-P1 and pBTM118c-DHFR as prepared above are inoculated into each well, and incubated for approximately 1 to 3 days with the solutions containing the hybrid ligands.

Cell growth in the wells is recorded after this growth period. The hybrid ligand compounds known to be present in those wells where growth is detected may subsequently be retested in a validation halo assay as described above in Example 4. In the case of pools of hybrid ligands, the pools may be fractioned by standard methodologies and individual hybrid ligands tested in halo assays and subsequently identified by standard methodologies. Where hybrid ligand specific growth can be ascertained, the compound linked to methotrexate to form this hybrid ligand is selected as being able to bind P1.

The sequence of the PCR product is confirmed by sequencing. Second, The PCR product is then digested with SalI and NotI and subcloned into the Cub-PLV vector (Stagljar et al. (1998) Proc. Natl. Acad. Sci. U.S.A., 95: 5187–92), so that Cub is downstream of the inserted DHFR and upstream of the reporter PLV while all three proteins are in-frame, yielding plasmid pDHFR-Cub-PLV. Third, the gene encoding the membrane anchor Sec62 is inserted upstream of DHFR following PCR amplification and sequence confirmation by sequencing of the gene using primers with flanking SalI restriction sites. Appropriate PCR primers for amplification of Sec62 from yeast (*S. cerevisiae*) genomic DNA are CR98 and CR99:

```
CR98 5'-GAT CGT CGA CAT GGT AGC CGA GCA AAC ACA GGA G-3'    (SEQ. ID No. 26)

CR99 5'-GAT CGT CGA CGT TTT GTT CGG CTT TTT CAT TGA TG-3'.  (SEQ. ID No. 27)
```

Upon cleavage of the fusion protein after the Cub moiety, PLV will be released from the fusion and its membrane-anchored location, and transfers to the nucleus where it activates transcription of genes under the control of a promoter comprising LexA-binding sites.

To construct plasmid pDHFR-Cub-GFP, the PLV moiety in pDHFR-Cub-PLV is replaced with a GFP cassette from pCK GFP—S65C using compatible restriction sites flanking both cassettes (Reichel, et al., PNAS, 1996, 93:5888–93). An alternative reporter plasmid, pDHFR-Cub-R-GFP is constructed such that a 20 amino acid leader sequence containing lysine is cloned between Cub and GFP such that the first amino acid of the leader-GFP fragment produced after cleavage of the Cub-R peptide bond is an arginine residue.

Plasmid pNubI-hCDK2 is constructed by digesting the hcdk2 PCR fragment produced in Example 3 with appropriate restriction enzymes and subcloning the product into plasmid pNubI (Laser et al., PNAS, 2000, 97:13732–7).

To construct a library of plasmids encoding the N-terminal half of ubiquitin fused to a library of polypeptides, a cDNA library is generated from poly A+ RNA isolated from human fetal brain (hFB) (Clontech, CAT# 6525-1) essentially essentially using a commercially available protocol and reagents (Superscript, Invitrogen, Carlsbad, Calif., USA, CAT. NO. 18248-013) but employing oligo-dT primers for first-strand synthesis as follows:

TT1-A: 5'-TTT TGT ACA TCT AGA TCG CGA GCG GCC GCC CTT TTT TTT TTT TV-3' (SEQ. ID No. 28)

Example 15

Methods of Identifying a Polypeptide that Binds to a User-Specified Ligand: a Three-Hybrid Assay System Based on the Ubiquitin Split Protein Sensor Technique The ubiquitin split protein sensor technique has been used to detect protein interactions in vivo or in vitro. It is generally useful for assaying for all kinds of protein-protein interactions, but is particularly useful in cases where a conventional yeast two-hybrid assay is problematic, i.e. where membrane proteins, transcriptional activators or repressors, etc., are involved. Further details of this technique may be taken, for example, from U.S. Pat. No. 5,585,245, U.S. Pat. No. 5,503,977 or Johnsson & Varshavsky (1997) in: *The Yeast Two-Hybrid System (Advances in Molecular Biology)*, Ed. Paul L. Bartel and Stanley Fields, Oxford University Press, pp 316–332. Here, we show how the ubiquitin split sensor principle may equally be employed in a three hybrid experiment to investigate interactions between proteins and small molecules.

Construction of Vectors for a Three Hybrid Assay System Based on Ubiquitin Split Protein Sensor Yeast strain JD53 (Dohmen et al., JBC, 1995, 270: 18099–109) is chosen for the experiments involving GFP as with V being A, G, or C at equal molar ratio. The resulting cDNA fragments were subcloned into plasmid pNubI as SalI/NotI restriction fragments (pADNX-N$_{ub}$IBC; Laser et al., PNAS, 2000, 97:13732–7) to yield a library of plasmids herein termed pNubI-hFB.

Quantification of the Degree of Cleavage of DHFR-Cub-GFP

The "bait-Cub-reporter" plasmid pDHFR-Cub-GFP (1 µg) is co-transformed with pNubI-hCDK2 into the yeast strain JD53 (Dohmen et al., JBC, 1995, 270:18099–109) by standard techniques (Burke at al., Methods in yeast genetics: A Cold Spring Harbor Laboratory course manual; Cold Spring Harbor Laboratory Press, 2000). Co-transformants containing both plasmids are selected on medium lacking leu and trp. Individual colonies are regrown in liquid media and $1\times10^4$, preferably $1\times10^5$, more preferably $1\times10^6$, or most preferably $1\times10^7$ cells inoculated into individual wells of microtitre plates containing SD medium lacking trp and leu but containing the dimerizing hybrid ligand GPC 285985 at a concentration of about 50 µM. GPC 285985 was added dissolved in DMSO to a final concentration of approximately 0.1% DMSO, DMSO alone was added to controls. After 1 to 3 days of incubation at 30° C., cleavage of the reporter moiety GFP from Cub is detected by Western blot analysis using GFP-specific antibodies (Clontech, Cat. No. 8369-1) and is observed only for cells from the GPC 285985 containing wells. Detection of the cleaved GFP moiety (approx. 29 kDa) is indicative of interaction of the hybrid ligand and the fusion proteins.

Repeating the above experiment but using the pDHFR-Cub-R-GFP instead of pDHFR-Cub-GFP demonstrates loss of GFP activity through N-end rule degradation following its cleavage from Cub brought about by formation of a trimeric complex of the DHFR-Cub-R-GFP and NubI-hCDK2 fusion proteins bridged by the hybrid ligand. The fluorescent intensity of GFP in those yeast cells exposed to the hybrid ligand GPC 285985 is reduced compared to those cells exposed only to DMSO. Fluorescent intensity is measured using a standard microtitre plate reader (Victor V, Perkin Elmer) or fluorescence cell-scanning/sorting (FACS) device for example from Cytomation or Beckton Coulter.

Quantification of the Degree of Cleavage of Sec62-DHFR-Cub-PL V by Screening for an Auxotrophic Marker The PLV moiety, when synthesized as a Sec62-DHFR-Cub-PLV fusion from plasmid PSDHFR-Cub-PLV, is tethered to the ER membrane outside the nucleus and thus, is not available for transcription activation of reporter genes. Only upon cleavage of the fusion protein after the Cub moiety, will PLV be released, serving as a transcription factor to activate reporter genes under the control of the promoter harboring lexA binding sites inside the nucleus (Stagljar et al. (1998) Proc. Natl. Acad. Sci. U.S.A., 95: 5187–92).

The "bait-Cub-reporter" plasmid PSDHFR-Cub-PLV (1 µg) is co-transformed with the library of plasmids pNub-hFB (5 µg) into the yeast strain L40 by standard techniques. Transformants are then plated onto 22×22 SD plates prepared with medium lacking leu and trp. After 3 days of incubation at 30° C., co-transformants are washed off the plates, mixed and frozen as small aliquots. $2\times10^6$ cells are plated on to SD plates lacking trp, leu and his, but containing 50 µM GPC 285985 and incubated for 2–5 days. Only cells containing both plasmids and exhibiting an active HIS3 gene (imidazole-glycerol-phosphate-dehydratase) can survive (first screen positive). The activation of HIS3 gene is dependent on interaction between pNub-hFB, GPC 285985 and pSDHFR-Cub-PLV, which triggers UBP-mediated cleavage of the PLV reporter from the bait fusion protein. The released PLV reporter will then shuttle to the nucleus where transcription of the reporter gene (HIS3) is initiated, leading to growth on SD medium lacking histidine.

First screen positive clones are picked and tested in a high-throughput halo assay analogous to that described in Example 10. Positive clones from this screen are identified by DNA sequencing and include clones containing genes expressing CDK2 and other genes.

A class of false-positives that will occur are proteins contained in the library, that interact with the membrane anchor Sec62. Therefore, a second screen without ligand is performed. Second-screen positives are solely dependent on the direct interaction between the anchor moiety Sec62 and the prey from the library. This class of false-positives has to be subtracted from the positive candidates from the first screen with the compound.

This class of false-positives may be eliminated, or at least the number of false-positives may be greatly reduced by minimizing the membrane anchor to just the minimal transmembrane domain of Sec62, that is sufficient to achieve secure membrane anchoring. This minimal domain may be determined by generating N- and C-terminal deletion constructs of Sec62, using standard laboratory methods.

Example 16

Methods of Identifying a Polypeptide that Binds to a User-Specified Ligand: a Three-Hybrid Assay System Based on a β-Lactamase Complementation Technique Assays based on the complementation of enzyme fragments fused to interacting proteins that regenerate enzymatic activity after dimerization are particularly well suited for monitoring inducible protein interactions (reviewed in Rossi, F. M., Blakely, B. T. & Blau, H. M. (2000) Trends Cell. Biol. 10, 119–122). These systems advantageously combine low-level expression of test proteins, generation of signal as direct result of the interaction, and enzymatic amplification of this system, resulting in high sensitivity and physiologically relevant assays. Assays based on enzyme-complementation may be performed in any cell type and in diverse cellular compartments such as the nucleus, secretoryvesicles, or plasma membrane. Therefore, these assays perfectly perform where classical 2-hybrid approaches fail (i.e., nuclear localized transcription factors, membrane proteins). The class A β-lactamases are particularly attractive candidates for enzyme complementation assays due to their monomeric nature and relatively small size. In addition, β-lactamases have been expressed successfully in prokaryotic and eukaryotic cells, making this system applicable to both classes of organisms. A pair of β-lactamase fragments (α197 and ω198) was recently identified that complement to produce detectable activity in bacteria when fused to two helices that form a leucine zipper (see Galarneau et al. (2002) Nature Biotech. 20:619–622 and references in Wehrman et al., Proc. Natl. Acad. Sci. U.S.A. (2002), 99:3469–3474).

The identification of the tripeptide, Asn-Gly-Arg (NGR) was recently reported, that produced a profound enhancement of β-lactamase activity mediated by different protein pairs in bacteria when introduced at the carboxyl terminus of the α197 fragment (Wehrman et al., Proc. Natl. Acad. Sci. U.S.A. (2002), 99:3469–3474).

It was reasoned that extension of the β-lactamase system into mammalian cells would provide significant advantages over other fragment complementation systems currently used [e.g., β-galactosidase and dihydrofolate reductase (reviewed in Rossi, F. M., Blakely, B. T. & Blau, H. M. (2000) Trends Cell. Biol. 10, 119–122)], because the fragments are small (<19 kDa), there is no endogenous β-lactamase activity, and a highly sensitive cell-permeable fluorescent substrate has been developed recently (Zlokarnik et al. (1998) Science -279:84–88).

Here, we show how the β3-lactamase complementation assay principle may equally be employed in a three hybrid experiment to investigate interactions between proteins and small molecules. Small molecules of the structure R1-Y—R2 are employed to mediate dimerization between a sensor protein P1, here DHFR tightly binding to methotrexate (here, R1), and a test protein P2, here hCDK2 binding to a moiety (R2) of compound GPC285985. The assay may equally be used to monitor interactions of proteins P2 expressed from a cDNA library with any dimerizing compound R1-Y—R2.

XhoI, are annealed and ligated to plasmids pcDNA3.1/Zeo and pcDNA3.1 linearized with KpnI/XhoI (from both plasmids a unique HindIII restriction site upstream of KpnI has previously been removed by standard procedures). Complementary oligonucleotides containing restriction site HindIII/NotI and coding in frame for a 15-amino-acid flexible polypeptide linker consisting of (GGGGS)$_3$ (SEQ. ID No. 33), are hybridized together and ligated into pcDNA3.1/Zeo and pcDNA3.1 linearized with HindIII/NotI. The PCR-generated products of α197 and ω198 are inserted upstream or downstream, and in frame with the 15-amino-acid linker, with KpnI/HindIII and NotI/XhoI, respectively. This leads to the creation of the construct pcDNA-α197-15aa-[N/X]/Zeo and the construct pcDNA-[K/H]-15aa-ω198, respectively. Interacting protein-coding sequences generated by PCR, containing either KpnI/HindIII or NotI/XhoI, are ligated upstream or downstream of the 15-amino-acid linker.

The plasmid pcDNA$_{DHFR}$-15aa-ω198, encoding a fusion protein comprising DHFR, a 15 amino acid linker sequence and the C-terminal part of β-lactamase is constructed as follows. First, an E. coli folA' (DHFR) fragment is PCR amplified from an E. coli genomic DNA library (Clontech, Cat# XL4001AB), using the primers CR104:

```
the primers CR104:
CR104  5'-GGG GGGTACCAT GAT CAG TCT GAT TGC GGC GTT AGC G-3'    (SEQ. ID No. 34)

and CR105:
CR105  5'-GGG GAAGCTTCC GCC GCT CCA GAA TCT CAA AG-3'.          (SEQ. ID No. 35)
```

Construction of Vectors for a Three Hybrid Assay System Based on β-Lactamase Complementation.

To create the β-lactamase fusion proteins for expression in mammalian cells, the α197-NGR fragment is amplified by PCR from pUC19 (Yanisch-Perron et al., Gene (1985) 33:103–119; commercially available through New England Biolabs, Beverly, Mass., USA) by using the forward primer CR100:

The sequence of the PCR product was confirmed by sequencing. Second, The PCR product is then digested with KpnI and HindIII and subcloned into pcDNA-[K/H]-15aa-ω198, upstream of the C-terminal β3-lactamase ω198 fragment, yielding plasmid pcDNA$_{DHFR}$-15aa-ω198.

Plasmid pcDNA-α197-15aa-hCDK2 is constructed by digesting a hcdk2 PCR fragment produced similarly as the one in Example 3 with appropriate restriction enzymes and

```
the forward primer CR100:
CR100  5'-GCA GGTACC CCA TGG TGA GTA TTC AAC ATT TCC GTG TCG-3'   (SEQ. ID No. 29)

and the reverse primer CR101:
CR101  5'-CCG AAGCTT TCT ACC ATT TTC GCC AGT TAA TAG TTT GC-3'    (SEQ. ID No. 30)
```

The ω198 fragment is amplified by using the primers CR102:

subcloning the product into plasmid pcDNA-α197-15aa-[N/X]/Zeo. The cDNA encoding hCDK2 is amplified from a

```
the primers CR102:
CR102  5'-CAC GGTACCC TAC TTA CTC TAG CTT CCC GGC AAC-3'    (SEQ. ID No. 31)

and the reverse primer CR103:
CR103  5'-CAC AAGCTT TTA CCA ATG CTT AAT CAG TGA GGC AC-3'  (SEQ. ID No. 32)
```

The sequences of the PCR products are confirmed by sequencing. Complementary oligonucleotides containing new restriction sites, including KpnI, HindIII, NotI, and human placenta MATCHMAKER cDNA library (Clontech, Cat# HL4025AH, Heidelberg, Germany) by PCR using the primers CR106:

the primers CR106:
CR106 5'-GG*GGTACC*GA GAA CTT CCA AAA GGT GG-3'   (SEQ. ID No. 36)

and CR107:
CR107 5'-CG*AAGCTT*T CAG AGT CGA AGA TGG GGT AC-3'   (SEQ. ID No. 37)

The sequence of the PCR product is confirmed by sequencing and the PCR fragment is cloned into the corresponding NotI and XhoI restriction sites of plasmid pcDNA-α197-15aa-[N/X].

To construct a library of plasmids encoding the N-terminal half of β-lactamase (α197), followed by the 15 amino acid linker sequence and fused in frame to a library of polypeptides, a cDNA library is generated from poly A+ RNA isolated from human fetal brain (hFB) (Clontech, CAT# 6525-1) essentially using a commercially available protocol and reagents (Superscript, Invitrogen, Carlsbad, Calif., USA, CAT. NO. 18248-013) but employing oligo-dT primers for first-strand synthesis as follows:

CR108: 5'-TTT TGT ACA TCT AGA TCG CGA *GGTACC* CCT TTT TTT TTT TTT TTV-3'   (SEQ. ID No. 38)

with V being A, G, or C at equal molar ratio. After second strand synthesis adapters are added to the cDNA by ligation. The adapters are produced by annealing oligos CR109:

annealing oligos CR109:
CR109 5'-*GGTACC* CAC GCG TCC G-3'   (SEQ. ID No. 39)

and CR110:
CR110 5'-CGG ACG CGT GGC-3'   (SEQ. ID No. 40).

The resulting cDNA fragments are digested with the restriction enzyme NotI and subcloned into plasmid pcDNA-α197-15aa-[N/X]/Zeo as NotI/XhoI restriction fragments to yield a library of plasmids herein termed pcDNA-α 197-15aa-hFB.

Protein-Compound Interaction Measured by the β-Lactamase Complementation Fluorogenic Assay: Human CDK2 Binding to GPC 285985.

HEK 293 cells are split 24 h before transfection at $1.8 \times 10^5$ cells onto 15 mm glass coverslips for microscopy (Merck, Germany) in six-well tissue culture plates (Coming Star) in DMEM (Invitrogen, Carlsbad, Calif., USA) enriched with 10% Cosmic calf serum (Hyclone). Cells are transiently co-transfected with plasmids pcDNA$_{DHFR}$-15aa-ο198 and pcDNA-al97-15aa-hCDK2 using Fugene 6 transfection reagent according to the manufacturer's instructions (Roche Diagnostics). Cells are grown for 48 hours selecting for the presence of both plasmids using Zeocin and Neomycin as selective agents. After 48 hours cells are again split at $1.8 \times 10^5$ cells. Aliquots of the cells are incubated 48 hours in the presence of the dimerizing hybrid ligand GPC 285985 at a concentration of about about 50 μM. GPC 285985 is added dissolved in DMSO to a final concentration of approximately 0.1% DMSO, DMSO alone is added to controls.

Cells are washed twice with PBS and once with a physiologic saline buffer (10 mM HEPES, 6 mM sucrose, 10 mM glucose, 140 mM NaCl, 5 mM KCl, 2 mM MgCl2, 2 mM CaCl$_2$, pH 7.35) before being loaded for one hour at room temperature with 1.5 μM CCF2/AM (Zlokarnik G. et al. (1998) Science 279:84–88). Cells are washed twice with the physiologic saline buffer. For microscopy, cell fluorescence is observed with FRET filter set XF89-2 (Omega Opticals, Brattleboro, Vt., USA) by excitation of CCF2 through a 365 nm filter (50 nm bandpass) with emission observed at 450 nm (65 nm bandpass; blue fluorescence) or 535 nm (45 nm bandpass; green fluorescence). Fluorescence microscopy is conducted on live HEK 293 cells with a Leica DMIRB/E (Leica, Germany) inverted microscope and a HCX PL Fluotar 40×/0.75 microscope lens. Images are taken with a color chilled 3 CCD camera (model C5810; Hamamatsu Photonics, Bridgewater, N.Y.).

Reconstitution of β-lactamase activity mediated by bridging between DHFR and hCDK2 with GPC 285985 compound, is detected as conversion of the fluorescence emission of the CCFC substrate from a bright green fluorescent signal (e.g. DMSO control samples) to a blue fluorescence.

Compound mediated dimerization can further be detected employing fluorescence spectroscopy or a colorimetric assay format (Zlokarnik G. et al. (1998) Science 279:84–88; and Galameau et al. (2002) Nature Biotech. 20:619–622). Preferably, detection is performed in an automated fashion, for example in a fluorescence assisted cell sorting (FACS) system.

Protein-Compound Interaction Measured by the β-Lactamase Complementation Fluorogenic Assay: Searching for Proteins Interacting with GPC 285985.

HEK 293 cells are split 24 h before transfection at $1.8 \times 10^5$ cells onto 15 mm glass coverslips for microscopy (Merck, Germany) in six-well tissue culture plates (Coming Star) in DMEM (Invitrogen, Carlsbad, Calif., USA) enriched with 10% Cosmic calf serum (Hyclone). Cells are transiently co-transfected with plasmids pcDNA$_{DHFR}$-15aa-ω198 and the library plasmids pcDNA-α197-15aa-hFB using Fugene 6 transfection reagent according to the manufacturer's instructions (Roche Diagnostics). Cells are grown for 48 hours selecting for the presence of both plasmids. After 48 hours cells were again split at $1.8 \times 10^5$ cells. Aliquots of the cells were incubated 48 hours in the presence of the dimerizing hybrid ligand GPC 285985 at a concentration of about 50 μM. GPC 285985 was added dissolved in DMSO to a final concentration of approximately 0.1% DMSO, DMSO alone was added to controls.

Fluorescence microscopy and sample preparation was performed as described in the previous section. Reconstitution of β-lactamase activity mediated by bridging between DHFR and library clones with GPC 285985 compound was detected as conversion of a bright green fluorescent signal (DMSO control samples) to blue fluorescence. Cells from positive samples were collected by centrifugation, cell membranes were lysed and plasmid DNA was isolated by standard procedures. Plasmid DNA from positive clones was analyzed by DNA sequencing.

Equivalents

Those skilled in the art will recognize, or be able to ascertain using no more than routine experimentation, numerous equivalents to the specific procedures described herein. Such equivalents are considered to be within the scope of this invention and are covered by the following claims.

TABLE 2

Inhibitors of kinases

| Structure | Reference |
|---|---|
| 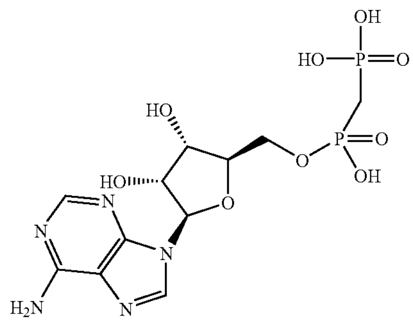 | Science 1997, 278(5336): 286–90 |
| | |
| | |
| | |

TABLE 2-continued
Inhibitors of kinases
| Structure | Reference |
|---|---|
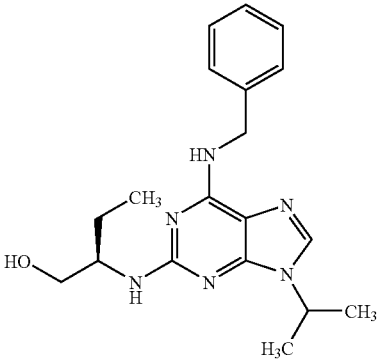
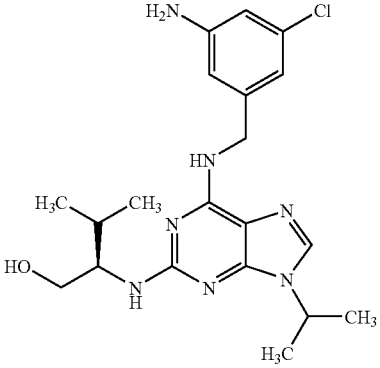
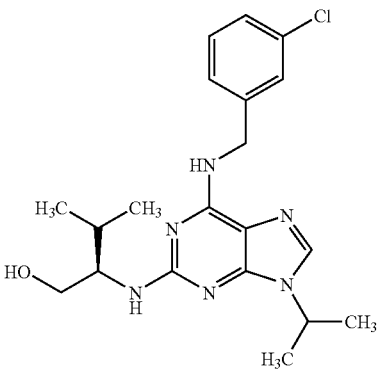
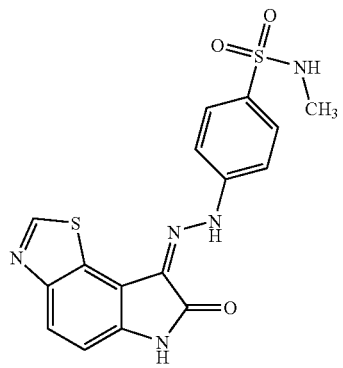

TABLE 2-continued

Inhibitors of kinases

| Structure | Reference |
|---|---|
| 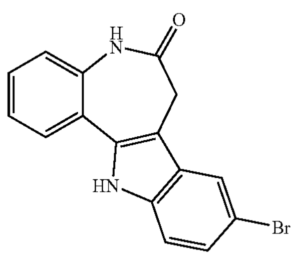 | Cancer Res. 1999, 59, 2566 |

TABLE 2-continued
Inhibitors of kinases
| Structure | Reference |
|---|---|
| 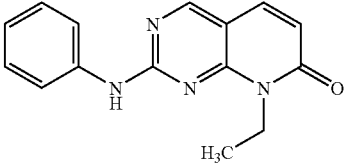 | |
| 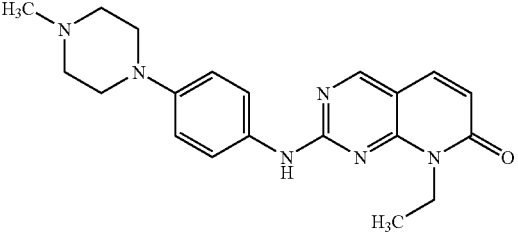 | |
| 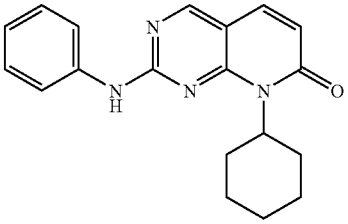 | |
| 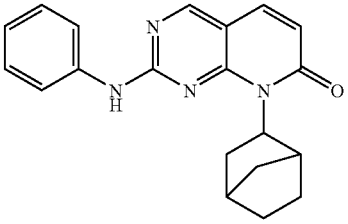 | |
| 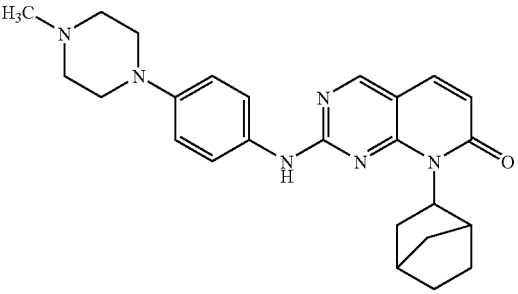 | |

TABLE 2-continued
Inhibitors of kinases
| Structure | Reference |
|---|---|
| 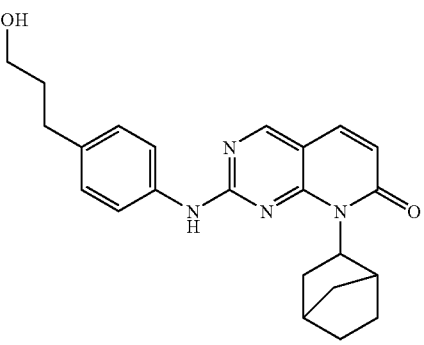 | |
| 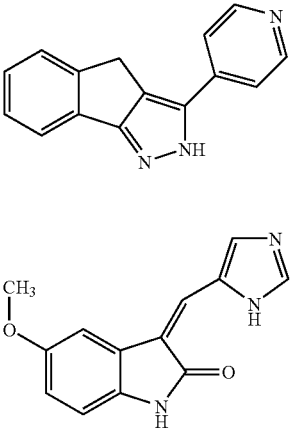 | Bioorg. Med. Chem Lett. 2002, 12, 221–224 |
| 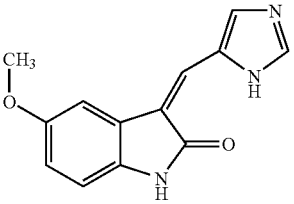 | |
| 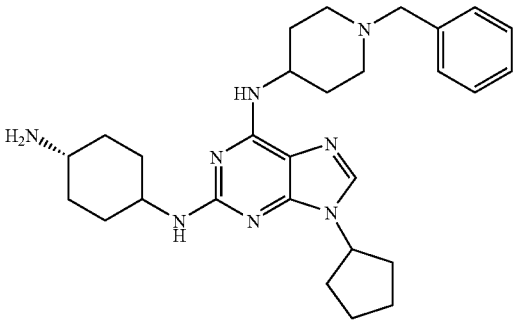 | |
| 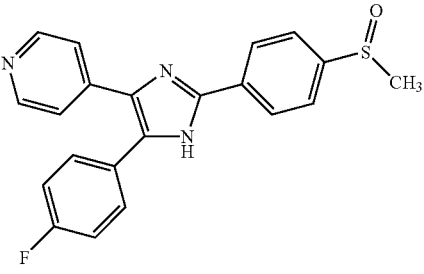 | |

TABLE 2-continued

Inhibitors of kinases

| Structure | Reference |
|---|---|
| | |
| 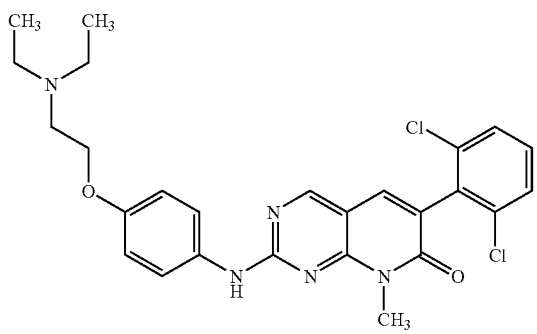 | J. Med. Chem. 1998, 41, 3276 |

TABLE 2-continued

Inhibitors of kinases

| Structure | Reference |
|-----------|-----------|

TABLE 2-continued

Inhibitors of kinases

| Structure | Reference |
|---|---|

TABLE 2-continued

Inhibitors of kinases

| Structure | Reference |
|---|---|

TABLE 2-continued
Inhibitors of kinases
| Structure | Reference |
|---|---|
| 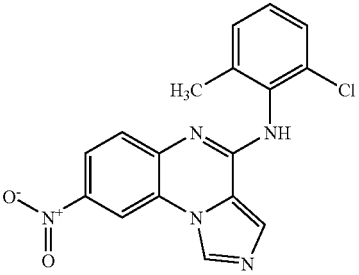 | |
| 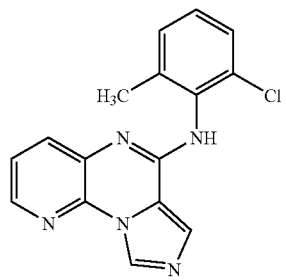 | |
| 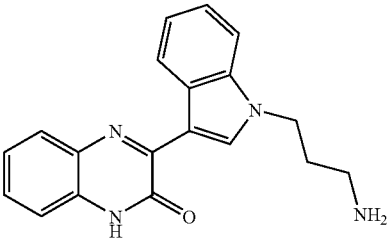 | |
| 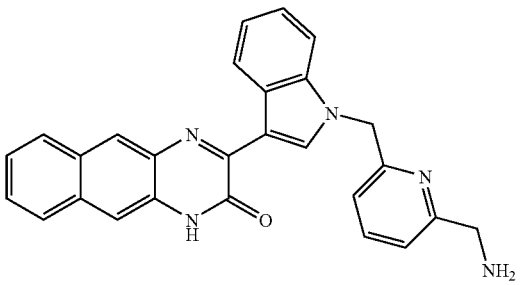 | |
| 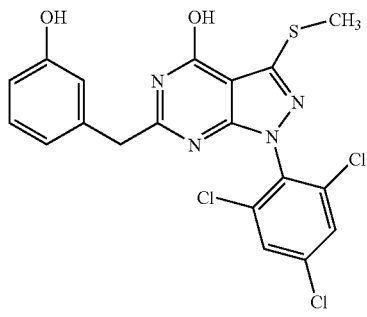 | |

TABLE 2-continued

Inhibitors of kinases

| Structure | Reference |
| --- | --- |
| | |
| 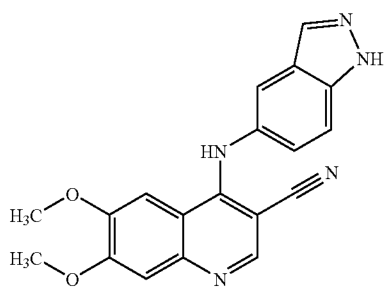 | Bior. Med. Chem. Lett. 2001, 11, 1401–1405 |
| | |
| | |

TABLE 2-continued

Inhibitors of kinases

| Structure | Reference |
|---|---|

TABLE 2-continued
Inhibitors of kinases
| Structure | Reference |
|---|---|
| 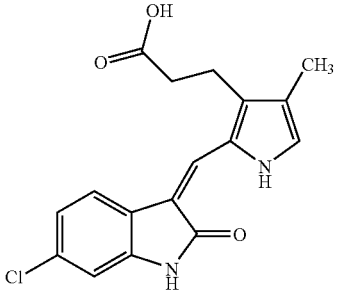 | |
| 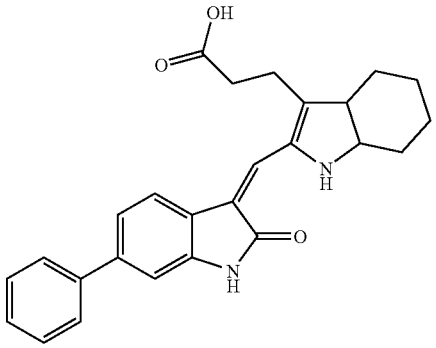 | |
| 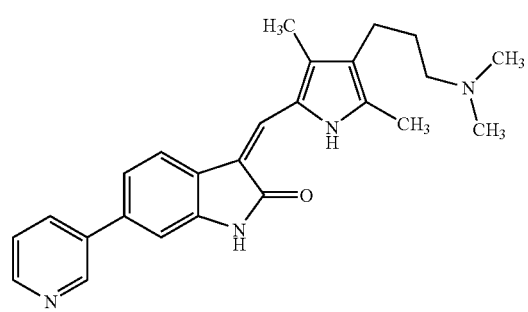 | |
| 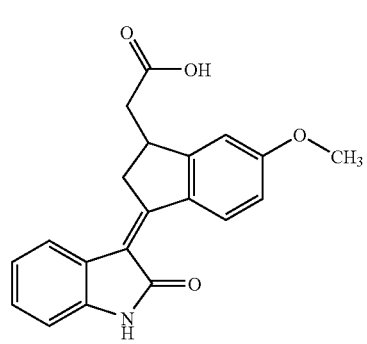 | |

TABLE 2-continued

Inhibitors of kinases

| Structure | Reference |
|---|---|

TABLE 2-continued
Inhibitors of kinases
| Structure | Reference |
|---|---|
| 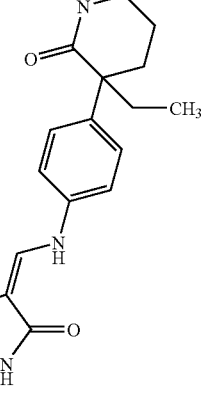 | |
| 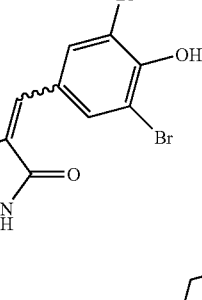 | Bioorg. Med. Chem. Lett. 2000, 10, 223 |
| 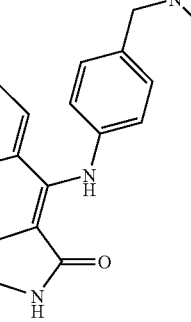 | |
| 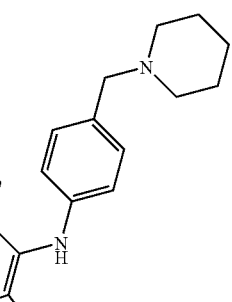 | |

TABLE 2-continued
Inhibitors of kinases
| Structure | Reference |
|---|---|
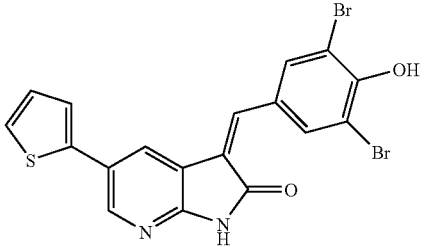
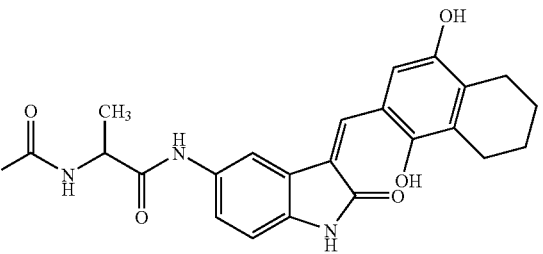
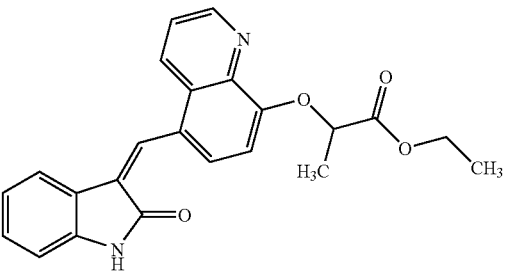
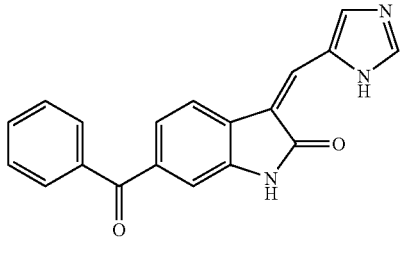
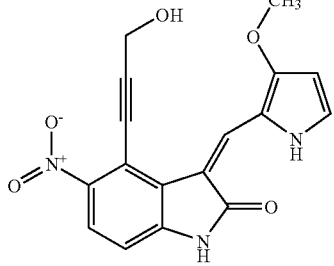

TABLE 2-continued

Inhibitors of kinases

| Structure | Reference |
|---|---|

TABLE 2-continued

Inhibitors of kinases

| Structure | Reference |
|---|---|
| | |
| | Bioorg. Med. Chem. Lett. 2001, 11, 9–12 |
| | Bioorg. Med. Chem. Lett. 2001, 11, 9–12 |
| 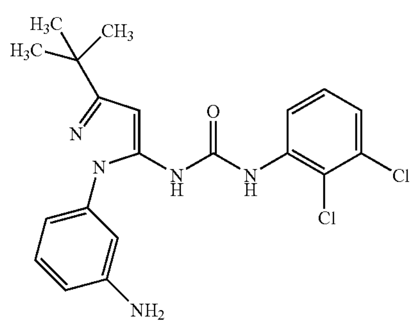 | Bioog. Med. Chem. Lett. 2000, 10, 2051–2054 |
| | |

TABLE 2-continued

Inhibitors of kinases

| Structure | Reference |
|---|---|

TABLE 2-continued
Inhibitors of kinases
| Structure | Reference |
|---|---|
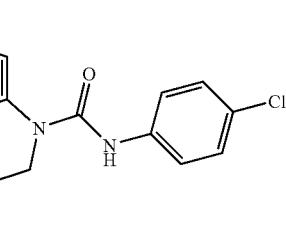
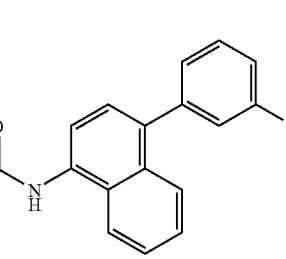
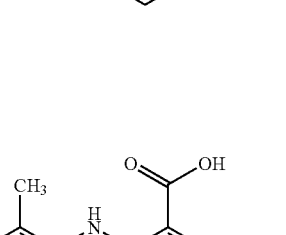
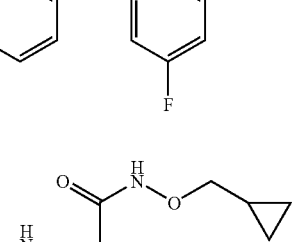
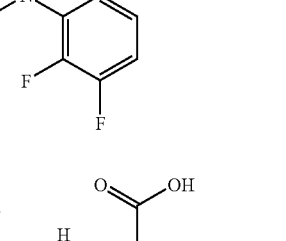

TABLE 2-continued
Inhibitors of kinases
| Structure | Reference |
|---|---|
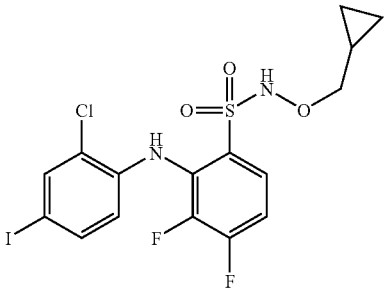
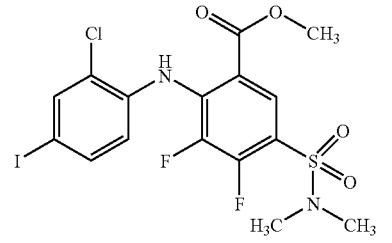
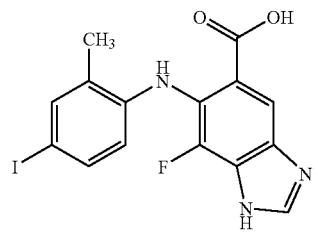
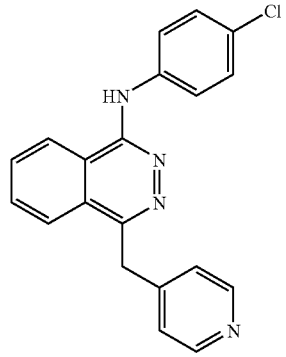

TABLE 2-continued

Inhibitors of kinases

| Structure | Reference |
|---|---|
| | |
| 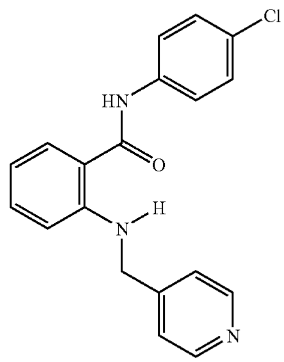 | WO 01/081311 |
| | |
| | |

TABLE 2-continued
Inhibitors of kinases
| Structure | Reference |
|---|---|
| 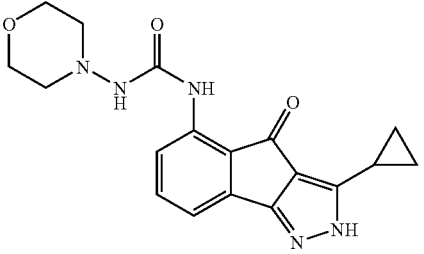 | |
| 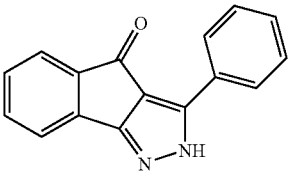 | WO 9917770 |
| 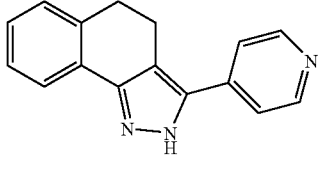 | |
| 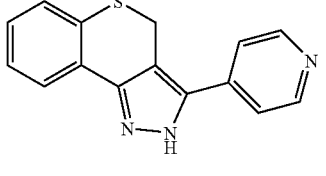 | |
| 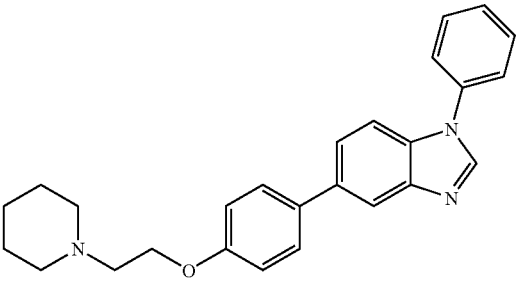 | |
| 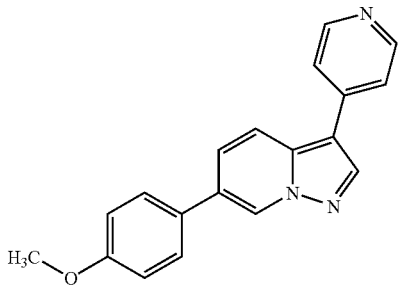 | |

TABLE 2-continued

Inhibitors of kinases

| Structure | Reference |
|---|---|

TABLE 2-continued

Inhibitors of kinases

| Structure | Reference |
|---|---|
| 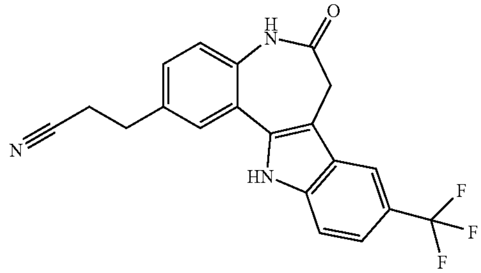 | Bioorg. Med. Chem. Lett., 2000, 10, 567–569 |

TABLE 2-continued

Inhibitors of kinases

| Structure | Reference |
|-----------|-----------|

TABLE 2-continued
Inhibitors of kinases
| Structure | Reference |
|---|---|
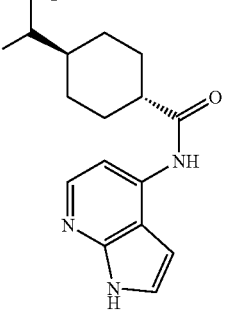
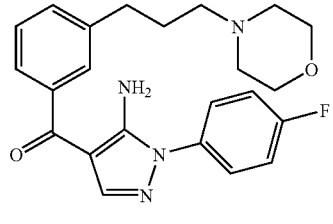
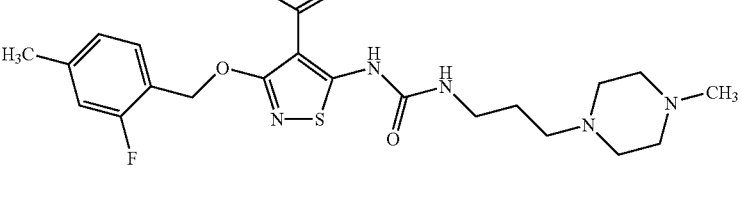
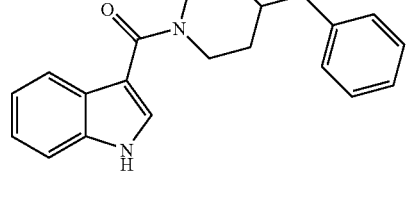
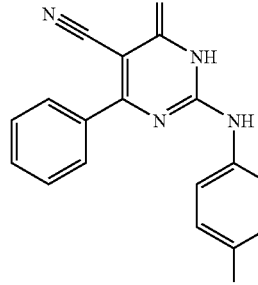

TABLE 2-continued
Inhibitors of kinases
| Structure | Reference |
|---|---|
| 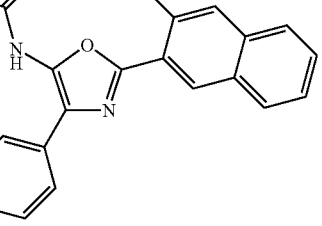 | |
| 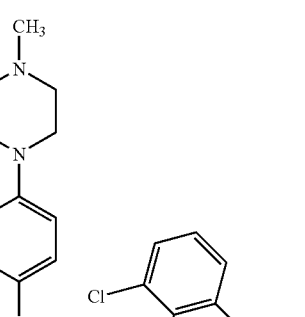 | |
| 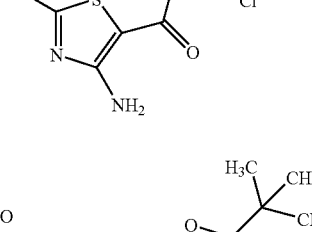 | |
| 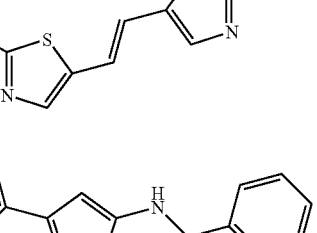 | |
| 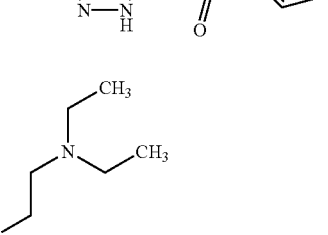 | |

TABLE 2-continued
Inhibitors of kinases
| Structure | Reference |
|---|---|
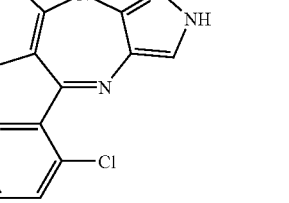
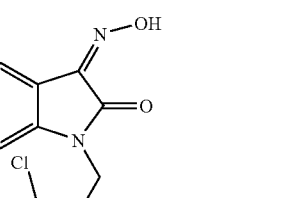
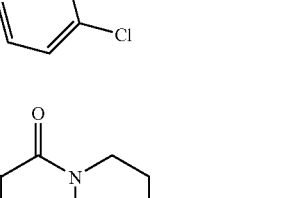
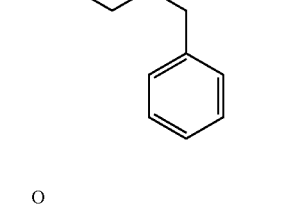
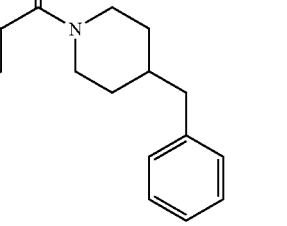

TABLE 2-continued
Inhibitors of kinases
| Structure | Reference |
|---|---|
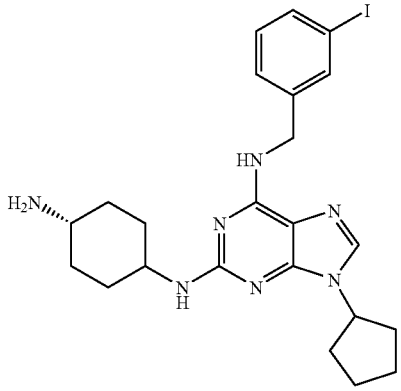
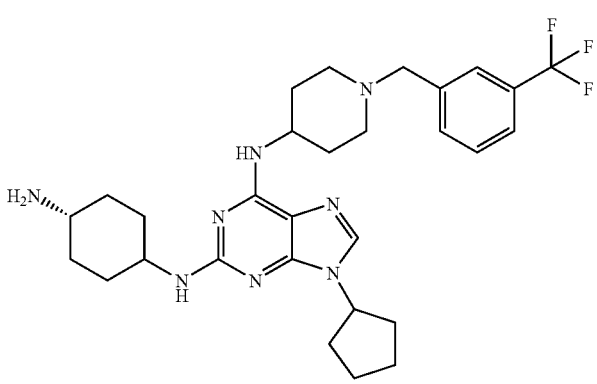
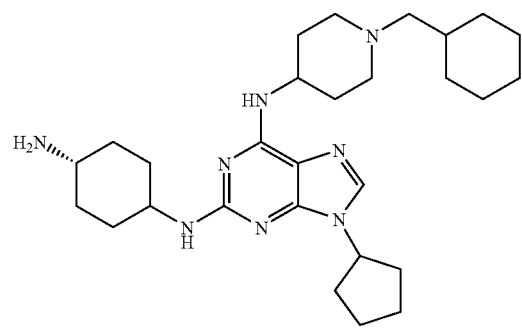
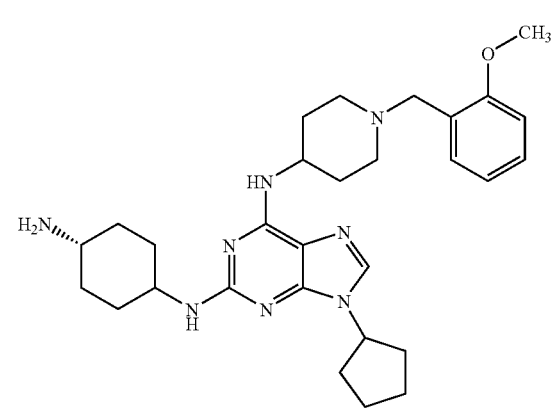

TABLE 2-continued
Inhibitors of kinases
| Structure | Reference |
|---|---|
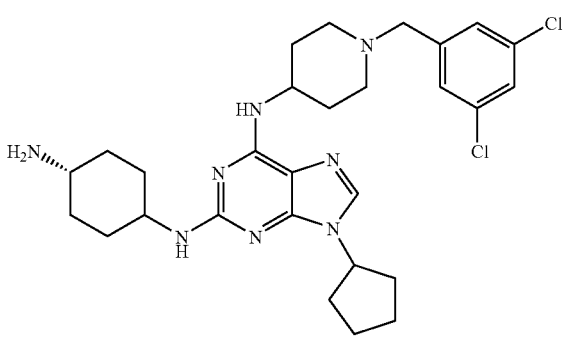
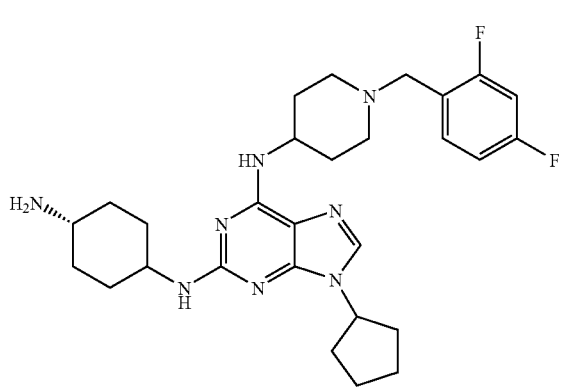
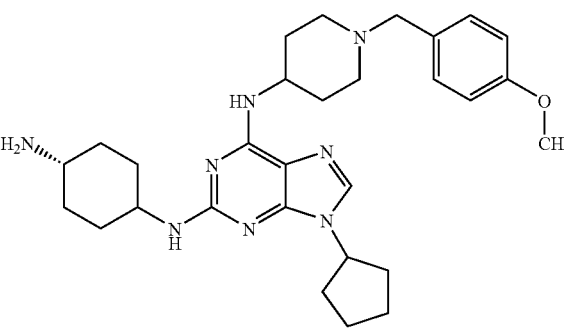
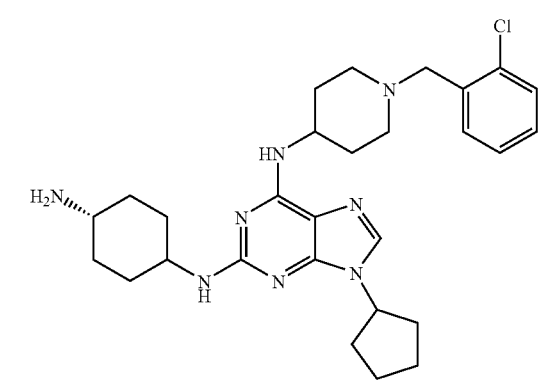

TABLE 2-continued

Inhibitors of kinases

| Structure | Reference |
| --- | --- |
| | |
| | Bioorg. Med. Chem. Lett. 2001, 11, 1401–1405 |
| | Bioorg. Med. Chem. Lett. 2001, 11, 1401–1405 |

TABLE 2-continued

Inhibitors of kinases

| Structure | Reference |
| --- | --- |
| | Bioorg. Med. Chem. Lett. 2001, 11, 1401–1405 |
| | Bioorg. Med. Chem. Lett. 2001, 11, 1401–1405 |
| | Bioorg. Med. Chem. Lett. 2001, 11, 1401–1405 |
| | |

TABLE 2-continued

Inhibitors of kinases

| Structure | Reference |
|---|---|
| (structure) | Bioorg. Med. Chem. Lett. 2001, 11, 1401–1405 |
| (structure) | Bioorg. Med. Chem. Lett. 2001, 11, 1401–1405 |
| (structure) | Bioorg. Med. Chem. Lett. 2001, 11, 1401–1405 |

TABLE 2-continued

Inhibitors of kinases

| Structure | Reference |
|---|---|

TABLE 2-continued

Inhibitors of kinases

| Structure | Reference |
|---|---|

TABLE 2-continued

Inhibitors of kinases

| Structure | Reference |
|-----------|-----------|

TABLE 2-continued
Inhibitors of kinases
| Structure | Reference |
|---|---|
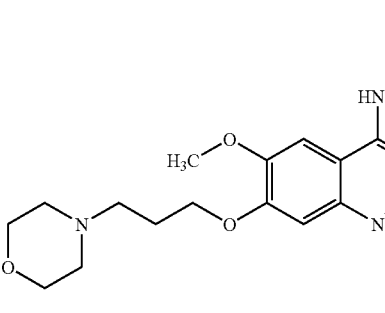

TABLE 2-continued
Inhibitors of kinases
| Structure | Reference |
|---|---|
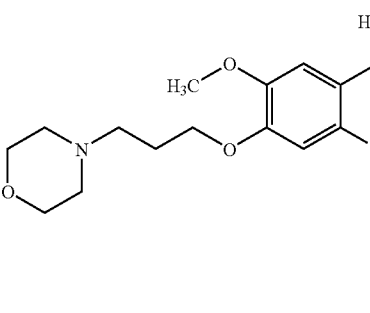
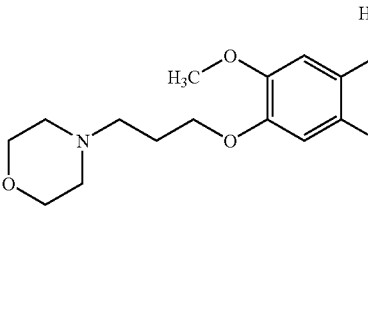
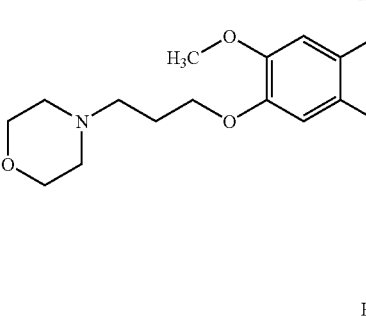
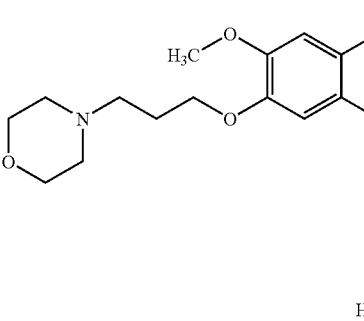
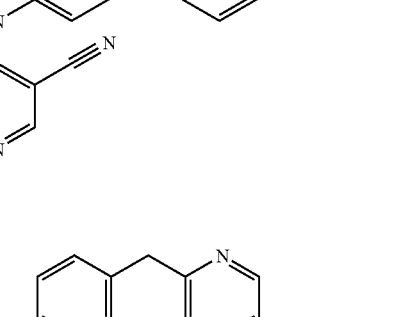

TABLE 2-continued
Inhibitors of kinases
| Structure | Reference |
|---|---|
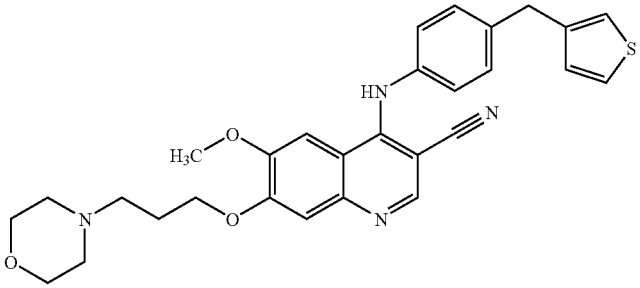
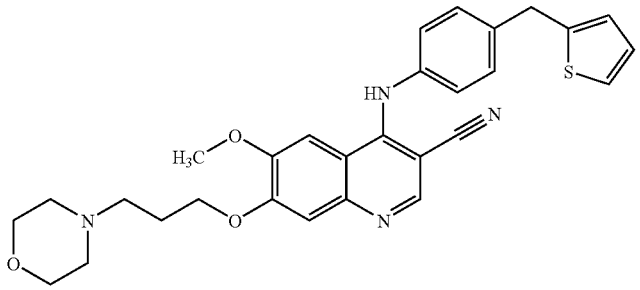
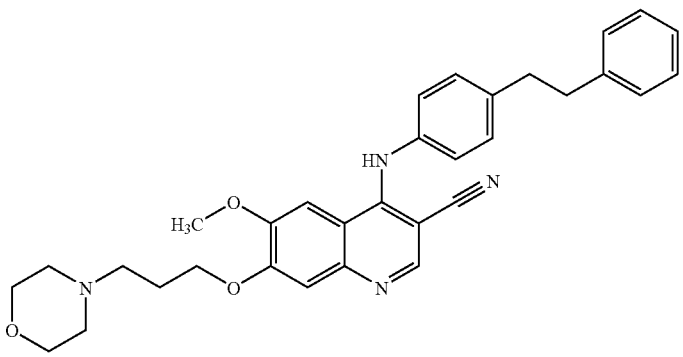
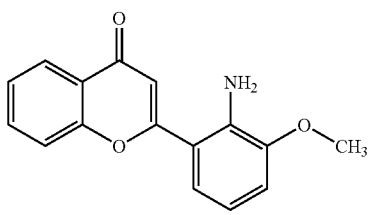
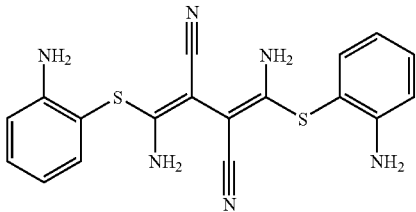

TABLE 2-continued
| Structure | Reference |
|---|---|
| 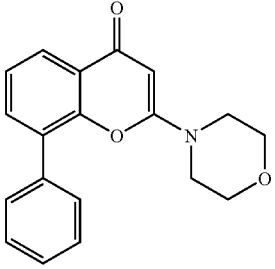 | |
| 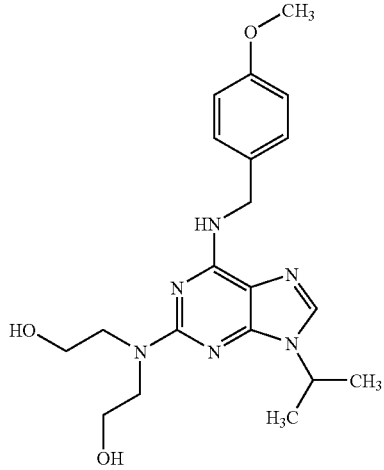 | |
| 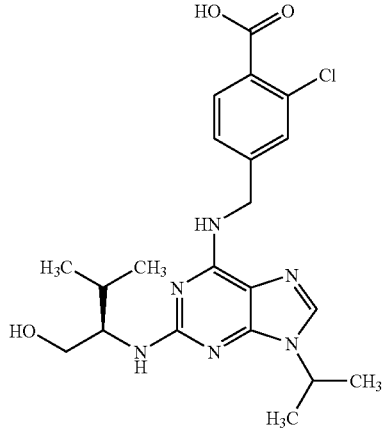 | |
| 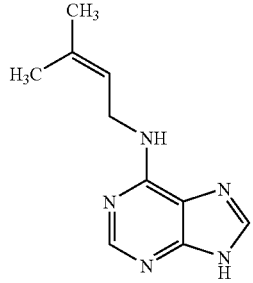 | |

TABLE 2-continued

Inhibitors of kinases

| Structure | Reference |
|---|---|
| 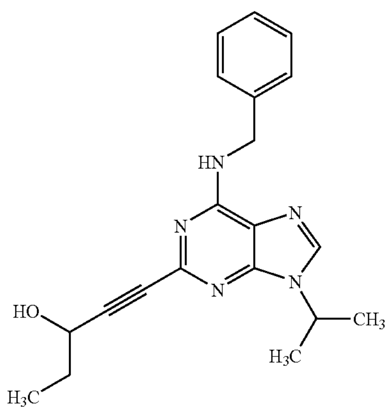 | J. Med. Chem. 2000, 43, 4089–4108 |

TABLE 2-continued
Inhibitors of kinases
| Structure | Reference |
|---|---|
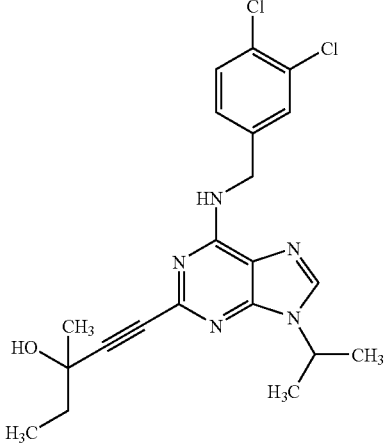
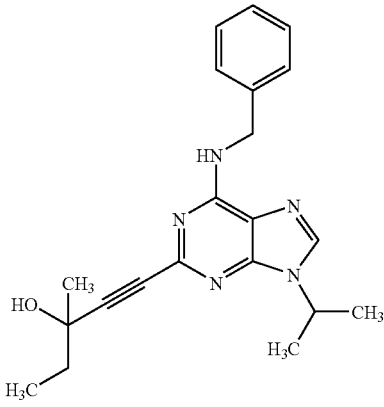
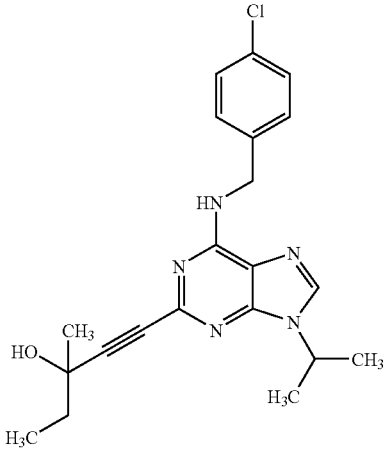

TABLE 2-continued

Inhibitors of kinases

| Structure | Reference |
|---|---|

TABLE 2-continued

Inhibitors of kinases

| Structure | Reference |
|---|---|

TABLE 2-continued

Inhibitors of kinases

| Structure | Reference |
|-----------|-----------|

TABLE 2-continued

Inhibitors of kinases

| Structure | Reference |
|---|---|

TABLE 2-continued

Inhibitors of kinases

| Structure | Reference |
|---|---|

TABLE 2-continued

Inhibitors of kinases

| Structure | Reference |
|---|---|
| | |
| | |
| 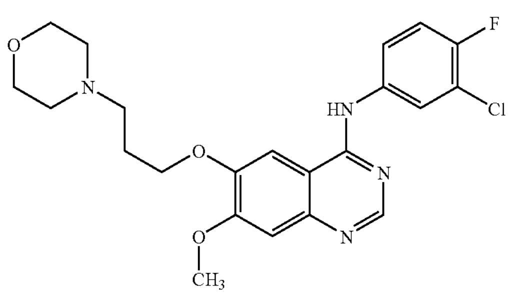 | Bioorg. Med. Chem. Lett. 2001, 11, 1922–1914 |
| | |

TABLE 2-continued
Inhibitors of kinases
| Structure | Reference |
|---|---|
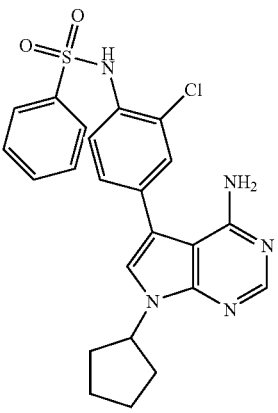
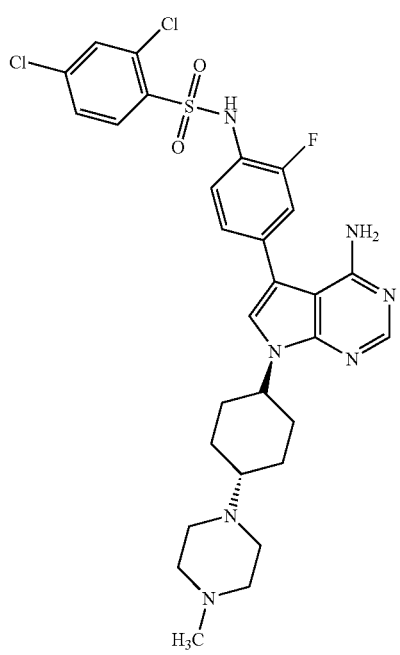
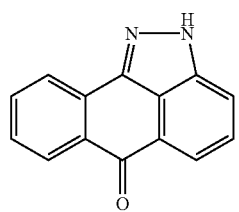

TABLE 2-continued

Inhibitors of kinases

| Structure | Reference |
|---|---|

TABLE 2-continued

Inhibitors of kinases

| Structure | Reference |
|---|---|

TABLE 2-continued
Inhibitors of kinases
| Structure | Reference |
|---|---|
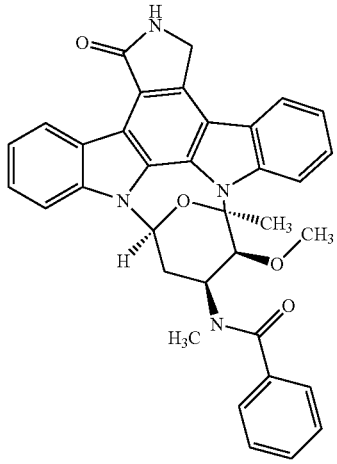
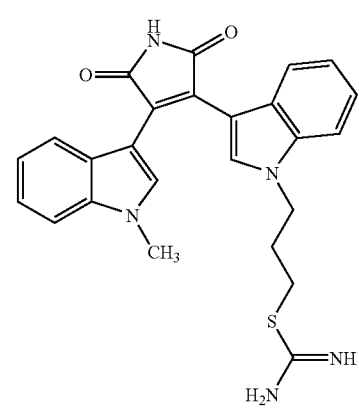
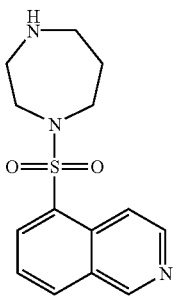

TABLE 2-continued
Inhibitors of kinases
| Structure | Reference |
|---|---|
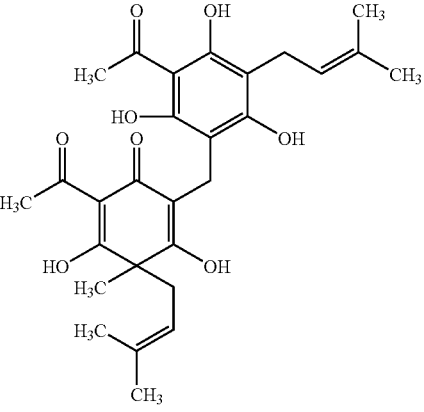
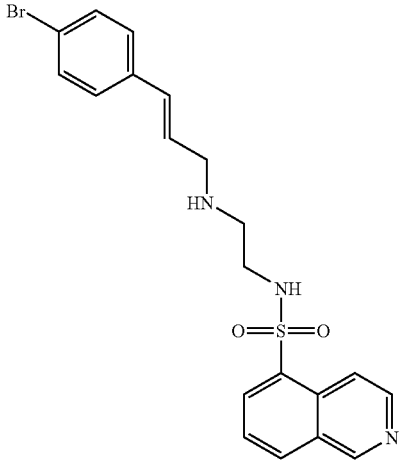
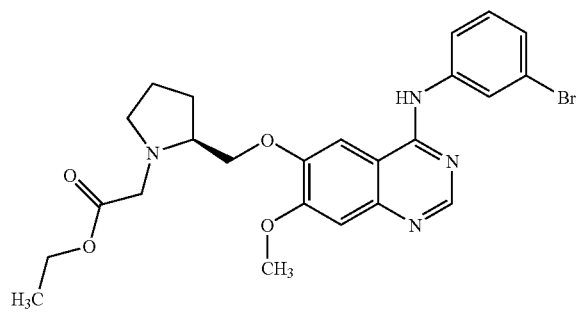

TABLE 2-continued

Inhibitors of kinases

| Structure | Reference |
|-----------|-----------|

| TABLE 2-continued |
|---|
| Inhibitors of kinases |

| Structure | Reference |
|---|---|

TABLE 2-continued
Inhibitors of kinases
| Structure | Reference |
|---|---|
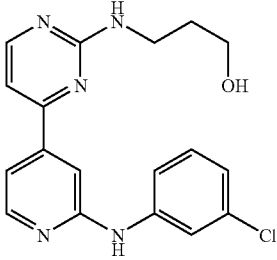
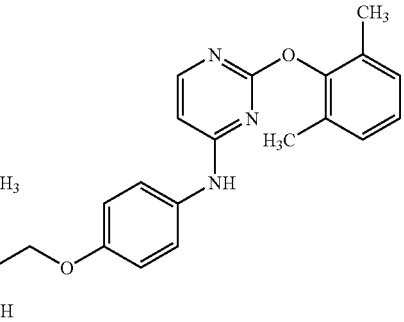
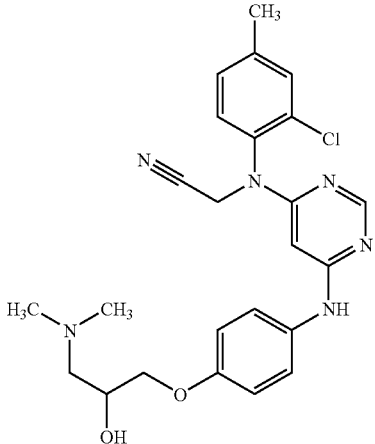
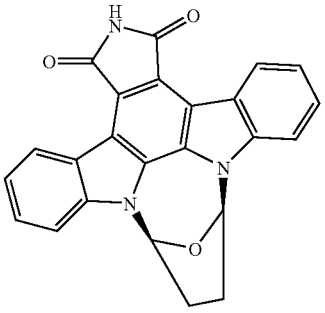

TABLE 2-continued
Inhibitors of kinases
| Structure | Reference |
|---|---|
| 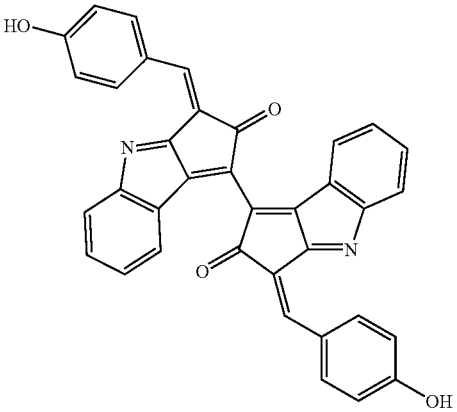 | |
| 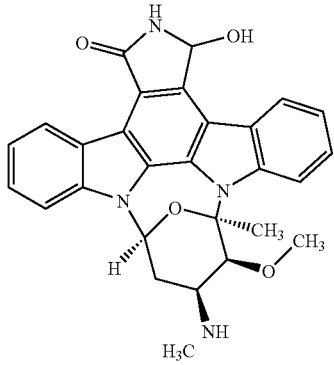 | |
| 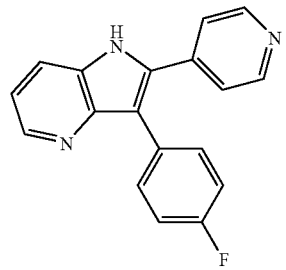 | WO 9920624 |
| 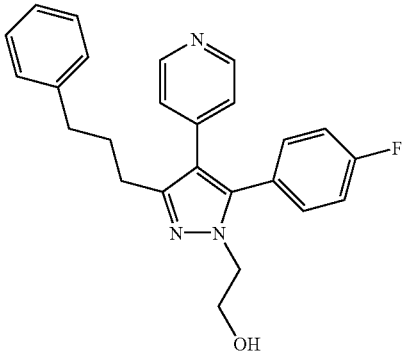 | |

TABLE 2-continued

Inhibitors of kinases

| Structure | Reference |
|---|---|

TABLE 2-continued

Inhibitors of kinases

| Structure | Reference |
|-----------|-----------|

TABLE 2-continued

Inhibitors of kinases

| Structure | Reference |
| --- | --- |
| | J. Med. Chem. 2001, 44, 3965–3977 |
| | J. Med. Chem. 2001, 44, 3965–3977 |
| | J. Med. Chem. 2001, 44, 3965–3977 |
| | J. Med. Chem. 2001, 44, 3965–3977 |

TABLE 2-continued

Inhibitors of kinases

| Structure | Reference |
|---|---|
| | J. Med. Chem. 2001, 44, 3965–3977 |
| | J. Med. Chem. 2001, 44, 3965–3977 |
| | J. Med. Chem. 2001, 44, 3965–3977 |
| | J. Med. Chem. 2001, 44, 3965–3977 |

TABLE 2-continued
Inhibitors of kinases
| Structure | Reference |
|---|---|
| 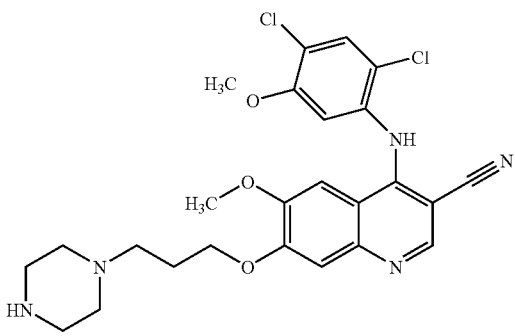 | J. Med. Chem. 2001, 44, 3965–3977 |
| 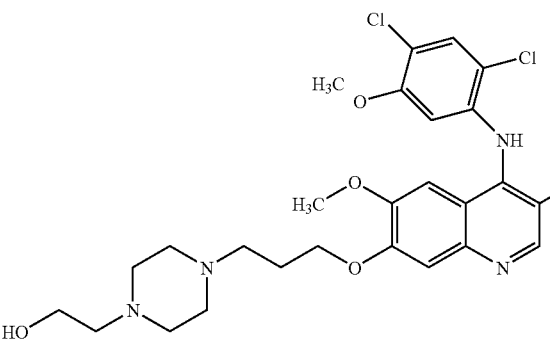 | J. Med. Chem. 2001, 44, 3965–3977 |
| 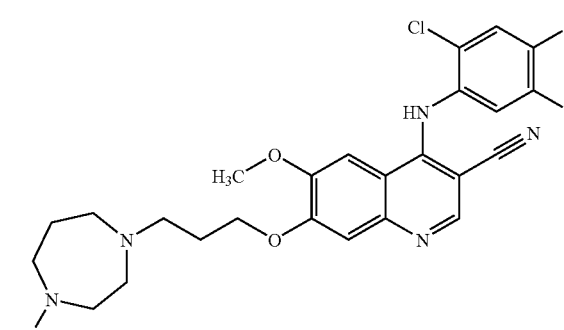 | J. Med. Chem. 2001, 44, 3965–3977 |
| 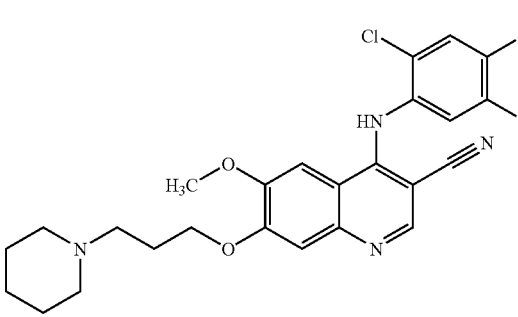 | J. Med. Chem. 2001, 44, 3965–3977 |

TABLE 2-continued

Inhibitors of kinases

| Structure | Reference |
|---|---|
| | J. Med. Chem. 2001, 44, 3965–3977 |
| | J. Med. Chem. 2001, 44, 3965–3977 |
| | J. Med. Chem. 2001, 44, 3965–3977 |
| | J. Med. Chem. 2001, 44, 3965–3977 |
| | J. Med. Chem. 2001, 44, 3965–3977 |

TABLE 2-continued

Inhibitors of kinases

| Structure | Reference |
| --- | --- |
| (structure) | J. Med. Chem. 2001, 44, 3965–3977 |
| (structure) | J. Med. Chem. 2001, 44, 3965–3977 |
| (structure) | J. Med. Chem. 2001, 44, 3965–3977 |
| (structure) | J. Med. Chem. 2001, 44, 3965–3977 |
| (structure) | J. Med. Chem. 2001, 44, 3965–3977 |
| (structure) | J. Med. Chem. 2001, 44, 3965–3977 |

TABLE 2-continued
Inhibitors of kinases
| Structure | Reference |
|---|---|
| 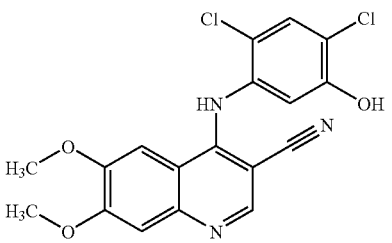 | J. Med. Chem. 2001, 44, 3965–3977 |
| 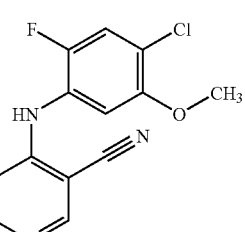 | J. Med. Chem. 2001, 44, 3965–3977 |
| 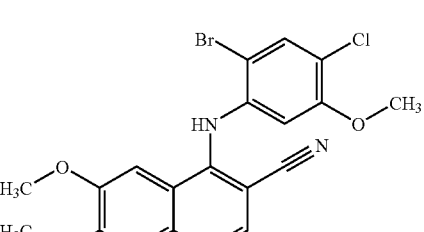 | J. Med. Chem. 2001, 44, 3965–3977 |
| 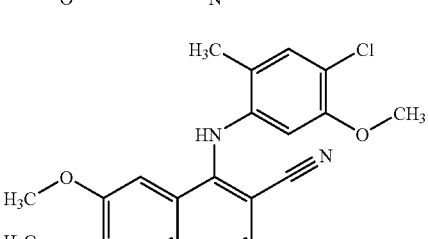 | J. Med. Chem. 2001, 44, 3965–3977 |
| 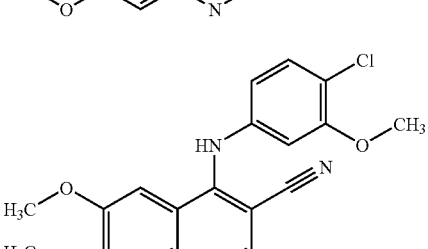 | J. Med. Chem. 2001, 44, 3965–3977 |
| 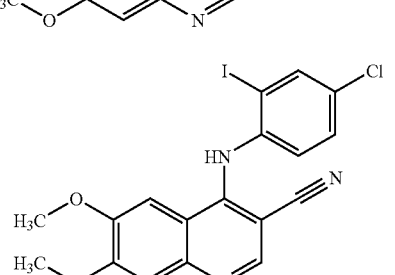 | J. Med. Chem. 2001, 44, 3965–3977 |

TABLE 2-continued

Inhibitors of kinases

| Structure | Reference |
|---|---|
| | J. Med. Chem. 2001, 44, 3965–3977 |
| | J. Med. Chem. 2001, 44, 3965–3977 |
| | J. Med. Chem. 2001, 44, 3965–3977 |
| | |
| | |
| | |

TABLE 2-continued

Inhibitors of kinases

| Structure | Reference |
|---|---|

TABLE 2-continued

Inhibitors of kinases

| Structure | Reference |
|---|---|
| | |
| | |
| | |
| 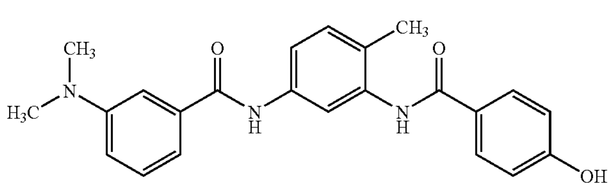 | Chem. Biol. 1999, 6, 559<br>J. Biol, Chem. 1999, 276, 17420,<br>WO 9822103 |
| 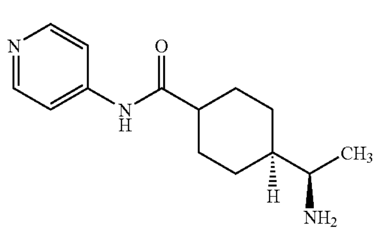 | Nature, 1998, 389, 990 |

TABLE 2-continued

Inhibitors of kinases

| Structure | Reference |
|---|---|

TABLE 2-continued

Inhibitors of kinases

| Structure | Reference |
|---|---|

TABLE 2-continued

Inhibitors of kinases

| Structure | Reference |
|---|---|

TABLE 2-continued

Inhibitors of kinases

| Structure | Reference |
|---|---|

TABLE 2-continued

Inhibitors of kinases

| Structure | Reference |
|-----------|-----------|

TABLE 2-continued

Inhibitors of kinases

| Structure | Reference |
|---|---|

TABLE 2-continued

Inhibitors of kinases

| Structure | Reference |
|---|---|

TABLE 2-continued
Inhibitors of kinases
| Structure | Reference |
|---|---|
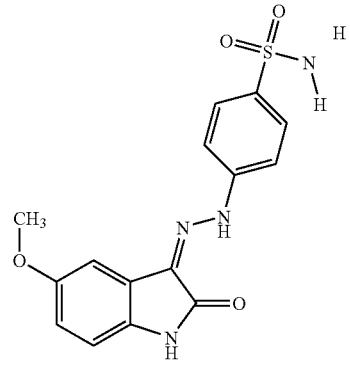
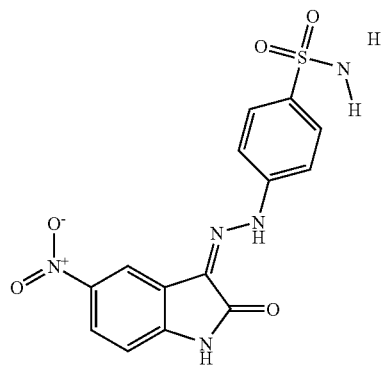
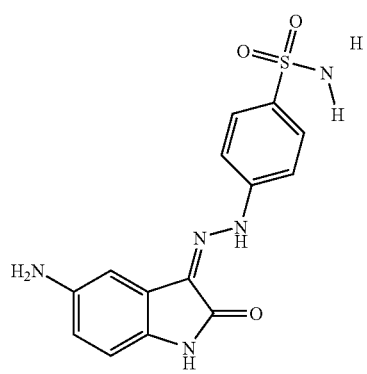
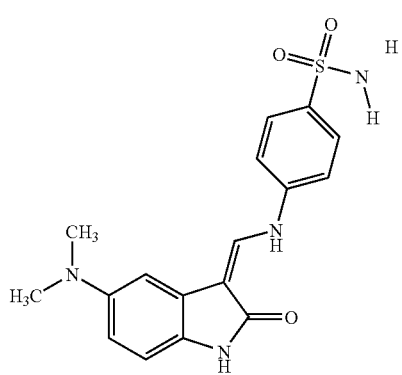

TABLE 2-continued

Inhibitors of kinases

| Structure | Reference |
|---|---|

TABLE 2-continued

Inhibitors of kinases

| Structure | Reference |
|---|---|

TABLE 2-continued
Inhibitors of kinases
| Structure | Reference |
| --- | --- |
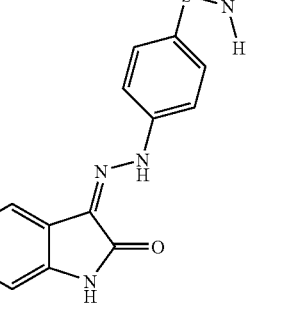
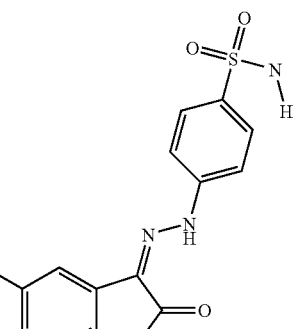
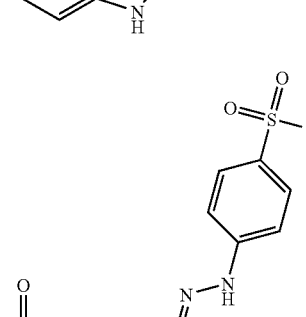
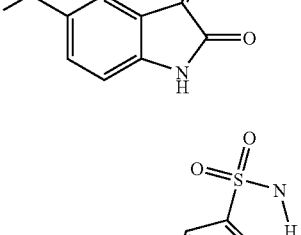

TABLE 2-continued

Inhibitors of kinases

| Structure | Reference |
|---|---|

TABLE 2-continued

Inhibitors of kinases

| Structure | Reference |
|-----------|-----------|

TABLE 2-continued

Inhibitors of kinases

| Structure | Reference |
|---|---|

TABLE 2-continued
Inhibitors of kinases
| Structure | Reference |
|---|---|
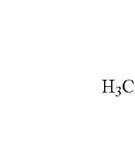

TABLE 2-continued
Inhibitors of kinases
| Structure | Reference |
|---|---|
| 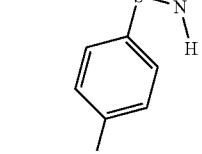 | |
| 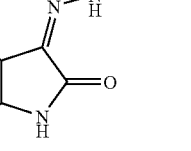 | |
| 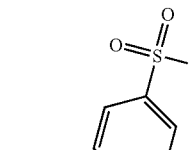 | |
| 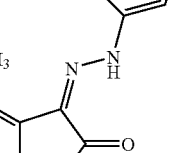 | |

TABLE 2-continued

Inhibitors of kinases

| Structure | Reference |
|-----------|-----------|

TABLE 2-continued
Inhibitors of kinases
| Structure | Reference |
|---|---|
| 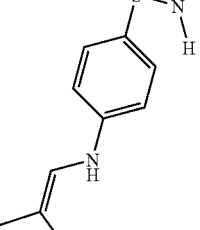 | |
| 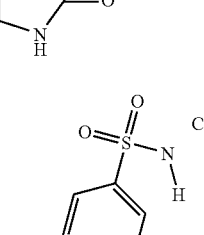 | |
| 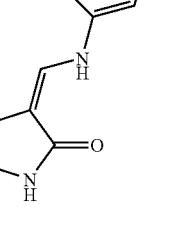 | |
| 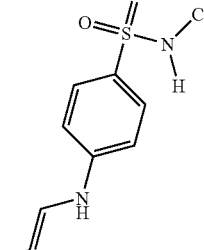 | |

TABLE 2-continued

Inhibitors of kinases

| Structure | Reference |
|-----------|-----------|

TABLE 2-continued
Inhibitors of kinases
| Structure | Reference |
|---|---|
| 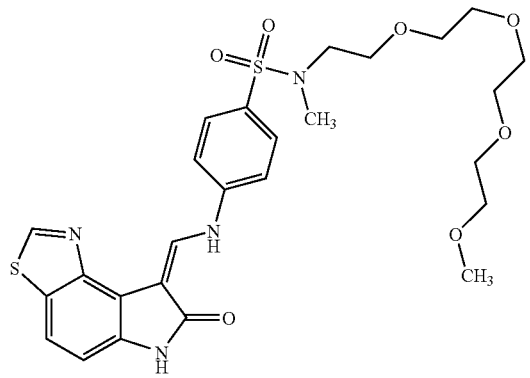 | |
| 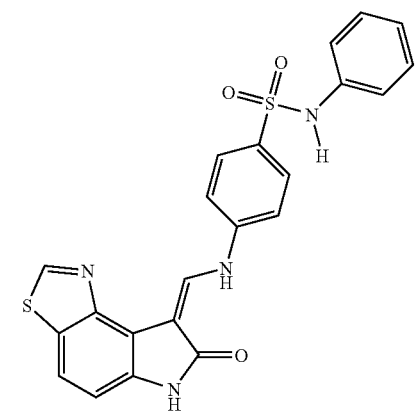 | |
| 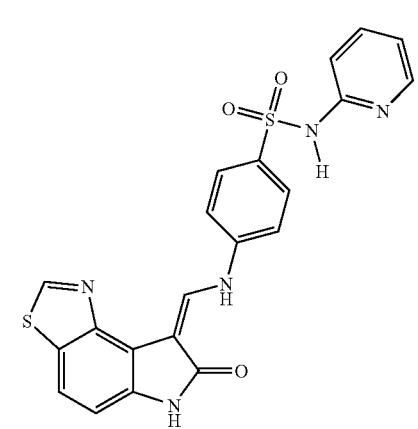 | |

/ 307 308
TABLE 2-continued
Inhibitors of kinases
| Structure | Reference |
|---|---|
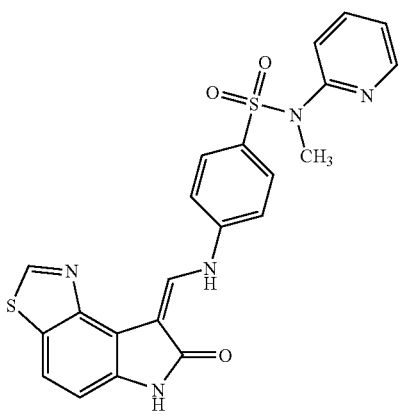
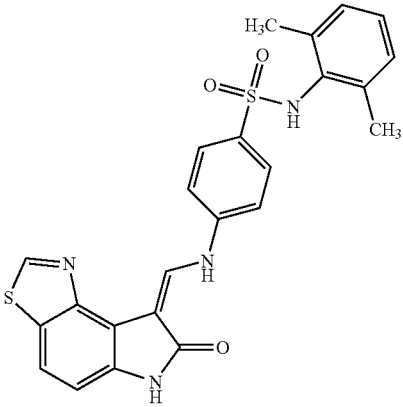
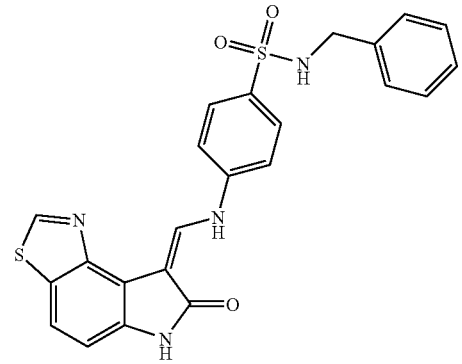

TABLE 2-continued
Inhibitors of kinases
| Structure | Reference |
|---|---|
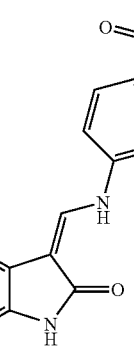

TABLE 2-continued
Inhibitors of kinases
| Structure | Reference |
|---|---|
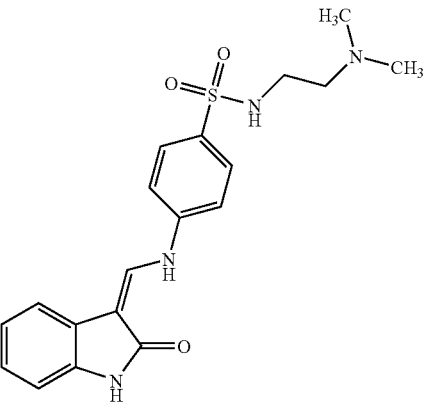
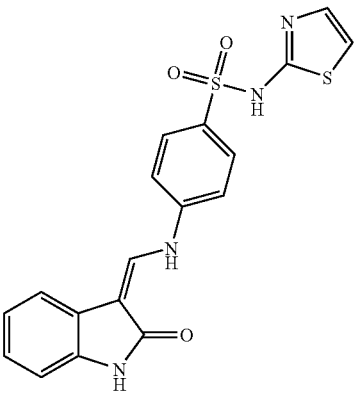
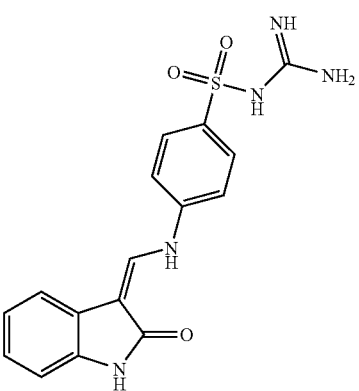

TABLE 2-continued

Inhibitors of kinases

| Structure | Reference |
|-----------|-----------|

TABLE 2-continued

Inhibitors of kinases

| Structure | Reference |
|---|---|
| 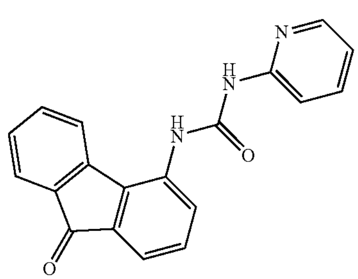 | J. Med. Chem. 2001, 44, 4615 |

TABLE 2-continued

Inhibitors of kinases

| Structure | Reference |
|---|---|
| | J. Med. Chem. 2001, 44, 4615 |
| | J. Med. Chem. 2001, 44, 4615 |
| | J. Med. Chem. 2001, 44, 4628 |
| | J. Med. Chem. 2001, 44, 4628 |
| | J. Med. Chem. 2001, 44, 4628 |

TABLE 2-continued
Inhibitors of kinases
| Structure | Reference |
|---|---|
| 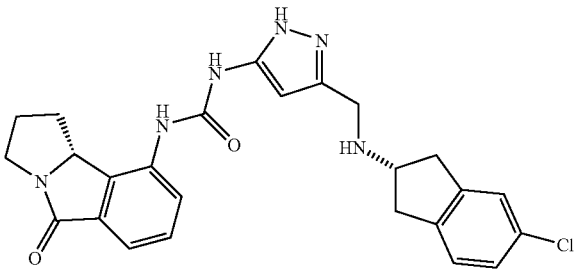 | J. Med. Chem. 2001, 44, 4628 |
| 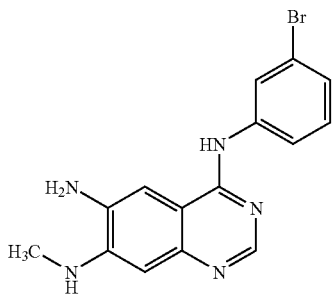 | |
| 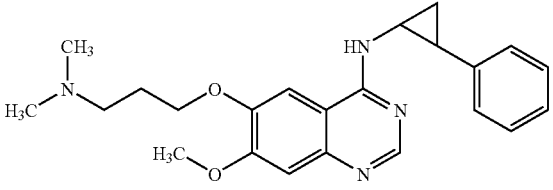 | |
| 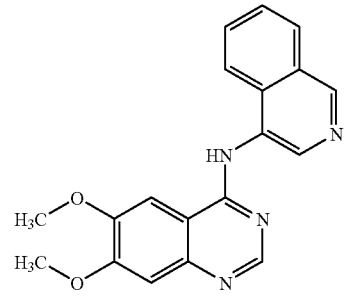 | |
| 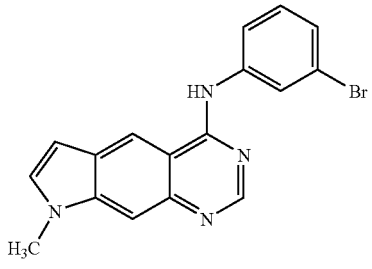 | |

TABLE 2-continued
Inhibitors of kinases
| Structure | Reference |
|---|---|
| 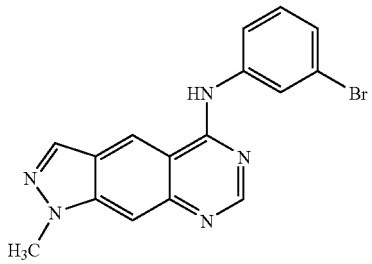 | |
| 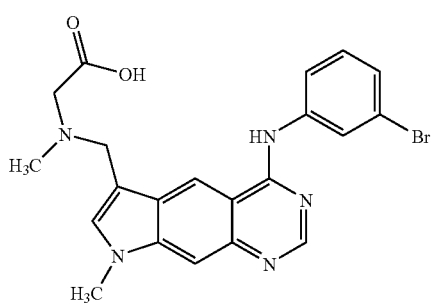 | |
| 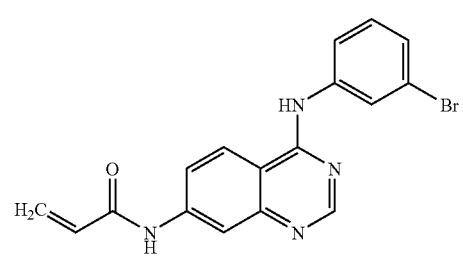 | |
| 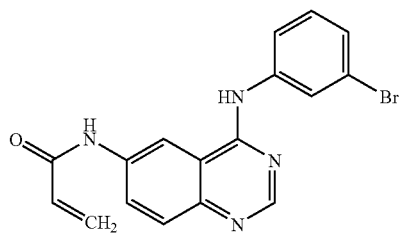 | |
| 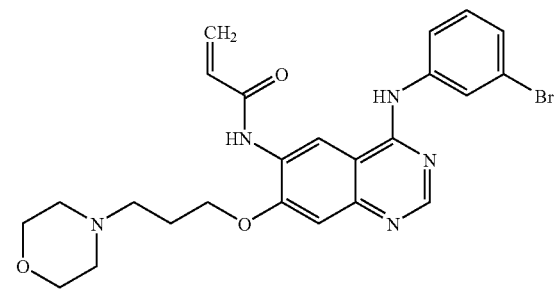 | Proc. Am. Assoc. Can Res. 1999, 40, 117 & 121 |

TABLE 2-continued
Inhibitors of kinases
| Structure | Reference |
|---|---|
| 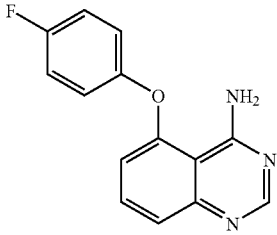 | |
| 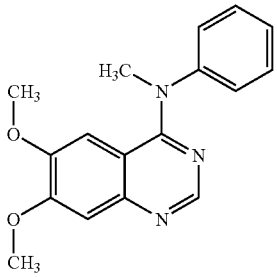 | |
| 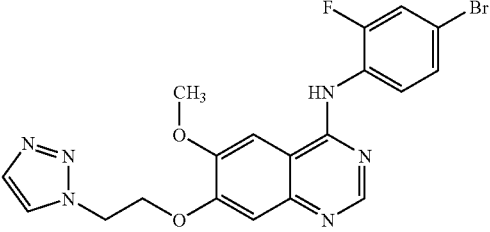 | Proc. Am. Assoc. Can. Res. 1999, 90, 69 |
| 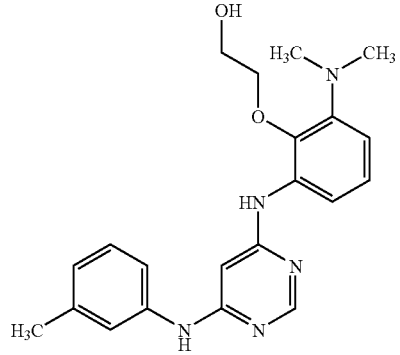 | |

TABLE 2-continued
Inhibitors of kinases
| Structure | Reference |
|---|---|
| 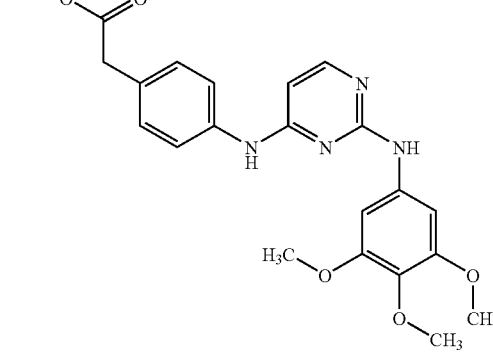 | |
| 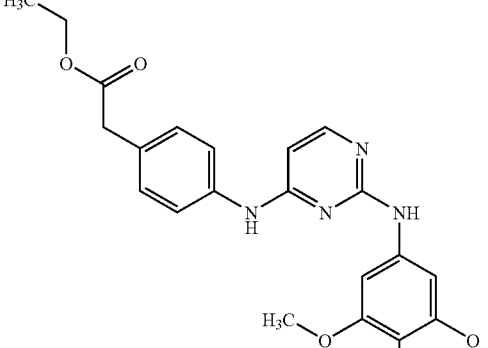 | |
| 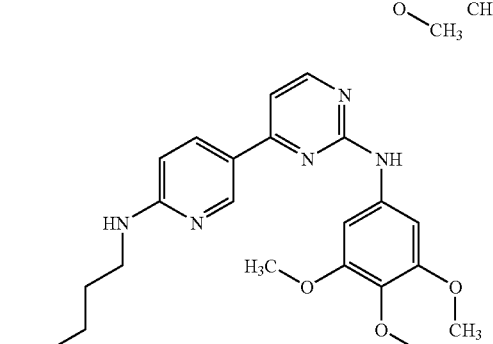 | |
| 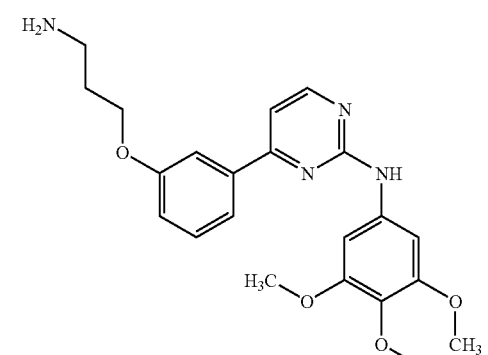 | |

TABLE 2-continued
Inhibitors of kinases
| Structure | Reference |
|---|---|
| 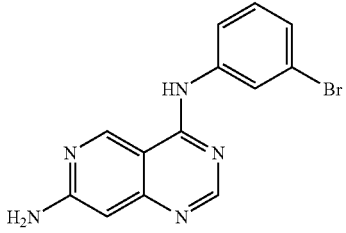 | J. Med. Chem. 1995, 38, 3780 |
| 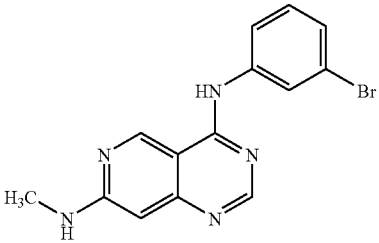 | J. Med. Chem. 1995, 38, 3780 |
| 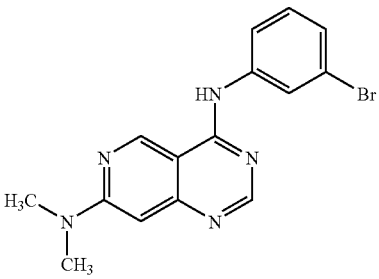 | J. Med. Chem. 1995, 38, 3780 |
| 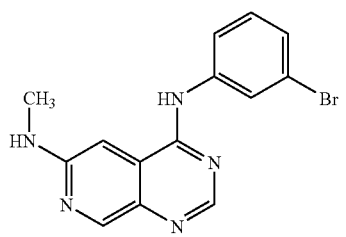 | J. Med. Chem. 1995, 38, 3780 |
| 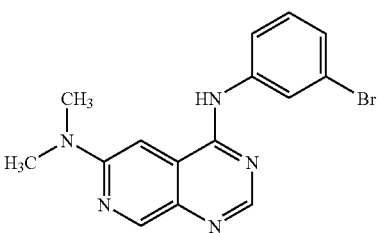 | J. Med. Chem. 1995, 38, 3780 |

TABLE 2-continued

Inhibitors of kinases

| Structure | Reference |
|-----------|-----------|
| 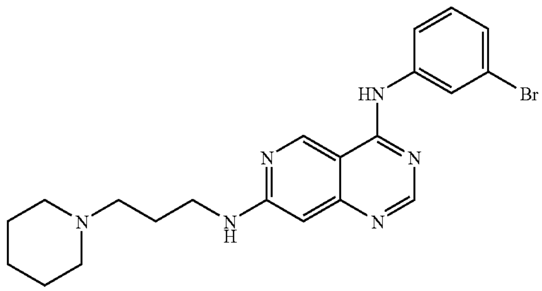 | J. Med. Chem. 1997, 40, 3915 |
| 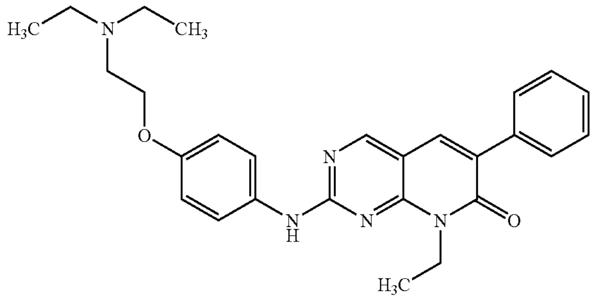 | J. Med. Chem. 1998, 41, 4365 |
| 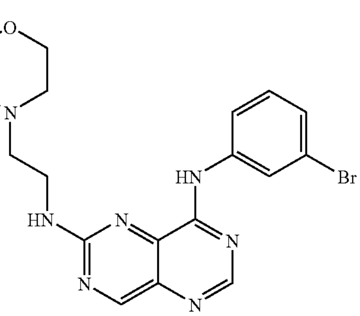 | J. Med. Chem. 1997, 40, 1820 |

TABLE 2-continued

Inhibitors of kinases

| Structure | Reference |
|---|---|
| | |
| | |
| 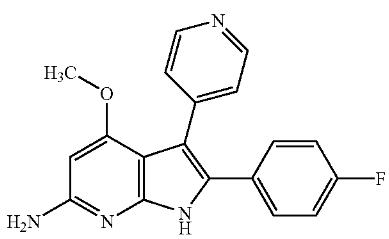 | J. Med. Chem. 1998. 41, 4196 |
| | |
| | |

TABLE 2-continued

Inhibitors of kinases

| Structure | Reference |
|---|---|

TABLE 2-continued

Inhibitors of kinases

| Structure | Reference |
|-----------|-----------|

TABLE 2-continued

Inhibitors of kinases

| Structure | Reference |
|-----------|-----------|

TABLE 2-continued

Inhibitors of kinases

| Structure | Reference |
|---|---|
|  |  |
| 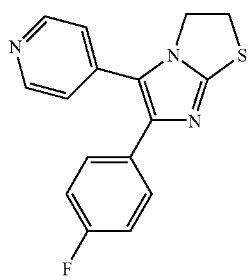 | Ann. N.Y. Acad. Sci. 1993, 696, 149 |
|  |  |
|  |  |

TABLE 2-continued

Inhibitors of kinases

| Structure | Reference |
| --- | --- |
| 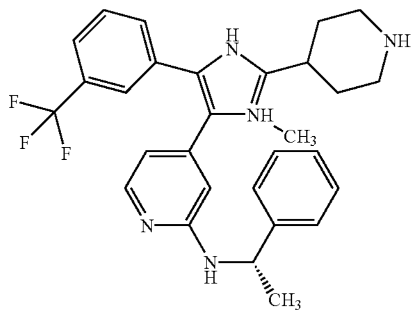 | J. Med. Chem. 1996, 39, 5215 |
| 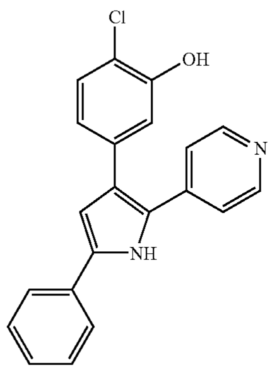 | Proc. Am. Assoc. Can. Res. 1998, 39, 558. |
| 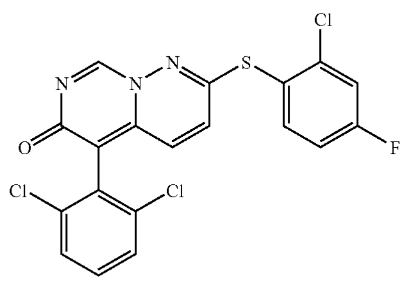 | J. Med. Chem. 2001, 44, 3417 |
| 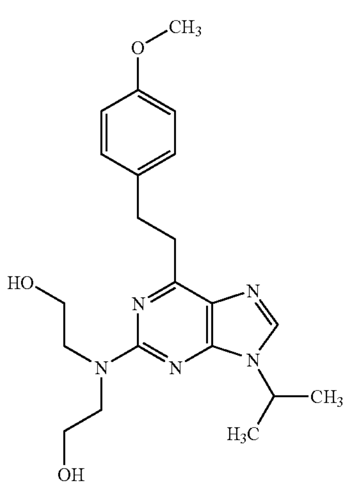 | J. Biol. Chem. 1997, 272, 29207 |

TABLE 2-continued
Inhibitors of kinases
| Structure | Reference |
|---|---|
| 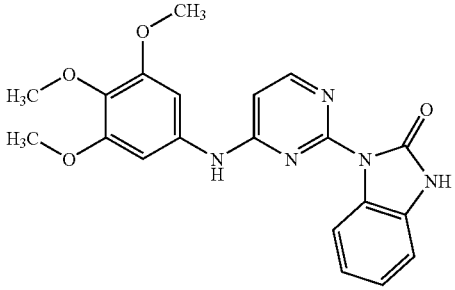 | WO 01/060816 |
| 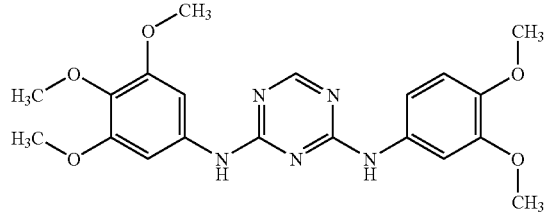 | WO 01/025220 |
| 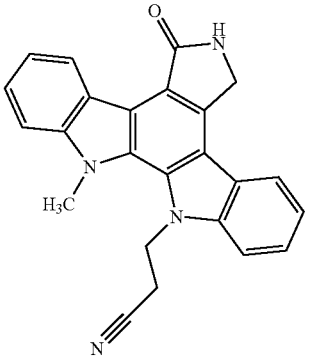 | |
| 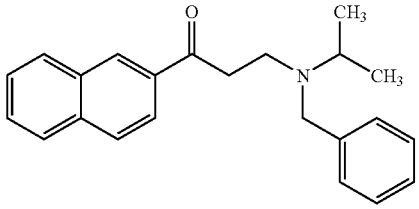 | Bioorg. Med. Chem. Lett. 2000, 10, 575–579 |
| 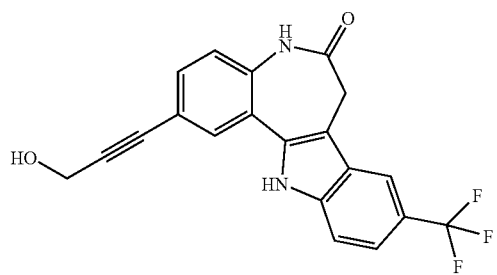 | Bioorg. Med. Chem. Lett. 2000, 10, 567–569 |

TABLE 2-continued

Inhibitors of kinases

| Structure | Reference |
|---|---|
| | |
| 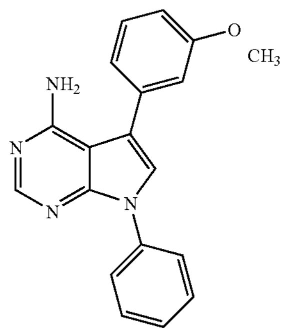 | Bioorg. Med. Chem. Lett. 2000, 10m 945–949 |
| 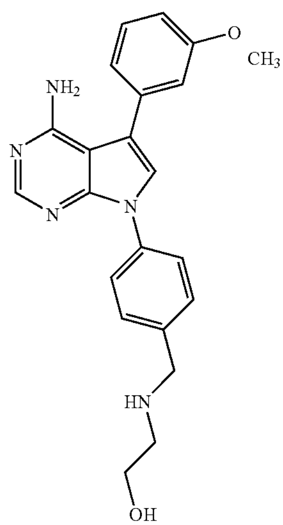 | Bioorg. Med. Chem. Lett. 2000, 10, 945–949 |

TABLE 2-continued
Inhibitors of kinases
| Structure | Reference |
| --- | --- |
| 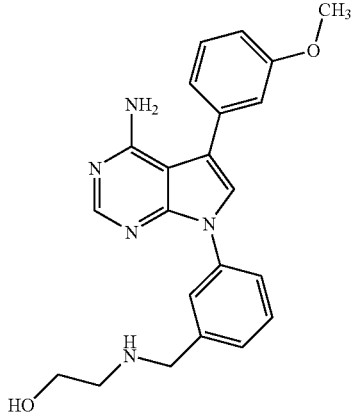 | Bioorg. Med. Chem. Lett. 2000, 10, 945–949 |
| 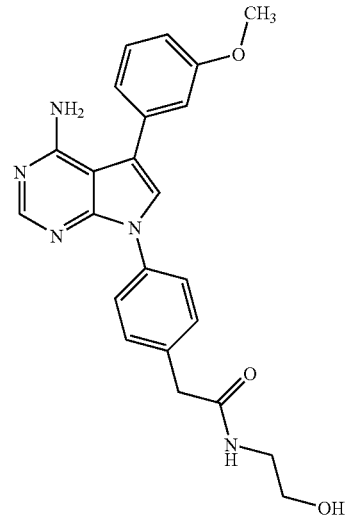 | Bioorg. Med. Chem. Lett. 2000, 10, 945–949 |
| 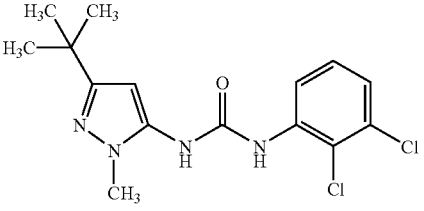 | Bioorg. Med. Chem. Lett. 2000, 10, 2047–2050 |
| 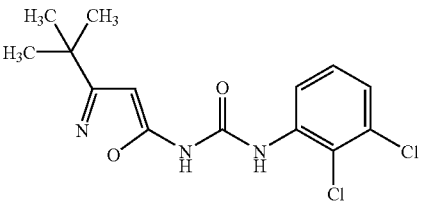 | Bioorg. Med. Chem. Lett. 2000, 10, 2047–2050 |

TABLE 2-continued

Inhibitors of kinases

| Structure | Reference |
|-----------|-----------|
| 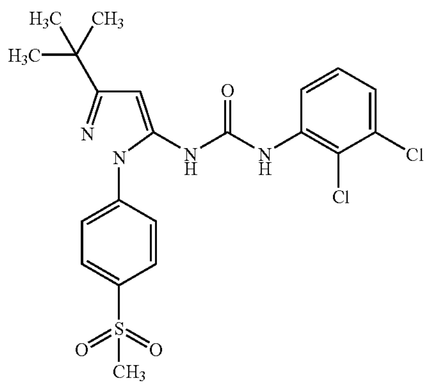 | Bioorg. Med. Chem. Lett. 2000, 10, 2051–2054 |
| 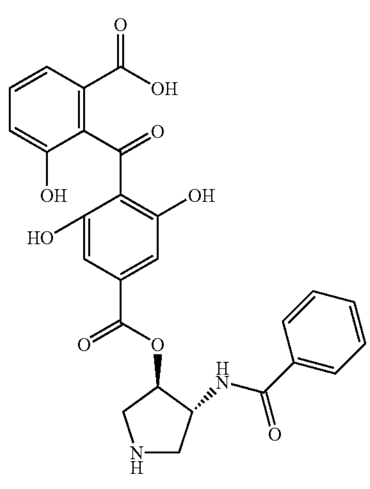 | Bioorg. Med. Chem. Lett. 1996, 6, 1759–1764 |

TABLE 2-continued
Inhibitors of kinases
| Structure | Reference |
|---|---|
| 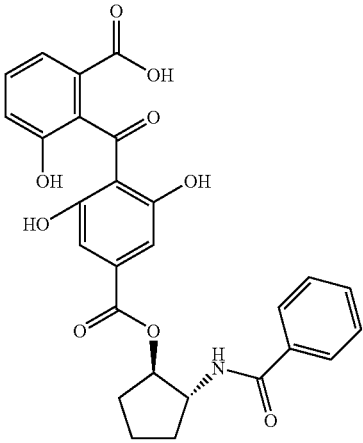 | Bioorg. Med. Chem. Lett. 1996, 6, 1759–1764 |
| 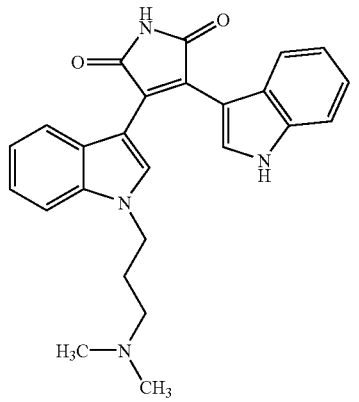 | J. Biol. Chem. 1991, 266, 15771 |
| 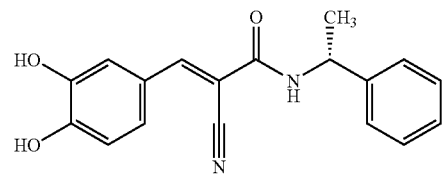 | J. Med. Chem. 1991, 34, 1896 |
| 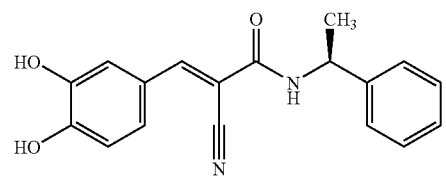 | J. Med. Chem. 1991, 34, 1896 |
| 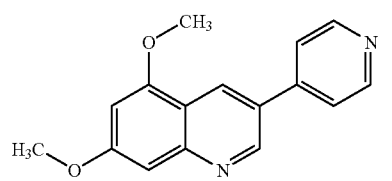 | J. Med. Chem. 1994, 37, 2627 |

TABLE 2-continued

Inhibitors of kinases

| Structure | Reference |
| --- | --- |
| 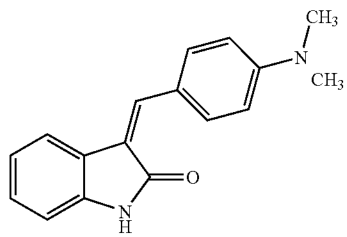 | J. Med. Chem. 1999, 41, 2588 |
| 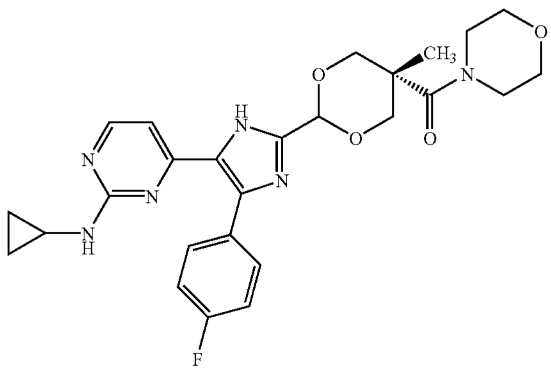 | Bioorg. Med. Chem. Lett. 2001, 11, 693–696 |
| | |
| 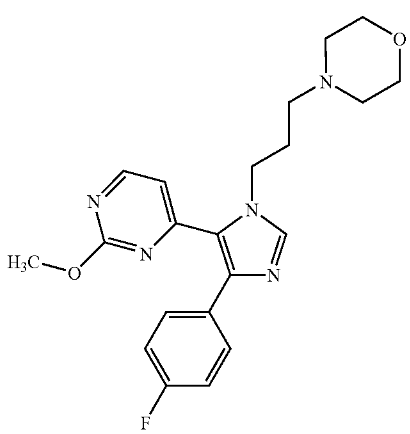 | Bioorg. Med. Chem. Lett. 1998, 8, 3111–3116 |

TABLE 2-continued
Inhibitors of kinases
| Structure | Reference |
|---|---|
| 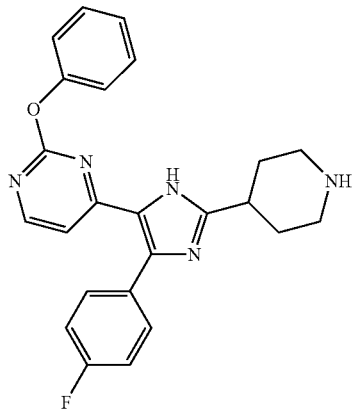 | Bioorg. Med. Chem. Lett. 2001, 11, 1123–1126 |
| 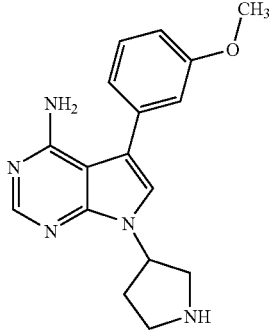 | Bioorg. Med. Chem. Lett. 2001, 11, 853–856 |
| 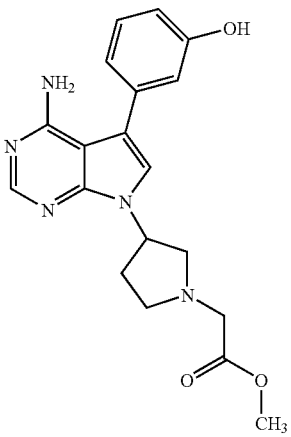 | Bioorg. Med. Chem. Lett, 2001, 11, 853–856 |

TABLE 2-continued

Inhibitors of kinases

| Structure | Reference |
|---|---|
|  | Bioorg. Med. Chem. Lett. 2001, 11, 853–856 |
|  | Bioorg. Med. Chem. Lett. 2001, 11, 853–856 |
|  | Bioorg. Med. Chem. Lett. 2001, 11, 853–856 |

TABLE 2-continued

Inhibitors of kinases

| Structure | Reference |
|---|---|
| | |
| 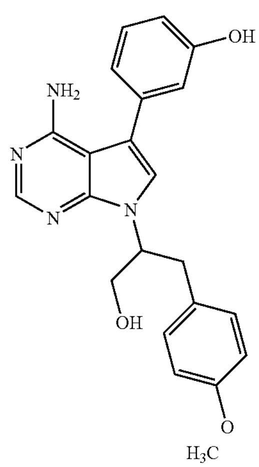 | Bioorg. Med. Chem. Lett. 2001, 11, 849–852 |
| 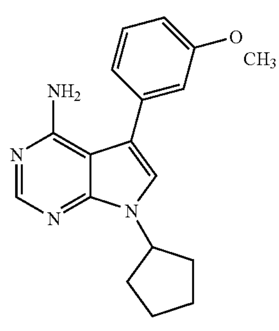 | Bioorg. Med. Chem. Lett. 2001, 11, 840–852 |

TABLE 2-continued
Inhibitors of kinases
| Structure | Reference |
|---|---|
| 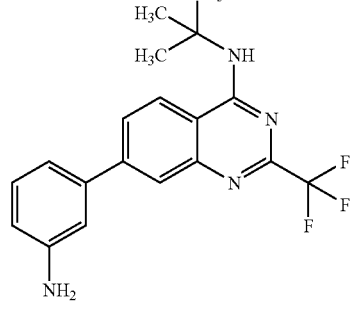 | Bioorg. Med. Chem. Lett. 2001, 11, 1157–1160 |
| 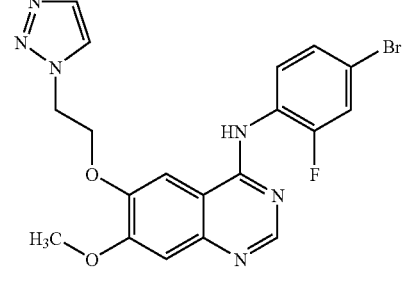 | J. Med. Chem. 2001, 44, 2133–2138 |
| 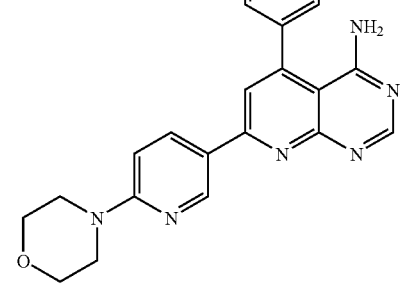 | WO 01/37835 |

TABLE 2-continued
Inhibitors of kinases
| Structure | Reference |
|---|---|
| 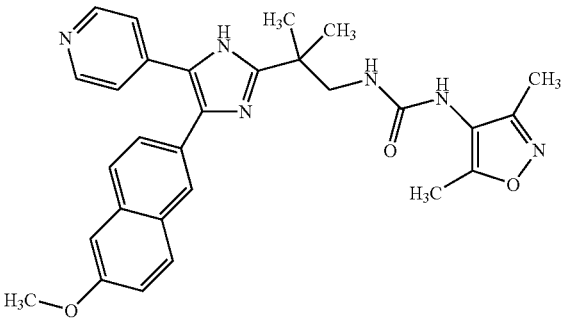 | |
| 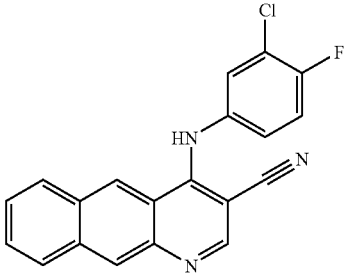 | US 01/051620 |
| 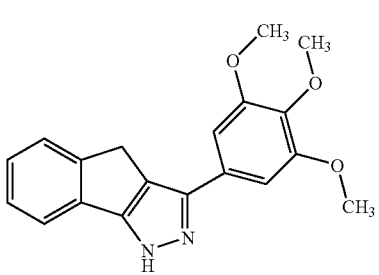 | WO 01/087846 |
| 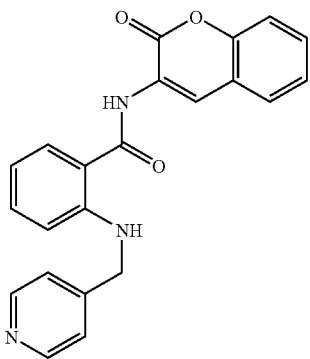 | WO 01/085719 |

TABLE 2-continued
Inhibitors of kinases
| Structure | Reference |
| --- | --- |
| 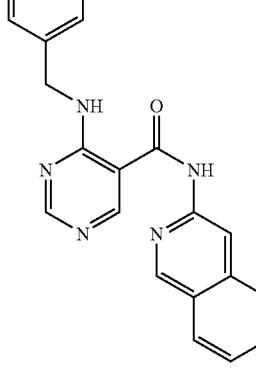 | WO 01/085715 |
| 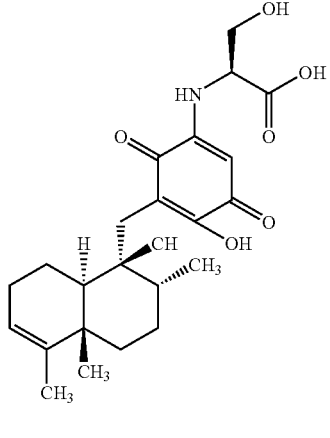 | J. Am. Chem. Soc. 2001, 123, 11586–11593 |
| 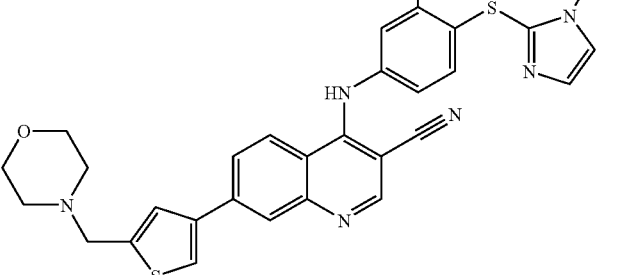 | WO 01/072711 |

TABLE 2-continued

Inhibitors of kinases

| Structure | Reference |
|---|---|
| 22 | WO 01/058899 |
| 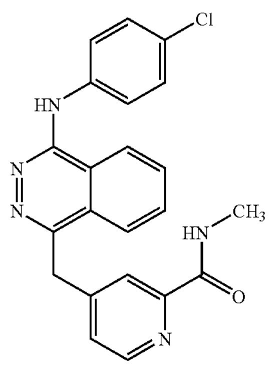 | WO 01/010859 |
| 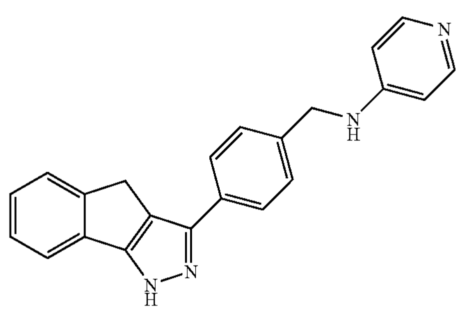 | WO 00/059901 |
| 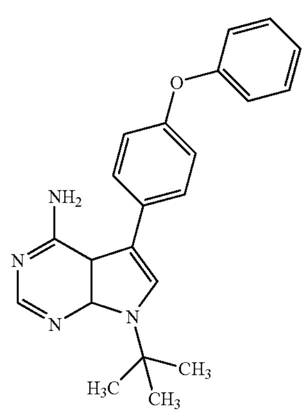 | Bioorg. Med. Chem. Lett. 2000, 10, 2167–2170 |

TABLE 2-continued

Inhibitors of kinases

| Structure | Reference |
|---|---|
| 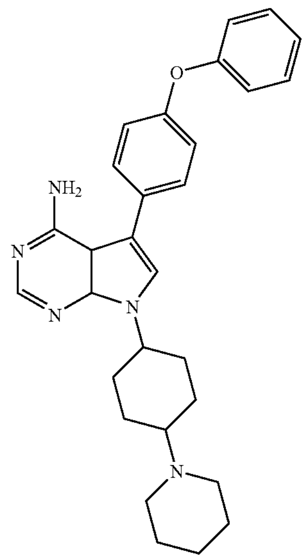 | WO 00/017203 |
| 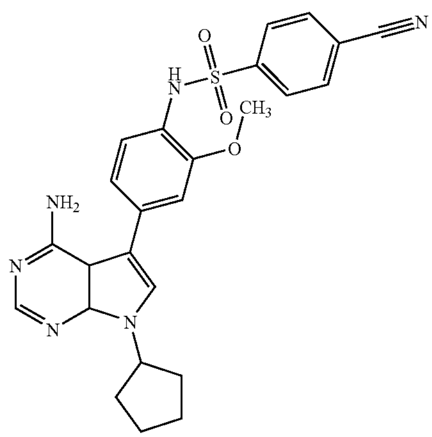 | WO 00/017202 |
| 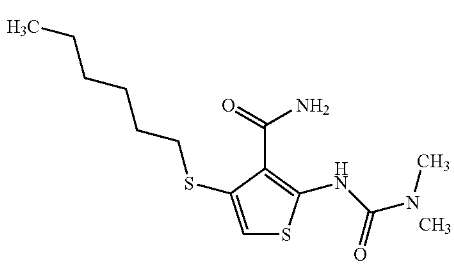 | WO 9962890 |
| 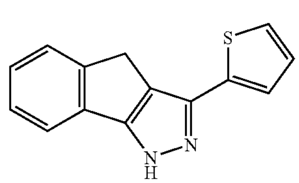 | WO 9917769 |

TABLE 2-continued

Inhibitors of kinases

| Structure | Reference |
|---|---|
| 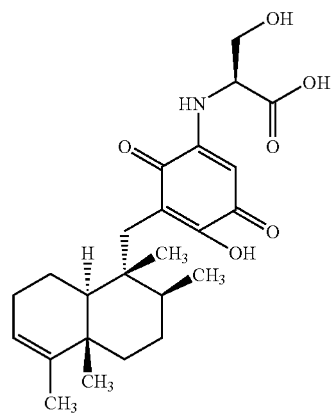 | J. Am. Chem. Soc. 2001, 123, 11586–11593 |
| 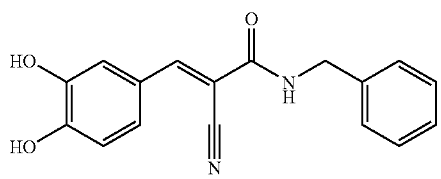 | Atherosclerosis (Shannon, Ireland) (2002), 160(1), 123–132. |
| | |
| | |
| 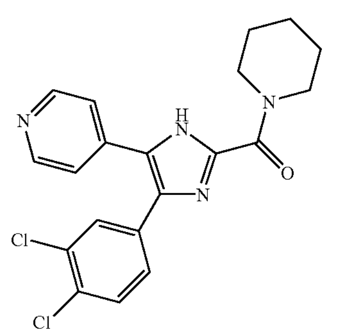 | WO 01/066540 |

TABLE 2-continued

Inhibitors of kinases

| Structure | Reference |
|---|---|
| (structure) | WO 01/066539 |
| (structure) | US 6187799 |
| (structure) | WO 99/32106 |
| (structure) | WO 99/32455 |

| Structure | Reference |
|---|---|
| (structure) | WO 99/32436 |
| (structure) | WO 99/17759 |
| (structure) | Biochem. Biophys. Res. Commun. 1987, 147, 322 |
| (structure) | Biochem. Biophys. Res. Commun. 1987, 147, 322 |
| (structure) | Biochem. Biophys. Res. Commun. 1987, 147, 322 |

TABLE 2-continued
Inhibitors of kinases
| Structure | Reference |
| --- | --- |
| 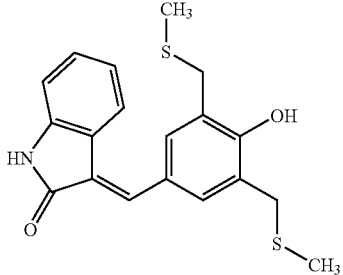 | Biochem. Biophys. Res. Commun. 1987, 147, 322 |
| 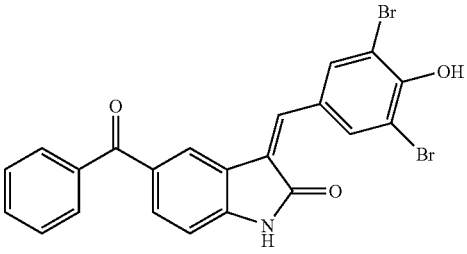 | Bioorg. Med. Chem. Lett. 2000, 10, 223–226 |
| 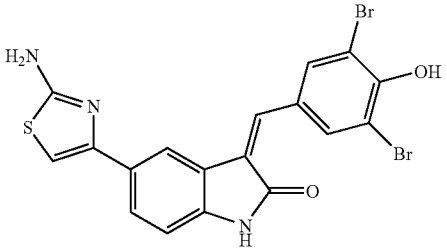 | Bioorg. Med. Chem. Lett. 2000, 10, 223–226 |
| 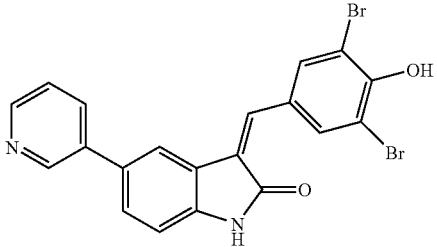 | Bioorg. Med. Chem. Lett. 2000, 10, 223–226 |
| 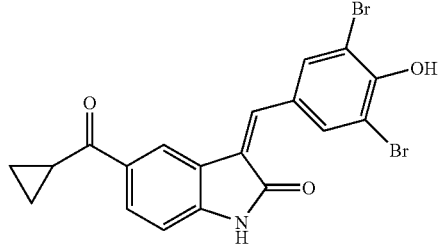 | Bioorg. Med. Chem. Lett. 2000, 10, 223–226 |

TABLE 2-continued

Inhibitors of kinases

| Structure | Reference |
|---|---|
| | Bioorg. Med. Chem. Lett. 2000, 10, 223–226 |
| | Bioorg. Med. Chem. Lett. 2000, 10, 223–226 |
| | Bioorg. Med. Chem. Lett. 2000, 10, 223–226 |
| | Bioorg. Med. Chem. Lett. 2000, 10, 223–226 |
| | Bioorg. Med. Chem. Lett. 2000, 10, 223–226 |

TABLE 2-continued

Inhibitors of kinases

| Structure | Reference |
| --- | --- |
| (structure) | Bioorg. Med. Chem. Lett. 2000, 10, 223–226 |
| (structure) | Bioorg. Med. Chem. Lett. 2000, 10, 223–226 |
| (structure) | Bioorg. Med. Chem. Lett. 2000, 10, 461–464 |
| (structure) | Bioorg. Med. Chem. Lett. 2000, 10, 461–464 |
| (structure) | Bioorg. Med. Chem. Lett. 2000, 10, 461–464 |
| (structure) | Bioorg. Med. Chem. Lett. 2001, 11, 1401–1405 |

TABLE 2-continued
Inhibitors of kinases
| Structure | Reference |
| --- | --- |
| 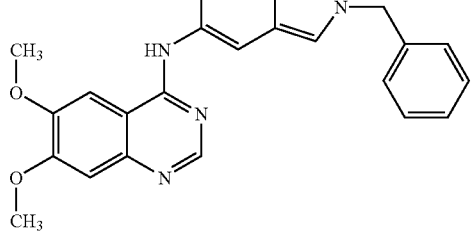 | Bioorg. Med. Chem. Lett. 2001, 11, 1401–1405 |
| 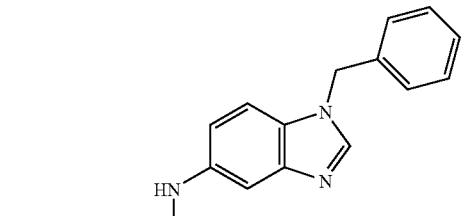 | Bioorg. Med. Chem. Lett. 2001, 11, 1401–1405 |
| 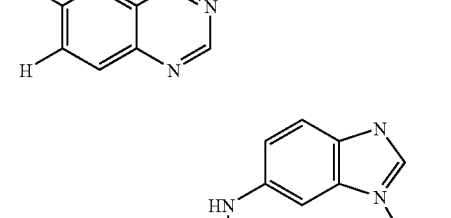 | Bioorg. Med. Chem. Lett. 2001, 11, 1401–1405 |
| 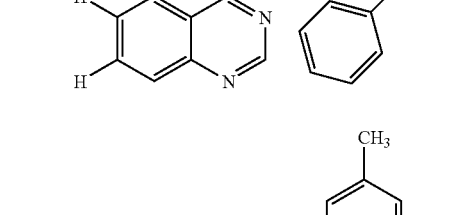 | Bioorg. Med. Chem. Lett. 2001, 11, 1911–1914 |
| 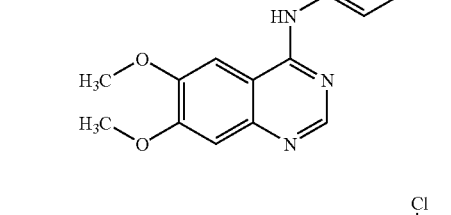 | Bioorg. Med. Chem. Lett. 2001, 11, 1911–1914 |

TABLE 2-continued

Inhibitors of kinases

| Structure | Reference |
|---|---|
| | Bioorg. Med. Chem. Lett. 2001, 11, 1911–1914 |
| | Bioorg. Med. Chem. Lett. 2001, 11, 1911–1914 |
| | Bioorg. Med. Chem. Lett. 2001, 11, 1911–1914 |
| | Bioorg. Med. Chem. Lett. 2001, 11, 1911–1914 |
| | Bioorg. Med. Chem. Lett. 2001, 11, 1911–1914 |

TABLE 2-continued

Inhibitors of kinases

| Structure | Reference |
|---|---|
| | Bioorg. Med. Chem. Lett. 2001, 11, 1911–1914 |
| | Bioorg. Med. Chem. Lett. 2001, 11, 1911–1914 |
| | Bioorg. Med. Chem. Lett. 2001, 11, 1911–1914 |
| | Bioorg. Med. Chem. Lett. 2001, 11, 1911–1914 |
| | Bioorg. Med. Chem. Lett. 2001, 11, 1911–1914 |

TABLE 2-continued
Inhibitors of kinases
| Structure | Reference |
|---|---|
| 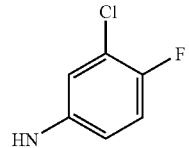 | Bioorg. Med. Chem. Lett. 2001, 11, 1911–1914 |
| 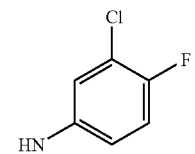 | Bioorg. Med. Chem. Lett. 2001, 11, 1911–1914 |
| 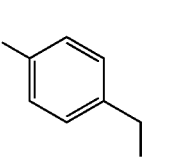 | Bioorg. Med. Chem. Lett. 2001, 11, 9–12 |
| 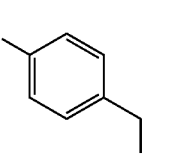 | Bioorg. Med. Chem. Lett. 2001, 11, 9–12 |
| 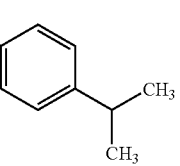 | Bioorg. Med. Chem. Lett. 2001, 11, 9–12 |
| 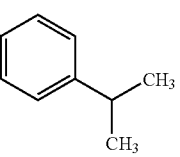 | Bioorg. Med. Chem. Lett. 2001, 11, 9–12 |
| 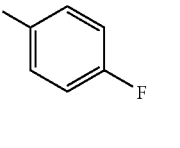 | Bioorg. Med. Chem. Lett. 2001, 11, 9–12 |

TABLE 2-continued
Inhibitors of kinases
| Structure | Reference |
|---|---|
| 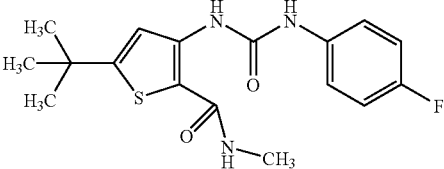 | Bioorg. Med. Chem. Lett. 2001, 11, 9–12 |
| 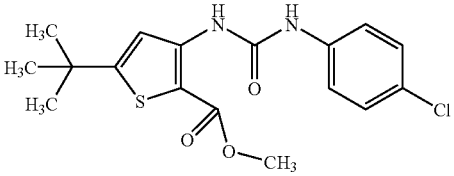 | Bioorg. Med. Chem. Lett. 2001, 11, 9–12 |
| 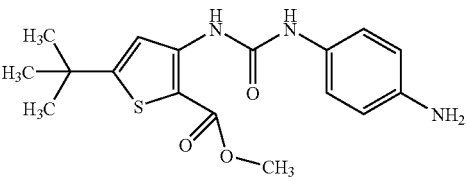 | Bioorg. Med. Chem. Lett. 2001, 11, 9–12 |
| 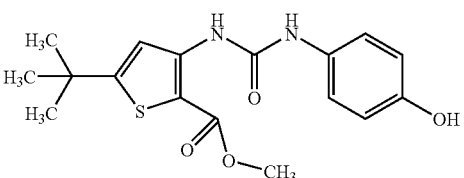 | Bioorg. Med. Chem. Lett. 2001, 11, 9–12 |
| 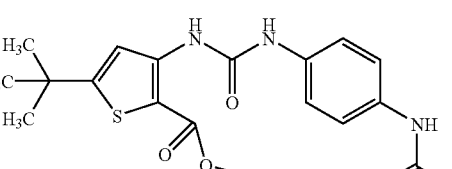 | Bioorg. Med. Chem. Lett. 2001, 11, 9–12 |
| 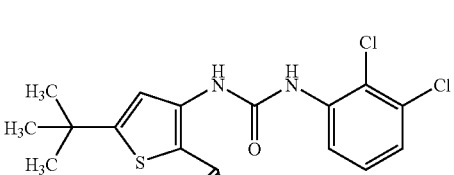 | Bioorg. Med. Chem. Lett. 2001, 11, 9–12 |
| 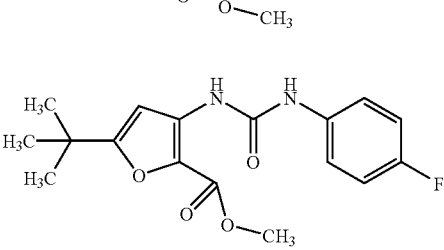 | Bioorg. Med. Chem. Lett. 2001, 11, 9–12 |

TABLE 2-continued

Inhibitors of kinases

| Structure | Reference |
|---|---|
| | Bioorg. Med. Chem. Lett. 2001, 11, 9–12 |
| | Bioorg. Med. Chem. Lett. 2001, 11, 9–12 |
| | Bioorg. Med. Chem. Lett. 2001, 11, 9–12 |
| | Bioorg. Med. Chem. Lett. 2001, 11, 9–12 |
| | Bioorg. Med. Chem. Lett. 2001, 11, 9–12 |
| | Bioorg. Med. Chem. Lett. 2001, 11, 9–12 |
| | Bioorg. Med. Chem. Lett. 2001, 11, 9–12 |

TABLE 2-continued

Inhibitors of kinases

| Structure | Reference |
| --- | --- |
| | Bioorg. Med. Chem. Lett. 2001, 11, 9–12 |
| | Bioorg. Med. Chem. Lett. 2001, 11, 9–12 |
| | Bioorg. Med. Chem. Lett. 2001, 11, 9–12 |
| | Bioorg. Med. Chem. Lett. 2001, 11, 9–12 |
| | Bioorg. Med. Chem. Lett. 2001, 11, 9–12 |
| | Bioorg. Med. Chem. Lett. 2001, 11, 9–12 |
| | Bioorg. Med. Chem. Lett. 2001, 11, 9–12 |

TABLE 2-continued

Inhibitors of kinases

| Structure | Reference |
|---|---|
| 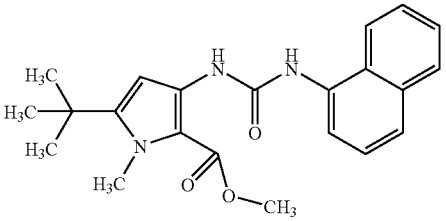 | Bioorg. Med. Chem. Lett. 2001, 11, 9–12 |
| 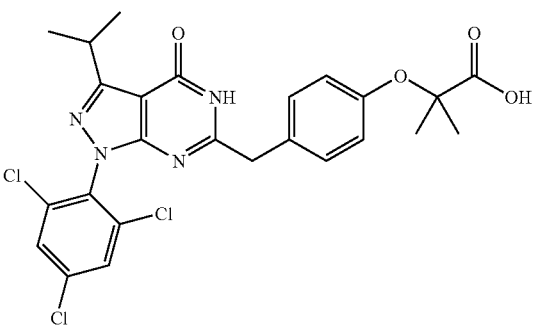 | |
| 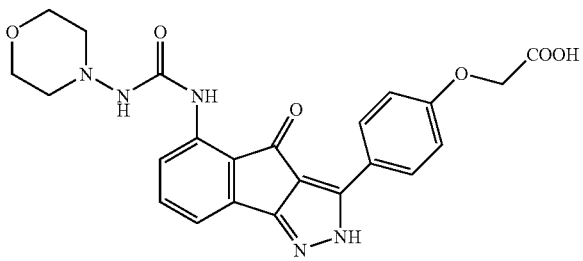 | |

We claim:

1. A hybrid ligand represented by the general formula: R1-Y—R2, wherein:
   (i) R1 represents a first ligand selected from: a steroid, retinoic acid, beta-lactam antibiotic, cannabinoid, nucleic acid, polypeptide, FK506, FK506 derivative, rapamycin, tetracycline, methotrexate, novobiocin, maltose, glutathione, biotin, vitamin D, dexamethasone, estrogen, progesterone, cortisone, testosterone, nickel, 2,4-diaminopteridine or cyclosporin, or a derivative thereof with structural modifications that retain a biological activity thereof;
   (ii) Y represents a polyethylene linker having the general formula $(CH_2—X—CH_2)_n$, where X represents O, S, SO, or $SO_2$, and n is an integer from 2 to 25; and,
   (iii) R2 represents a user-specified second ligand different from R1 selected from: a peptide, nucleic acid, carbohydrate, polysaccharide, lipid, prostaglandin, acyl halide, alcohol, aldehyde, alkane, alkene, alkyne, alkyl, alkyl halide, alkaloid, amine, aromatic hydrocarbon, sulfonate ester, carboxylate acid, aryl halide, ester, phenol, ether, nitrile, carboxylic acid anhydride, amide, quaternary ammonium salt, imine, enamine, amine oxide, cyanohydrin, organocadmium, aldol, organometallic, aromatic hydrocarbon, nucleoside, or a nucleotide.

2. The hybrid ligand of claim 1, wherein the first ligand binds to a polypeptide.

3. The hybrid ligand of claim 2, wherein the binding affinity corresponds to a ligand/polypeptide dissociation constant $K_D$ of less than 1 µM.

4. The hybrid ligand of claim 2, wherein the first ligand is capable of forming a covalent bond with the polypeptide.

5. The hybrid ligand of claim 1, wherein X is O.

6. The hybrid ligand of claim 1, wherein Y is $(CH_2—O—CH_2)_n$, where n=2 to 5.

7. The hybrid ligand of claim 1, wherein R1 is dexamethasone.

8. The hybrid ligand of claim 1, wherein R1 is methotrexate, a methotrexate derivative, FK506, an FK506 derivative or a 2,4-diaminopteridine derivative.

9. The hybrid ligand of claim 1, wherein R1 is methotrexate and Y is $(CH_2—O—CH_2)_n$, where n=2 to 5.

10. The hybrid ligand of claim 1, wherein R2 is a ligand selected from: a compound with a known biological effect, a compound with an unknown mechanism of action, a compound which binds to more than one polypeptide, a drug candidate compound, or a compound that binds to an unknown protein.

11. The hybrid ligand of claim 1, wherein R2 binds to or inhibits a kinase.

12. A hybrid ligand represented by the general formula: R1-Y—R2, wherein:
   (i) R1 represents a first ligand selected from: a steroid, retinoic acid, beta-lactam antibiotic, cannabinoid, nucleic acid, polypeptide, FK506, FK506 derivative, rapamycin, tetracycline, methotrexate, novobiocin, maltose, glutathione, biotin, vitamin D, dexamethasone, estrogen, progesterone, cortisone, testosterone, nickel, or 2,4-diaminopteridine or cyclosporin, or a derivative thereof with structural modifications that retain a biological activity thereof;
   (ii) Y represents a linker; and,
   (iii) R2 represents a user-specified second ligand different from R1 selected from: a peptide, nucleic acid, carbohydrate, polysaccharide, lipid, prostaglandin, acyl halide, alcohol, aldehyde, alkane, alkene, alkyne, alkyl, alkyl halide, alkaloid, amine, aromatic hydrocarbon, sulfonate ester, carboxylate acid, aryl halide, ester, phenol, ether, nitrile, carboxylic acid anhydride, amide, quaternary ammonium salt, imine, enamine, amine oxide, cyanohydrin, organocadmium, aldol, organometallic, aromatic hydrocarbon, nucleoside, or a nucleotide;
   wherein R2 binds to or inhibits a kinase.

13. The hybrid ligand of claim 12, wherein the kinase is a cyclin dependent kinase.

14. The hybrid ligand of claim 12, wherein R2 is a ligand selected from Table 2, or a derivative thereof with structural modifications that retain a biological activity thereof.

15. The hybrid ligand of claim 12 wherein Y represents a polyethylene linker having the general formula $(CH_2—X—CH_2)_n$, where X represents O, S, SO, or $SO_2$, and n is an integer from 2 to 25.

16. A fusion polypeptide, comprising segments P1, Cub-Z, and RM, in an order wherein Cub-Z is closer to the N-terminus of the fusion polypeptide than RM, wherein
   (i) P1 is a ligand binding polypeptide that binds to a non-peptide ligand of a hybrid ligand, which has the general formula R1-Y—R2, where R1 and R2 are ligands, and Y is a linker,
   (ii) Cub is a carboxy-terminal subdomain of ubiquitin,
   (iii) Z is an amino acid residue,
   (iv) RM is a reporter moiety.

17. A fusion polypeptide, comprising segments P1 and Nux, wherein
   (i) Nux is the amino-terminal subdomain of a wild-type ubiquitin or a reduced-associating mutant ubiquitin amino-terminal subdomain, and
   (ii) P1 is a ligand binding polypeptide that binds to a non-peptide ligand of a hybrid ligand, which has the general formula R1-Y—R2, where R1 and R2 are ligands, R1 is different from R2, and at least one of R1 and R2 is not a peptide, and Y is a linker.

18. The fusion polypeptide of claim 16 or 17, wherein the non-peptide ligands are: a steroid, retinoic acid, beta-lactam antibiotic, cannabinoid, nucleic acid, FK506, FK506 derivative, rapamycin, tetracycline, methotrexate, 2,4-diaminopteridine derivative, novobiocin, maltose, glutathione, biotin, vitamin D, dexamethasone, estrogen, progesterone, cortisone, testosterone, nickel, cyclosporin, or a derivative thereof with structural modifications that retain a biological activity thereof; or a carbohydrate, polysaccharide, lipid, prostaglandin, acyl halide, alcohol, aldehyde, alkane, alkene, alkyne, alkyl, alkyl halide, alkaloid, amine, aromatic hydrocarbon, sulfonate ester, carboxylate acid, aryl halide, ester, phenol, ether, nitrile, carboxylic acid anhydride, amide, quaternary ammonium salt, imine, enamine, amine oxide, cyanohydrin, organocadmium, aldol, organometallic, aromatic hydrocarbon, nucleoside, or a nucleotide.

19. The fusion polypeptide of claim 16, wherein Z is a non-methionine amino acid.

20. The fusion polypeptide of claim 16, wherein RM is: a polypeptide capable of emitting light upon excitation, a polypeptide with an enzymatic activity, a detectable tag or a transcription factor.

21. The fusion polypeptide of claim 16, wherein RM is: green fluorescent protein, URA3 or PLV.

22. A nucleic acid encoding the fusion polypeptide of any one of claims 16 or 17.

23. A composition, comprising:
(i) a hybrid ligand of the general formula R1-Y—R2, where R1 and R2 are ligands, R1 is different from R2 and at least one of R1 and R2 is not a peptide, Y is a linker; and,
(ii) at least one of two fusion polypeptides comprising:
  (a) a first fusion polypeptide comprising segments P2, Cub-Z, and RM, in an order wherein Cub-Z is closer to the N-terminus of the first fusion polypeptide than RM, wherein P2 is a ligand binding polypeptide that may bind to ligand R1 or R2 of the hybrid ligand, Cub is a carboxy-terminal subdomain of ubiquitin and RM is a reporter moiety, and Z is an amino acid residue;
  (b) a second fusion polypeptide comprising segments Nux and P1, wherein Nux is the amino-terminal subdomain of a wild-type ubiquitin or a reduced-associating mutant ubiquitin amino-terminal subdomain, and P1 is a ligand binding polypeptide that may bind to ligand R1 or R2 of the hybrid ligand.

24. A composition, comprising:
(i) a hybrid ligand represented by the general formula: R1-Y—R2, wherein:
  (a) R1 represents a first ligand selected from: a steroid, retinoic acid, beta-lactam antibiotic, cannabinoid, nucleic acid, polypeptide, FK506, FK506 derivative, rapamycin, tetracycline, methotrexate, 2,4-diaminopteridine derivative, novobiocin, maltose, glutathione, biotin, vitamin D, dexamethasone, estrogen, progesterone, cortisone, testosterone, nickel, or cyclosporin, or a derivative thereof with minor structural modifications that retain a biological activity thereof;
  (b) Y represents a polyethylene linker having the general formula $(CH_2—X—CH_2)_n$, where X represents O, S, SO, or $SO_2$, and n is an integer from 2 to 25;
  (c) R2 represents a user-specified second ligand different from R1 selected from: a peptide, nucleic acid, carbohydrate, polysaccharide, lipid, prostaglandin, acyl halide, alcohol, aldehyde, alkane, alkene, alkyne, alkyl, alkyl halide, alkaloid, amine, aromatic hydrocarbon, sulfonate ester, carboxylate acid, aryl halide, ester, phenol, ether, nitrile, carboxylic acid anhydride, amide, quaternary ammonium salt, imine, enamine, amine oxide, cyanohydrin, organocadmium, aldol, organometallic, aromatic hydrocarbon, nucleoside, or a nucleotide;

(ii) at least one fusion polypeptide selected from:
  (a) a first fusion polypeptide comprising: a ligand binding domain P1 and a domain selected from the group consisting of: a DNA binding domain and a transcriptional activation domain, wherein the ligand binding domain binds the first ligand R1; and,
  (b) a second fusion polypeptide comprising: a candidate ligand-binding domain P2 for the user-specified ligand R2 and a domain selected from the group consisting of: a DNA binding domain and a transcriptional activation domain.
wherein one of the first and second fusion polypeptides contains a DNA binding domain and the other fusion polypeptide contains a transcription activation domain.

25. A composition comprising:
(i) A hybrid ligand represented by the general formula: R1-Y—R2, wherein:
  (a) R1 represents a first ligand selected from: a steroid, retinoic acid, beta-lactam antibiotic, cannabinoid, nucleic acid, polypeptide, FK506, FK506 derivative, rapamycin, tetracycline, methotrexate, 2,4-diaminopteridine derivative, novobiocin, maltose, glutathione, biotin, vitamin D, dexamethasone, estrogen, progesterone, cortisone, testosterone, nickel, or cyclosporin or a derivative thereof with structural modifications that retain a biological activity thereof.
  (b) Y represents a polyethylene linker having the general formula $(CH_2—X—CH_2)_n$, where X represents O, S, SO, or $SO_2$, and n is an integer from 2 to 25;
  (c) R2 represents a user-specified second ligand different from R1 selected from: a peptide, nucleic acid, carbohydrate, polysaccharide, lipid, prostaglandin, acyl halide, alcohol, aldehyde, alkane, alkene, alkyne, alkyl, alkyl halide, alkaloid, amine, aromatic hydrocarbon, sulfonate ester, carboxylate acid, aryl halide, ester, phenol, ether, nitrile, carboxylic acid anhydride, amide, quaternary ammonium salt, imine, enamine, amine oxide, cyanohydrin, organocadmium, aldol, organometallic, aromatic hydrocarbon, nucleoside, or a nucleotide; and
(ii) a fusion polypeptide that includes:
  (a) at least one ligand binding domain; and,
  (b) a functional domain heterologous to the ligand binding domain which by itself is not capable of inducing or allowing the detection of a detectable event, but which is capable of inducing or allowing the detection of a detectable event when brought into proximity of a second functional domain.

26. The composition of any one of claims 23 to 25, wherein the composition is a complex.

27. The composition of any one of claims 23 to 25, wherein the composition is provided in an environment chosen from: a cell, a container, a kit, a solution or a growth medium.

28. A kit comprising:
(i) a compound of general structure R1-Y-L, wherein;
  (a) Y is of the general structure $(CH_2—X—CH_2)_n$, wherein X represents O, S, SO, or $SO_2$, and n is an integer from 2 to 25;
  (b) R1 is selected from: steroid, retinoic acid, beta-lactam antibiotic, cannabinoid, nucleic acid, polypeptide, FK506, FK506 derivative, rapamycin, tetracycline, methotrexate, novobiocin, maltose, glutathione, biotin, vitamin D, dexamethasone, estrogen, progesterone, cortisone, testosterone, nickel, 2,4-diaminopteridine or cyclosporin, or a derivative thereof with structural modifications that retain a biological activity thereof, and, (c) L is a chemical group that can be substituted by a different chemical group, and (ii) instructions to use the compound for the synthesis of a hybrid ligand R1-Y—R2 where R1 is different from R2, and at least one of R1 and R2 is not a peptide.

29. A composition comprising:
(i) a hybrid ligand of general structure R1-Y—R2, wherein R1 represents a first ligand selected from: steroid, retinoic acid, beta-lactam antibiotic, cannabinoid, nucleic acid, polypeptide, FK506, FK506 derivative, rapamycin, tetracycline, methotrexate, novobiocin, maltose, glutathione, biotin, vitamin D, dexamethasone, estrogen, progesterone, cortisone, testosterone, nickel, 2,4-diaminopteridine or cyclosporin, or a derivative thereof with structural modifications that retain a biological activity thereof; Y is a linker having the general formula $(CH_2—X—CH_2)_2$; and R2 represents a user-specified second ligand different from R1 selected from: a peptide, nucleic acid, carbohydrate, polysaccharide, lipid, prostaglandin, acyl halide, alcohol, aldehyde, alkane, alkene, alkyne, alkyl, alkyl halide, alkaloid, amine, aromatic hydrocarbon, sulfonate ester, carboxylate acid, aryl halide, ester, phenol, ether, nitrile, carboxylic acid anhydride, amide, quaternary ammonium salt, imine, enamine, amine oxide, cyanohydrin, organocadmium, aldol, organometallic, aromatic hydrocarbon, nucleoside, or a nucleotide, and
(ii) a fusion polypeptide, comprising at least two domains which are not found in combination in nature, wherein
  (a) one domain is a user specified polypeptide, and
  (b) a second domain is a DNA binding domain.

30. The composition of claim 29, wherein n is an integer from 2 to 25.

31. The composition of claim 29, wherein X=O, S, SO or $SO_2$.

32. The composition of claim 29, wherein R1 represents a first ligand selected from: a steroid, retinoic acid, beta-lactam antibiotic, cannabinoid, FK506, FK506 derivative, rapamycin, tetracycline, methotrexate, novobiocin, maltose, glutathione, vitamin D, dexamethasone, estrogen, progesterone, cortisone, testosterone, 2,4-diaminopteridine derivative or cyclosporin, or a derivative of one of the above with structural modifications that retain a biological activity thereof.

33. A composition comprising
(i) a polypeptide comprising a fragment of a β-lactamase and a user specified polypeptide, and
(ii) a second polypeptide comprising a second fragment of a β-lactamase and a domain chosen from the group consisting of: β-lactamase, a steroid receptor, retinoic acid receptor, cannabinoid receptor, FKB12, Tet-R, DHFR, GyrB, maltose binding protein, glutathione-S-transferase, vitamin D receptor, glucocorticoid receptor, estrogen receptor, progesterone receptor, testosterone receptor, or a fragment of one of the above, which fragment retains the binding capacity to its respective ligand,
wherein said first and second fragments of a β-lactamase individually possess no β-lactamase activity, and wherein the enzymatic activity of a β-lactamase is reconstituted when P1 and P2 are brought into close spatial proximity.

34. The composition of claim 33, further comprising a hybrid ligand of general structure R1-Y—R2, wherein Y is a linker.

35. The composition of claim 34, wherein Y is of the general structure $(CH_2—X—CH_2)_n$, and n is an integer from 2 to 25.

36. The composition of claim 35, wherein X=O, S, SO or $SO_2$.

37. The composition of claim 34, wherein R1 represents a first ligand selected from: a steroid, retinoic acid, beta-lactam antibiotic, cannabinoid, nucleic acid, polypeptide, FK506, FK506 derivative, rapamycin, tetracycline, methotrexate, novobiocin, maltose, glutathione, biotin, vitamin D, dexamethasone, estrogen, progesterone, cortisone, testosterone, nickel, 2,4-diaminopteridine derivative or cyclosporin, or a derivative of one of the above with structural modifications that retain a biological activity thereof.

* * * * *

UNITED STATES PATENT AND TRADEMARK OFFICE
CERTIFICATE OF CORRECTION

PATENT NO. : 7,135,550 B2
APPLICATION NO. : 10/234985
DATED : November 14, 2006
INVENTOR(S) : Come et al.

Page 1 of 1

It is certified that error appears in the above-identified patent and that said Letters Patent is hereby corrected as shown below:

Claim 12, Column 411, line 67, please delete "nucleic acid, polypeptide".

Claim 24, Column 413, line 50, please delete "minor".

Claim 31, Column 415, line 36, please correct "29" to read --30--.

Signed and Sealed this

Sixth Day of March, 2007

JON W. DUDAS
*Director of the United States Patent and Trademark Office*

SEQUENCE LISTING

<160> NUMBER OF SEQ ID NOS: 41

<210> SEQ ID NO 1
<211> LENGTH: 31
<212> TYPE: DNA
<213> ORGANISM: Artificial Sequence
<220> FEATURE:
<223> OTHER INFORMATION: Oligonucleotide ON-284

<400> SEQUENCE: 1
gatcttggag ccacccgcag ttcgaaaaat a                               31

<210> SEQ ID NO 2
<211> LENGTH: 31
<212> TYPE: DNA
<213> ORGANISM: Artificial Sequence
<220> FEATURE:
<223> OTHER INFORMATION: 5' phosphorylated oligonucleotide

<400> SEQUENCE: 2
agcttatttt tcgaactgcg ggtggctcca a                               31

```
<210> SEQ ID NO 3
<211> LENGTH: 53
<212> TYPE: DNA
<213> ORGANISM: Artificial Sequence
<220> FEATURE:
<223> OTHER INFORMATION: Oliogonucleotide ON-286

<400> SEQUENCE: 3
gcgggctagc taactaatgg aggatacata atgaaacca gtaacgttat acg        53

<210> SEQ ID NO 4
<211> LENGTH: 46
<212> TYPE: DNA
<213> ORGANISM: Artificial Sequence
<220> FEATURE:
<223> OTHER INFORMATION: Oligonucleotide ON-287

<400> SEQUENCE: 4
cgttccgagc tcactgcccg ctctcgagtc gggaaacctg tcgtgc               46

<210> SEQ ID NO 5
<211> LENGTH: 51
<212> TYPE: DNA
<213> ORGANISM: Artificial Sequence
<220> FEATURE:
<223> OTHER INFORMATION: Oligonucleotide ON-295

<400> SEQUENCE: 5
cctccatatg aattgtgagc gctcacaatt cggtacagcc ccatcccacc c          51

<210> SEQ ID NO 6
<211> LENGTH: 51
<212> TYPE: DNA
<213> ORGANISM: Artificial Sequence
<220> FEATURE:
<223> OTHER INFORMATION: Oligonucleotide ON-296

<400> SEQUENCE: 6
cgccatcgat caattgtgag cgctcacaat tcaggatgtg tgtgatgaag a          51

<210> SEQ ID NO 7
<211> LENGTH: 5
<212> TYPE: PRT
<213> ORGANISM: Artificial Sequence
<220> FEATURE:
<223> OTHER INFORMATION: 5-amino spacer sequence

<400> SEQUENCE: 7

Gly Ala Asp Gly Ala
1               5

<210> SEQ ID NO 8
<211> LENGTH: 13
<212> TYPE: PRT
<213> ORGANISM: Artificial Sequence
<220> FEATURE:
<223> OTHER INFORMATION: Dynorphin B

<400> SEQUENCE: 8

Tyr Gly Gly Phe Leu Arg Arg Gln Phe Lys Val Val Thr
1               5                   10

<210> SEQ ID NO 9
<211> LENGTH: 72
<212> TYPE: DNA
<213> ORGANISM: Artificial Sequence
```

```
<220> FEATURE:
<223> OTHER INFORMATION: Oligonucleotide ON-312

<400> SEQUENCE: 9
tcgagagcgg gcaggggcc gacggggcct acggtggttt cctgcgtcgt cagttcaaag      60
ttgtaaccta at                                                         72

<210> SEQ ID NO 10
<211> LENGTH: 72
<212> TYPE: DNA
<213> ORGANISM: Artificial Sequence
<220> FEATURE:
<223> OTHER INFORMATION: Oligonucleotide ON-313

<400> SEQUENCE: 10
ctagattagg ttacaacttt gaactgacga cgcaggaaac caccgtaggc cccgtcggcc      60
ccctgcccgc tc                                                         72

<210> SEQ ID NO 11
<211> LENGTH: 15
<212> TYPE: DNA
<213> ORGANISM: Artificial Sequence
<220> FEATURE:
<223> OTHER INFORMATION: Oligonucleotide ON-335

<400> SEQUENCE: 11
gggcctaatt aatta                                                      15

<210> SEQ ID NO 12
<211> LENGTH: 22
<212> TYPE: DNA
<213> ORGANISM: Artificial Sequence
<220> FEATURE:
<223> OTHER INFORMATION: Oligonucleotide ON-336

<400> SEQUENCE: 12
agcttaatta attaggcccc gt                                              22

<210> SEQ ID NO 13
<211> LENGTH: 44
<212> TYPE: DNA
<213> ORGANISM: Artificial Sequence
<220> FEATURE:
<223> OTHER INFORMATION: primer

<400> SEQUENCE: 13
ttttgtacat ctagatcgcg aaagcttctt ttttttttt tttv                       44

<210> SEQ ID NO 14
<211> LENGTH: 12
<212> TYPE: DNA
<213> ORGANISM: Artificial Sequence
<220> FEATURE:
<223> OTHER INFORMATION: Oligonucleotide ON-369

<400> SEQUENCE: 14
agcagcagca gc                                                         12

<210> SEQ ID NO 15
<211> LENGTH: 15
<212> TYPE: DNA
<213> ORGANISM: Artificial Sequence
<220> FEATURE:
<223> OTHER INFORMATION: Oligonucleotide ON-370
```

<400> SEQUENCE: 15
gctgctgctg ctcgt                                                          15

<210> SEQ ID NO 16
<211> LENGTH: 36
<212> TYPE: DNA
<213> ORGANISM: Artificial Sequence
<220> FEATURE:
<223> OTHER INFORMATION: primer

<400> SEQUENCE: 16
ggggtcgaca tgatcagtct gattgcggcg ttagcg                                   36

<210> SEQ ID NO 17
<211> LENGTH: 37
<212> TYPE: DNA
<213> ORGANISM: Artificial Sequence
<220> FEATURE:
<223> OTHER INFORMATION: primer

<400> SEQUENCE: 17
gggggcggcc gcttaccgcc gctccagaat ctcaaag                                  37

<210> SEQ ID NO 18
<211> LENGTH: 48
<212> TYPE: DNA
<213> ORGANISM: Artificial Sequence
<220> FEATURE:
<223> OTHER INFORMATION: primer

<400> SEQUENCE: 18
ggggtcgaca tgggtggtgg tggtggtggt gcaggagtct cacaagac                      48

<210> SEQ ID NO 19
<211> LENGTH: 30
<212> TYPE: DNA
<213> ORGANISM: Artificial Sequence
<220> FEATURE:
<223> OTHER INFORMATION: primer

<400> SEQUENCE: 19
gggggcggcc gcttttttgat gaaacagaag                                         30

<210> SEQ ID NO 20
<211> LENGTH: 23
<212> TYPE: DNA
<213> ORGANISM: Artificial Sequence
<220> FEATURE:
<223> OTHER INFORMATION: primer

<400> SEQUENCE: 20
gggtcgacgc atggagaact tcc                                                 23

<210> SEQ ID NO 21
<211> LENGTH: 22
<212> TYPE: DNA
<213> ORGANISM: Artificial Sequence
<220> FEATURE:
<223> OTHER INFORMATION: primer

<400> SEQUENCE: 21
gggcggccgc tcagagtcga ag                                                  22

<210> SEQ ID NO 22
<211> LENGTH: 24
<212> TYPE: DNA
<213> ORGANISM: Artificial Sequence
<220> FEATURE:
<223> OTHER INFORMATION: primer

<400> SEQUENCE: 22
gggtcgacgc atggctacct ctcg                                          24

<210> SEQ ID NO 23
<211> LENGTH: 26
<212> TYPE: DNA
<213> ORGANISM: Artificial Sequence
<220> FEATURE:
<223> OTHER INFORMATION: primer

<400> SEQUENCE: 23
gggcggccgc tcaggctgta ttcagc                                        26

<210> SEQ ID NO 24
<211> LENGTH: 37
<212> TYPE: DNA
<213> ORGANISM: Artificial Sequence
<220> FEATURE:
<223> OTHER INFORMATION: primer

<400> SEQUENCE: 24
gggggtcgac atgatcagtc tgattgcggc gttagcg                            37

<210> SEQ ID NO 25
<211> LENGTH: 37
<212> TYPE: DNA
<213> ORGANISM: Artificial Sequence
<220> FEATURE:
<223> OTHER INFORMATION: primer

<400> SEQUENCE: 25
gggggcggcc gcttaccgcc gctccagaat ctcaaag                            37

<210> SEQ ID NO 26
<211> LENGTH: 34
<212> TYPE: DNA
<213> ORGANISM: Artificial Sequence
<220> FEATURE:
<223> OTHER INFORMATION: primer

<400> SEQUENCE: 26
gatcgtcgac atggtagccg agcaaacaca ggag                               34

<210> SEQ ID NO 27
<211> LENGTH: 35
<212> TYPE: DNA
<213> ORGANISM: Artificial Sequence
<220> FEATURE:
<223> OTHER INFORMATION: primer

<400> SEQUENCE: 27
gatcgtcgac gttttgttcg gcttttttcat tgatg                             35

<210> SEQ ID NO 28
<211> LENGTH: 47
<212> TYPE: DNA
<213> ORGANISM: Artificial Sequence
<220> FEATURE:
<223> OTHER INFORMATION: primer

```
<400> SEQUENCE: 28
ttttgtacat ctagatcgcg agcggccgcc cttttttttt tttttv              47

<210> SEQ ID NO 29
<211> LENGTH: 39
<212> TYPE: DNA
<213> ORGANISM: Artificial Sequence
<220> FEATURE:
<223> OTHER INFORMATION: primer

<400> SEQUENCE: 29
gcaggtaccc catggtgagt attcaacatt tccgtgtcg                      39

<210> SEQ ID NO 30
<211> LENGTH: 38
<212> TYPE: DNA
<213> ORGANISM: Artificial Sequence
<220> FEATURE:
<223> OTHER INFORMATION: primer

<400> SEQUENCE: 30
ccgaagcttt ctaccatttt cgccagttaa tagtttgc                       38

<210> SEQ ID NO 31
<211> LENGTH: 36
<212> TYPE: DNA
<213> ORGANISM: Artificial Sequence
<220> FEATURE:
<223> OTHER INFORMATION: primer

<400> SEQUENCE: 31
cacgcggccg cctacttact ctagcttccc ggcaac                         36

<210> SEQ ID NO 32
<211> LENGTH: 35
<212> TYPE: DNA
<213> ORGANISM: Artificial Sequence
<220> FEATURE:
<223> OTHER INFORMATION: primer

<400> SEQUENCE: 32
cacctcgagt taccaatgct taatcagtga ggcac                          35

<210> SEQ ID NO 33
<211> LENGTH: 15
<212> TYPE: PRT
<213> ORGANISM: Artificial Sequence
<220> FEATURE:
<223> OTHER INFORMATION: polypeptide linker

<400> SEQUENCE: 33

Gly Gly Gly Gly Ser Gly Gly Gly Gly Ser Gly Gly Gly Gly Ser
 1               5                  10                  15

<210> SEQ ID NO 34
<211> LENGTH: 37
<212> TYPE: DNA
<213> ORGANISM: Artificial Sequence
<220> FEATURE:
<223> OTHER INFORMATION: primer

<400> SEQUENCE: 34 gggggggtacc atgatcagtc tgattgcggc gttagcg                       37
```

<210> SEQ ID NO 35
<211> LENGTH: 32
<212> TYPE: DNA
<213> ORGANISM: Artificial Sequence
<220> FEATURE:
<223> OTHER INFORMATION: primer

<400> SEQUENCE: 35
ggggaagctt ccgccgctcc agaatctcaa ag                             32

<210> SEQ ID NO 36
<211> LENGTH: 29
<212> TYPE: DNA
<213> ORGANISM: Artificial Sequence
<220> FEATURE:
<223> OTHER INFORMATION: primer

<400> SEQUENCE: 36
gggcggccgc gagaacttcc aaaaggtgg                                 29

<210> SEQ ID NO 37
<211> LENGTH: 29
<212> TYPE: DNA
<213> ORGANISM: Artificial Sequence
<220> FEATURE:
<223> OTHER INFORMATION: primer

<400> SEQUENCE: 37
cgctcgagtc agagtcgaag atggggtac                                 29

<210> SEQ ID NO 38
<211> LENGTH: 45
<212> TYPE: DNA
<213> ORGANISM: Artificial Sequence
<220> FEATURE:
<223> OTHER INFORMATION: primer

<400> SEQUENCE: 38
ttttgtacat ctagatcgcg actcgagcct ttttttttt ttttv                45

<210> SEQ ID NO 39
<211> LENGTH: 16
<212> TYPE: DNA
<213> ORGANISM: Artificial Sequence
<220> FEATURE:
<223> OTHER INFORMATION: Oligonucleotide CR109

<400> SEQUENCE: 39
ggccgccacg cgtccg                                               16

<210> SEQ ID NO 40
<211> LENGTH: 12
<212> TYPE: DNA
<213> ORGANISM: Artificial Sequence
<220> FEATURE:
<223> OTHER INFORMATION: Oligonucleotide CR110

<400> SEQUENCE: 40
cggacgcgtg gc                                                   12

<210> SEQ ID NO 41
<211> LENGTH: 132
<212> TYPE: DNA
<213> ORGANISM: Artificial Sequence
<220> FEATURE:
<223> OTHER INFORMATION: Cloning vector pACT2

```
<400> SEQUENCE: 41
aaaaaagaga tctgtatggc ttacccatac gatgttccag attacgctag cttgggtggt          60
catatggcca tggaggcccc ggggatccga attcgagctc gagagatcta tgaatcgtag         120
atactgaaaa ac                                                              132
```